United States Patent
Sinskey et al.

(10) Patent No.: US 8,679,782 B2
(45) Date of Patent: Mar. 25, 2014

(54) PRODUCTION OF TRIACYLGLYCERIDES, FATTY ACIDS, AND THEIR DERIVATIVES

(75) Inventors: Anthony John Sinskey, Boston, MA (US); Daniel MacEachran, Cambridge, MA (US); Kazuhiko Kurosawa, Somerville, MA (US); Paolo Boccazzi, Cambridge, MA (US); Jason W. Holder, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 84 days.

(21) Appl. No.: 13/378,479

(22) PCT Filed: Jun. 15, 2010

(86) PCT No.: PCT/US2010/001717
§ 371 (c)(1),
(2), (4) Date: Mar. 6, 2012

(87) PCT Pub. No.: WO2010/147642
PCT Pub. Date: Dec. 23, 2010

(65) Prior Publication Data
US 2012/0171735 A1   Jul. 5, 2012

Related U.S. Application Data

(60) Provisional application No. 61/268,707, filed on Jun. 15, 2009, provisional application No. 61/281,239, filed on Nov. 13, 2009.

(51) Int. Cl.
*C12P 21/06* (2006.01)

(52) U.S. Cl.
USPC ...................................................... 435/69.1

(58) Field of Classification Search
USPC ...................................................... 435/69.1
See application file for complete search history.

(56) References Cited

U.S. PATENT DOCUMENTS

| | | |
|---|---|---|
| 5,429,942 A | 7/1995 | Kock et al. |
| 5,514,583 A | 5/1996 | Picataggio et al. |
| 5,712,133 A | 1/1998 | Picataggio et al. |
| 5,726,053 A | 3/1998 | Picataggio et al. |
| 5,789,210 A | 8/1998 | Ho et al. |
| 5,900,496 A | 5/1999 | Hou |
| 5,922,581 A | 7/1999 | Hoshino et al. |
| 6,025,169 A | 2/2000 | Nakamura et al. |
| 6,110,715 A | 8/2000 | Chida et al. |
| 6,566,107 B1 | 5/2003 | Zhang |
| 6,825,002 B2 | 11/2004 | Tsubokura et al. |
| 6,955,911 B2 | 10/2005 | Ryuno et al. |
| 7,118,896 B2 | 10/2006 | Kalscheuer et al. |
| 7,223,575 B2 | 5/2007 | Zhang et al. |
| 7,226,735 B2 | 6/2007 | Jeffries et al. |
| 7,253,001 B2 | 8/2007 | Wahlbom et al. |
| 7,285,403 B2 | 10/2007 | Jeffries et al. |
| 7,288,402 B2 | 10/2007 | Osswald et al. |
| 7,354,755 B2 | 4/2008 | Zhang et al. |
| 7,491,521 B2 | 2/2009 | Osswald et al. |
| 7,977,075 B2 | 7/2011 | Causey et al. |
| 2001/0036660 A1 | 11/2001 | Tsuda et al. |
| 2003/0162271 A1 | 8/2003 | Zhang et al. |
| 2005/0032159 A1 | 2/2005 | Ichige et al. |
| 2005/0153411 A1 | 7/2005 | Wahlbom et al. |
| 2005/0239165 A1 | 10/2005 | Lorenz et al. |
| 2006/0110805 A1 | 5/2006 | Fotheringham et al. |
| 2007/0190629 A1 | 8/2007 | Wahlbom et al. |
| 2008/0081358 A1 | 4/2008 | Viitanen et al. |
| 2008/0261287 A1 | 10/2008 | Winkler et al. |
| 2008/0293100 A1 | 11/2008 | Wendisch et al. |
| 2009/0047721 A1 | 2/2009 | Trimbur et al. |

FOREIGN PATENT DOCUMENTS

| | | |
|---|---|---|
| EP | 1 549 736 B1 | 4/2009 |
| WO | WO 97/13842 A1 | 4/1997 |
| WO | WO 03/078643 A1 | 9/2003 |
| WO | WO 2004/037973 A2 | 5/2004 |
| WO | WO 2005/113774 A2 | 12/2005 |
| WO | WO 2006/009434 A1 | 1/2006 |
| WO | WO 2008/006037 A2 | 1/2008 |
| WO | WO 2008/081959 A1 | 7/2008 |
| WO | WO 2008/124162 A2 | 10/2008 |
| WO | WO 2008/151149 A2 | 12/2008 |
| WO | WO 2009/009391 A2 | 1/2009 |

OTHER PUBLICATIONS

Genbank Submission; UNIPROT, Accession No. Q0SEX5; McLeod et al.; Sep. 5, 2006. 1 page.
Alvarez et al., Cloning and characterization of a gene involved in triacylglycerol biosynthesis and identification of additional homologous genes in the oleaginous bacterium *Rhodococcus opacus* PD630. Microbiology. Aug. 2008;154(Pt 8):2327-35.
Alvarez et al., Triacylglycerols in prokaryotic microorganisms. Appl Microbiol Biotechnol. Dec. 2002;60(4):367-76. Epub Oct. 12, 2002.
Aristidou et al., Metabolic engineering applications to renewable resource utilization. Curr Opin Biotechnol. Apr. 2000;11(2):187-98.
Azócar et al., Biotechnological processes for biodiesel production using alternative oils. Appl Microbiol Biotechnol. Oct. 2010;88(3):621-36. Epub Aug. 10, 2010.
Ciapina et al., Biosurfactant production by *Rhodococcus erythropolis* grown on glycerol as sole carbon source. Appl Biochem Biotechnol. Mar. 2006;131(1-3):880-6.
Hahn-Hägerdal et al., Metabolic engineering of *Saccharomyces cerevisiae* for xylose utilization. Adv Biochem Eng Biotechnol. 2001;73:53-84.
Holder et al., Comparative and functional genomics of *Rhodococcus opacus* PD630 for biofuels development. PLoS Genet. Sep. 2011;7(9):e1002219. Epub Sep. 8, 2011.
Jeffries et al., Engineering yeasts for xylose metabolism. Curr Opin Biotechnol. Jun. 2006;17(3):320-6. Epub May 18, 2006.
Jin et al., Improvement of xylose uptake and ethanol production in recombinant *Saccharomyces cerevisiae* through an inverse metabolic engineering approach. Appl Environ Microbiol. Dec. 2005;71(12):8249-56.

(Continued)

*Primary Examiner* — Karen Cochrane Carlson
(74) *Attorney, Agent, or Firm* — Wolf, Greenfield & Sacks, P.C.

(57) ABSTRACT

The invention relates to production of triacylglycerols in cells.

18 Claims, 93 Drawing Sheets

(56) References Cited

OTHER PUBLICATIONS

Kawaguchi et al., Engineering of a xylose metabolic pathway in *Corynebacterium glutamicum*. Appl Environ Microbiol. May 2006;72(5):3418-28.

Kurosawa et al., High glucose cultivation of *Rhodococcus opacus* PD630 in batch-culture for biodiesel production. Journal of Biotechnology, in press 2010.

Kurosawa et al., High-cell-density batch fermentation of *Rhodococcus opacus* PD630 using a high glucose concentration for triacylglycerol production. J Biotechnol. Jun. 2010;147(3-4):212-8. Epub Apr. 20, 2010.

Kurosawa et al., Rhodostreptomycins, antibiotics biosynthesized following horizontal gene transfer from *Streptomyces padanus* to *Rhodococcus fascians*. J Am Chem Soc. Jan. 30, 2008;130(4):1126-7. Epub Jan. 8, 2008.

MacEachran et al., The *Rhodococcus opacus* PD630 heparin-binding hemagglutinin homolog TadA mediates lipid body formation. Appl Environ Microbiol. Nov. 2010;76(21):7217-25. Epub Sep. 17, 2010.

Madhavan et al., Alcoholic fermentation of xylose and mixed sugars using recombinant *Saccharomyces cerevisiae* engineered for xylose utilization. Appl Microbiol Biotechnol. Apr. 2009;82(6):1037-47. Epub Jan. 6, 2009.

McLeod et al., The complete genome of *Rhodococcus* sp. RHA1 provides insights into a catabolic powerhouse. Proc Natl Acad Sci U S A. Oct. 17, 2006;103(42):15582-7. Epub Oct. 9, 2006.

Meijnen et al., Engineering *Pseudomonas putida* S12 for efficient utilization of D-xylose and L-arabinose. Appl Environ Microbiol. Aug. 2008;74(16):5031-7. Epub Jun. 27, 2008.

Ohta et al., Metabolic engineering of *Klebsiella oxytoca* M5A1 for ethanol production from xylose and glucose. Appl Environ Microbiol. Oct. 1991;57(10):2810-5.

Riesenberg et al., High-cell-density cultivation of microorganisms. Appl Microbiol Biotechnol. Apr. 1999;51(4):422-30.

Rittmann et al., Engineering of a glycerol utilization pathway for amino acid production by *Corynebacterium glutamicum*. Appl Environ Microbiol. Oct. 2008;74(20):6216-22. Epub Aug. 29, 2008.

Shaw et al., Metabolic engineering of a thermophilic bacterium to produce ethanol at high yield. Proc Natl Acad Sci U S A. Sep. 16, 2008;105(37):13769-74. Epub Sep. 8, 2008.

Van Maris et al., Development of efficient xylose fermentation in *Saccharomyces cerevisiae*: xylose isomerase as a key component. Adv Biochem Eng Biotechnol. 2007;108:179-204.

Voss et al., High cell density cultivation of *Rhodococcus opacus* for lipid production at a pilot-plant scale. Appl Microbiol Biotechnol. May 2001;55(5):547-55.

Wältermann et al., Mechanism of lipid-body formation in prokaryotes: how bacteria fatten up. Mol Microbiol. Feb. 2005;55(3):750-63.

Wältermann et al., *Rhodococcus opacus* strain PD630 as a new source of high-value single-cell oil? Isolation and characterization of triacylglycerols and other storage lipids. Microbiology. May 2000;146 ( Pt 5):1143-9.

Wang et al., Establishment of a xylose metabolic pathway in an industrial strain of *Saccharomyces cerevisiae*. Biotechnol Lett. Jun. 2004;26(11):885-90.

Wisselink et al., Novel evolutionary engineering approach for accelerated utilization of glucose, xylose, and arabinose mixtures by engineered *Saccharomyces cerevisiae* strains. Appl Environ Microbiol. Feb. 2009;75(4):907-14. Epub Dec. 12, 2008.

Yanase et al., Genetic engineering of *Zymobacter palmae* for production of ethanol from xylose. Appl Environ Microbiol. Apr. 2007;73(8):2592-9. Epub Feb. 16, 2007.

Zhang et al., Metabolic Engineering of a Pentose Metabolism Pathway in Ethanologenic *Zymomonas mobilis*. Science. Jan. 13, 1995;267(5195):240-3.

Triacylglycerols (TAGs)

- Actinomycetes accumulate stored lipids as TAGS.

- 10-80% cell dry weight in *Rhodococcus* is Fatty Acid
  - *opacus* PD630
    - >70% from sugar
    - >80% from oil sources

- Stored lipids accumulate as mostly C16-C18:1 in TAGs (C53) that can be converted to biodiesel and other fuels.
  - by methanolysis
  - or ethanolysis
  - Physical methods

Lipid Bodies (LB) in *Rhodococcus opacus* PD630

*Rhodococcus opacus* PD630

Alvarez et al. (1996) Arch. Microbiol.

Cultured from gas works plant on phenyldecane as sole carbon source. 55(3):750-63

Fig. 1

Addition of glucose at 120 hours increases total fatty acids and CDW 3 assemblies of the *R. opacus* PD630 Genome

| | Paired ends | 022309 assembly | FASI edit reassembly |
|---|---|---|---|
| numberOfScaffolds | 20 | 16 | 17 |
| numberOfBases | 9,086,342 | 9,173,585 | 9,175,513 |
| avgScaffoldSize | 454,317 | 573,349 | 539,736 |
| N50ScaffoldSize | 1,079,462 | 1,224,274 | 1,224,624 |
| largestScaffoldSize | 2,321,171 | 2,335,733 | 2,333,867 |
| numberOfContigs | 363 | 367 | 339 |
| numberOfBases | 9,019,691 | 9,049,865 | 9,056,225 |
| avgContigSize | 24,847 | 24,659 | 26,714 |
| N50ContigSize | 57,861 | 50,344 | 63,408 |
| largestContigSize | 183,062 | 195,783 | 195,783 |
| Q40PlusBases | 99.84% | 99.90% | 99.90% |
| allContigMetrics\|numberOfContigs | 1,390 | 757 | 711 |
| allContigMetrics\|numberOfBases | 9,210,670 | 9,126,833 | 9,129,612 |
| scaffoldedLargeContigs | 295 | 333 | 309 |
| percentOfLargeCtgs | 81.27% | 90.74% | 91.15% |
| singletonLCScaffolds | 3 | 1 | 2 |
| nonSingletonScaffolds | 17 | 15 | 15 |
| Percent Of LargeCtgs 500 bp | 80.44% | 90.46% | 90.56% |

Fig. 15

EC numbers to gene copy #s
Search for hard wiring of lipid production through Comparative genomics reaction
ATP + acetyl-CoA + HCO3- = ADP + phosphate + malonyl-CoA
malonyl-CoA + [acyl-carrier protein] = CoA + malonyl-[acyl-carrier protein]
acetyl-CoA + n malonyl-CoA + 4n NADPH + 4n H+ = long-chain-acyl-CoA + n CoA + n CO2 + 4n NADP+
acetyl-CoA + n malonyl-CoA + 2n NADPH + 2n H+ = a long-chain fatty acid + (n+1) CoA + n CO2 + 2n NADP+
an acyl-[acyl-carrier protein] + malonyl-[acyl-carrier protein] = a 3-oxoacyl-[acyl-carrier protein] + CO2 + [acyl-carrier protein]
a (Z)-hexadec-11-enoyl-[acyl-carrier protein] + a malonyl-[acyl-carrier protein] = a (Z)-3-oxooctadeca-13-enoyl-[acyl-carrier protein] + CO2 + an [acyl-carrier protein]
acetyl-[acyl-carrier protein] + a malonyl-[acyl-carrier protein] = an acetoacetyl-[acyl-carrier protein] + CoA + CO2
3-oxoacyl-[acyl-carrier protein] + NADPH + H+ = (3R)-3-hydroxyacyl-[acyl-carrier protein] + NADP+

| EC_number | CGB1 | H37Rv | Smeg | NCF1 | R_eutr | SM_COEL | S_averm | RHA1 | R_opacus | Description |
|---|---|---|---|---|---|---|---|---|---|---|
| EC:6.4.1.2 | 3 | 2 | 2 | 1 | 3 | 1 | 1 | 1 | 4 | 5 acetyl-CoA carboxylase |
| EC:2.3.1.39 | 2 | 2 | 2 | 1 | 1 | 1 | 1 | 1 | 1 | 2 [acyl-carrier-protein] S-malonyltransferase |
| EC:2.3.1.86 | 0 | 15 | 28 | 16 | 1 | 3 | 4 | 22 | 0 | 23 fatty-acyl-CoA synthase |
| EC:2.3.1.85 | 2 | 0 | 0 | 0 | 0 | 0 | 0 | 0 | 0 | 0 fatty-acid synthase |
| EC:2.3.1.41 | 2 | 4 | 4 | 2 | 1 | 5 | 5 | 5 | 3 | 3 beta-ketoacyl-acyl-carrier-protein synthase I |
| EC:2.3.1.179 | 0 | 0 | 2 | 1 | 1 | 2 | 2 | 2 | 1 | 2 beta-ketoacyl-acyl-carrier-protein synthase II |
| EC:2.3.1.180 | 0 | 0 | 2 | 3 | 1 | 5 | 5 | 5 | 3 | 5 beta-ketoacyl-acyl-carrier-protein synthase III |
| EC:1.1.1.100 | 6 | 5 | 48 | 18 | 15 | 17 | 17 | 17 | 51 | 50 3-oxoacyl-[acyl-carrier-protein] reductase |

Fig. 17

Applying StatGraphics to optimize carbon/nitrogen ratio of the production medium

- Box-Wilson central composite design (CCD)
- Define max and min values for experimental factors (glucose, $(NH_4)_2SO_4$) based on experimental results
- Run all conditions statistically calculated by StatGraphics

- Response surface plot of experimental design conditions
- The optimal C/N ratio was predicted to be 17.8
- Maximum production of fatty acids 25.4 g/L Experimental confirmation of optimal production by *R. opacus* PD630 on glucose with Sixfors system Defined medium containing 240 g L$^{-1}$ glucose and 13.4 g L$^{-1}$ (NH$_4$)$_2$SO$_4$. Total fatty acids (filled circles), CDW (open diamonds), residual glucose (filled squares), residual (NH$_4$)$_2$SO$_4$ (open triangles).

Triplicate independent fermentations

Optimal tFA production and yield by *R. opacus* PD630 on glucose with the Sixfors system

| glucose [g/l] | (NH4)2SO4 [g/l] | C/N ratio [g/g] | CDW^a [g/l] | tFA^b [g/l] | FA [%CDW] | Y_{f/u}^c |
|---|---|---|---|---|---|---|
| 0 | 7.5 | 0.0 | 0 | 0 | 0 | 0.00 |
| 15.3 | 12.8 | 1.2 | 7.02 | 1.08 | 14.7 | 0.14 |
| 35.2 | 2.2 | 16.0 | 9.69 | 4.93 | 54.0 | 0.14 |
| 35.2 | 12.8 | 2.8 | 12.52 | 2.28 | 25.9 | 0.06 |
| 120 | 0 | 120.0 | 0 | 0 | 0 | 0.00 |
| 120 | 7.5 | 16.0 | 35.9 | 16.2 | 48.8 | 0.14 |
| 120 | 7.5 | 16.0 | 37.4 | 18.6 | 49.8 | 0.15 |
| 120 | 7.5 | 16.0 | 39.7 | 14.0 | 35.4 | 0.12 |
| 120 | 7.5 | 16.0 | 42.7 | 21.6 | 51.8 | 0.18 |
| 120 | 10 | 12.0 | 36.2 | 17.32 | 47.8 | 0.14 |
| 120 | 15 | 8.0 | 31.36 | 8.18 | 27.7 | 0.07 |
| 120 | 20 | 6.0 | 27.76 | 7.86 | 33.3 | 0.07 |
| 160 | 7.5 | 21.3 | 41.75 | 20.82 | 49.9 | 0.13 |
| 200 | 7.5 | 26.7 | 42.88 | 21.69 | 50.6 | 0.11 |
| 200 | 15 | 13.3 | 71.78 | 16.51 | 21.8 | 0.08 |
| 200 | 20 | 10.0 | 73.42 | 15.46 | 22.4 | 0.08 |
| 200 | 30 | 6.7 | 77.41 | 12.57 | 19.5 | 0.06 |
| 205 | 2.2 | 93.2 | 10.58 | 3.11 | 28.9 | 0.02 |
| 205 | 7.5 | 27.3 | 33.4 | 16.58 | 53.9 | 0.08 |
| 205 | 12.8 | 16.0 | 51.34 | 24.73 | 48.2 | 0.12 |
| 240 | 2.2 | 109.1 | 9.09 | 2.77 | 42.1 | 0.01 |
| 240 | 7.5 | 32.0 | 42.63 | 17.76 | 44.1 | 0.07 |
| 240 | 13.45 | 17.8 | 85.93 | 26.45 | 36.5 | 0.11 |
| 240 | 13.45 | 17.8 | 74.87 | 20.81 | 33.9 | 0.09 |
| 240 | 13.45 | 17.8 | 72.10 | 29.26 | 44.7 | 0.12 |

Max Yield → (120, 7.5, 16.0 rows)
Max tFA → (240, 13.45, 17.8 rows)

Fig. 30

Xylose utilization

| | Xylose | | |
|---|---|---|---|
| | 0.4% | 2% | 10% |
| R. opacus PD630 | − | − | − |
| Streptomyces | | | |
| coelicolor BAA-471 | + | − | |
| avermitilis ATCC 31267 | + | ± | |
| padanus MITKK-103 | − | | |
| | + | + | − |

+, growth; ±, faint growth; −, no growth

R. opacus PD630 does not utilize xylose

Construct a strain with the ability to metabolize and accumulate lipids in high amounts.

Fig. 31

Sequence of insert DNA in pAL358

```
GATCCCTGATGTGTGCCCCTAGTGGGGCTCGGGCCGGCGACCACGAGGCGGCGGCCGACCACGAGGCATGGCGAGGTGACGCAGGTCATGACGTCAGCATAGGAGGGTCGCCG
CAAAGGCGCCCATGCATGCCGACTGCTCCTGCGCGGCCCTCGCCGCCGCGACGCACGCCGAACGGCACGCACGCGTCGAGGCACGCCGTACGCGCCGTACCCCGGCCTTCTTCGT
CAGCGCCTCGCTCGTGCAGCCCGTCAGCGCGTCGGCGCAGGCGGTGGTCCATCGCCAGCGGTGCTCGAGGTGCTCGGCCGTCGAGGGCCGCGGCACGCCGGCGCACGCCGCCATCGA
CATCGAAGTCCTCGAACGCCGGAGTCCTCAGCGCCGGTCGGCGCACGCGGTTCTTGAGGATCAGGTAGTTGCGCATGCAGGAGTCAGCAGCCCGCGAGGCCCACACGCCGTCGAGTCCCGTCC
GCACCTCCGGGTCGAAGTCAAGTGCCCGGGCACTGGCGTCGGGCCGTCCGTTGAGGTCGATGTGGAAGAGTCTTCCCGCCCACAGGCCTGCGCATGCCGTGCCGGCGGAAGTTCAGGCGGCCATCT
GCGCGGCCTTGAAGTCAAGTGCCCGGGCACTGGCGTCGGGCCGTCCGTTGAGGTCGATGTGGAAGAGTCTTCCCGCCCACAGGCCTGCGCATGCCGTGCCGGCGGAAGTTCAGGCGGCCATCT
CCTGGTCGTACTTGATGCCGACCTCCGGGTTGACGCGTACAGCTCCGGGCGTCCGATGTGGAGCGCTCCAGGCGCTCGATGAAGGGCAGGGCGTGGCCGACGGTCGGAGGGCGTCGG
GCTCGTTGGGGCTTGGCTCGATGGCGAAGCGGAGGTCGTAGCCCTGGCCGCCCACCGGCGAACCGGAGGTCGTAGCCCTGGCCGACATACGTCTTGGCCACCAGTTCGGCCCAGTTGCGGATCGTCTTGC
GCACGCGTACCGGGCGCTGGCGCCGACTCGCGCGGTCGTTGATGTGCGACTCGAACGCCGTTGGCGGTGGAAGACGGGTCGAAGACTCAGGTCGTCGTCCTGCCAGCGAGCTCGTGAAGTTCACTCCGTAGGCC
TGGCGTCCAGGGCCTGCAGGGCCTCGACCGGTCACCGTTGATGTGGCGAAGCGCTTGATGTGGGTCGAGGGCGGTGGCGTCGCGAACGGGTCCTCGCCGGGGTCCCTACCATTTCGTCATGGGCGTTTACAAATTAGTATGCGACCACGCCCTCTG
CCAGTCGGCGCTGCACCGTTGCGACCGTTGAAGCTCATGGCGCGGCTTCGGGCGGTCTTGCCGCTACGACTATTTCGTCATGGGCGTTTACAAATTAGTATGCGACCACGCCCTCTG
TGAACCTGTCTGCCCACAAGGTGTCTTCGACACAGATGTCTTCGACAGATGTCTTCCTGCGGCCGGCGTCCCAGTCCACCAGTCCACCAGTCCTCACCCAGTCCTCACCCACCGCCGGCCACCGCGGCCACCGCGGCCACCGCGGCCACC
CGCGAAGAGGAGAACCCATGTGCAGCGAGAACCGCAGCGCCGACACCGTCCACCACCGCGCGACACCGGCGACCGTCCGCCGTGCCCGTGCCCAGTGACGAGGCGGGGTGAGAACGCACGCACGGGCTCGACCAGCGTCCGTCGCCCGGGCGCTGCC
GACAGGTGGTGGCGACGCGGCCGCACGAGCCGGCGCGGCGACGGCGGCACCGCGACACCGCGATCTCGTCGGCTGGTGGAGAACACCGCGGCCCCCGAAGGCTTGGGCCCCAGCGCCGCAACGCACGGACACTGGGCGTGCCCGGCGCTGACCG
AGTGCGGTGACGCGGCCGCACGAGCCGGCGCGGCGACGGCGGCACCGCGACACCGCGATCTCGTCGGCTGGTGGAGAACACCGCGGCCCCCGAAGGCTTGGGCCCCAGCGCCGCAACGCACGGACACTGGGCGTGCCCGGCGCTGACCG
TCTGGAACGATGTCCGCCCGCGGAGTGGGCTTGGCTCCGAGCACGAACCGGAGGCGGCGACCGGCGACCGACCGCTCGAGGGCGACCGAGCGACTACCTCGGCGGCGACACTCTGGCGGACACTCTGGCGCGTCGGGCCACGGTG
TCACGCGAGCAAGTGGGCTTGGCTCCGAGCACGAACCGGAGGCGGCGACCGGCGACCGACCGCTCGAGGGCGACCGAGCGACTACCTCGGCGGCGACACTCTGGCGGACACTCTGGCGCGTCGGGCCACGGTG
GCAGGCCCGTCACCGATCCCGGGCCGTGGTGCGTCCGGGTGAGGTGCGCGGAGCCTGCTGCCCGGGACCGTACTGAGCCTGCCGCTGGCCTGGAACCTGAAACTGCACCCCGCTGACCCGGGAGTGCCGGCAGGTGCGTCCTCAGATCTCCGCC
CGCTGCTGCCCCGGGTGGTGCGTCCGGGTGAGGTGCGCGGAGCCTGCTGCCCGGGACCGTACTGAGCCTGCCGCTGGCCTGGAACCTGAAACTGCACCCCGCTGACCCGGGAGTGCCGGCAGGTGCGTCCTCAGATCTCCGCC
ACAACGCGGCCGGCCGCGTGGGCGGCCGCTTGCCGCACGCCTCGGGGACTACTGAGCCTGCCGCTGGCCTGGAACCTGAAACTGCACCCCGCTGACCCGGGAGTGCCGGCAGGTGCGTCCTCAGATCTCCGCC
ATCCACCCGGTGGACCGCGGAGCCGTCGCAGCCCGTGCTGTCTGATCGGCGGCGGTCCCTCCAGGCGCGGCCGTGCTCAGGCGCCAGAGACCGGCCAGAGACCGGCCAGAGACCGGCCAGAGACCCTGCGCCGCGGCCTGCGCC
TGGCCCTGGACCGCGGAGCCGTCGCAGCCCGTGCTGTCTGATCGGCGGCGGTCCCTCCAGGCGCGGCCGTGCTCAGGCGCCAGAGACCGGCCAGAGACCGGCCAGAGACCGGCCAGAGACCCTGCGCCGCGGCCTGCGCC
ACGGGCTGCCGCCGACGACCCCGTCGTGCTGATCGGCGTGAGCTGCTGAGGAGCTGCGAGGAGGACAGCAGCGTGGCCTGCAGACCGTGGCCTGTCCGCAGAGCGGCGAGTCGGCGCCCGAGTGCCGCGACGGCGAGAGG
TGGCGGAGGAAGAGGCCAAGGAGCTGAGGAGCTGAGGAGCTGAGGAGCTGCGAGGAGGACAGCAGCGTGGCCTGCAGACCGTGGCCTGTCCGCAGAGCGGCGAGTCGGCGCCCGAGTGCCGCGACGGCGAGAGG
AGTCCTACGCGAGCCAAGGCGACGACCACGAGACGCCCTCCGCCGCTCGCCGCGCCTCGCCGCGCCTCGCCTCAGCGTCAGCGCCCAGACCCGCGACCAGCGCCGAGATCGCCGCTTCGAGACGAGCCGGACGAACTGCC
ACGCGGCCAGTCCGAGCGCGGCCACTCGCCTCGCCGCGCCTCGCCTCAGCGTCAGCGCCCAGACCCGCGACCAGCGCCGAGATCGCCGCTTCGAGACGAGCCGGACGAACTGCC
AGCAGTCCGAGCGCGGCCACTCGCCTCGCCGCGCCTCGCCTCAGCGTCAGCGCCCAGACCCGCGACCAGCGCCGAGATCGCCGCTTCGAGACGAGCCGGACGAACTGCCGCCAAGGCGGAGAAGCTGC
GCACCGACGCGCGGACCTGGGCGCCGGGGCCCCTCGCCGTCAGCCGCAGCGGTGAGCCCGACAGCCCCGACCAACCTCACCGGGCCCCACGCCGCCAAGGCGGACCGCATCCGTTCCG
AGTCCGACGCGGACCTGGGCGCCGGGGCCCCTCGCCGTCAGCCGCAGCGGTGAGCCCGACAGCCCCGACCAACCTCACCGGGCCCCACGCCGCCAAGGCGGACCGCATCCGTTCCG
CCGCCGCCGGACGCGGAGGACGCGGCGTTTCTCGGGGTTCGCGCAGCGACGAGCCGGATAGGTTCCGCGCCTTCGAAAGCCCCCTGCTTCAAGTGGC
AGGGGGCTTTGTCCCGTTCTAGCGTGCGGGCAT
```

Fig. 33

Fatty acid production of *R. opacus* PD630 (WT) and the transformants (Xsp) with *S. padanus* library.

| Strain | Production (fatty acid/dried cell mass)* | |
| --- | --- | --- |
| | from xylose | from glucose |
| PD630 (WT) | no growth | excellent |
| Xsp8, 10 and 12 | good | excellent |
| Xsp1 | good | good |
| Xsp15 and 21 | poor | excellent |
| Xsp23, 25, 26, 27, 33, 36 and 37 | poor | poor |

*; excellent, 44-51%: good, 30-35%: poor, 10-15%.

The strain was cultured at 30 °C for 4 days in defined medium containing 1.6% xylose or glucose with 0.10 % $(NH_4)_2SO_4$ and 10 μg/mL gentamicin.

Fig. 34

Fermentation results in the transformants

| Strain | CDW [g/L] | rCDW [g/L] | tFA [g/L] | FA [%/CDW] |
|---|---|---|---|---|
| Xsp1 | 19.3 | 12.1 | 7.3 | 37.5 |
| Xsp8 | 25.6 | 14.2 | 11.4 | 44.6 |
| Xsp10 | 24.2 | 16.4 | 7.8 | 32.3 |
| Xsp12 | 32.0 | 21.4 | 10.7 | 33.3 |

Medium conditions: 120 g/L xylose, 7.5 g/L $(NH_4)_2SO_4$

Fig. 35

Co-metabolism in transformant Xsp8

| Medium conditions* | CDW [g/L] | rCDW [g/L] | tFA [g/L] | FA [%/CDW] |
|---|---|---|---|---|
| 120 g/L xylose 0 g/L glucose | 25.6 | 14.2 | 11.4 | 44.6 |
| 60 g/L xylose 60 g/L glucose | 31.2 | 17.7 | 13.5 | 43.3 |
| 30 g/L xylose 90 g/L glucose | 39.5 | 25.3 | 14.2 | 36.0 |
| 0 g/L xylose 120 g/L glucose | 33.0 | 16.6 | 16.4 | 49.6 |

* medium contained 0.75% $(NH_4)_2SO_4$

Fig. 36

Fermentation results

| Medium conditions* | Cell dried weight [g/L] | Fatty acids content [%/CDW] | Total fatty acids [g/L] |
|---|---|---|---|
| 120 g/L xylose 0 g/L glucose | 28.4 | 42.2 | 12.0 |
|  | 25.6 (26.0) | 44.6 (43.8) | 11.4 (11.3) |
|  | 24.0 | 44.6 | 10.6 |
| 60 g/L xylose 60 g/L glucose | 35.3 | 43.1 | 15.2 |
|  | 31.2 (34.4) | 43.3 (39.8) | 13.5 (13.6) |
|  | 36.8 | 32.9 | 12.1 |
| 0 g/L xylose 120 g/L glucose | 33.0 | 49.6 | 16.4 |
|  | 40.4 (37.0) | 38.9 (40.7) | 15.7 (14.9) |
|  | 37.6 | 33.6 | 12.6 |

*: medium contained 7.5 g/L $(NH_4)_2SO_4$.   ( ): average

Fig. 37

StatGraphics was used to optimize C/N ratio

- The original and coded values of the independent variables were applied in the factorial design

| Trial | Coded values | | Original values | |
|---|---|---|---|---|
| | xylose [g/L] | $(NH_4)_2SO_4$ [g/L] | xylose [g/L] | $(NH_4)_2SO_4$ [g/L] |
| 1 | -1.41 | 0 | -0.914 | 5.054 |
| 2 | 0 | 0 | 90.006 | 5.054 |
| 3 | -1 | +1 | 25.716 | 8.664 |
| 4 | +1.41 | 0 | 180.926 | 5.054 |
| 5 | 0 | 0 | 90.006 | 5.054 |
| 6 | +1 | +1 | 154.296 | 8.664 |
| 7 | +1 | -1 | 154.296 | 1.444 |
| 8 | -1 | -1 | 25.716 | 1.444 |
| 9 | 0 | -1.41 | 90.006 | -0.051 |
| 10 | 0 | 0 | 90.006 | 5.054 |
| 11 | 0 | +1.41 | 90.006 | 10.159 |

Fig. 42

Overview of total fatty acids obtained in fermentations

| Xylose [g/L] | (NH4)2SO4 [g/L] | C/N ratio [g/g] | tFA [g/L] |
|---|---|---|---|
| 0.0 | 5.1 | 0.0 | 0.0 |
| 25.7 | 1.4 | 18.4 | 3.5 |
| | 8.7 | 3.0 | 1.4 |
| 90.0 | 0.0 | 0.0 | 0.0 |
| | 5.1 | 17.6 | 6.1 |
| | 5.1 | 17.6 | 6.7 |
| | 5.1 | 17.6 | 6.8 |
| | 10.2 | 8.8 | 5.2 |
| 154.3 | 1.4 | 110.2 | 2.0 |
| | 8.7 | 17.7 | 7.8 |
| 180.9 | 5.1 | 35.5 | 3.9 |

Fig. 43

Transformation of the plasmid with xylA and xylB into R. opacus
Defined medium containing 4 % xylose and 0.14 % (NH$_4$)$_2$SO$_4$ with 10 µg/mL gentamicin for 10 days at 30°C Fatty acid production of the Xsp8C-retransformants with the plasmid

| Strain | Xylose [g/L] | Glucose [g/L] | Broth [pH] | Residue [g/100 mL] Xylose | Residue [g/100 mL] Glucose | DCM [g/L] | Fatty acid production [g/L] | Fatty acid production [%/DCM] |
|---|---|---|---|---|---|---|---|---|
| Xsp8 | 16 | 0 | 6.2 | 2.8 | nd | 5 | 1.5 | 30 |
|  | 0 | 16 | 6.1 | nd | 0.0 | 4.5 | 2.1 | 46 |
| Xsp8C-1 | 16 | 0 | 6.1 | 0.4 | nd | 4.7 | 1.9 | 39 |
|  | 0 | 16 | 6.1 | nd | 0.7 | 4.8 | 1.9 | 40 |
| Xsp8C-2 | 16 | 0 | 6.1 | 8.0 | nd | 3.4 | 0.9 | 28 |
|  | 0 | 16 | 6.8 | nd | 14.8 | nd (no growth) | nd | nd |
| Xsp8C-3 | 16 | 0 | 6.1 | 3.1 | nd | 4.6 | 1.6 | 36 |
|  | 0 | 16 | 6.1 | nd | nd | 5.4 | 2.5 | 47 |
| Xsp8C-4 | 16 | 0 | 6.0 | 10.6 | nd | 2.1 | 0.4 | 21 |
|  | 0 | 16 | 6.1 | nd | nd | 6.6 | 3.3 | 50 |
| Xsp8C-5 | 16 | 0 | 6.1 | 6.7 | nd | 3.2 | 0.4 | 12 |
|  | 0 | 16 | 6.1 | nd | nd | 6.5 | 2.1 | 32 |

The strain was cultured at 30 °C for 5 days in the defined medium with 0.1% $(NH_4)_2SO_4$ and 10 µg/ml gentamicin:

Fig. 45

Statistical analysis

- The optimal C/N ratio were obtained by applying StatGraphics
- An optimal C/N ratio of 16.9 was predicted
- Under the optimal condition 7.7 g/L fatty acids could be produced in theory

Lignin experiment

- Lignin alkali (Sigma Adrich)
- Different lignin concentrations were used to identify an inhibiting effect
- Due to the lignin insolubility the cell growth was proven by colony forming units (CFU/mL)

Catabolic pathways for the degradation of lignin-derived compounds by *Sphingmonas paucimobilis*

We identified two genes, *xylA*, which encodes xylose isomerase, and *xylB*, encoding xylulose kinase and cellulose binding protein domain tFA production of *R. opacus* PD630 transformed with pPB80

| Carbon source Bolus at day 2 | | | DCM (g/L) | tFatty acid production | |
|---|---|---|---|---|---|
| 1% | 2% | OD$_{660}$ | | (g/L) | (%/DCM) |
| Glycerol | Glycerol | 3.9 | 1.0 | 0.1 | 8 |
| Glucose | Glycerol | 10.5 | 4.0 | 0.9 | 23 |
| Gluconate | Glycerol | 9.4 | 4.0 | 1.1 | 27 |
| Gluconate | Gluconate | 7.6 | 4.0 | 1.7 | 42 |

- *R. opacus* PD630 (pPB80) grow on glycerol as sole carbon source but does not accumulate TAGs

Fig. 57

Integration of *glpK* and *g3pdh* onto *R. opacus* chromosome via homologous recombination

- pDPM9 has 1Kb (3' and 5') flanking regions of the *penP* gene
- SacI fragment from pPB80 cloned into pDM9 to obtain pDP1
- pDP1 conjugated into *R. opacus* and plated onto defined medium plus glycerol and gentamycin

TAGs production by *R. opacus glpK and g3pdh* potential integrants

Six potential integrant strains (G, H, H2, J2, L2, T2) were grown in TAGs accumulating defined medium containing 2.25% (w/v) glycerol as sole carbon source, 0.14% (NH$_4$)$_2$SO$_4$ and gentamycin

| Strain | OD660 | pH | CDW g/l | TAG (%CDW) Dens. | TAG (%CDW) FAME |
|---|---|---|---|---|---|
| G | 4.54 | 6.12 | 1.8 | 26.8 | 20.0 |
| H | 5.6 | 3.77 | 3.4 | 34.6 | 26.8 |
| H2 | 6.18 | 4.32 | 3.1 | 28.0 | 26.1 |
| J2 | 5.2 | 4.17 | 3.2 | 27.7 | ND |
| L2 | 3.28 | 3.48 | 3.2 | 36.2 | 27.0 |
| T2 | 6.04 | 3.62 | 2.4 | 33.1 | 24.9 |

TAGs

Lipid accumulation in *R. opacus* GspC transformants analyzed GC FAME

| Flask | Strain | carbon | Cultivation [Days] | Broth [pH] | [OD₆₆₀] | DCM [g/L] | Fatty acid production [g/L] | [%/DCM] |
|---|---|---|---|---|---|---|---|---|
| 1 | GspC1-2 | glycerol | 6 | 6.2 | 10.6 | 4.0 | 1.4 | 34 |
| 2 | GspC1-5 | glycerol | 6 | 6.1 | 8.3 | 3.1 | 0.5 | 16 |
| 3 | GspC15-1 | glycerol | 6 | 6.1 | 8.6 | 3.3 | 0.5 | 16 |
| 4 | GspC15-3 | glycerol | 6 | 6.1 | 5.7 | 2.4 | 0.3 | 12 |

Strains cultured with aeration (200 rpm) at 30 °C in defined medium: 0.1 % $(NH_4)_2SO_4$, 1.6% glycerol

- Several *R. opacus* PD630 GspC transformants grew on glycerol and one GspC1-2 accumulated TAGs (34 % CDW)

Fig. 62

Fatty acid composition profile growing in the optimal conditions

| C14:0 | C15:0 | C16:0 | C16:1 | C17:0 | C17:1 | C18:0 | C18:1 |
|---|---|---|---|---|---|---|---|
| 1.9 | 5.6 | 27.7 | 10.8 | 8.7 | 15.9 | 4.8 | 24.7 |

Fatty acid analysis of lyophilized cells was done by GC after derivatization to fatty acid methyl esters by sulfuric acid-catalyzed methanolysis. Values are percentages of total fatty acids.

Fig. 64

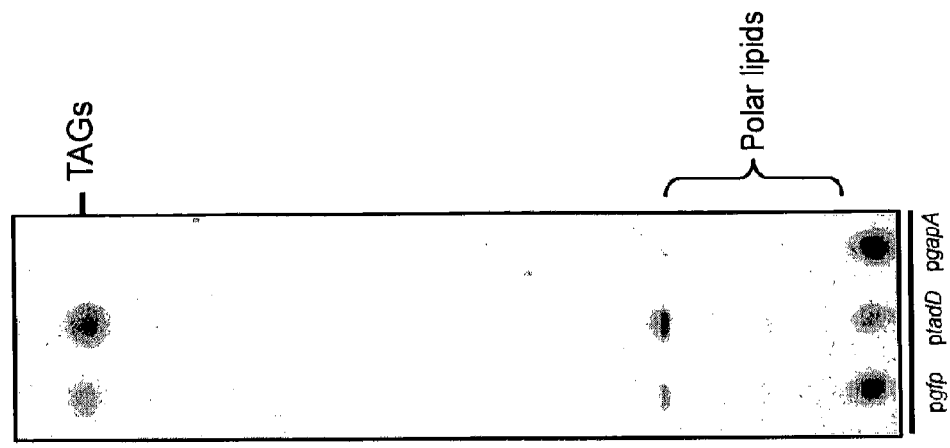
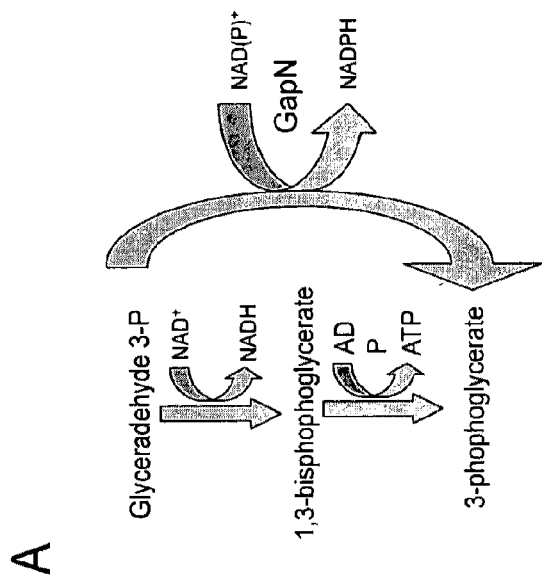
Fig. 78

```
R. opacus PD630 TadA      ------------MTDQKTIDSVKTSLYAAVGAGDVVVQAVADVVAQVRSRAESTQGDVEERVGGAKE     55
R. jostii RHA1 ro02104    ------------MTDQKTIDSVKTSLYAAVGAGDVVVQAVADVVAQVRSRAESTQGDVEERVGGAKE     55
R. opacus B4 ROP 18230    ------------MTDQKTIDSVKTSLYAAVGAGDVVVQAVADVVAQVRSRAESTQGDVEERVGGAKE     55
M. smegmatis HbhA         ---MADKTQPTVEELKAPILAAVGAADLALATVNELIATLLERAGARSDAEAARVEESRA           57
M. tuberculosis HbhA      MKGIPMAENSNIDDIKAPLLAALGAADLALATVNELITNLRERAEEFTRDTRSRVEESRA           60
                                      : .::::*.* **::**.*:.: .:* *.*** .: .:* **.

R. opacus PD630 TadA      RIAGLQEEVTEGVENLRDRLAGLPSELPEELAELREKFTADELRKVAEAYLKVASDLYTS        115
R. jostii RHA1 ro02104    RIAGLQEEVTEGVENLRDRLAGLPSELPEELAELREKFTADELRKVAEAYLKVASDLYTS        115
R. opacus B4 ROP 18230    RPAGLQEEVTEGVENLRDRLAGLPSELPEELAELREKFTADELRKVAEAYLKVASDLYTS        115
M. smegmatis HbhA         RLTKLQEELPSQFGELREKLNSD--------BLRKKLNSEELRKAAESYADQATATYNK        108
M. tuberculosis HbhA      RLTKLQEDLPEQLTELREKFT---------------AEELRKAAEGYLEAATSRYNE         102
                          *:. ****::. . .:**:::                 ::****:**::.*:.  *:

R. opacus PD630 TadA      LAERGEDTVERIRKQPVVEEGIGRAEFTAFGDAVELTEEALGTVARQTRAVGEQAAKLAGR      175
R. jostii RHA1 ro02104    LAERGEDTVERIRKQPVVEEGIGRAEFTAFGDAVELTEEALGTVARQTRAVGEQAAKLAGR      175
R. opacus B4 ROP 18230    LAERGEDTVERIRKQPVVEEGIGRAEFTAFGDAVELTEEALGTVARQTRAVGEQAAKLAGL      175
M. smegmatis HbhA         LVERGEAALERLRNQPALEEAATRVETYTDQAVELTQEALGTVASQTVASQTRAVGERAAKLVGV      168
M. tuberculosis HbhA      LVERGEAALERLRSQQSFEEVSARAEXYVDQAVELTQEALGTVASQTRAVGERAAKLVGI      162
                          *.****  :**:*.: ..:*     *  . *****:*******:**.*** ****:**:

R. opacus PD630 TadA      ASGRISDTAEGLGEAIADAGDEAALKVLDLGDQAEEASKDAADRVAATAADVQAQ-DKAA      235
R. jostii RHA1 ro02104    ASGRISDTAEGLGEAIADAGDEAALKVLDLGDQAEEASKDAADRVTATAADVQARD-DKAA     235
R. opacus B4 ROP 18230    ASGRISDTAEGLGEAIADAGDEAALKVLDLGDQAEEASKDAADRVTATAADV---DKTA      232
M. smegmatis HbhA         ELPKRAEAAA---------------------------ETASEAAAETAEPVK-KAPAP      204
M. tuberculosis HbhA      ELPK----------------------------------------------------PAKKAB     175
                          * *                                                   *.*:*

R. opacus PD630 TadA      QAKRAPA----KKAAPAKRAASTPAPAPAKVAPPAKKAAPAKKA                    276
R. jostii RHA1 ro02104    PAKHAPA----KKAAPAKRAAVSRAADAKKAAPAAPAGKAA BAKKA                 276
R. opacus B4 ROP 18230    PAKHAAPAKKAA---KKAAPAKKAAATEPAPA--KKAAPAKKAAAPAGKAA BAKKA       274
M. smegmatis HbhA         PAKQRAPA---KKATPAKS--KAPAPA-----------------                    232
M. tuberculosis HbhA      PAKKAAPA---KRAAAKKAPAKKAAA-----------------                    204
                          *:*::**   ***.. *: ** * *.:*

Fig. 82
```

TadA can mediate yeast agglutination
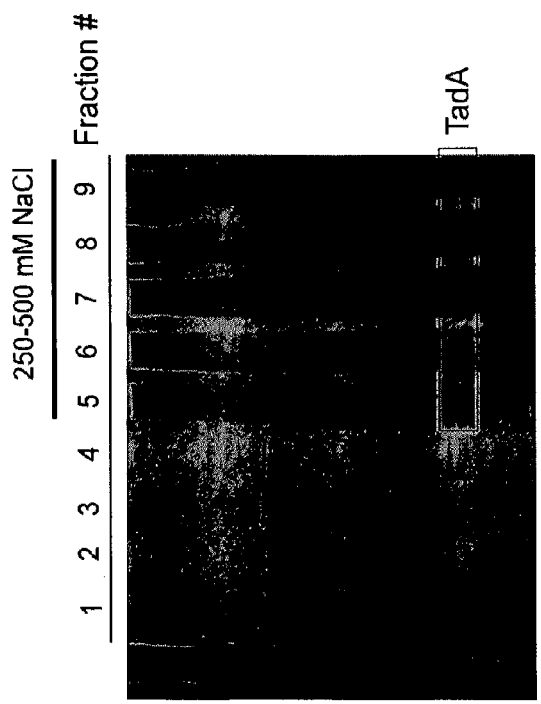
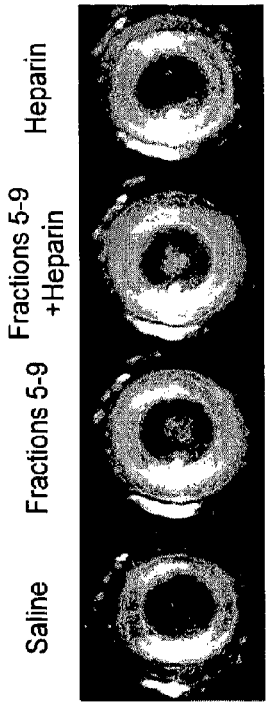
Fig. 85

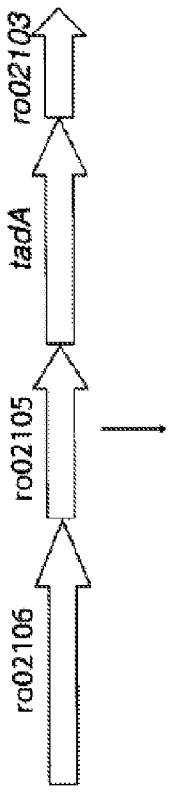
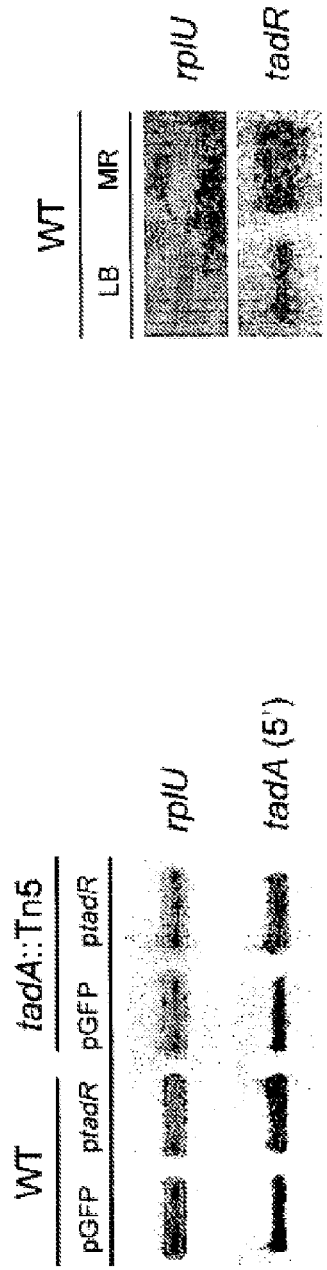
Fig. 89

SEQUENCE LISTING

<160> NUMBER OF SEQ ID NOS: 29

<210> SEQ ID NO 1
<211> LENGTH: 3603
<212> TYPE: DNA
<213> ORGANISM: Artificial Sequence
<220> FEATURE:
<223> OTHER INFORMATION: Synthetic Polynucleotide

<400> SEQUENCE: 1

```
gatccctgat gtgtgcccct agtgggccgg ttccccgggt cgggcggcga ccacggagca      60
tggcgaggtg acgcaggtca tgacgtcagc ataggagggt cgccgcaaag gcgcccatgt     120
catgcgcgac tgtcctgcgc ggccgtcctg cgcgacggaa cggccggggg cacggcacgc     180
```

-continued

```
gtacgcgccg taccccggc cttctttcgt cagcgcctcg cgctcgtggc cgtcagccgc    240
gcgcgcccag caggtggtcc atcgccagct ggtcgaggtg ctcgaacgcc ataccgcgcg    300
cggcggcggc atcgacatcg aagtcctcga acgccgagcg gtcggcgagc agggcgtcca    360
ggccgtcggc cgcggtcgcc tgggccagct ggtccgacg cgcggcacgc agcgcctcct    420
gcacctccgg gtcggcacgg aaggcggccg cacggtcctt gaggatcagg tagttgcgca    480
tgcagcccgc ggccgaggcc cacacgccgt cgaagtcctc ggtccgcggc ggcttgaagt    540
cgaagtgccg cgggccctcg taaccggcgg tctccaggag gtcgaccagc cagaacgccg    600
cccgcaggtc gccggcgccg aaccgcaggt cctggtcgta cttgatgccg gactggccgt    660
tgaggtcgat gtggaagagc ttgcccgccc acagggcctg cgcgatgccg tgcgggaagt    720
tcaggccggc catctgctcg tggccgacct ccgggttgac gccgtacagc tccgggcgct    780
ccaggcgctc gatgaaggcc agggcgtggc cgacggtggg cagcaggatg tcgccgcggg    840
gctcgttggg cttgggctcg atggcgaagc ggaggtcgta gccctgggcg atgacgtact    900
cgccgaggag gtcgaacgcc tccttcatgc ggtcgagggc gtcgcgcacg tccttggcgc    960
caccggactc ggcgccctca cggccacccc aggcgacata cgtcttggca cccagttcgg   1020
ccgccaggtc gatgttgcgg atcgtcttgc gcagcgcgta ccggcgtacg tcgcggtcgt   1080
tggcggtgaa gccgccgtcc ttgaagacgg ggtgggtgaa gaggttcgtg gtggccatgg   1140
gcaccgtcat gccggtggcg tccagggcct ggcggaagcg cttgatgtgc gactcgcgct   1200
cggtgtcgga ggacccgaag gggatcaggt cgtcgtcgtg gaaggtcact ccgtaggcgc   1260
ccagctcggc caggcgctgc accgtctcga ccgggtcgag ggcggggcgg gtggcgtcgc   1320
cgaacgggtc ccttccctgc cagccgacgg tccacagacc gaaggtgaac ctgtcctcgg   1380
gggtgggctg gaagctcatg gcgcggctcc ttgttccgta cgactatttc gtcatggccg   1440
tttacaaatt agtatgcgac cacgcctctg ggaagagaca aggtgtcttc gaccacaagg   1500
tgtcttcgac agatgtcttc cacgggcgcc ctcgggggtg tcctcgggag cgccccacag   1560
cacatcccgc tgagccgcgg aagagggaga accccatgtc agcagcggag ggtccgctcg   1620
tcgtcggcgt ggacacgtcc acccagtcca cgaaggccct ggtcgtcgac gcggccaccg   1680
gacaggtggt ggcgagcggc caggcgccgc acaccgtcac caccggcggg ggccgggaga   1740
gcgatccgcg ccagtggtgg gacgccctgt gcgaggcgct cgccagtgc ggtgacgcgg    1800
cgcacgaggc ggccgcgatc tcggtcggcg gacagcagca cggcctggtc acgctggacg   1860
agcggggtga gccggtgcgg ccggcgctgc tctggaacga tgtccgctcc gcgccgcagg   1920
cccgtcggct ggtggaggaa ctgggcggcc cgaaggcttg ggccgaacgc accggcagcg   1980
tgccggggc ctcgttcacg gcgagcaagt gggcttggct cgccgagcac gaaccggagg    2040
cggcccgcgc gaccagggcc gtacggctcc cccacgacta cctcaccgag cgcctgaccg   2100
ggcaggccgt caccgatcgc ggtgacgcct ccggcaccgg ctggtgggcg tccggcacgg   2160
agcggtacga cgaggacact ctggcgcacc tcgggctcga cccggcgctg ctgccccggg   2220
tggtgcgtcc gggtgaggtg gccgggaccg tacgcgacgg acacggtctg cctttctcca   2280
agggcacgtt ggtggcctcg ggcaccggtg acaacgcggc ggccgcgctg ggcctcgggc   2340
tgctgcccgg caccccggta ctgagcctcg ggacctccgg cacggtgtac gccgtgtccc   2400
ggcaccgccc ggccgatccc accggtacgg tggcgggctt cgccgacgcg cgcggggact   2460
ggctgccgct ggcctgcacc ctgaactgca cgctcgccgt cgaccgcgtc gcgactctgc   2520
tgggcctgga ccgcgaggcc gtcgcgcccg gcggctccgt gacgctcctg ccgttcctgg   2580
```

```
acggcgaacg caccccgac ctgccgaacg cctccggtct gctgcacggg ctgcgccacg    2640
acacgacccc gggccagctg ctccaggcgg cgtacgacgg tgcggtgcac tccctgctcg    2700
gcgcgctcga cctggtcctc gacgaggacg cggaccgcga cagcccgctg ctgctgatcg    2760
gcggcggcgc gcggggccac gcctggcagc agaccgtgcg acggctgtcc ggacggccgg    2820
tccagatcct gcgcctggcc gaggaagagg ccaaggagct gcgtgaggag cccgccgcg     2880 cggccgaaca gcaccgcgag ctggccgagt cggccgccca gcaggtgcgt aacgacgcc     2940 agtcctacgc caccgagcgc aaggcgaagg cggaggacga gggctcccgg atcgtcgaga    3000
aggccaaggg cgaggcctct cagctgcgtg ccgacgcgca aggacgcg cagtccaagc     3060 gtgaggaggc ggacgccctc ttcgaggaga cccgcgccaa ggccgcgcag ccgccgccg    3120 acttcgagac gaacctggcc aagcgccgcg agcagtccga gcgcgacctg gcctcgcgtc    3180
agcagaaggc ggagaagcgg ctcgcggaga tcgagcaccg cgccgagcag ctgcgcctgg    3240
aggcggagaa gctgcgcacc gacgcgggagc cgcgcccg ccagacggtg gagaccgcgc    3300
agcgccaggc cgaggacatc gtggccgacg ccaacgccaa ggcggaccgc atccgttccg    3360
agtccgagcg cgagctggcg cccctcacca accgccgcga cagcatcaac gcccagctga    3420
cgaacgtgcg cgagatgctg gcgacgctga ccggcgcggc ggtggccgcc gccggcacga    3480
cgggtgagga cgagccggtt tctcgtgggg ttccggcgca gcagaccga tagggttccg     3540 cgccttcgaa agcccctgc ttcaagtggc aggggcttt gtcccgttct agcgtggcgg     3600
cat                                                                   3603

<210> SEQ ID NO 2
<211> LENGTH: 517
<212> TYPE: DNA
<213> ORGANISM: Streptomyces padanus

<400> SEQUENCE: 2
cctgcaccct gaactgcacg ctcgccgtcg accgcgtcgc gactctgctg ggcctggacc      60
gcgaggccgt cgcgcccggc ggctccgtga cgctcctgcc gttcctggac ggcgaacgca     120 ccccccgacct gccgaacgcc tccggtctgc tgcacgggct cgccacgac acgaccccgg     180 gccagctgct ccaggcggcg tacgacggtg cggtgcactc cctgctcggc gcgctcgacc     240
tggtcctcga cgaggacgcg gaccgcgaca gcccgctgct gctgatcggc ggcggcgcgc     300
ggggccacgc ctggcagcag accgtgcgac ggctgtccgg acggccggtc cagatcctgc     360
gcctggccga ggaagaggcc aaggagctgc gtgaggaggc ccgccgcgcg ccgaacagc     420 accgcgagct ggccgagtcg gccgcccagc aggtgcgtaa cgacgccgag tcctacgcca     480
ccgagcgcaa ggcgaaggcg gaggacgagg gctcccg                            517

<210> SEQ ID NO 3
<211> LENGTH: 432
<212> TYPE: DNA
<213> ORGANISM: Streptomyces padanus
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
```

```
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (266)..(267)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (317)..(318)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (397)..(398)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (428)..(432)
<223> OTHER INFORMATION: n is a, c, g, or t

<400> SEQUENCE: 3
nnnnnnnnnn nnnnngcacg ctcgccgtcn accgcgtcgc gactctgctg ggcctggacc     60
gcgaggccgt cgcgcccggc ggctccgtga cnctcctgcc gttcctggac ggcgaacgca    120
cccccgacct gcctaacgcc tccggtctgc tgcacgggct gcgccacgac acgaccccng    180
gccagctgct ccaggcggcg tacgacggtg cggtgcactc cctgctcggc gcgctcgacc    240
tggtcctcga ctaggacncg naccgnnaca gcccgctgct gctgatcggc ggcggcgcgc    300
ggggccncgc ctggcannag accgtgcgac ggctgtccgg acggncggtn cagatccctg    360
cgnccaanga actggtcacc ctggggggcgg cggtccnngn ggccgggctg ctgaccggag    420
aggatcannn nn                                                        432

<210> SEQ ID NO 4
<211> LENGTH: 478
<212> TYPE: PRT
<213> ORGANISM: Rhodoccus opacus

<400> SEQUENCE: 4

Met Ser Ile Ala Ala Asp Ser Leu Ser Asn Ile Thr Pro Pro Gly Leu
 1               5                  10                  15
```

```
Thr Ile Asp Gly Glu Ile Thr Thr Ala Ala Val Ile Pro Val Ile
             20                  25                  30

Asn Pro Ala Thr Glu Ser Ala Phe Ile Glu Val Pro Asp Ala Gly Val
         35                  40                  45

Glu Gln Leu Asp Ala Ala Val Ser Ala Ala Arg Arg Ala Ala Lys His
 50                  55                  60

Trp Ala Thr His Asp Leu Pro Phe Arg Gln Gly Ile Val Leu Arg Leu
 65                  70                  75                  80

Val Asp His Val Arg Ala Asn Ile Asp Glu Leu Ala Arg Leu Val Thr
                 85                  90                  95

Leu Glu Gln Gly Lys Pro Leu Ala Lys Ala Ala Gly Glu Ile Glu Ser
            100                 105                 110

Gly Leu Arg Gly Leu Glu Arg Tyr Ala Ser Trp Asp Ile Pro Val Glu
            115                 120                 125

Val Ile Arg Asp Asn Asp Asp Glu Leu Ile Glu Val His Arg Ala Pro
            130                 135                 140

Val Gly Val Val Gly Gly Ile Thr Ala Trp Asn Tyr Pro Leu Leu Leu
145                 150                 155                 160

Ala Leu Trp Lys Ile Gly Pro Ala Leu Ile Thr Gly Asn Pro Ile Ile
                165                 170                 175

Val Lys Pro Ser Pro Leu Thr Pro Val Ala Thr Leu Arg Leu Gly Glu
            180                 185                 190

Leu Ala Gln Gln Ile Leu Pro Pro Gly Val Leu Gln Val Leu Ser Gly
            195                 200                 205

Gly Asp Asp Leu Gly Arg Ala Met Thr Ala His Thr Gly Ile Asp Lys
            210                 215                 220

Ile Thr Phe Thr Gly Ser Glu Arg Ala Gly Lys Ser Ile Met Ala Gly
225                 230                 235                 240

Ala Gly Ala Thr Leu Lys Arg Leu Thr Leu Glu Leu Gly Gly Asn Asp
                245                 250                 255

Pro Gly Ile Val Leu Asp Asp Val Asp Val Ala Ser Ile Ala Ala Asp
            260                 265                 270

Leu Tyr Trp Gly Ala Leu Ser Asn Cys Gly Gln Val Cys Ala Gly Leu
            275                 280                 285

Lys Arg Leu Tyr Val Pro Gln His Leu Ala Pro Ala Ile Glu Glu Ala
            290                 295                 300

Leu Ala Glu Val Ala Lys Gly Val Lys Val Gly Asn Gly Leu Asp Asp
305                 310                 315                 320

Gly Val Asp Met Gly Pro Val Gln Asn Ala Ala Gln Phe Thr Lys Val
                325                 330                 335

Arg Gly Tyr Val Asp Asp Ala Ala Asn Arg Gly Ala Asp Val Tyr Phe
            340                 345                 350

Arg Gly Glu Val Pro Glu Gly Pro Gly Tyr Phe His Pro Val Thr Leu
            355                 360                 365

Val Arg Gly Val Asp Asp Ser Val Pro Leu Val Arg Glu Glu Gln Phe
            370                 375                 380

Gly Pro Val Leu Pro Ile Leu Thr Tyr Thr Asp Ile Asp Asp Val Ile
385                 390                 395                 400

Ala Arg Ala Asn Asp Ser Glu Leu Ala Leu Gly Ala Ser Val Trp Ser
                405                 410                 415

Ser Asp Glu Gln Arg Ala Thr Glu Val Ala Glu Arg Val Glu Ala Gly
            420                 425                 430

Thr Val Trp Val Asn Gln His Pro Met Leu Ser Ser Asp Val Pro Phe
```

```
                435                 440                 445
Gly Gly Val Lys Gln Ser Gly Leu Gly Val Glu Gln Ser Ile His Gly
        450                 455                 460

Val Leu Glu Tyr Thr Asn Tyr Arg Val Leu Arg Val Lys Arg
465                 470                 475

<210> SEQ ID NO 5
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 5
gcggctgcag atgagtatcg ccgcagattc tctgtc                            36

<210> SEQ ID NO 6
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 6
ccgcggaatt ctttatcgtt tgacccgcag cactctg                           37

<210> SEQ ID NO 7
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 7
gcggctgcag atgactgtcc gggtaggcgt aaacg                             35

<210> SEQ ID NO 8
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 8
ccgcggaatt ctttagagag acttggcgac gagaccgatg                        40

<210> SEQ ID NO 9
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 9
gcgggaattc aggaggtctc tctcatgagt atcgccgcag attctctgtc c           51

<210> SEQ ID NO 10
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 10
ccgcaagctt ttaatgatga tgatgatgat gtcgtttgac ccgcagcact ctctag      56
```

<210> SEQ ID NO 11
<211> LENGTH: 276
<212> TYPE: PRT
<213> ORGANISM: Rhodoccus opacus

<400> SEQUENCE: 11

Met Thr Asp Gln Lys Thr Ile Asp Ser Val Lys Thr Ser Leu Tyr Ala
1               5                   10                  15

Ala Val Gly Ala Gly Asp Val Val Gln Ala Val Ala Asp Val Val
        20                  25                  30

Ala Gln Val Arg Ser Arg Ala Glu Ser Thr Gln Gly Asp Val Glu Glu
        35                  40                  45

Arg Val Gly Gly Ala Lys Glu Arg Ile Ala Gly Leu Gln Glu Glu Val
50                  55                  60

Thr Glu Gly Val Glu Asn Leu Arg Asp Arg Leu Ala Gly Leu Pro Ser
65                  70                  75                  80

Glu Leu Pro Glu Glu Leu Ala Glu Leu Arg Glu Lys Phe Thr Ala Asp
                85                  90                  95

Glu Leu Arg Lys Val Ala Glu Ala Tyr Leu Lys Val Ala Ser Asp Leu
            100                 105                 110

Tyr Thr Ser Leu Ala Glu Arg Gly Glu Asp Thr Val Glu Arg Ile Arg
        115                 120                 125

Lys Gln Pro Val Val Glu Glu Gly Ile Gly Arg Ala Glu Thr Ala Phe
130                 135                 140

Gly Asp Ala Val Glu Leu Thr Glu Glu Ala Leu Gly Thr Val Ala Arg
145                 150                 155                 160

Gln Thr Arg Ala Val Gly Glu Gln Ala Ala Lys Leu Ala Gly Arg Ala
                165                 170                 175

Ser Gly Arg Ile Ser Asp Thr Ala Glu Gly Leu Gly Glu Ala Ile Ala
            180                 185                 190

Asp Ala Gly Asp Glu Ala Ala Leu Lys Val Leu Asp Leu Gly Asp Gln
        195                 200                 205

Ala Glu Glu Ala Ser Lys Asp Ala Ala Asp Arg Val Ala Ala Thr Ala
210                 215                 220

Ala Asp Val Gln Ala Gln Ala Asp Lys Ala Gln Ala Lys His Ala
225                 230                 235                 240

Ala Pro Ala Lys Lys Ala Ala Pro Ala Lys Ala Ala Thr Pro Ala
                245                 250                 255

Pro Ala Pro Ala Lys Lys Val Ala Ala Pro Ala Lys Lys Ala Ala Pro
            260                 265                 270

Ala Lys Lys Ala
        275

<210> SEQ ID NO 12
<211> LENGTH: 97
<212> TYPE: PRT
<213> ORGANISM: Rhodoccus opacus

<400> SEQUENCE: 12

Met Ile Gln Val Asp Gly Val Val Ser Val Ile Leu Leu Val Ile Arg
1               5                   10                  15

Ile Val Ala Leu Gly Gly Ala Ala Tyr Ala Leu Phe His Ala Ala Arg
        20                  25                  30

Gln Arg Lys Asp Ala Phe Thr Ala Val Asp Lys Leu Ser Lys Pro Ile
        35                  40                  45

Trp Leu Ser Ile Leu Ala Val Ala Phe Leu Val Leu Leu Leu Phe Pro

```
                    50                  55                  60
Ala Val Gln Leu Phe Gly Ile Val Ala Val Ala Val Cys Val Tyr
 65                  70                  75                  80

Leu Val Asp Val Arg Pro Arg Val Asp Val Gln Arg Gly Pro Arg
                 85                  90                  95

Trp

<210> SEQ ID NO 13
<211> LENGTH: 168
<212> TYPE: PRT
<213> ORGANISM: Rhodoccus opacus

<400> SEQUENCE: 13

Met Ala Ser Asp Asp Arg Asp Ala Ala Gly Ala Gly Asp Leu Ala Ala
 1               5                  10                  15

Arg Val Val Ser Asn Ala Ala His Asp Ile Gly Gly Phe Ile Arg Ala
                20                  25                  30

Gln Arg Glu Ala Ala Gln Val Ser Met Arg Gln Leu Ala Gln Leu Ala
             35                  40                  45

Gly Val Ser Asn Pro Tyr Leu Ser Gln Ile Glu Arg Gly Leu Arg Lys
 50                  55                  60

Pro Ser Ala Glu Val Leu Gly Gln Ile Ala Lys Gly Leu Arg Val Ser
 65                  70                  75                  80

Ser Glu Val Leu Tyr Val Gln Ala Gly Tyr Leu Glu Gln Arg Pro His
                 85                  90                  95

Gly Pro Leu Arg Asp Ala Leu Leu Ala Asp Thr Ala Ile Thr Glu Arg
                100                 105                 110

Gln Lys Gln Val Leu Leu Glu Ile Tyr Glu Ser Phe Cys Arg Glu Asn
             115                 120                 125

Glu Ser Ala Glu Ala Ala Glu Ser Arg Thr Ser Glu Leu Arg Thr Glu
 130                 135                 140

Glu His Gln Arg Ser Asp Ser Gln Thr Pro Glu Pro Glu Pro Pro Thr
145                 150                 155                 160

Val Glu Gln Glu Lys Ala Asp Asp
                165

<210> SEQ ID NO 14
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 14
cggatctgcc ctggcttcag gagatcggaa gacgtgagcg gataacaatt tcacacagg      59

<210> SEQ ID NO 15
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 15
cgaattgctg cgcgtaacca ccacacccgc cgcgcttagg atcgtcggca ccgtcacgg      59

<210> SEQ ID NO 16
<211> LENGTH: 82
<212> TYPE: DNA
<213> ORGANISM: Artificial Sequence
```

```
<220> FEATURE:
<223> OTHER INFORMATION: Synthetic Oligonucleotide

<400> SEQUENCE: 16
gctcgaggca tgcagaaagg aggccatatg ggactgcatg catcatcatc atcatcatat      60
gactgaccag aagaccatcg ac                                               82

<210> SEQ ID NO 17
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 17
ccatgattac gccaagcttg gtaccgagct cggttcaagc cttcttggcc ggagcagcc       59

<210> SEQ ID NO 18
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 18
atgaccatga ttacgccaag cttggtaccg agctcggttc agtcggcctg agcctggacg      60
tcgg                                                                   64

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
ggcaaaatgg tggaagggcg                                                  20

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
ggccttgctg ttcttctacg gc                                               22

<210> SEQ ID NO 21
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 21
caaaacagcc aagcttttaa tgatgatgat gatgatgagc cttcttggcc ggagcagcc       59

<210> SEQ ID NO 22
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 22
```

```
tacccgtttt tttgggcagc gaattcagga ggtctctctc atgactgacc agaagaccat      60
cgacagc                                                                67

<210> SEQ ID NO 23
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 23
cgccaaaaca gccaagcttt taatgatgat gatgatgatg gtcggcctga gcctggacgt      60
cggcagcggt ggcggcgacg c                                                81

<210> SEQ ID NO 24
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 24
cagaccgctt ctgcgttctg atttaatctg                                       30

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 25
cgctaaccaa accggtaacc ccgc                                             24

<210> SEQ ID NO 26
<211> LENGTH: 276
<212> TYPE: PRT
<213> ORGANISM: Rhodococcus jostii

<400> SEQUENCE: 26

Met Thr Asp Gln Lys Thr Ile Asp Ser Val Lys Thr Ser Leu Tyr Ala
1               5                   10                  15

Ala Val Gly Ala Gly Asp Val Val Gln Ala Val Ala Asp Val Val
            20                  25                  30

Ala Gln Val Arg Ser Arg Ala Glu Ser Thr Gln Gly Asp Val Glu Glu
        35                  40                  45

Arg Val Gly Gly Ala Lys Glu Arg Ile Ala Gly Leu Gln Glu Glu Val
    50                  55                  60

Thr Glu Gly Val Glu Asn Leu Arg Asp Arg Leu Ala Gly Leu Pro Ser
65                  70                  75                  80

Glu Leu Pro Glu Glu Leu Ala Glu Leu Arg Glu Lys Phe Thr Ala Asp
                85                  90                  95

Glu Leu Arg Lys Val Ala Glu Ala Tyr Leu Lys Val Ala Ser Asp Leu
            100                 105                 110

Tyr Thr Ser Leu Ala Glu Arg Gly Glu Asp Thr Val Glu Arg Ile Arg
        115                 120                 125

Lys Gln Pro Val Val Glu Glu Gly Ile Gly Arg Ala Glu Thr Ala Phe
    130                 135                 140

Gly Asp Ala Val Glu Leu Thr Glu Glu Ala Leu Gly Thr Val Ala Arg
145                 150                 155                 160
```

-continued

```
Gln Thr Arg Ala Val Gly Glu Gln Ala Ala Lys Leu Ala Gly Arg Ala
                165                 170                 175

Ser Gly Arg Ile Ser Asp Thr Ala Glu Gly Leu Gly Glu Ala Ile Ala
            180                 185                 190

Asp Ala Gly Asp Glu Ala Ala Leu Lys Val Leu Asp Leu Gly Asp Gln
        195                 200                 205

Ala Glu Glu Ala Ser Lys Asp Ala Ala Asp Arg Val Thr Ala Thr Ala
    210                 215                 220

Ala Asp Val Gln Ala Arg Ala Asp Lys Ala Ala Pro Ala Lys His Ala
225                 230                 235                 240

Ala Pro Ala Lys Lys Ala Ala Pro Ala Lys Ala Ala Ala Thr Pro Ala
                245                 250                 255

Pro Ala Pro Ala Lys Lys Ala Ala Ala Pro Ala Lys Lys Ala Ala Pro
            260                 265                 270

Ala Lys Lys Ala
        275

<210> SEQ ID NO 27
<211> LENGTH: 274
<212> TYPE: PRT
<213> ORGANISM: Rhodoccus opacus

<400> SEQUENCE: 27

Met Thr Asp Gln Lys Thr Ile Asp Ser Val Lys Thr Ser Leu Tyr Ala
1               5                   10                  15

Ala Val Gly Ala Gly Asp Val Val Gln Ala Val Ala Asp Val Val
            20                  25                  30

Ala Gln Val Arg Ser Arg Ala Glu Ser Thr Gln Gly Asp Val Glu Glu
        35                  40                  45

Arg Val Gly Gly Ala Lys Glu Arg Phe Ala Gly Leu Gln Glu Glu Val
    50                  55                  60

Thr Glu Gly Val Glu Asn Leu Arg Asp Arg Leu Ala Gly Leu Pro Ser
65                  70                  75                  80

Glu Leu Pro Glu Glu Leu Ala Glu Leu Arg Glu Lys Phe Thr Ala Asp
                85                  90                  95

Glu Leu Arg Lys Val Ala Glu Ala Tyr Leu Lys Val Ala Ser Asp Leu
            100                 105                 110

Tyr Thr Ser Leu Ala Glu Arg Gly Glu Asp Thr Val Glu Arg Ile Arg
        115                 120                 125

Lys Gln Pro Val Val Glu Gly Ile Gly Arg Ala Glu Thr Ala Phe
    130                 135                 140

Gly Asp Ala Val Glu Leu Thr Glu Glu Ala Leu Gly Thr Val Ala Arg
145                 150                 155                 160

Gln Thr Arg Ala Val Gly Glu Gln Ala Ala Lys Leu Ala Gly Leu Ala
                165                 170                 175

Ser Gly Arg Ile Ser Asp Thr Ala Glu Gly Leu Gly Glu Ala Ile Ala
            180                 185                 190

Asp Ala Gly Asp Glu Ala Ala Leu Lys Val Leu Asp Leu Gly Asp Gln
        195                 200                 205

Ala Glu Glu Ala Ser Lys Asp Ala Ala Asp Arg Val Thr Ala Thr Ala
    210                 215                 220

Ala Asp Val Ala Asp Lys Thr Ala Pro Ala Lys His Ala Ala Pro Ala
225                 230                 235                 240

Pro Ala Lys Lys Ala Ala Pro Ala Lys Ala Ala Thr Pro Ala Pro
                245                 250                 255
```

```
Ala Lys Lys Ala Ala Pro Ala Pro Ala Lys Lys Ala Ala Pro Ala Lys
            260                 265                 270

Lys Ala

<210> SEQ ID NO 28
<211> LENGTH: 232
<212> TYPE: PRT
<213> ORGANISM: Mycobacterium smegmatis

<400> SEQUENCE: 28

Met Ala Asp Lys Thr Gln Pro Thr Val Glu Glu Leu Lys Ala Pro Leu
1               5                   10                  15

Leu Ala Ala Val Gly Ala Ala Asp Leu Ala Leu Ala Thr Val Asn Glu
            20                  25                  30

Ile Ile Ala Thr Leu Leu Glu Arg Ala Gly Glu Ala Arg Ser Asp Ala
        35                  40                  45

Glu Ala Arg Val Glu Glu Ser Arg Ala Arg Leu Thr Lys Leu Gln Glu
    50                  55                  60

Glu Leu Pro Ser Gln Phe Gly Glu Leu Arg Glu Lys Leu Asn Ser Asp
65                  70                  75                  80

Glu Leu Arg Lys Lys Leu Asn Ser Glu Glu Leu Arg Lys Ala Ala Glu
                85                  90                  95

Ser Tyr Ala Asp Gln Ala Thr Ala Thr Tyr Asn Lys Leu Val Glu Arg
            100                 105                 110

Gly Glu Ala Ala Leu Glu Arg Leu Arg Asn Gln Pro Ala Leu Glu Glu
        115                 120                 125

Ala Ala Thr Arg Val Glu Thr Tyr Thr Asp Gln Ala Val Glu Leu Thr
    130                 135                 140

Gln Glu Ala Leu Gly Thr Val Ala Ser Gln Thr Arg Ala Val Gly Glu
145                 150                 155                 160

Arg Ala Ala Lys Leu Val Gly Val Glu Leu Pro Lys Arg Ala Glu Ala
                165                 170                 175

Ala Ala Glu Thr Ala Ser Glu Ala Ala Ala Glu Thr Ala Glu Pro Val
            180                 185                 190

Lys Lys Ala Ala Ala Pro Ala Ala Lys Lys Ala Ala Pro Ala Lys Lys
        195                 200                 205

Ala Ala Pro Ala Lys Lys Ala Thr Pro Ala Lys Ser Ala Ala Lys Ala
    210                 215                 220

Pro Ala Lys Lys Val Thr Gln Lys
225                 230

<210> SEQ ID NO 29
<211> LENGTH: 204
<212> TYPE: PRT
<213> ORGANISM: Mycobacterium tuberculosis
<220> FEATURE:
<221> NAME/KEY: misc_feature
<222> LOCATION: (129)..(129)
<223> OTHER INFORMATION: Xaa can be any naturally occurring amino acid

<400> SEQUENCE: 29

Met Lys Gly Ile Pro Met Ala Glu Asn Ser Asn Ile Asp Asp Ile Lys
1               5                   10                  15

Ala Pro Leu Leu Ala Ala Leu Gly Ala Ala Asp Leu Ala Leu Ala Thr
            20                  25                  30

Val Asn Glu Leu Ile Thr Asn Leu Arg Glu Arg Ala Glu Glu Thr Arg
        35                  40                  45
```

-continued

```
Thr Asp Thr Arg Ser Arg Val Glu Glu Ser Arg Ala Arg Leu Thr Lys
    50                  55                  60

Leu Gln Glu Asp Leu Pro Glu Gln Leu Thr Glu Leu Arg Glu Lys Phe
65              70                  75                  80

Thr Ala Glu Glu Leu Arg Lys Ala Ala Glu Gly Tyr Leu Glu Ala Ala
                85                  90                  95

Thr Ser Arg Tyr Asn Glu Leu Val Glu Arg Gly Glu Ala Ala Leu Glu
                100                 105                 110

Arg Leu Arg Ser Gln Gln Ser Phe Glu Glu Val Ser Ala Arg Ala Glu
            115                 120                 125

Xaa Tyr Val Asp Gln Ala Val Glu Leu Thr Gln Glu Ala Leu Gly Thr
    130                 135                 140

Val Ala Ser Gln Thr Arg Ala Val Gly Glu Arg Ala Ala Lys Leu Val
145                 150                 155                 160

Gly Ile Glu Leu Pro Lys Lys Ala Ala Pro Ala Lys Lys Ala Ala Pro
            165                 170                 175

Ala Lys Lys Ala Ala Pro Ala Lys Lys Ala Ala Lys Lys Ala Ala Pro
            180                 185                 190

Ala Lys Lys Ala Ala Ala Lys Lys Val Thr Gln Lys
            195                 200
```

PRODUCTION OF TRIACYLGLYCERIDES, FATTY ACIDS, AND THEIR DERIVATIVES

RELATED APPLICATIONS

This application is a national stage filing under 35 U.S.C. §371 of international application PCT/US2010/001717, filed Jun. 15, 2010, which was published under PCT Article 21(2) in English, and claims the benefit under 35 U.S.C. §119(e) of U.S. provisional application Ser. No. 61/268,707, filed on Jun. 15, 2009, and U.S. provisional application Ser. No. 61/281,239, filed on Nov. 13, 2009, the entire disclosures of which are incorporated by reference herein in their entirety.

FIELD OF THE INVENTION

The invention relates to the production of triacylglycerols in cells.

BACKGROUND OF THE INVENTION

Biodiesel, monoalkyl esters of long-chain fatty acids with short-chain alcohols derived from triacylglycerols (TAGs), can be produced from renewable biomass sources (Canakci and Sanli, *J Ind Microbial Biotechnol* 2008, 35:431-441, Du et al., *Appl Microbiol Biotechnol* 2008, 79:331-337, Vasudevan and Briggs, *J Ind Microbial Biotechnol* 2008, 35:421-430). Reports on the production of microbial oils by oleaginous microorganisms such as yeast, fungi, bacteria and microalgae have increased due to heightened awareness of the needs for alternative oil sources in the form of high energy molecules from renewable resources (Alvarez and Steinbüchel, *Appl Microbiol Biotechnol* 2002, 60:367-376, Antoni et al., *Appl Microbiol Biotechnol* 2007, 77:23-35; Li et al., *Appl Microbiol Biotechnol* 2008, 80:749-756; Hu et al., *Plant J* 2008, 54:621-639).

*Rhodococcus opacus* PD630 (*R. opacus* PD630) grown on gluconate medium is capable of accumulating TAGs up to 76% of the cell dry weight (CDW) (Alvarez et al., *Arch Microbiol* 1996, 165:377-386, Wältermann et al, *Microbiology* 2000, 146:1143-1149). It has also been reported that *R. opacus* PD630 grown in a fed-batch condition on a medium containing sugar beet molasses and sucrose as carbon sources reached a cell density of 37.4 g CDW $l^{-1}$ with a fatty acid content of 51.9% of the CDW (Voss and Steinbüchel, *Appl Microbiol Biotechnol* 2001, 55:547-555).

Currently, the development of second generation biofuel technologies that can be produced sustainably by using lignocellulosic biomass have been accelerated due to food-fuel conflict avoidance and use of wastes or unutilized materials (Stein, *J Am Diet Assoc* 2007, 107:1870-1878; Tollefson, *Nature* 2008, 451:880-883). Lignocellulosic biomass includes xylan that is a xylose polymer. However, the use of xylose-based media for the growth of *R. opacus* PD630 cultures has not been possible, owing to the inability of *R. opacus* PD630 to metabolize xylose.

Similarly, synthesis of biodiesel from plant oil has led to the production of large quantities of glycerol. As world production of biodiesel is increasing exponentially, large quantities of low cost glycerol that could be used as a substrate for bioprocesses will be available. Although *R. opacus* PD630 can utilize glucose and other carbon sources for growth, it does not utilize glycerol as sole carbon source.

SUMMARY OF INVENTION

Described herein are methods for producing high yields of triacylglycerols (TAGs) from cells. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells. Methods involve batch-culture fermentations using pH controlled environmental conditions that allow for an increase of glucose and $(NH_4)_2SO_4$ in the production medium, resulting in a dramatic increase in fatty acid production. Also described herein are recombinant *Rhodococcus* strains that are capable of efficiently metabolizing xylose and glycerol. These microorganisms, and methods of using such microorganisms, hold great potential as a future source of industrial biodiesel derived from renewable biomass resources. Also described herein are methods for increasing TAG production in cells by overexpressing novel genes involved in TAG accumulation.

Aspects of the invention relate to methods for producing triacylglycerols by culturing a population of cells in culture medium comprising a glucose concentration between 40 g $l^{-1}$ and 300 g $l^{-1}$ and a carbon/nitrogen ratio between 1.2/1 and 109/1 for a time sufficient for the cells to produce triacylglycerols, and optionally collecting the triacylglycerols from the culture medium. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the glucose concentration is between 60 g $l^{-1}$ and 300 g $l^{-1}$, or between 120 g $l^{-1}$ and 300 g $l^{-1}$. In some embodiments, the carbon to nitrogen ratio is between 10/1 and 20/1, and in certain embodiments is approximately 17.8/1. In some embodiments, the cell is cultured in medium with a pH between 4.0 and 9.0, and in certain embodiments with a pH of approximately 7.0. In some embodiments the cell is cultured at a temperature of between 20° C. and 45° C., and in certain embodiments at a temperature of approximately 30° C. In some embodiments, the cell is cultured in the presence of xylose and/or glycerol.

Further aspects of the invention relate to methods for producing triacylglycerols by culturing a population of cells in culture medium comprising a xylose concentration between 40 g $l^{-1}$ and 300 g $l^{-1}$ and a carbon/nitrogen ratio between 1.2/1 and 109/1 for a time sufficient for the cells to produce triacylglycerols, and optionally collecting the triacylglycerols from the culture medium. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells.

In some embodiments, the cells are genetically modified. In certain embodiments, the cells recombinantly express a gene encoding xylose isomerase and/or a gene encoding xylulose kinase. The gene encoding xylose isomerase and/or the gene encoding xylulose kinase can be a prokaryotic gene such as a *Streptomyces padanus* gene. In some embodiments, the gene encoding xylose isomerase and/or the gene encoding xylulose kinase is expressed from a plasmid or is integrated into the genome of the cell. In some embodiments, the gene encoding xylose isomerase is xylA. In some embodiments, the gene encoding xylulose kinase is xylB, or a fusion between xylB or a portion thereof and CBP or a portion thereof.

In some embodiments, the cell is cultured in the presence of glucose. In certain embodiments, the glucose is at a concentration of 40 g l$^{-1}$ or more, or 200 g l$^{-1}$ or more. In some embodiments, the cell is cultured in medium with a pH between 4.0 and 9.0, and in certain embodiments, with a pH of approximately 7.0. In some embodiments, the cell is cultured at a temperature of between 20° C. and 45° C., and in certain embodiments, at a temperature of approximately 30° C. In some embodiments, the carbon to nitrogen ratio is between 10/1 and 20/1, and in certain embodiments, it is approximately 16.9/1.

Further aspects of the invention relate to methods for producing triacylglycerols including culturing a population of cells in culture medium comprising a glycerol concentration between 40 g l$^{-1}$ and 300 g l$^{-1}$ and a carbon/nitrogen ratio between 1.2/1 and 109/1 for a time sufficient for the cells to produce triacylglycerols, and optionally collecting the triacylglycerols from the culture medium. The cell can be any type of eukaryotic or prokaryotic cell. In some embodiments, the cells are oleaginous cells. In certain embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells.

In some embodiments, the cells are genetically modified. In certain embodiments, the cells recombinantly express a gene encoding glycerol kinase and/or a gene encoding glycerol-3-phosphate dehydrogenase. The gene encoding glycerol kinase and/or the gene encoding glycerol-3-phosphate dehydrogenase can be a prokaryotic gene such as a *Rhodococcus* gene. In certain embodiments, the gene encoding glycerol kinase and/or the gene encoding glycerol-3-phosphate dehydrogenase is a *Rhodococcus erythropolis* AN12 gene. In some embodiments, the gene encoding glycerol kinase and/or the gene encoding glycerol-3-phosphate dehydrogenase is expressed from a plasmid. In other embodiments, the gene encoding glycerol kinase and/or the gene encoding glycerol-3-phosphate dehydrogenase is integrated into the genome of the cell.

In some embodiments, the cell is cultured in the presence of glucose. In certain embodiments, the glucose is at a concentration of 40 g l$^{-1}$ or more, or 200 g l$^{-1}$ or more. In some embodiments, the cell is cultured in medium with a pH between 4.0 and 9.0, and in certain embodiments, a pH of approximately 7.0. In some embodiments, the cell is cultured at a temperature of between 20° C. and 45° C., and in certain embodiments, at a temperature of approximately 30° C. In some embodiments, the carbon to nitrogen ratio is between 10/1 and 20/1, and in certain embodiments, it is approximately 17.8/1 or 16.9/1.

Further aspects of the invention relate to cells that recombinantly express a gene encoding xylose isomerase and/or a gene encoding xylulose kinase. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the gene encoding xylose isomerase and/or the gene encoding xylulose kinase is a prokaryotic gene, such as a *Streptomyces padanus* gene. The gene encoding xylose isomerase and/or the gene encoding xylulose kinase can be expressed from a plasmid or can be integrated into the genome of the cell. In some embodiments, the gene encoding xylose isomerase is xylA, and the gene encoding xylulose kinase is xylB, or a fusion between xylB or a portion thereof and CBP or a portion thereof.

Aspects of the invention relate to producing triacylglycerols by culturing cells associated with the invention, and optionally recovering the triacylglycerols from the cells. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the cell is cultured in the presence of glucose. In certain embodiments, the glucose is at a concentration of 40 g l$^{-1}$ or more or 200 g l$^{-1}$ or more. In some embodiments the cell is cultured in the presence of xylose. The cell can be cultured in medium with a pH between 4.0 and 9.0. In certain embodiments, the pH is approximately 7.0. The cell can also be cultured at a temperature of between 20° C. and 45° C. In certain embodiments the temperature is approximately 30° C. The carbon to nitrogen ratio of the media in which the cell is cultured can be between 1.2/1 and 109/1. In some embodiments, the carbon to nitrogen ratio is between 10/1 and 20/1. In certain embodiments, the carbon to nitrogen ratio is approximately 17.8/1 or approximately 16.9/1.

Aspects of the invention relate to methods for producing triacylglycerols, including obtaining or producing a genetically modified cell that recombinantly expresses a gene encoding xylose isomerase and/or a gene encoding xylulose kinase, culturing a population of said cells in a culture medium for a time sufficient for the cells to produce triacylglycerols, and optionally collecting the triacylglycerols from the culture medium. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the gene encoding xylose isomerase and/or the gene encoding xylulose kinase is a prokaryotic gene, such as a *Streptomyces padanus* gene.

The gene encoding xylose isomerase and/or the gene encoding xylulose kinase can be expressed from a plasmid or can be integrated into the genome of the cell. In some embodiments, the gene encoding xylose isomerase is xylA, and the gene encoding xylulose kinase is xylB, or a fusion between xylB or a portion thereof and CBP or a portion thereof. In some embodiments, the cell is cultured in the presence of glucose. In certain embodiments, the glucose is at a concentration of 40 g l$^{-1}$ or more, or 200 g l$^{-1}$ or more. In some embodiments, the cell is cultured in the presence of xylose. The cell can be cultured in medium with a pH between 4.0 and 9.0. In certain embodiments, the pH is approximately 7.0. The cell can also be cultured in media with a temperature of between 20° C. and 45° C. In certain embodiments, the temperature is approximately 30° C. The carbon to nitrogen ratio can be between 1.2/1 and 109/1. In some embodiments, the carbon to nitrogen ratio is between 10/1 and 20/1. In certain embodiments, the carbon to nitrogen ratio is approximately 17.8/1 or 16.9/1.

Further aspects of the invention relate to cells that recombinantly express a gene encoding glycerol kinase and/or a gene encoding glycerol-3-phosphate dehydrogenase. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the gene encoding glycerol kinase and/or the gene encoding glycerol-3-phosphate dehydrogenase is a prokaryotic gene, such as a *Rhodococcus erythropolis* AN12 gene. The gene encoding glycerol kinase and/or the gene encoding glycerol-3-phosphate dehydrogenase can be expressed from a plasmid or can be integrated into the genome of the cell. Aspects of the invention relate to methods for producing triacylglycerols by culturing such cells, and optionally recovering the triacylglycerols from the cells. In some embodiments, the cell is cultured in the presence of glucose. In certain embodiments the glucose is at a concentration of 40 g l$^{-1}$ or 200 g l$^{-1}$ or more. In some embodiments, the cell is cultured in the presence of glycerol. The cell can be cultured in medium with a pH between 4.0 and 9.0. In certain embodiments, the pH is approximately 7.0. The cell can also be cultured at a temperature of between 20° C. and 45° C. In certain embodiments, the temperature is approximately 30° C. The carbon to nitrogen ratio can be between 1.2/1 and 109/1. In some embodiments, the carbon to nitrogen ratio is between 10/1 and 20/1. In certain embodiments, the carbon to nitrogen ratio is approximately 17.8/1 or approximately 16.9/1.

Aspects of the invention relate to methods for producing triacylglycerols, including obtaining or producing a genetically modified cell that recombinantly expresses a gene encoding glycerol kinase and/or a gene encoding glycerol-3-phosphate dehydrogenase, culturing a population of said cells in a culture medium for a time sufficient for the cells to produce triacylglycerols, and optionally collecting triacylglycerols from the culture medium. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the gene encoding glycerol kinase and/or the gene encoding glycerol-3-phosphate dehydrogenase is a prokaryotic gene, such as a *Rhodococcus erythropolis* AN12 gene.

The gene encoding glycerol kinase and/or the gene encoding glycerol-3-phosphate dehydrogenase can be expressed from a plasmid or can be integrated into the genome of the cell. In some embodiments, the cell is cultured in the presence of glucose. In certain embodiments, the glucose is at a concentration of 40 g l$^{-1}$ or more or 200 g l$^{-1}$ or more. In some embodiments, the cell is cultured in the presence of glycerol. The cell can be cultured in medium with a pH between 4.0 and 9.0. In certain embodiments, the pH is approximately 7.0. The cell can also be cultured at a temperature of between 20° C. and 45° C. In certain embodiments, the temperature is approximately 30° C. The carbon to nitrogen ratio can be between 1.2/1 and 109/1. In some embodiments, the carbon to nitrogen ratio is between 10/1 and 20/1. In certain embodiments, the carbon to nitrogen ratio is approximately 17.8/1 or approximately 16.9/1.

Aspects of the invention relate to methods for producing triacylglycerols, including culturing a population of oleaginous cells in culture medium comprising a glucose concentration between 120 g l$^{-1}$ and 300 g l$^{-1}$ and a carbon/nitrogen ratio of approximately 17.8/1 for a time sufficient for the cells to produce triacylglycerols, and optionally collecting the triacylglycerols from the culture medium.

Further aspects of the invention relate to methods for producing triacylglycerols, including obtaining or producing a genetically modified cell that overexpresses a gene encoding for an aldehyde dehydrogenase protein, culturing a population of said cells in a culture medium for a time sufficient for the cells to produce triacylglycerols, and optionally collecting the triacylglycerols from the culture medium. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some embodiments, the gene encoding for an aldehyde dehydrogenase protein is expressed recombinantly. In certain embodiments, the aldehyde dehydrogenase protein is a non-phosphorylative glyceraldehyde-3 phosphate dehydrogenase (GapN) protein. In some embodiments, the cell is cultured in the presence of glucose. In certain embodiments, the glucose is at a concentration of 40 g l$^{-1}$ or more or 200 g l$^{-1}$ or more. In certain embodiments, the glucose concentration is between 60 g l$^{-1}$ and 300 g l$^{-1}$, or between 120 g l$^{-1}$ and 300 g l$^{-1}$. In some embodiments, the cell is cultured in the presence of glycerol. The cell can be cultured in medium with a pH between 4.0 and 9.0. In certain embodiments, the pH is approximately 7.0. The cell can also be cultured at a temperature of between 20° C. and 45° C. In certain embodiments, the temperature is approximately 30° C. The carbon to nitrogen ratio can be between 1.2/1 and 109/1. In some embodiments, the carbon to nitrogen ratio is between 10/1 and 20/1. In certain embodiments, the carbon to nitrogen ratio is approximately 17.8/1 or approximately 16.9/1.

In some embodiments, the gene encoding for the aldehyde dehydrogenase protein is a bacterial gene such as an *Actinomycetes* gene. In some embodiments, the *Actinomycetes* gene is a *Rhodococcus* gene such as a *Rhodococcus opacus* gene. In certain embodiments, the *Rhodococcus opacus* gene is a *Rhodococcus opacus* PD630 gene. The gene encoding for an aldehyde dehydrogenase protein can be expressed on a plasmid and/or integrated into the genome of the cell.

In some embodiments, the cell has reduced expression of a glyceraldehyde 3-phosphate dehydrogenase (GapA) protein relative to a wild-type cell. In certain embodiments, the cell expresses a mutated form of the glyceraldehyde 3-phosphate dehydrogenase (GapA) protein and/or the glyceraldehyde 3-phosphate dehydrogenase (GapA) protein in the cell is deleted.

Further aspects of the invention relate to methods for producing triacylglycerols, including obtaining or producing a genetically modified cell that overexpresses one or more of tadR, tadA and tadB, culturing a population of said cells in a culture medium for a time sufficient for the cells to produce triacylglycerols, and optionally collecting the triacylglycerols from the culture medium.

The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells. In some embodiments, tadR, tadA and/or tadB is expressed recombinantly.

In some embodiments, the cell is cultured in the presence of glucose. In certain embodiments, the glucose is at a concentration of 40 g $l^{-1}$ or more or 200 g $l^{-1}$ or more. In certain embodiments, the glucose concentration is between 60 g $l^{-1}$ and 300 g $l^{-1}$, or between 120 g $l^{-1}$ and 300 g $l^{-1}$. In some embodiments, the cell is cultured in the presence of glycerol. The cell can be cultured in medium with a pH between 4.0 and 9.0. In certain embodiments, the pH is approximately 7.0. The cell can also be cultured at a temperature of between 20° C. and 45° C. In certain embodiments, the temperature is approximately 30° C. The carbon to nitrogen ratio can be between 1.2/1 and 109/1. In some embodiments, the carbon to nitrogen ratio is between 10/1 and 20/1. In certain embodiments, the carbon to nitrogen ratio is approximately 17.8/1 or approximately 16.9/1.

In some embodiments, the tadR, tadA and/or tadB gene is a bacterial gene such as an *Actinomycetes* gene. In some embodiments the *Actinomycetes* gene is a *Rhodococcus* gene such as a *Rhodococcus opacus* gene. In certain embodiments, the *Rhodococcus opacus* gene is a *Rhodococcus opacus* PD630 gene. The tadR, tadA and/or tadB gene can be expressed on a plasmid and/or integrated into the genome of the cell.

Further aspects of the invention relate to isolated *Rhodococcus* TadA polypeptides. In some embodiments, the isolated polypeptide is at least 80% identical, or at least 90% identical to SEQ ID NO:11. In certain embodiments, the isolated polypeptide is a *Rhodococcus opacus* polypeptide such as a *Rhodococcus opacus* PD630 polypeptide. Aspects of the invention also include polypeptides that comprise SEQ ID NO:11. Aspects of the invention also include nucleic acids that encode for TadA polypeptides or portions thereof.

Further aspects of the invention relate to isolated *Rhodococcus* TadD polypeptides. In some embodiments, the isolated polypeptide is at least 80% identical, or at least 90% identical to SEQ ID NO:4. In certain embodiments, the isolated polypeptide is a *Rhodococcus opacus* polypeptide such as a *Rhodococcus opacus* PD630 polypeptide. Aspects of the invention also include polypeptides that comprise SEQ ID NO:4. Aspects of the invention also include nucleic acids that encode for TadD polypeptides or portions thereof.

Further aspects of the invention relate to isolated *Rhodococcus* TadB polypeptides. In some embodiments, the isolated polypeptide is at least 80% identical, or at least 90% identical to SEQ ID NO:12. In certain embodiments, the isolated polypeptide is a *Rhodococcus opacus* polypeptide such as a *Rhodococcus opacus* PD630 polypeptide. Aspects of the invention also include polypeptides that comprise SEQ ID NO:12. Aspects of the invention also include nucleic acids that encode for TadB polypeptides or portions thereof.

Further aspects of the invention relate to isolated *Rhodococcus* TadR polypeptides. In some embodiments, the isolated polypeptide is at least 80% identical, or at least 90% identical to SEQ ID NO:13. In certain embodiments, the isolated polypeptide is a *Rhodococcus opacus* polypeptide such as a *Rhodococcus opacus* PD630 polypeptide. Aspects of the invention also include polypeptides that comprise SEQ ID NO:13. Aspects of the invention also include nucleic acids that encode for TadR polypeptides or portions thereof.

These and other aspects of the invention, as well as various embodiments thereof, will become more apparent in reference to the drawings and detailed description of the invention.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 presents an image depicting lipid bodies in *R. opacus* PD630. (Alvarez et al., *Arch Microbiol* 1996, 165:377-386)

FIG. 15 is a table depicting 3 assemblies of the *R. opacus* PD630 genome.

FIG. 17 is a table indicating genes associated with lipid production, identified using comparative genomics.

FIG. 30 is a table depicting optimal glucose, $(NH_4)_2SO_4$ and carbon:nitrogen ratio (C/N, w/w) of the defined medium tested for fermentations for bioprocess production of triacylglycerols.

FIG. 31 presents a table depicting xylose utilization by *R. opacus* PD630 and various species of *Streptomyces*.

FIG. 33 presents the nucleotide sequence (positions 1-3603; SEQ ID NO:1) of the whole insert 3603 bp fragment on the pAL358 plasmid in transformant-Xsp1, 8, 10 and 12. The xylA ORF1 is included in the 1167 nucleotides region (233-1399). The xylB ORF2 is included in the 1938 nucleotides region (1596-3533) with a cellulose-binding protein sequence (2829-3633, boldface).

FIG. 34 presents a table depicting fatty acid production in *R. opacus* PD630 (wt) and in transformant strains (Xsp) transformed with an *S. padanus* library.

FIG. 35 presents a table depicting fatty acid production in the transformant strains.

FIG. 36 presents a table depicting results of co-metabolism in transformant strains.

FIG. 37 presents a table depicting fermentation results.

FIG. 42 depicts a table indicating the use of StatGraphics to optimize the C/N ratio.

FIG. 43 presents a table depicting an overview of the total fatty acids obtained from the fermentations.

FIG. 45 presents a table summarizing fatty acid production by Xsp8C-retransformants.

FIG. 57 presents a table depicting total fatty acid production in *R. opacus* PD630 transformed with pPB80.

FIG. 62 presents a table summarizing lipid accumulation in *R. opacus* GspC transformants analyzed by GC FAME.

FIG. 64 presents a table showing fatty acid composition profiles. Fatty acid analysis of lyophilized cells was conducted by gas chromatography (GC) after derivatization to fatty acid methyl esters by sulfuric acid-catalyzed methanolysis. Values are percentages of total fatty acids.

FIG. 75A presents Sudan Black staining of wild type (WT) and 44B2 colonies grown on minimal medium supplemented with 4% glucose and 0.15% ammonium sulphate. The lipophilic dye Sudan Black was used to identify transposon mutants that accumulated less TAGs than the wild type strain. Strains accumulating less TAGs absorb and retain less of the dye than the wild type strain as can be seen in the 44B2 mutant colony. FIG. 75B presents thin-layer chromatography of the wild type and 44B2 mutant grown for varying lengths of time. Lipid extracts from the two strains from progressive time points were resolved using a two solvent system to separate TAGs from other lipid species followed by charring. TAG standards were used to identify the Rf value for TAGs under the chromatographic conditions used. The 44B2 mutant accumulates less TAGs than the wild type at all time points while the relevant abundance of other lipids remains largely unchanged.

FIG. 76A presents SDS-PAGE analysis of purified TadD. A c-terminal hexa-histidine tagged variant of TadD was expressed recombinantly in *E. coli* and purified using nickel affinity chromatography. FIG. 76B presents a schematic and a graph showing that purified TadD reduces NAD(P)+ in the presence of glyceraldehyde 3-phosphate (G3P). The purified histidine-tagged variant of TadD was incubated with G3P and NAD(P)+ and NAD(P)H formation was monitored as an increase in absorbance at 340 nm. Values are expressed as a change in absorbance at 340 nm per mg of protein per minute. A marked increase in specific activity in fractions containing the TadD protein as compared to those from cells harboring the empty vector was observed.

FIG. 77A shows lipid accumulation increase under nitrogen limiting conditions. Lipids were extracted from wild type *R. opacus* PD630 and the TadD mutant and were grown in either LB or minimal medium supplemented with either 1% or 0.15% ammonium sulphate and assayed using GC-FAMEs analysis. An increase in total fatty acids was observed in when wild type *R. opacus* PD630 was grown under nitrogen limiting conditions as compared to nitrogen replete conditions. Additionally, the TadD mutant demonstrated decreased lipid accumulation as compared to the wild type, as shown above. FIG. 77B shows ND-G3PDH activity in crude lysates from cultures grown under identical conditions to those described above. Cultures from above were lysed and the crude lysates assayed for ND-G3PDH activity. As with the total fatty acids, a significant increase in the ND-G3PDH activity was observed in cells grown under nitrogen limiting conditions as compared to those grown under nitrogen replete conditions. Furthermore, significantly lower ND-G3PH activity was observed in the TadD mutant. FIG. 77C shows that NAD(P)+/NAD(P)H ratios decrease during early nitrogen limitation. Wild type *R. opacus* PD630 and the TadD mutant were grown in minimal medium supplemented with either 1% or 0.15% ammonium sulphate, and the resulting cell lysates were assayed for NAD(P)+ and NAD(P)H concentrations. Consistent with the data concerning ND-G3PDH activity, a decrease in the ratio of NAD(P)+/NAD(P)H was observed under nitrogen limitation as compared to nitrogen replete conditions. Additionally, no change was seen in the ratio of NAD(P)+/NAD(P)H in the TadD mutant. FIG. 77D shows that the ratio of NAD+/NADH increases under nitrogen limiting conditions. Cell lysates from above were also assayed for NAD+ and NADH concentrations. A marked increase in the ratio of NAD+ to NADH was observed under nitrogen limiting conditions as compared to nitrogen replete conditions, while no difference was observed in the TadD mutant. The NAD+/NADH ratio in the TadD mutant is significantly lower than that observed for the wild type.

FIG. 78 shows that overexpression of a predicted *R. opacus* PD630 GapA homolog results in a decrease in TAG accumulation. FIG. 78A depicts a schematic based on the hypothesis that GapA and GapN compete for G3P during glycolysis in *R. opacus* PD630. FIG. 78B shows that extrachromosomal expression of GapA results in a decrease in TAG accumulation. Lipid extracts from wild type *R. opacus* PD630 expressing either GFP, TadD or the *R. jostii* RHA1 GapA homolog encoded by the ro07177 gene were grown in minimal medium supplemented with spectinomycin and anhydrotetracycline and were resolved using TLC. As described above, expression of the TadD resulted in an increase in TAGs while expression of the ro07177 protein resulted in a dramatic decrease in TAGs as compared to the wild type strain expressing the GFP protein.

FIG. 80A shows a Sudan Black B staining colony phenotype of wild type *R. opacus* and the tadA::Tn5 mutant. Colonies were grown for 120 h and stained with the lipophilic dye Sudan Black B. The lighter staining of the tadA::Tn5 mutant is suggestive of decreased TAG accumulation. FIG. 80B shows thin-layer chromatography analysis of lipids in wild-type *R. opacus* and the tadA::Tn5 mutant. Strains were grown in minimal medium and samples removed and lyophilized at 24, 48, 72, 96 and 120 h followed by resolution using TLC. The tadA::Tn5 mutant demonstrates decreased TAG accumulation at all time points when compared to the parental strain. FIG. 80C shows complementation analysis of the tadA::Tn5 mutant. Expression of wild-type tadA (pDPM78), but not the truncation mutant (pDPM80), compensated for the observed decrease in TAG accumulation in the tadA::Tn5 mutant (see Table 9).

FIG. 82 shows an alignment of the predicted amino acid sequence of the TadA protein and the mycobacterial heparin-binding hemagglutinin protein (HbhA). The predicted amino acid sequence of the TadA protein from *R. opacus* PD630 (SEQ ID NO:11), the ro02104 protein from *R. jostii* RHA1 (SEQ ID NO:26), the ROP 18230 protein from *Rhodococcus opacus* B4 (SEQ ID NO:27) and the HbhA protein from *M. smegmatis* MC2 155 (SEQ ID NO:28) and *M. tuberculosis* CDC1551 (SEQ ID NO:29) were aligned using ClustalW. The predicted lysine rich heparin-binding domains are highlighted in gray. The region deleted in the AC-terminus TadA mutants is highlighted in gray.

FIG. 85 demonstrates yeast agglutination mediated by TadA.

FIG. 87A reveals that TadA agglutinates lipid bodies in vitro. Increasing concentrations of purified WT and ΔC-terminus TadA were incubated with purified lipid bodies resulting in increased sedimentation of the lipid bodies. Concentration of protein in each well corresponds to the bar graph below. FIG. 87B demonstrates quantitation of lipid body aggregation. Aliquots were removed from the above lipid body aggregation experiments and their absorbance at 600 nm was analyzed. Increased concentration of the WT TadA and not the ΔC-terminus mutant, was associated with a decreased optical density. FIG. 87C demonstrates fluorescent microscopy of lipid body aggregates from lipid body aggregation assays. Lipid bodies and their aggregates from the lipid body aggregation assay were stained with Nile Red and observed using fluorescent microscopy. Lipid bodies incubated with TadA were found primarily as large aggregates while lipid bodies incubated with either the buffer control and the ΔC-terminus mutant were primarily observed as medium-sized aggregates. FIG. 87D demonstrates Western blotting of the lipid body aggregation assay. Western blots were performed on lipid bodies which had been incubated with either WT or the ΔC-terminus TadA-His. Both the WT and ΔC-terminus TadA were found to associate with lipid bodies in vitro.

FIG. 89 presents a schematic and gels depicting transcriptional regulation of tadA.

DETAILED DESCRIPTION

Figure 2:
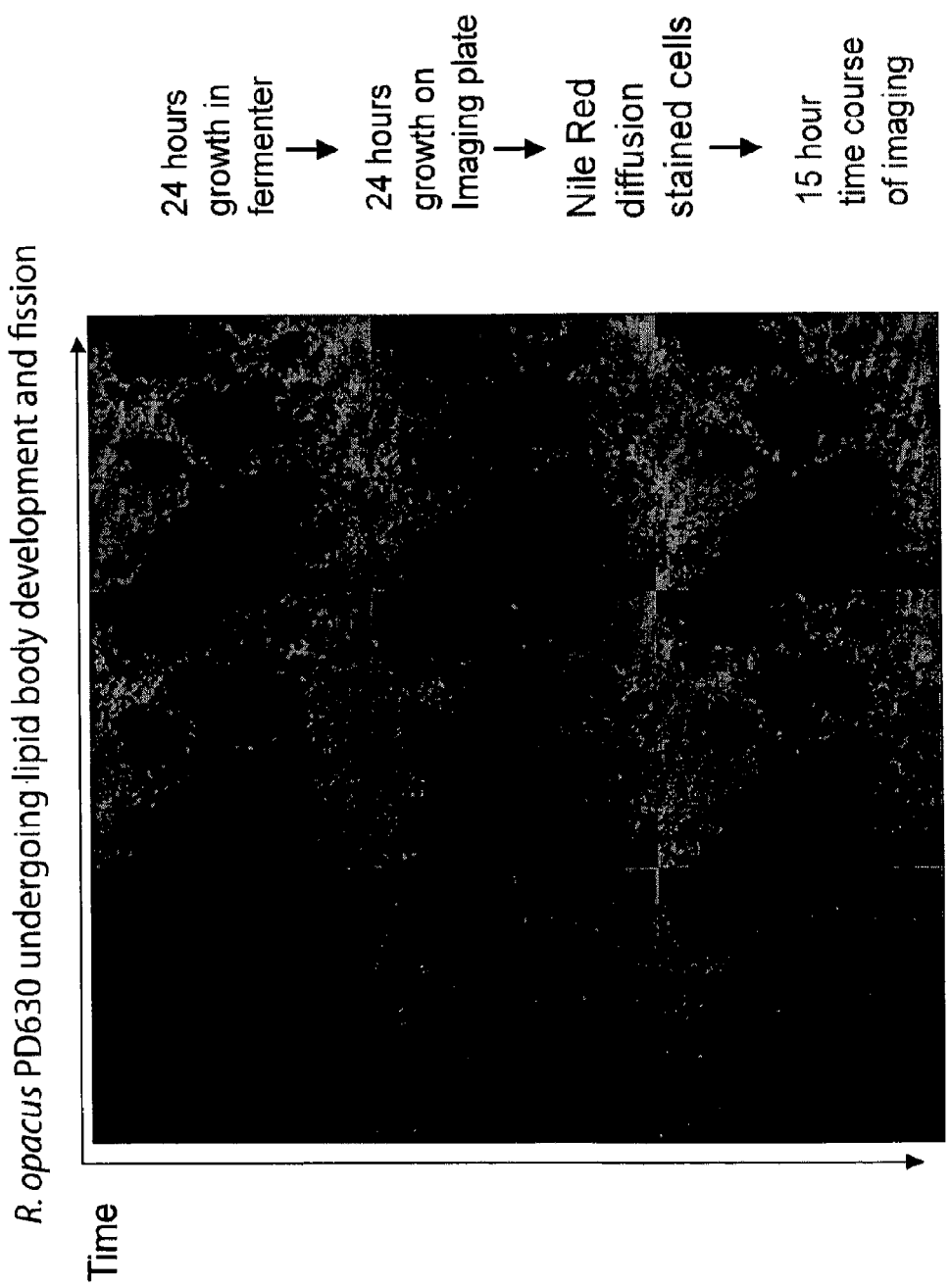
FIG. 2 presents an image of Nile Red diffusion stained cells showing *R. opacus* PD630 undergoing lipid body development and fission.

Aspects of the invention relate to methods for production of TAGs in cells. Described herein are methods for high titer production of TAGs in glucose-containing medium. Surprisingly, it was found that the oleaginous microorganism *R. opacus* PD630 has the ability to grow to a high density (72 g l$^{-1}$) and produce TAGs in defined media containing high glucose concentrations (up to 300 g l$^{-1}$ of glucose). Further described are recombinant microorganisms and methods of using such microorganisms for production of TAGs in medium containing xylose and glycerol. Surprisingly, metabolic engineering of *R. opacus* PD630 strains to recombinantly express genes involved in xylose metabolism, including xylA and xylB, allowed for growth and TAG production on xylose-containing media. The xylB gene was expressed as a novel recombinant gene fusion product with a gene encoding for a predicted cellulose binding protein (CBP). Also described herein are methods for increasing production of TAGs in cells by overexpressing novel genes involved in TAG accumulation.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Certain methods of the invention relate to the production of TAGs. As used herein, a TAG (triacylglycerol) refers to a glyceride in which the glycerol is esterified with three fatty acids. As used herein, a fatty acid refers to an organic acid made up of molecules containing a carboxyl group at the end of a hydrocarbon chain. The fatty acid components of the TAG can have chains of varying lengths. For example, in some embodiments the carbon content of the fatty acid may vary from 2 to 34 carbons. Several non-limiting examples of fatty acids include myristic acid, pentadecanoic acid, palmitic acid, palmitoleic acid, heptadecanoic acid, cis-10Heptadecanoic acid, stearic acid, oleic acid, caproic acid, linoleic acid, linolenic acid, elcosenoic acid, behenic acid and erucic acid.

It should be appreciated that methods described herein for the production of TAGs encompass the use of any type of cell. The cell can be any type of eukaryotic or prokaryotic cell. In some embodiments, the cells are oleaginous cells. In some embodiments, the oleaginous cells are bacterial cells. For example, the cells can be *Actinomycetes* cells such as *Rhodococcus* cells. In certain embodiments, the *Rhodococcus* cells are *Rhodococcus opacus* cells such as *Rhodococcus opacus* PD630 cells. In other embodiments, the *Rhodococcus* cells are *Rhodococcus* sp. RHA1 cells.

In some aspects, methods described herein use oleaginous microorganisms for the production of TAGs. As used herein an oleaginous microorganism refers to a microorganism that can accumulate at least 20% of its dry cell weight as oil. An oleaginous microorganism can be a species of yeast, fungi, microalgae or bacteria. For example, an oleaginous species of yeast can be a species belonging to the genera of *Yarrowia, Candida, Rhodotorula, Rhodosporidium, Cryptococcus, Trichosporon, Lipomyces, Codermyces* and *Pichia*. Several non-limiting examples of oleaginous yeast species include *Rhodotorula glutinis, Cryptococcus curvatus, Cryptococcus albidus, Candida valida, Candida utilis, Codermyces poitrasii, Rhodosporidium toruloides, Lipomyces starkeyi, Pichia angusta* and *Yarrowia lipolytica*.

An oleaginous species of fungi can be, for example, a species belonging to the genera of *Mortierella, Cunninghamella, Mucor, Phycomyces* or *Pythium*. Several non-limiting examples of oleaginous fungus species include *Mortierella ramanniana* var. *angulispora, Cunninghamella echinulata, Mucor circinelloides, Mortierella alpina, Mortierella elongate,* and *Pythium ultimum*.

An oleaginous species of microalgae can be, for example, a species belonging to the genera of *Cyclotella, Hantzschia, Nitzschia, Chlorella, Scenedesmus, Ankistrodesmus, Botryococcus, Navicula, Ochromonas, Coscinodiscus, Dunaliella, Phaeodactylum* and *Euglena*. Several non-limiting examples of oleaginous microalgae species include *Nitzschia palea, Nitzschia closterium, Cyclotella cryptica, Chlorella pyrenoi-* dosa, *Botryococcus braunii, Navicula pelliculosa, Ochromonas danica, Coscinodiscus eccentricus, Dunaliella* spp., *Phaeodactylum tricornutum* and *Euglena gracilis*.

An oleaginous microorganism can also be a species of bacteria such as a species belonging to the genera of *Rhodococcus, Acinetobacter, Streptomyces, Nocardia*, or *Mycobacterium*. In some embodiments, the oleaginous microorganism used for TAG production is a species of *Rhodococcus* such as *Rhodococcus opacus*, for example *Rhodococcus opacus* PD630 (*R. opacus* PD630) or *Rhodococcus jostii*, for example *Rhodococcus jostii* RHA1 (*R. jostii* RHA1). In species of *Rhodococcus*, 10-80% of cell dry weight is fatty acid. The stored lipids that accumulate in *Rhodococcus* mainly consist of C16-C18.1 in TAGs that can be converted to biodiesel and other fuels. *R. opacus* PD630 undergoes a developmental process leading to abundant lipid storage involving: increased lipid accumulation that can be detected by lipophilic dyes such as Nile Red, morphological changes from elongated rods to rotund cocci, and cell shortening as the cells develop under defined media conditions. Shorter fragmented cells filled with lipid bodies can be separated using buoyant density separations.

Aspects of the invention relate to the use of controlled growth conditions to maximize lipid body production. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include antibiotics, IPTG for gene induction, and ATCC Trace Mineral Supplement.

Several non-limiting examples of growth conditions that affect fermentation include: agitation speed, oxygen content, pH, temperature, glucose concentration, nitrogen concentration and the carbon to nitrogen (C/N) ratio. In some embodiments, the agitation speed of the culture is between 300 and 1200 rpm. In other embodiments the agitation speed can be more than 1200 rpm. For example the agitation speed can be approximately 300, 400, 500, 600, 700, 800, 900, 1000, 1100, 1200 or more than 1200 rpm. In some embodiments the oxygen content of the culture is above 80% with pure $O_2$. The pH of the culture can be between 4.0 and 9.0. For example the pH can be approximately 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9, including any intermediate value. In certain embodiments, the pH is approximately 6.9 or 7.0. In some embodiments, the temperature of the culture is between 20 and 45° C. For example, the temperature can be approximately 20, 21, 22, 23, 24, 25, 26, 27, 28, 29, 30, 31, 32, 33, 34, 35, 36, 37, 38, 39, 40, 41, 42, 43, 44 or 45° C., including any intermediate value. In certain embodiments, the temperature is approximately 30° C.

The glucose concentration in the culture media can be between 30 and 300 g $l^{-1}$. In some embodiments, the glucose concentration is between 40 and 240 g $l^{-1}$. For example, in certain embodiments, the glucose concentration can be approximately 40, 50, 60, 70, 80, 90, 100, 110, 120, 130, 140, 150, 160, 170, 180, 190, 200, 210, 220, 230, 240 or more than 240 g $l^{-1}$, including any intermediate value. In some embodiments the concentration of nitrogen is between 2 and 30 g $l^{-1}$. For example, in certain embodiments, the concentration of nitrogen can be approximately 2, 3, 4, 5, 6, 7, 8, 9, 10, 11, 12, 13, 14, 15, 16, 17, 18, 19, 20, 21, 22, 23, 24, 25, 26, 27, 28, 29 or 30 g $l^{-1}$, including any intermediate value. The C/N ratio can be between 1.2/1 and 109/1. For example, in certain embodiments, the C/N ratio can be approximately 1.2/1, 5/1, 10/1, 15/1, 20/1, 25/1, 30/1, 35/1, 40/1, 45/1, 50/1, 55/1, 60/1, 65/1, 70/1, 75/1, 80/1, 85/1, 90/1, 95/1, 100/1, 105/1 or 109/1, including any intermediate value. In some embodiments the C/N ratio is between 5/1 and 20/1. For example, in certain embodiments, the C/N ratio can be approximately 5/1, 6/1, 7/1, 8/1, 9/1, 10/1, 11/1, 12/1, 13/1, 14/1, 15/1, 16/1, 17/1, 18/1, 19/1, or 20/1, including any intermediate value. In certain embodiments the C/N ratio can be approximately 17.8/1.

Several non-limiting factors that can be analyzed to evaluate lipid production in cell culture include glucose consumption, nitrogen consumption, cell dry weight and total fatty acid production. In some embodiments, these parameters are measured in g $l^{-1}$. In certain embodiments, maximum production of fatty acids is achieved, in the presence of glucose, using a defined medium with a C/N (w/w) balance of approximately 17.8/1, containing approximately 240.0 g $l^{-1}$ glucose and approximately 13.45 g $l^{-1}$ $(NH_4)_2SO_4$. In certain embodiments, maximum fatty acid production under these conditions is approximately 25 g $l^{-1}$ and the yield of fatty acid production per gram of glucose consumed is approximately 0.1 (±0.02) g. In some embodiments, the maximum yield of total fatty acids per gram of glucose is approximately 0.15 (±0.03) g, achieved using conditions that include a defined medium with a C/N ratio of approximately 16/1, containing approximately 120.0 g $l^{-1}$ glucose and approximately 7.5 g $l^{-1}$ $(NH_4)_2SO_4$.

The growth conditions described herein, for example those presented in Example 1, including high cell density, high glucose concentration and an optimized C/N ratio, attain significant effects because they result in a significant increase in fatty acid production over previously tested growth conditions.

Aspects of the invention include multi-phase (fed batch) fermentation methods for production and harvesting of lipid bodies from cells such as oleaginous cells. As used herein, a "fed-batch" method refers to a process involving feeding a growth-limiting nutrient substrate to a culture. Example 4 describes bolus addition of glucose late in fermentation, conducted under optimal or high Nitrogen:Carbon (N:C) ratios in *Rhodococcus* species including *R. opacus* PD630 and *R. jostii* RHA1. As used herein, "bolus" addition refers to administration of a substance in a large dose. In some embodiments, bolus addition of glucose late in fermentation provides advantages such as increased lipid yields, increased purity, decreased retention time in the fermenter and ease of separation of lipid products. Example 4 demonstrates that *R. jostii* RHA1 had a more robust conversion of glucose after fed-batch feeding in both optimal and high N:C ratio fermentations, demonstrating that the biomass of *Rhodococcus* retains significant catalytic activity for the biosynthesis of storage lipids long after free ammonium has disappeared from the culture medium. In some embodiments, glucose is fed to a culture that is grown in optimal N:C ratio at approximately 72 hours.

It should be appreciated that the lipids produced by the methods described herein can be purified by many different means. Example 5 demonstrates that nitrogen limitation results in weakening of cell walls, leading to easier recovery of intracellular contents such as TAGs. Control of media and characterization of kinetics of storage lipid production and cell weakening allows for the production and harvesting of valuable stored lipids that can be used for the chemical conversion to Fatty Acid Methyl Esters (FAMEs), routinely used as biodiesel fuel.

Another aspect of the invention relates to the creation of recombinant microorganisms that can metabolize xylose and the use of such microorganisms in TAG production. As presented in Example 2, transformation of R. opacus PD630 cells with a library of DNA from Streptomyces padanus (S. padanus), a bacterial species that can metabolize xylose, led to the production of transformant strains of R. opacus PD630 that can metabolize xylose and produce high yields of TAGs in the presence of xylose-containing media.

The transformant strains of R. opacus PD630 described herein, that were isolated for their ability to metabolize xylose, include a region of DNA from the S. padanus library that contains the xylA (xylose isomerase) gene and the xylB (xylulose kinase) gene. Interestingly, the xylB gene is truncated and fused to a portion of a gene encoding for a predicted cellulose binding protein (CBP), likely due to a recombination event that occurred between these genes in the S. padanus library. The S. padanus gene encoding for the predicted cellulose binding protein is herein referred to as the CBP gene. Thus this recombination event led to the production of a novel gene that comprises a portion of the xylB gene and a portion of the CBP gene.

It should be appreciated that the xylA, xylB and CBP genes, or portions thereof, expressed in a cell, such as an R. opacus PD630 cell, can be obtained from a variety of sources. In the Examples section included herein, these genes are obtained from S. padanus MITKK-103, deposited with accession number NRRL30828. In some embodiments, xylA and/or xylB is obtained from S. coelicolor or S. avermitilis. In certain embodiments, xylA is obtained from S. coelicolor and xylB is obtained from S. avermitilis. As one of ordinary skill in the art would be aware, homologous genes could be obtained from other species and could be identified by homology searches, for example through a protein BLAST search, available at the NCBI interne site (www.ncbi.nlm.nih.gov). Additionally, as one of ordinary skill in the art would be aware, any suitable functional screen or assay could be used to identify functional homologs of these genes, or to identify other distinct genes that can confer the ability of a cell to grow on xylose. A xylA, xylB or CBP gene, or portions thereof can be PCR amplified from DNA from any source which contains the given gene or portions thereof. In some embodiments, one or more of the genes or portions thereof is synthetic. Any means of obtaining xylA, xylB or CBP or portions thereof is compatible with the instant invention.

The invention encompasses any cell, such as a Rhodococcus cell that recombinantly expresses one or more genes that permit growth on xylose as a carbon source, and uses thereof In some embodiments, the one or more genes that permit growth on xylose as a carbon source include xylA and/or xylB or portions thereof In some embodiments, the Rhodococcus cell that recombinantly expresses xylA and/or xylB or portions thereof is an R. opacus cell. In some embodiments the R. opacus cell that recombinantly expresses xylA and/or xylB or portions thereof is an R. opacus PD630 cell.

The invention also encompasses any type of cell that recombinantly expresses xylA and a gene fusion comprising a xylB gene or a portion thereof fused to a CBP gene or a portion thereof The cell can be prokaryotic or eukaryotic. In some embodiments the cell is a bacterial cell such as a Rhodococcus cell. In certain embodiments the cell is an R. opacus cell such as an R. opacus PD630 cell. In other embodiments the cell is a fungal cell (including yeast cells) such as an S. cerevisiae cell. In other embodiments the cell is a mammalian cell or a plant cell. It should be appreciated that some cells compatible with the invention may express an endogenous copy of one or more of the genes. In some embodiments a cell may express an endogenous copy of one or more of the genes as well as a recombinant copy of one or more of the genes.

Parameters discussed above related to growth conditions of bacteria for TAG production are also applicable for growth of recombinant R. opacus PD630 cells on xylose-containing media. In some embodiments cultures are maintained with an agitation speed between 300 and 1200 rpm, an oxygen content of above 80% with pure oxygen, a pH of approximately 6.9 and a temperature of approximately 30° C. The concentration of xylose can range from 30 to 200 g l$^{-1}$. For example, the xylose concentration can be approximately 30, 40, 50, 60, 70, 80, 90, 100, 110, 120, 130, 140, 150, 160, 170, 180, 190, or 200 g l$^{-1}$, including any intermediate value. In certain embodiments, the xylose concentration is approximately 180 g l$^{-1}$. In other embodiments, the xylose concentration is approximately 150 g l$^{-1}$. In other embodiments, the xylose concentration is approximately 120 g l$^{-1}$. In some embodiments, recombinant R. opacus PD630 cells that can metabolize xylose are grown on mixed media containing both xylose and glucose. In certain embodiments, the concentration of xylose and glucose is each approximately 60 g l$^{-1}$. In some embodiments, the C/N ratio of the xylose-containing media is approximately 16.9/1.

Significantly, as demonstrated in the Examples section, growth of the metabolically engineered R. opacus PD630 strains described herein in batch-culture, including approximately 12% xylose, can reach a cell density of approximately 26.9 g l$^{-1}$ CDW with a fatty acid content of approximately 43% of the CDW, accounting for approximately 11.7 g of fatty acids per liter after approximately 124 h of cultivation. The difficulty in achieving such an oleaginous organism that can produce a high yield of TAGs when grown in xylose-containing media is demonstrated by the fact that such an organism has never been identified as naturally occurring and has never successfully been engineered before.

Another aspect of the invention relates to the creation of recombinant microorganisms that can metabolize glycerol and the use of such microorganisms in TAG production. As presented in Example 3, transformation of R. opacus PD630 cells with a plasmid containing a genome fragment from Rhodococcus erythropolis AN12 (R. erythropolis AN12) allowed the transformed R. opacus PD630 cells to grow in the presence of glycerol as a sole carbon source and transform and store some of the glycerol as fatty acids. The plasmid contained two genes: glycerol kinase (glpK) and glycerol-3-phosphate dehydrogenase (g3pdh).

It should be appreciated that the glpK and g3pdh genes, or portions thereof, expressed in R. opacus PD630 can be obtained from a variety of sources. In the Examples section included herein, these genes are from R. erythropolis AN12. As one of ordinary skill in the art would be aware, homologous genes could be obtained from other species and could be identified by homology searches, for example through a protein BLAST search, available at the NCBI internet site (www.ncbi.nlm.nih.gov). Additionally, as one of ordinary skill in the art would be aware, any suitable functional screen or assay could be used to identify functional homologs of these genes, or to identify other distinct genes that can confer the ability of a cell to grow on glycerol. A glpK and/or g3pdh gene, or portions thereof can be PCR amplified from DNA from any source of DNA which contains the given gene or portions thereof. In some embodiments, one or more of the genes or portions thereof is synthetic. Any means of obtaining glpK or g3pdh or portions thereof is compatible with the instant invention.

The invention encompasses any type of cell, such as an oleaginous cell, that recombinantly expresses glpK and/or g3pdh or portions thereof. In some embodiments the cell is a bacterial cell such as a *Rhodococcus* cell. In certain embodiments the cell is an *R. opacus* cell such as an *R. opacus* PD630 cell. In other embodiments the cell is a fungal cell (including yeast) such as an *S. cerevisiae* cell. In other embodiments, it is a plant cell or a mammalian cell. It should be appreciated that some cells compatible with the invention may express an endogenous copy of one or more of the genes. In some embodiments a cell may express an endogenous copy of one or more of the genes as well as a recombinant copy of one or more of the genes. In some embodiments, one or both of the genes encoding glpK or g3pdh or portions thereof is expressed in a recombinant expression vector. Parameters discussed above related to growth conditions of bacteria for TAG production are also applicable for growth of recombinant *R. opacus* PD630 cells on glycerol-containing media.

According to aspects of the invention, high titers of TAGs are produced through culturing cells such as oleaginous microorganisms. As used herein "high titer" refers to a titer in the grams per liter (g $L^{-1}$) scale. The titer produced for a given TAG will be influenced by multiple factors including choice of media. In some embodiments the titer for production of total fatty acids is at least 1 g $L^{-1}$. For example the titer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more than 40 g $L^{-1}$, including any intermediate values.

The liquid cultures used to grow cells associated with the invention can be housed in any of the culture vessels known and used in the art. In some embodiments, large scale production in an aerated reaction vessel such as a stirred tank reactor can be used to produce large quantities of the TAGs associated with the invention. It should be appreciated that any means of purification of TAGs from cell culture media is compatible with the invention.

Aspects of the invention include strategies to optimize TAG production from a cell. Optimized production of a TAG refers to producing a higher amount of a TAG following pursuit of an optimization strategy than would be achieved in the absence of such a strategy. In embodiments that employ recombinant cells, one strategy for optimization is to increase expression levels of the recombinant genes through selection of appropriate promoters and ribosome binding sites. In some embodiments this may include the selection of high-copy number plasmids, or low or medium-copy number plasmids. The step of transcription termination can also be targeted for regulation of gene expression, through the introduction or elimination of structures such as stem-loops.

In some embodiments it may be advantageous to use a cell that has been optimized for production of one or more TAGs. For example it may be optimal to mutate the cell prior to or after introduction of recombinant gene products. In some embodiments, screening for mutations that lead to enhanced production of one or more TAGs may be conducted through a random mutagenesis screen, or through screening of known mutations. In some embodiments shotgun cloning of genomic fragments could be used to identify genomic regions that lead to an increase in production of one or more TAGs, through screening cells or organisms that have these fragments for increased production of one or more TAGs. In some cases one or more mutations may be combined in the same cell or organism.

Example 6 presents the results of a high-throughput genetic screen utilizing transposon mutagenesis to identify factors involved in optimization of TAG biosynthesis and accumulation in *R. opacus* PD630. As a result of this screen, a gene encoding for an aldehyde dehydrogenase protein was identified, the overexpression of which leads to an increase in TAG production. As used herein, an aldehyde dehydrogenase protein refers to an enzyme that catalyzes the oxidation (dehydrogenation) of aldehydes. Further characterization of this gene and its protein product demonstrated that the protein is capable of oxidizing glyceraldehyde-3 phosphate (G3P) to 3-phosphoglycerate (3-PG) while reducing NAD(P)$^+$ to NAD (P)H, suggesting it is a homolog of the non-phosphorylating glyceraldehyde-3 phosphate dehydrogenase (G3PDH) GapN.

The non-phosphorylative glyceraldehyde 3-phosphate dehydrogenase (GapN) family of enzymes, a sub-family of the larger aldehyde dehydrogenase family, was originally associated with green eukaryotes, plants and algae primarily, wherein it catalyzes the irreversible oxidation of glyceradehyde-3-phosphate (G3P) to 3-phosphoglycerate while concomitantly reducing NAD(P)$^+$ to NAD(P)H. While this family of enzymes was initially associated strictly with green eukaryotes, sequence and functional homologs have been identified in a number of eubacteria and archae. While not wishing to be bound by any theory, results presented in Example 6 suggest that the GapN enzyme, identified herein through genetic screening, is involved in the generation of NAD(P)H, utilized in the biosynthesis of fatty acids. These data also suggest that activation (or derepression) of the GapN protein may constitute an early switch from a vegetative lifestyle to a storage one.

Aspects of the invention relate to producing TAGs in cells that overexpress an aldehyde dehydrogenase protein. In some embodiments, the aldehyde dehydrogenase protein is a non-phosphorylative glyceraldehyde 3-phosphate dehydrogenase such as a GapN protein. A cell that overexpresses a GapN protein may endogenously express a gene encoding for a GapN protein and/or recombinantly express a gene encoding for a GapN protein. Expression of an endogenous gene can be upregulated using techniques known to one of ordinary skill in the art such as through increasing the transcription and/or translation of the gene and/or reducing the degradation rate of expression products of the gene, such as RNA or protein.

Recombinant expression of a GapN protein in a cell can involve expressing the gene encoding for the GapN protein on a plasmid and/or integrating the gene into the chromosomal DNA of the cell. In some embodiments, multiple copies of the gene encoding for a GapN protein are expressed recombinantly in the same cell. It should be appreciated that in expressing a GapN protein, or upregulating expression of a GapN protein, a full length protein or a biologically active portion thereof may be expressed. A biologically active portion of a GapN protein can be any portion of a GapN protein that achieves a biological function. For example, a biologically active portion of a GapN protein can be a portion of the protein that is capable of oxidizing glyceraldehyde-3 phosphate (G3P) to 3-phosphoglycerate (3-PG) while reducing NAD(P)$^+$ to NAD(P)H. In some embodiments, a biologically active form of a GapN protein may be a form that when expressed in a cell leads to increased TAG production in the cell.

It should be appreciated that the gene encoding for the GapN protein, or a biologically active portion thereof, can be obtained from a variety of sources. In the Examples section included herein, the gene encoding for the GapN protein is from *R. opacus* PD630, and is referred to as tadD. The *R. opacus* PD630 protein encoded by the tadD gene is referred to interchangeably herein as TadD or GapN since it is homologous to the GapN family of proteins. The protein sequence for *R. opacus* PD630 TadD/GapN is provided in Example 6. As one of ordinary skill in the art would be aware, homologous genes could be obtained from other species and could be identified by homology searches, for example through a protein BLAST search, available at the NCBI interne site (www.ncbi.nlm.nih.gov). Additionally, as one of ordinary skill in the art would be aware, any suitable functional screen or assay could be used to identify functional homologs of this genes. A gene encoding for GapN, or a biologically active portion thereof, can be PCR amplified from DNA from any source of DNA which contains the given gene or portion thereof. In some embodiments, the gene is synthetic. Any means of obtaining a gene encoding for a GapN protein or biologically active portion thereof is compatible with the instant invention.

The invention encompasses any type of cell, such as an oleaginous cell, that overexpresses an aldehyde dehydrogenase protein. In some embodiments, the aldehyde dehydrogenase protein is a non-phosphorylative glyceraldehyde 3-phosphate dehydrogenase such as a GapN protein. In some embodiments the cell is a bacterial cell such as a *Rhodococcus* cell. In certain embodiments the cell is an *R. opacus* cell such as an *R. opacus* PD630 cell. In other embodiments the cell is a fungal cell (including yeast) such as an *S. cerevisiae* cell. In other embodiments, it is a plant cell or a mammalian cell. Parameters discussed above related to growth conditions of bacteria for TAG production are applicable for growth of cells that overexpress a GapN protein.

Figure 79:
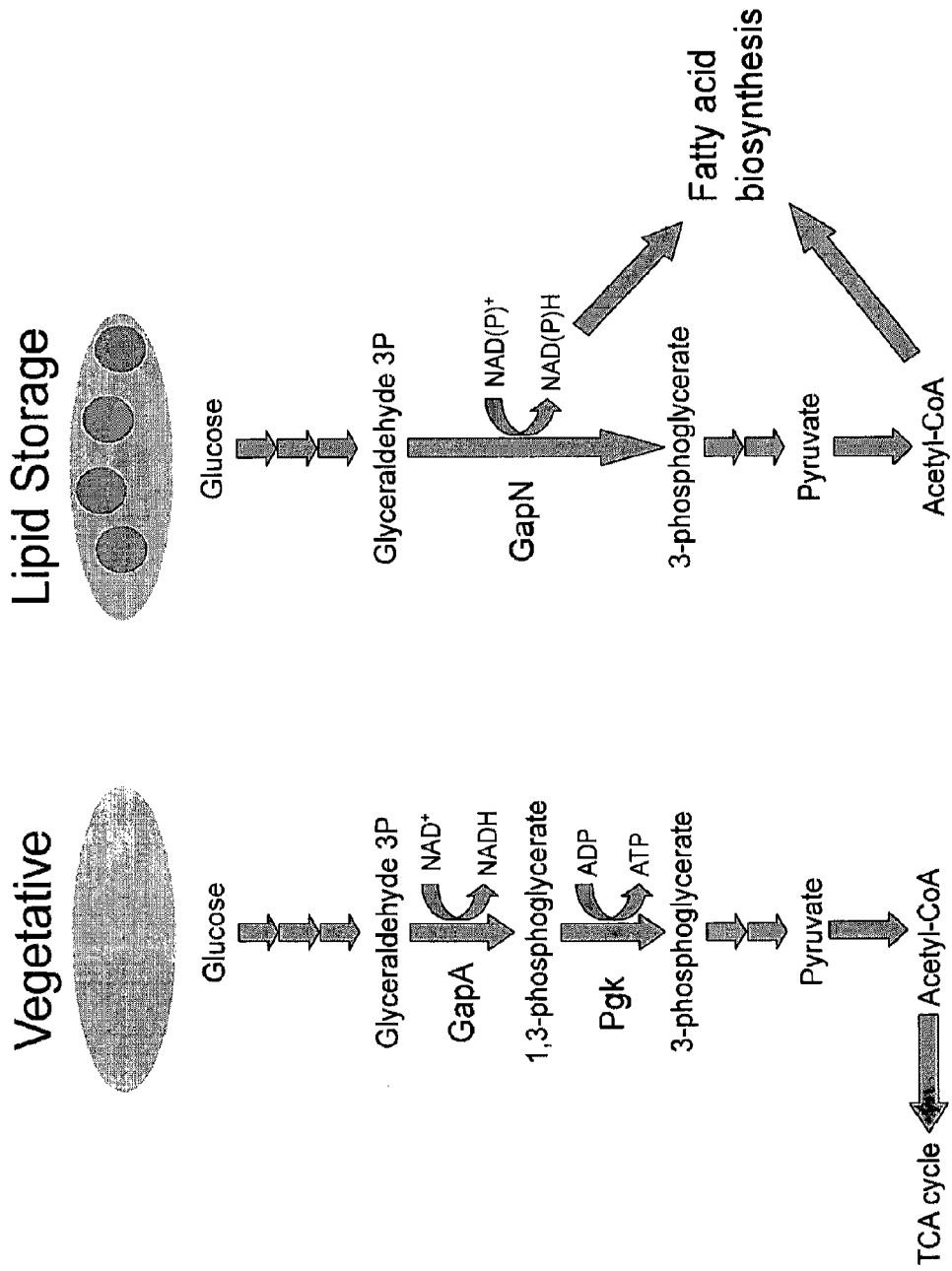
FIG. 79 presents a schematic of a proposed model for the role of TadD in TAG metabolism in *R. opacus* PD630. Under high nitrogen conditions (depicted on the left) glyceraldehyde 3-phosphate is metabolized to 3-phosphoglycerate by the canonical glyceraldehyde 3-phosphate dehydrogenase GapA and the phosphoglycerate kinase Pgk yielding NADH and ATP. Without wishing to be bound by any theory, under nitrogen limiting conditions, G3P may be metabolized to 3-phosphoglycerate by the non-phosphorylating, NAD(P)+-dependent glyceraldehyde 3-phosphate dehydrogenase TadD yielding NAD(P)H, a key redox molecule in fatty acid metabolism.

In contrast to GapN proteins, GapA proteins are canonical phosphorylative glyceraldehyde 3-phosphate dehydrogenase proteins that oxidize G3P to 1,3-bisphosphoglycerate (1,3BPG) while reducing $NAD^+$ to NADH. 1,3-BPG is subsequently dephosphorylated to 3-phosphoglycerate (3-PG) by the enzyme phosphoglycerate kinase yielding one molecule of adenosine triphosphate (ATP) (FIG. 79). Example 6 demonstrates that overexpression of a GapA protein results in a dramatic decrease in total fatty acid production in cells. Thus methods associated with the invention, for producing TAGs in cells, can involve reducing expression of a GapA protein. Reduction in protein level of a GapA protein can be achieved through any means known to one of ordinary skill in the art, such as by deleting the gene or mutating the gene. In some embodiments, a mutation in the gene can be a substitution or deletion of one or more nucleotides in the gene or a truncation of the gene and/or protein. Reduction in the protein level of a GapA protein can also be achieved indirectly by affecting the transcription and/or translation and/or degradation rate of expression products of the gene, such as RNA or protein. In some embodiments, a cell that produces TAGs overexpresses a GapN protein and has reduced expression of a GapA protein, or lacks expression of a GapA protein.

Example 7 presents additional novel genes uncovered in a genetic screen to identify TAG accumulation defective (Tad) mutants in *R. opacus* PD630. One of the genes identified through this screen was tadA. Although mutations in tadA do not affect growth rate, glucose, nitrogen consumption or pH, they have a striking effect on lipid body formation and accumulation in a cell. Significantly, overexpression of tadA leads to coalescence of lipid bodies. Further characterization of this gene and its protein product demonstrated that the protein is enriched in lipid body fractions and mediates yeast agglutination. The TadA protein shows similarity to the heparin-binding hemagglutinin family of proteins, particularly at the C-terminus, and thus is predicted to be a heparin-binding protein.

The gene immediately upstream of tadA in the *R. opacus* PD630 genome, named herein tadR, is also demonstrated in Example 7 to be involved in regulation of TAG production, at least in part through regulation of tadA expression. The tadR gene encodes for a predicted DNA binding protein, containing an XRE HTH DNA binding domain. tadR induces TAG accumulation independently of tadA, suggesting that it has other downstream targets involved in TAG accumulation other than tadA.

Figure 92:
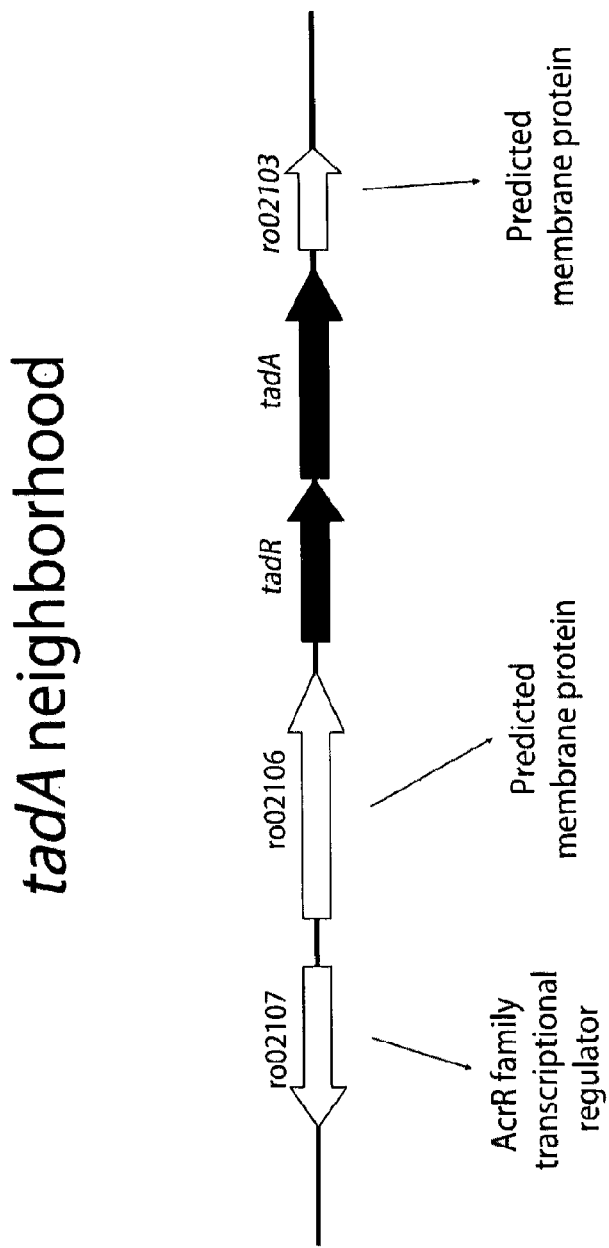
FIG. 92 presents a schematic depicting the operon containing tadR and tadA.
Figure 93:
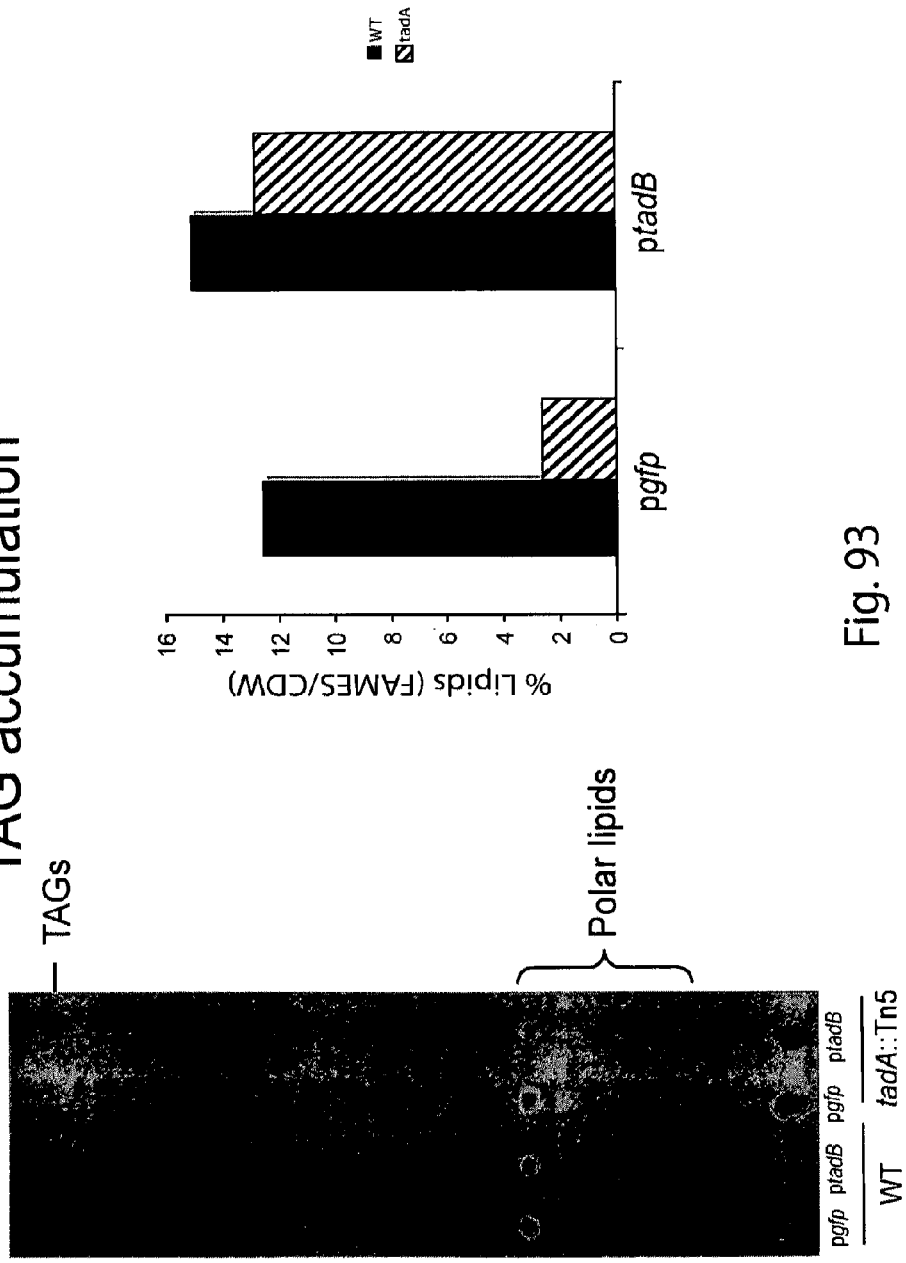
FIG. 93 demonstrates increased TAG accumulation in tadB mutants.

Other genes within the *R. opacus* PD630 operon containing tadA are shown in FIG. 92. Immediately downstream from tadA is a gene designated as ro02103, named herein tadB. This gene encodes for a predicted membrane protein. Significantly, when overexpressed, the tadB gene was also found to produce increased TAG accumulation (FIG. 93).

Aspects of the invention relate to producing TAGs in cells that overexpress one or more of tadR, tadA and tadB, and/or one or more of the other genes within the same operon as these genes (FIG. 92). In some embodiments, a cell overexpresses tadR, alone or in combination with overexpression of tadA and/or tadB. In other embodiments, a cell overexpresses tadA alone or in combination with overexpression of tadR and/or tadB. In other embodiments a cell overexpresses tadB alone or in combination with overexpression of tadR and/or tadA. In some embodiments a cell overexpresses the whole operon containing the tadA gene. A cell that overexpresses one or more of tadR, tadA and tadB may endogenously express one or more of these genes and/or recombinantly express one or more of these genes. Expression of an endogenous gene can be upregulated using techniques known to one of ordinary skill in the art such as through increasing the transcription and/or translation of the gene and/or reducing the degradation rate of expression products of the gene, such as RNA or protein.

Recombinant expression of one or more of tadR, tadA and tadB in a cell can involve expressing the gene encoding for tadR, tadA and/or tadB on a plasmid and/or integrating the gene for tadR, tadA and/or tadB into the chromosomal DNA of the cell. In some embodiments, multiple copies of tadR, tadA and/or tadB are expressed recombinantly in the same cell. In some embodiments, the operon comprising these genes is recombinantly expressed in a cell. It should be appreciated that in expressing tadR, tadA and/or tadB, or upregulating expression of tadR, tadA and/or tadB, a tadR, tadA and/or tadB gene encoding a full length protein or a biologically active portion thereof may be expressed. A biologically active portion of a Tad protein, such as TadA, TadR or TadB, can be any portion of a Tad protein that achieves a biological function. For example, a biologically active portion of a Tad protein can be a portion of the protein that when expressed in a cell leads to increased TAG production in the cell.

It should be appreciated that the tadR, tadA and/or tadB gene, or portion thereof, can be obtained from a variety of sources. In the Examples section included herein, the tadR, tadA and tadB genes are from *R. opacus* PD630. As one of ordinary skill in the art would be aware, homologous genes could be obtained from other species and could be identified by homology searches, for example through a protein BLAST search, available at the NCBI internet site (www.ncbi.nlm.nih.gov). Additionally, as one of ordinary skill in the art would be aware, any suitable functional screen or assay could be used to identify functional homologs of this genes. A tadR, tadA and tadB gene, or portion thereof, or the operon containing these genes can be PCR amplified from DNA from any source of DNA which contains the given gene or portion thereof. In some embodiments, the gene or operon is synthetic. Any means of obtaining a tadR, tadA or tadB gene or portion thereof, or operon containing these genes, is compatible with the instant invention.

The invention encompasses any type of cell, such as an oleaginous cell, that overexpresses one or more of tadR, tadA and tadB. In some embodiments, the cell is a bacterial cell such as a *Rhodococcus* cell. In certain embodiments, the cell is an *R. opacus* cell such as an *R. opacus* PD630 cell. In other embodiments, the cell is a fungal cell (including yeast) such as an *S. cerevisiae* cell. In other embodiments, it is a plant cell or a mammalian cell. Parameters discussed above related to growth conditions of bacteria for TAG production are applicable for growth of cells that overexpress tadR, tadA and/or tadB.

Optimization of protein expression may also require in some embodiments that a gene be modified before being introduced into a cell such as through codon optimization for expression in a bacterial cell. Codon usages for a variety of organisms can be accessed in the Codon Usage Database (http://www.kazusa.or.jp/codon/).

Protein engineering can also be used to optimize expression or activity of a protein. In certain embodiments a protein engineering approach could include determining the three dimensional (3D) structure of a protein such as an enzyme or constructing a 3D homology model for the protein based on the structure of a related protein. Based on 3D models, mutations in a protein can be constructed and incorporated into a cell or organism, which could then be screened for an increased production of one or more TAGs. In some embodiments TAG production in a cell could be increased through manipulation of proteins that act in the same pathway as the proteins associated with the invention. For example in some embodiments it may be advantageous to increase expression of a protein or other factor that acts upstream of a target protein such as a protein encoded for by one of the genes that is recombinantly expressed in cells associated with the invention. This could be achieved by over-expressing the upstream factor using any standard method.

Aspects of the invention thus involve recombinant expression of genes discussed above, functional modifications and variants of the foregoing, as well as uses relating thereto. Homologs and alleles of the nucleic acids associated with the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/ 0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity to the sequences of nucleic acids. For example, in some embodiments, homologs and alleles will share at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99% nucleotide identity. In general, homologs and alleles typically will share at least 80% amino acid identity to the sequences of polypeptides. For example, in some embodiments, homologs and alleles will share at least 80%, 81%, 82%, 83%, 84%, 85%, 86%, 87%, 88%, 89%, 90%, 91%, 92%, 93%, 94%, 95%, 96%, 97%, 98%, 99% or more than 99% amino acid identity.

The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also encompasses isolated polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. In some embodiments, 1, 2, 3, 4, 5, 6, 7, 8, 9, 10, 11, 12, 13, 14, 15, 16, 17, 18, 19, 20 or more than 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

A polypeptide or fragment thereof described herein can be synthetic. As used herein, the term "synthetic" means artificially prepared. A synthetic polypeptide is a polypeptide that is synthesized and is not a naturally produced polypeptide molecule (e.g., not produced in an animal or organism). It will be understood that the sequence of a natural polypeptide (e.g., an endogenous polypeptide) may be identical to the sequence of a synthetic polypeptide, but the latter will have been prepared using at least one synthetic step.

In some embodiments, one or more of the genes associated with the invention (for example, xylA, xylB, fusions of xylB and CBP, glpK, g3pdh, tadD, tadA, tadB and/or tadR), or portions thereof, is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that comprises any of the genes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in some embodiments include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. For example, heterologous expression of xylA and a fusion product comprising a portion of xylB and a portion of CBP for production of TAGs is demonstrated in the Examples section using the pXsp plasmid. The novel method for producing TAGs can also be expressed in other cells including bacterial cells, archaeal cells, and fungi cells (including yeast cells).

One or more nucleic acid molecules that encode genes associated with the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing one or more nucleic acid molecules associated with the claimed invention also may be accomplished by integrating the one or more nucleic acid molecules into the genome.

Further aspects of the invention relate to methods and compositions for preparing antibodies that specifically bind to polypeptides or fragments thereof described herein. As used herein, the term "antibody" refers to a glycoprotein that may include at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

Isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g., IgM or IgG1) that is encoded by heavy chain constant region genes. Antibodies of the invention can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

Antibodies of the present invention can be polyclonal, monoclonal, or a mixture of polyclonal and monoclonal antibodies. Antibodies of the invention can be produced by methods disclosed herein or by a variety of techniques known in the art. Polyclonal and monoclonal antibodies may be prepared using techniques that are known in the art. The term "monoclonal antibody," as used herein, refers to a preparation of antibody molecules of single molecular composition. A monoclonal antibody displays a single binding specificity and affinity for a particular epitope. The term "polyclonal antibody" refers to a preparation of antibody molecules that comprises a mixture of antibodies active that specifically bind a specific antigen.

A process of monoclonal antibody production may include obtaining immune somatic cells with the potential for producing antibody, in particular B lymphocytes, which have been previously immunized with the antigen of interest either in vivo or in vitro and that are suitable for fusion with a B-cell myeloma line. Mammalian lymphocytes typically are immunized by in vivo immunization of the animal (e.g., a mouse or other mammal) with the desired protein or polypeptide, or a fragment thereof, in the present invention. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rat, rabbit, hamster, sheep, goats, camels, llamas, frogs, etc. may also be used as hosts for preparing antibody-producing cells. (See; Goding in Monoclonal Antibodies: Principles and Practice, 2d ed., pp. 60-61, Orlando, Fla., Academic Press, 1986). Mouse strains that have human immunoglobulin genes inserted in the genome (and that cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with B cell myeloma cells or transformed cells, which are capable of replicating indefinitely in cell culture, thereby producing an immortal, immunoglobulin-secreting cell line. The B cell myeloma cells or transformed cells may be mouse or other suitable mammalian cells. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include, but are not limited to Ag8, P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984). Those of ordinary skill in the art will be aware of numerous routine methods to produce monoclonal antibodies.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, Eur. J. Immunol. 6:511 (1976), which is hereby incorporated by reference).

Methods for raising polyclonal antibodies are well known to those of ordinary skill in the art. As a non-limiting example, polyclonal antibodies may be raised by administering a polypeptide subcutaneously to New Zealand white rabbits which have first been bled to obtain pre-immune serum. The polypeptide can be inoculated with (e.g., injected at) a total volume of 100 µl per site at six different sites, typically with one or more adjuvants. The rabbits are then bled two weeks after the first injection and periodically boosted with the same antigen three times every six weeks. A sample of serum is collected 10 days after each boost. Polyclonal antibodies are recovered from the serum, preferably by affinity chromatography using the polypeptide to capture the antibody. This and other procedures for raising polyclonal antibodies are disclosed in E. Harlow, et al., editors, Antibodies: A Laboratory Manual (1988), which is hereby incorporated by reference. Those of ordinary skill in the art will be aware of numerous routine methods to produce polyclonal antibodies.

In other embodiments, antibodies may be recombinant antibodies. The term "recombinant antibody", as used herein, is intended to include antibodies that are prepared, expressed, created or isolated by recombinant means, such as antibodies isolated from an animal (e.g., a mouse, rat, rabbit, etc.) that is transgenic for another species' immunoglobulin genes, genetically engineered antibodies, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules encoding antibodies and vectors comprising the nucleic acid molecules as described herein. The vectors provided can be used to transform or transfect host cells for producing specific antibodies. In some embodiments, the vectors can include an isolated nucleic acid molecule encoding a heavy chain and/or a light chain of an antibody of the invention encoded by a nucleic acid molecule. In a further embodiment, plasmids are given which produce the antibodies or antigen-binding fragments described herein.

Antibodies or antigen-binding fragments of the invention are, preferably, isolated. "Isolated", as used herein with respect to antibodies and antigen-binding fragments thereof, is intended to refer to an antibody (or antigen-binding fragment thereof) that is substantially free of other antibodies (or antigen-binding fragments) having different antigenic specificities. An isolated antibody that specifically binds to an epitope, isoform or variant of a polypeptide described herein may, however, have cross-reactivity to other related antigens, e.g., a mutant form of the polypeptide, or a polypeptide from other species (e.g., a homolog). Moreover, an isolated antibody (or antigen-binding fragment thereof) may be substantially free of other cellular material and/or chemicals.

Antibodies of the invention include, but are not limited to antibodies that specifically bind to XylA, XylB, a fusion between XylB and CBP, GlpK, G3pdh, TadD/GapN, TadA, TadB and/or TadR, or portions thereof. As used herein, "specific binding" refers to antibody binding to a predetermined antigen with a preference that enables the antibody to be used to distinguish the antigen from others to an extent that permits the diagnostic and other assays described herein. The antibody may bind with an affinity that is at least two-fold greater than its affinity for binding to antigens other than the predetermined antigen. In some embodiments, an antibody specifically binds to a polypeptide with sub-nanomolar affinity. The binding affinities can be about $1\times10^{-6}$, $1\times10^{-7}$, $1\times10^{-8}$, $1\times10^{-9}$M or less, preferably about $1\times10^{-10}$ M or less, more preferably $1\times10^{-11}$M or less. In certain embodiments the binding affinity is less than about $5\times10^{-10}$ M.

In some aspects of the invention, an antibody or antigen-binding fragment thereof binds to a conformational epitope within the polypeptide. To determine if the selected antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. In some embodiments antibodies that bind to native protein but not denatured protein are those antibodies that bind conformational epitopes, and are preferred antibodies.

In some embodiments of the invention, antibodies competitively inhibit the specific binding of a second antibody to its target epitope. To determine competitive inhibition, a variety of assays known to one of ordinary skill in the art can be employed. These methods may include cell-based methods employing flow cytometry or solid phase binding analysis.

Other assays that evaluate the ability of antibodies to cross-compete in solid phase or in solution phase, also can be used.

Certain antibodies competitively inhibit the specific binding of a second antibody to its target epitope by at least about 10%, 20%, 30%, 40%, 50%, 60%, 70%, 80%, 90%, 95%, 99% or 100%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies of the invention may include antibodies that specifically bind to an epitope on a polypeptide defined by a second antibody. To determine the epitope, one can use standard epitope mapping methods known in the art. For example, fragments (polypeptides) of an antigen that bind the second antibody can be used to determine whether a candidate antibody binds the same epitope. For linear epitopes, overlapping polypeptides of a defined length (e.g., 5, 6, 7, 8 or more amino acids) may be synthesized. The polypeptides preferably are offset by 1 amino acid, such that a series of polypeptides covering every 4, 5, 6, 7, or 8 amino acid fragment (respectively) of a polypeptide sequence are prepared. Fewer polypeptides can be prepared by using larger offsets, e.g., 2 or 3 amino acids. In addition, longer polypeptides (e.g., 9-, 10- or 11-mers) can be synthesized. Binding of polypeptides to antibodies can be determined using standard methodologies including surface plasmon resonance (BIACORE) and ELISA assays. Other methods that use mass spectrometry to define conformational epitopes have been described and can be used (see, e.g., Baerga-Ortiz et al., Protein Science 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Polypeptide Combinatorial Libraries") of Current Protocols in Immunology, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment thereof of the invention can be linked to a detectable label. A detectable label of the invention may be attached to antibodies or antigen-binding fragments thereof of the invention by standard protocols known in the art. In some embodiments, the detectable labels may be covalently attached to an antibody or antigen-binding fragment thereof of the invention. The covalent binding can be achieved either by direct condensation of existing side chains or by the incorporation of external bridging moieties. Many bivalent or polyvalent agents are useful in coupling protein molecules to other proteins, polypeptides or amine functions, etc. For example, the literature is replete with coupling agents such as carbodiimides, diisocyanates, glutaraldehyde, and diazobenzenes. This list is not intended to be exhaustive of the various coupling agents known in the art but, rather, is exemplary of the more common coupling agents. Additional descriptions of detectable labels useful in the invention are provided elsewhere herein.

EXAMPLES

Example 1

Cultivation of Rhodococcus opacus PD630 with High Glucose Concentrations in Batch-Culture for Biodiesel Production Introduction Biodiesel, monoalkyl esters of long-chain fatty acids with short-chain alcohols derived from triacylglycerols (TAGs), is in the spotlight as a clean burning alternative fuel made from a variety of biomass sources because of the uncontrollable oil prices and the depletion of fossil fuel resources (Canakci and Sanli 2008; Du et al. 2008; Vasudevan and Briggs 2008).

Recently, there has been considerable interests on the production of microbial oils by oleaginous microorganisms, such as yeast, fungi, bacteria and microalgae (Li et al. 2008; Alvarez and Steinbüchel 2002; Hu et al. 2008). Bacteria belonging to the actinomycetes group, such as Streptomyces, Nocardia, Rhodococcus, Mycobacterium, were found to be able to accumulate TAGs in cells under favorable conditions (Alvarez and Steinbüchel 2002) (FIG. 1). The genus Rhodococcus has an extraordinary capacity for metabolizing recalcitrant organic compounds with environmental and biotechnological importance (Bell et al. 1998; Larkin et al. 2005). Steinbüchel et al. (Alvarez et al. 1996; Wältermann et al. 2000) demonstrated that Rhodococcus opacus DSMZ 44193 (PD630), grown under the right conditions on gluconate medium, is able to accumulate large amounts of triacylglycerols, up to 76% of the cell dry weight (CDW). It has been reported that R. opacus DSMZ 44193 grown in fed-batch conditions on a medium containing sugar beet molasses and sucrose as carbon sources, reached a cell density of 37.4 g CDW $l^{-1}$ with a fatty acids content of 51.9% of the CDW (Voss and Steinbüchel 2001). These findings suggest that R. opacus DSMZ 44193 can be cultivated on a cheap residual carbon source from agricultural crops for the production of a highly desirable biotechnology commodity such as biodiesel.

Recently, there has been a strong demand to accelerate the development of the so-called "Second Generation Biofuel Technologies" that can be produced sustainably to avoid the food-fuel conflict by using lignocellulosic biomass and waste or unutilized materials (Stein 2007; Tollefson 2008). Lignocellulosic biomass includes cellulose that is a glucose polymer. The purpose of this study was to screen for a high triacylglycerols producer, from bacteria belonging to the genera Rhodococcus, Streptomyces and Mycobacterium, capable of growing to high cell densities when cultivated on glucose as a single carbon source for biodiesel production. It was discovered herein that R. opacus DSMZ 44193 has the uncommon capability, not previously reported, to accumulate large amounts of triacylglycerols under the right growth conditions in batch-culture with very high concentrations of glucose. Here the fermentative production of triacylglycerols by R. opacus DSMZ 44193 on high glucose concentrations is described, as is the experimental design protocol used to achieve the cultural conditions necessary for both high cell density and TAGs accumulation. In particular, the importance of the carbon to nitrogen ratio of the medium composition in order to achieve high yields of triacylglycerols is demonstrated.

Materials and Methods

Strain and Media

Rhodococcus opacus DSMZ 44193 (PD630; Wältermann at al., 2000) used in this study was obtained from Deutsche Sammlung von Mikroorganismen und Zellkulturen GmnH (DSMZ, Germany). The culture media used were Luria-Bertani broth (LB) and a phosphate-buffered defined medium which contained per liter: 40 g glucose, 1.4 g $(NH_4)_2SO_4$, 1.0 g $MgSO_4.7H_2O$, 0.015 g $CaCl_2.2H_2O$, 1.0 ml trace element solution, 1.0 ml stock A so and 35.2 ml 1.0 M phosphate buffer. The trace element solution, stock A solution and phosphate buffer were the same as those described by Chartrain et al. (1998). Glucose, $MgSO_4.7H_2O$ and $CaCl_2.2H_2O$ were dissolved in deionized water and sterilized by autoclave then, stock A, trace elements and $(NH_4)_2SO_4$, were added to the cooled medium as filter sterilized stock solutions. Modifications of the defined medium for optimization of TAGs production are stated below in the text. The strain was routinely maintained on Luria-Bertani (LB) agar (2% w/v) medium at 4° C. and preserved in 20% (v/v) glycerol at −80° C.

Preparation of Seed Culture

A loopful of cells from a single colony grown on an LB agar plate at 30° C. for 3 days was used to inoculate 50 ml of defined medium in a 250-ml baffled flask. The culture was then incubated on a rotary shaker (250 rpm) at 30° C. for 2 days until a constant absorbance of approximately 10. The optical density was determined with a Spectronic 20 Genesys spectrophotometer (Spectronic Instruments Inc., Rochester, N.Y.) at 660 nm (OD660).

Culture Conditions

Flask experiments were carried out in triplicate using 500-ml baffled flasks containing 100 ml of defined medium incubated on a rotary shaker (250 rpm) at 30° C. Unless otherwise stated, cultures were inoculated with a seed culture to reach an initial $OD_{660}$ of about 0.03 ($7.5 \times 10^6$ cfu/ml). Fermentor experiments were performed with a Sixfors bioreactor system (Infors AG CH-4103, Bottmingen, Switzerland) at 30° C. Cultures were cultivated into 500 ml fermentor vessels containing 300 ml working volume of defined medium inoculated with a seed culture to a starting $OD_{660}$ of about 0.3. The pH value in the medium was controlled at 7.0±0.1 by addition of 2 M NaOH. Dissolved oxygen was measured with an Ingold polarographic probe and maintained at above 80% $O_2$ saturation by adjusting the agitation speed up to 1200 rpm and by automatically adjusting the mixture of air and pure oxygen flow via flow controllers while maintaining air gas flow at 0.1 vvm. To prevent foam formation, polypropylene glycol P2'000 (Fluka) was manually added to each vessel when needed.

Response Surface Methodology Experimental Design and Statistical Analysis

Figure 24:
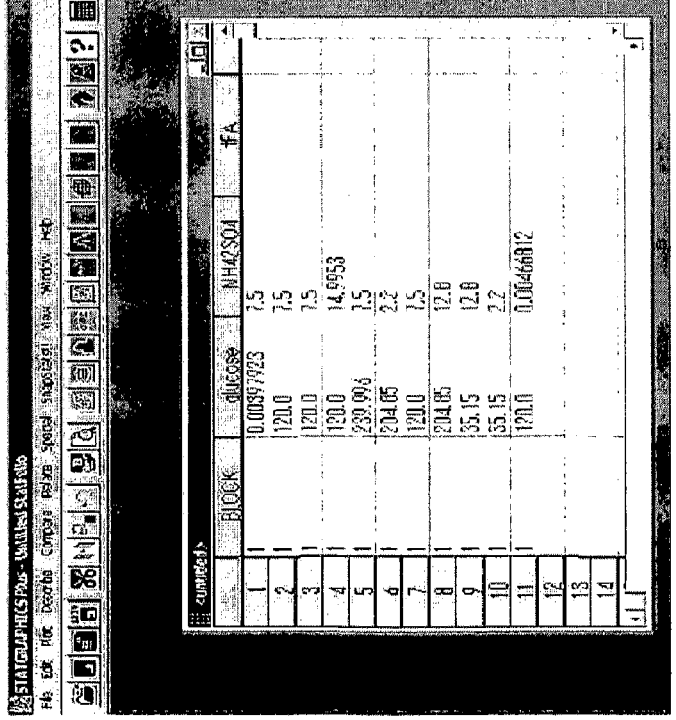
FIG. 24 is a schematic depicting the use of StatGraphics to optimize the carbon:nitrogen ratio of the production medium.

The crucial parameter of carbon/nitrogen ratio of the defined medium to obtain the maximum production of fatty acids was optimized by response surface methodology based on the Box-Wilson central composition design (CCD). The design matrix of the experimental conditions was subjected to regression analysis using software StatGraphics (StatPoint, Inc., USA) (FIG. 24). The design class chosen to perform the experiments was a response surface with eleven proofs and a triplicate central point. The range and concentrations of glucose and $(NH_4)_2SO_4$ levels of the variables investigated are shown in Table 1. The defined medium utilized was the same as described before.

Analytical Procedures

Cell growth was estimated by measuring the optical density or the cell dry weight (CDW). The CDW was determined after lyophilization of culture biomass obtained by centrifugation of 10 ml of culture broth at 5,000 rpm for 15 min and by washing the cell pellet twice in deionized water. The lyophilized cell pellet was also used to analyze the fatty acids concentration. The supernatants of culture broth samples separated by centrifugation were used for analyses of residual glucose and $(NH_4)_2SO_4$ after filtration through a pore-size filter. The residual glucose concentrations were measured by high-performance liquid chromatography (HPLC) (Agilent 1100 system) fitted with an Aminex HPX-87H column (300× 7.8 mm, BIO-RAD, USA) coupled to a refractive index (RI) detector. The column was eluted with 5 mM $H_2SO_4$ as mobile phase at 40° C. and a flow rate of 0.6 ml/min. Residual ammonia concentrations were determined by the Ammonia Assay kit (Sigma, St. Louis, Mo.) according to the manufacturer's instructions.

For the analysis of total lipids, fatty acids were converted to methyl esters by methanolysis followed by gas chromatography (GC) (Brandl et al. 1988; Wältermann et al. 2000). 10 mg of lyophilized cells was resuspended in 1 ml of methanol containing 15% (v/v) $H_2SO_4$ and 1 ml of chloroform. Methanolysis was carried out in a 100° C. heating block for 2.5 h. After cooling to room temperature, 0.5 ml of deionized water was added to the solution and then vortexed for 1 min. The organic phase containing fatty acid methyl esters (FAMEs) was analyzed by using an Agilent 6850 series II GC system equipped with an Agilent DB-Wax column (30 m×0.32 mm, 0.5 µm thick film) with hydrogen as carrier gas. A 2 µl portion of the organic phase was injected with a 30:1 split ratio using the autosampler. The inlet was maintained at 250° C. The oven was held at 80° C. for 5 min, heated to 220° C. at 20° C./min, and then held at 220° C. for 5 min. Peak detection was performed by a flame ionization detector, which was maintained at 300° C. The fatty acids were identified and quantified by comparisons to standard fatty acid methyl esters (Sigma, St. Louis, Mo.). Fatty acids content was defined as the percentage of the ratio of fatty acids to dry cell mass weight (% DCM).

Chemicals

All chemicals used were reagent-grade and obtained from Sigma-Aldrich (St. Louis, Mo.), unless otherwise noted. All media components were purchased from BD Diagnostic Systems (Difco, Sparks, Md.).

Results

Genomic Analysis of R. opacus PD630

Figure 3:
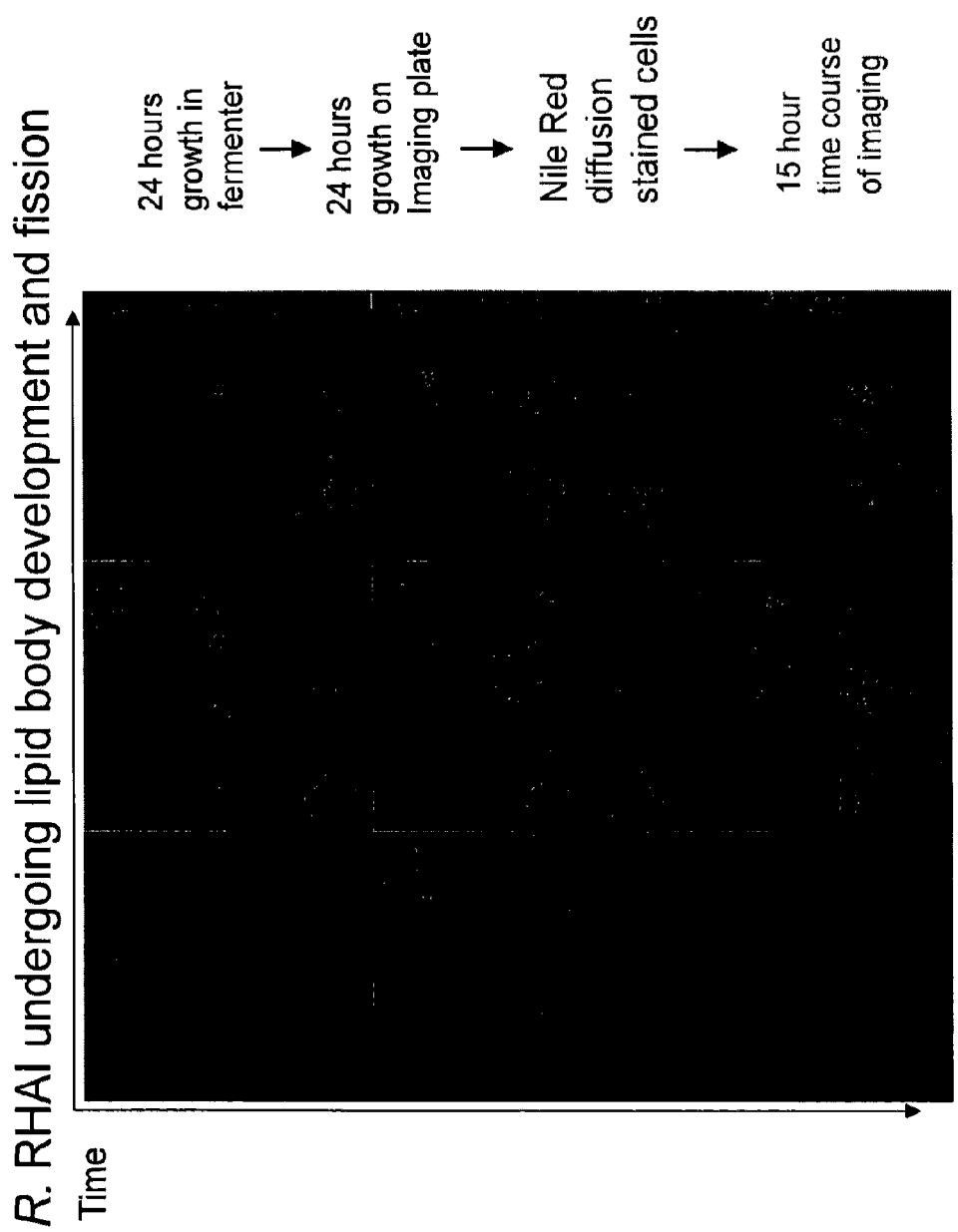
FIG. 3 presents an image of Nile Red diffusion stained cells showing *R. jostii* RHAI undergoing lipid body development and fission.
Figure 4:
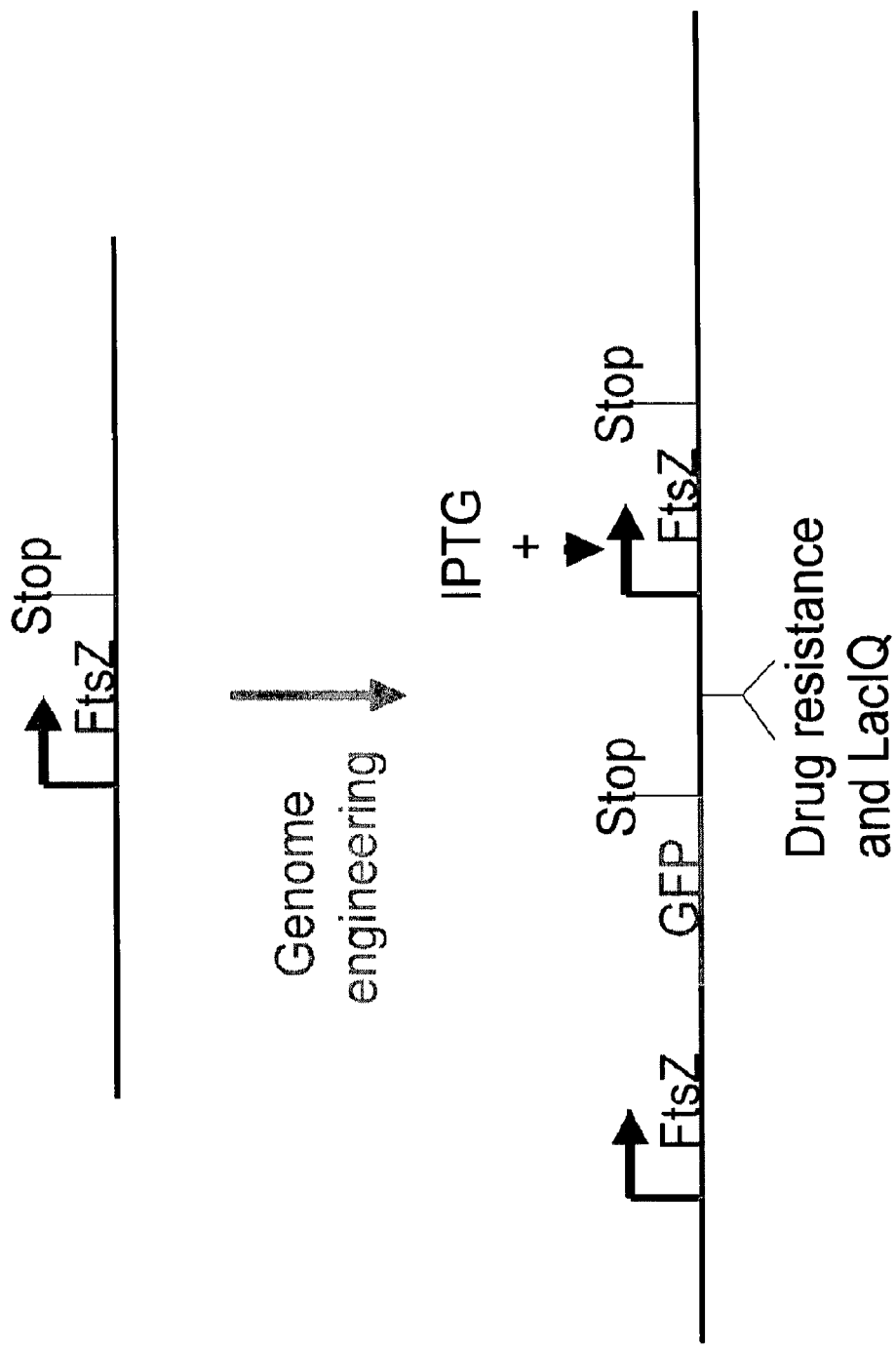
FIG. 4 is a schematic depicting genetic engineering.
Figure 5:
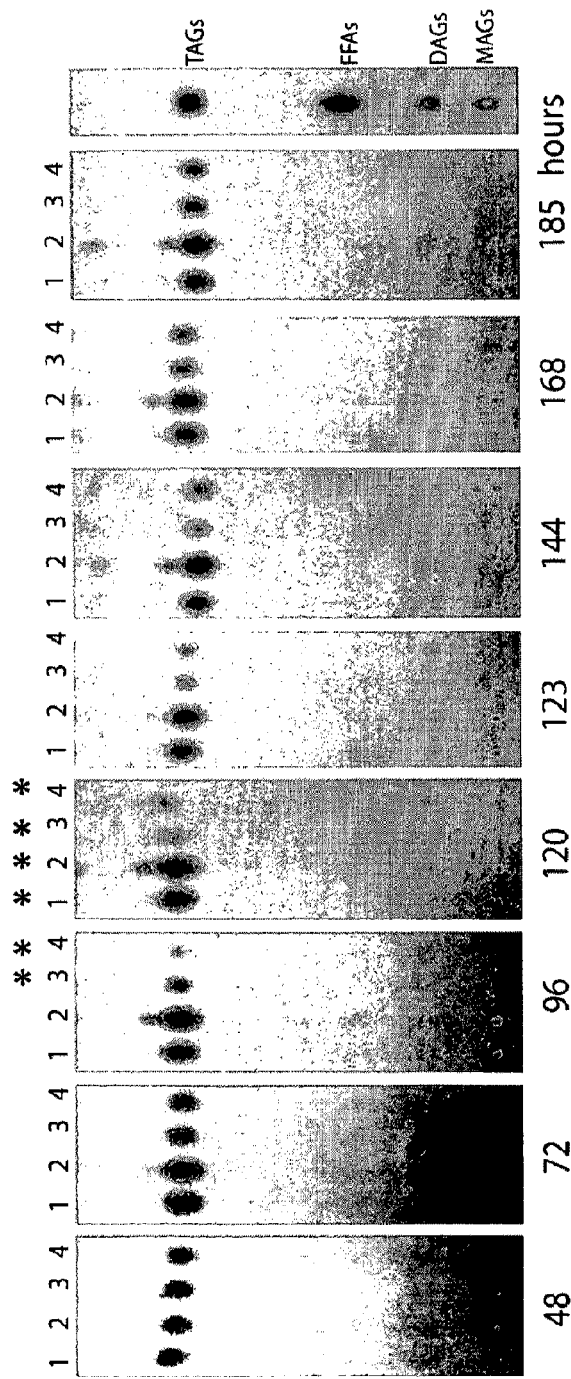
FIG. 5 is a depiction of fermentation lipids evaluated by thin-layer chromatography (TLC). Fermentation conditions tested include: *R. opacus* with 12% glucose and a carbon:nitrogen (C/N) ratio of 17.8:1; *R. jostii* RHA1 with 12% glucose and a C/N ratio of 17.8:1; *R. opacus* with 12% glucose and a C/N ratio of 5:1; and *R. jostii* RHA1 with 12% glucose and a C/N ratio of 5:1.
Figure 6:
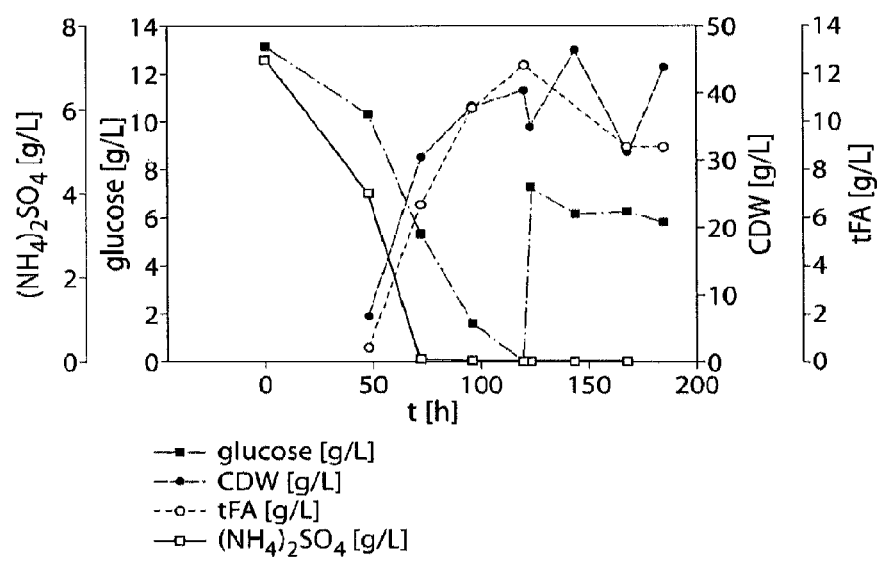
FIG. 6 is a graph depicting a time course of fatty acid production by *R. opacus* PD630 grown in medium containing 120 g $l^{-1}$ glucose and 6.7 g $l^{-1}$ $(NH_4)_2SO_4$.
Figure 7:
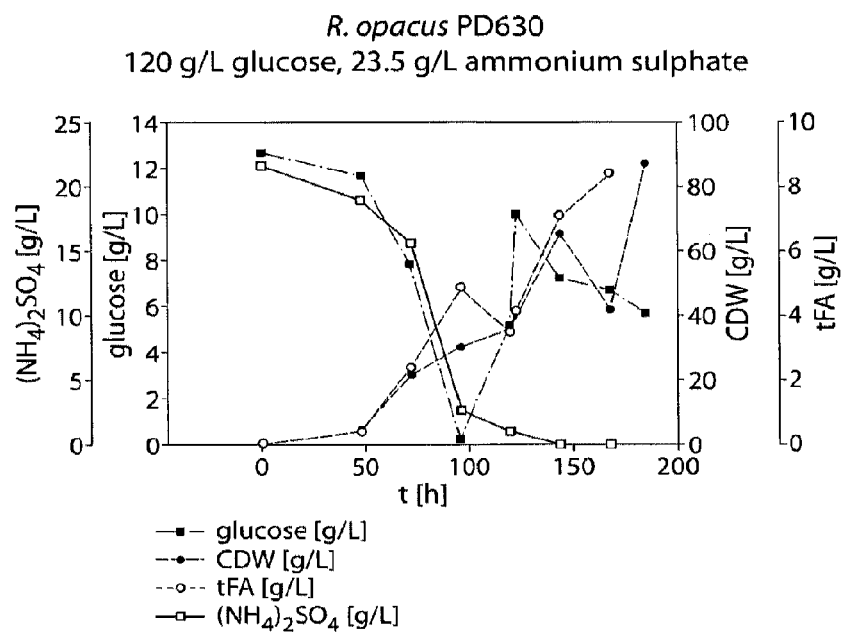
FIG. 7 is a graph depicting a time course of fatty acid production by *R. opacus* PD630 grown in medium containing 120 g $l^{-1}$ glucose and 23.5 g $l^{-1}$ $(NH_4)_2SO_4$.
Figure 8:
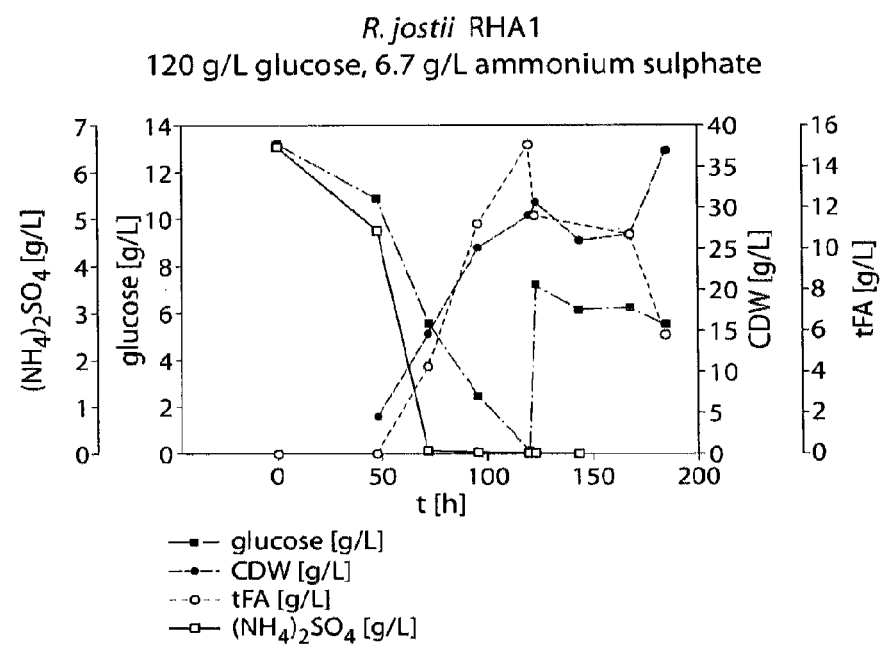
FIG. 8 is a graph depicting a time course of fatty acid production by *R. jostii* RHA1 grown in medium containing 120 g $l^{-1}$ glucose and 6.7 g $(NH_4)_2SO_4$.
Figure 9:
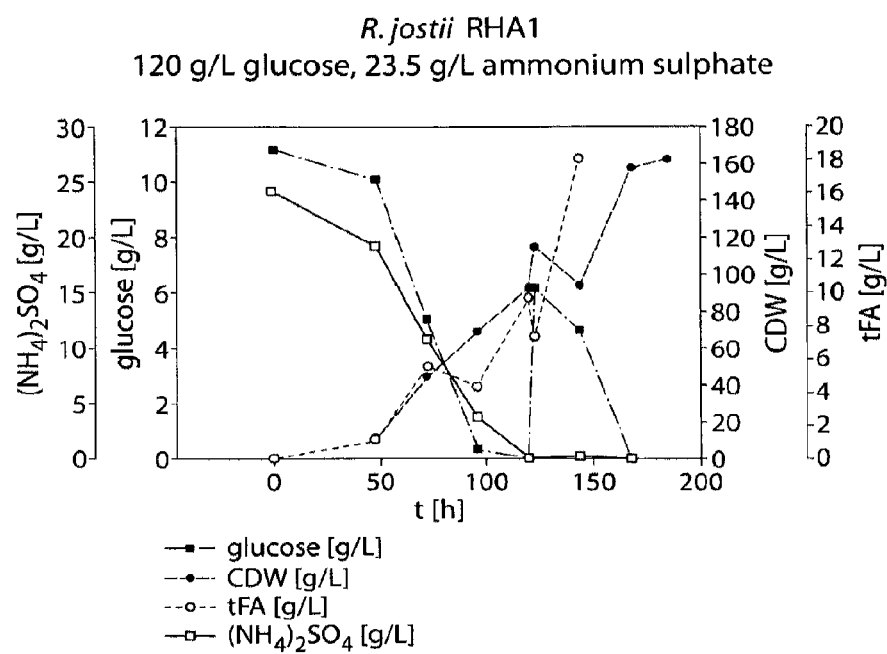
FIG. 9 is a graph depicting a time course of fatty acid production by *R. jostii* RHA1 grown in medium containing 120 g $l^{-1}$ glucose and 23.5 g $l^{-1}$ $(NH_4)_2SO_4$.
Figure 11:
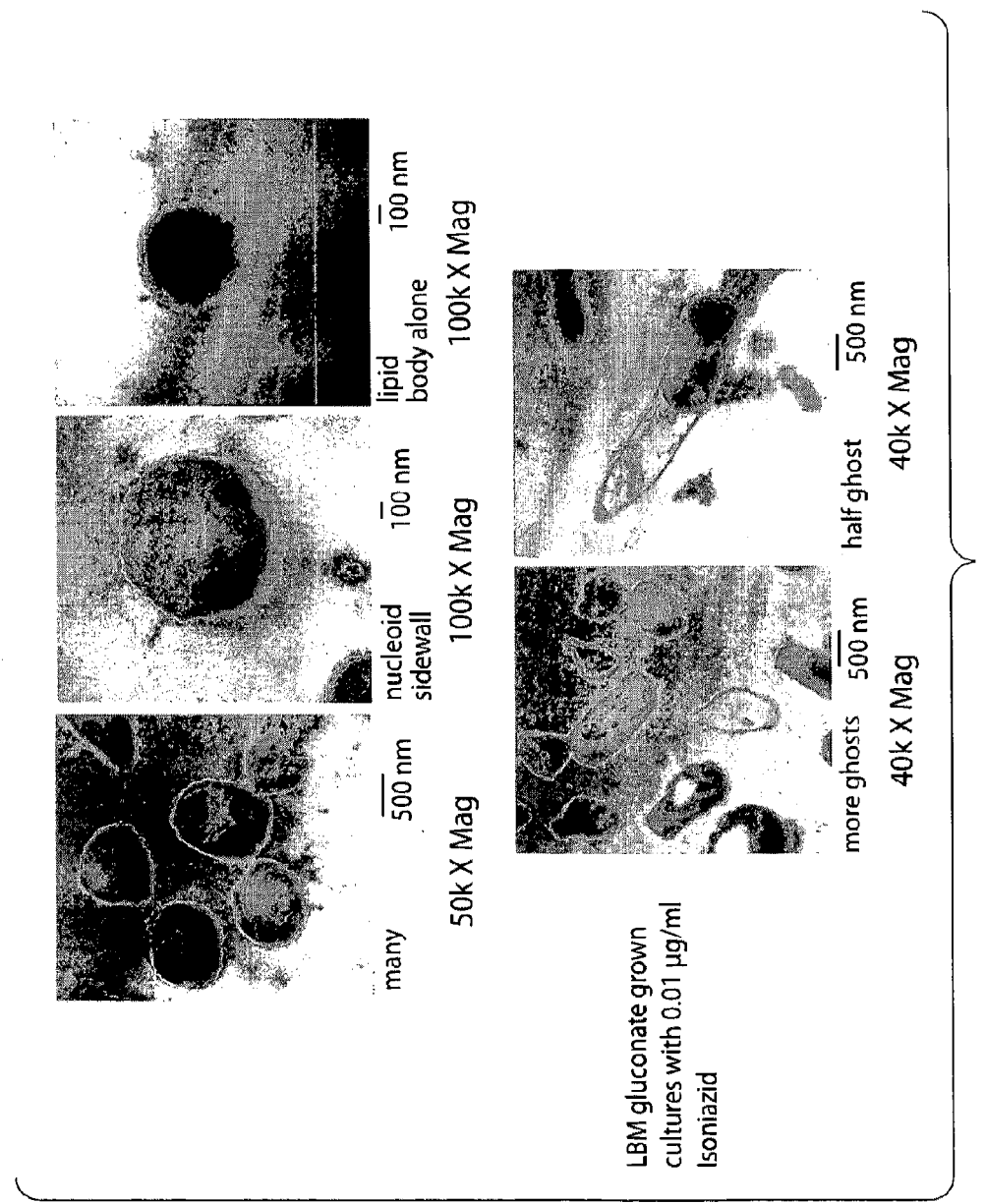
FIG. 11 presents images of cells grown in LBM gluconate with 0.01 μg/ml isoniazid.
Figure 12:
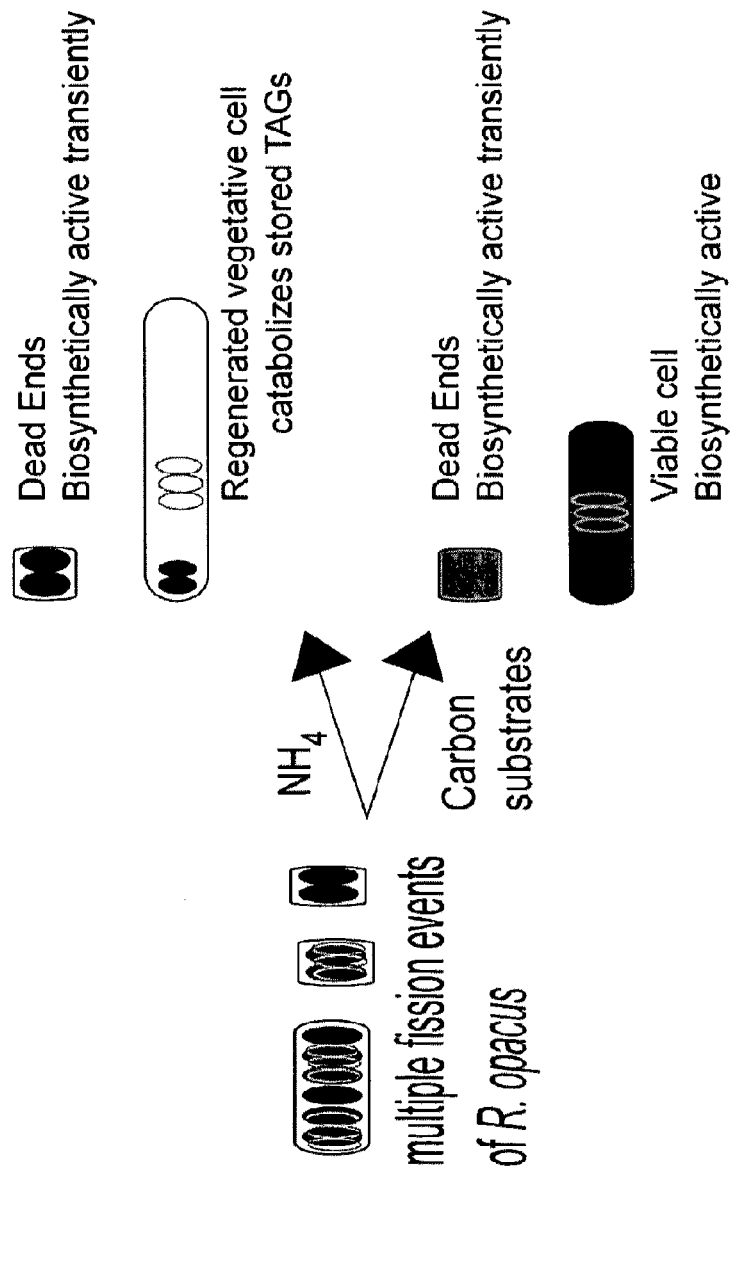
FIG. 12 is a schematic depicting cell fate possibilities under conditions of nitrogen starvation.

Lipid body development and fission in R. opacus PD630 and R. jostii RHA1 is shown in FIGS. 2 and 3. FIG. 4 presents a genetic engineering schematic. FIG. 5 demonstrates the evaluation of fermentation lipids by thin-layer chromatography. FIG. 11 depicts cells grown in LBM gluconate with 0.01 µg/ml isoniazid. FIG. 12 depicts cell fate possibilities under conditions of nitrogen starvation.

Figure 13:
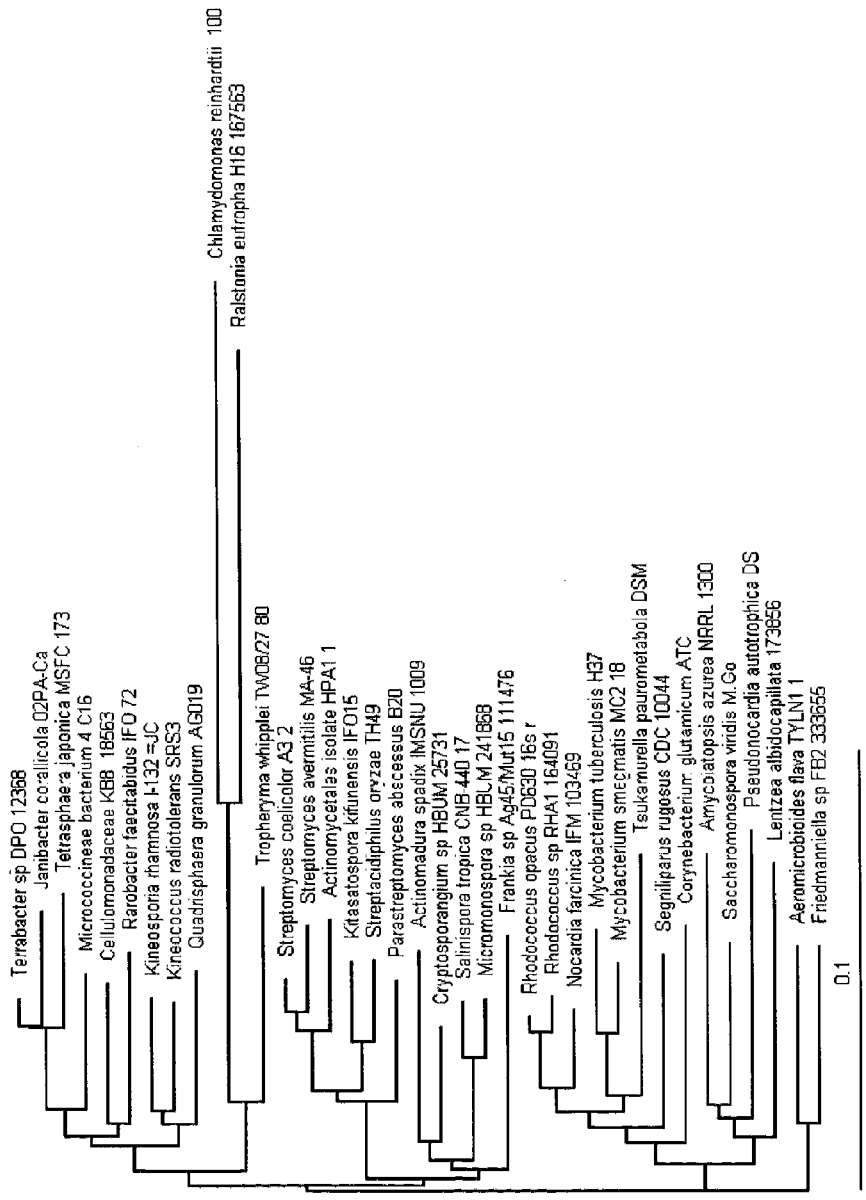
FIG. 13 is a phylogenetic tree depicting actinomycetes in 16s rRNA in a variety of prokaryotic species.
Figure 14:
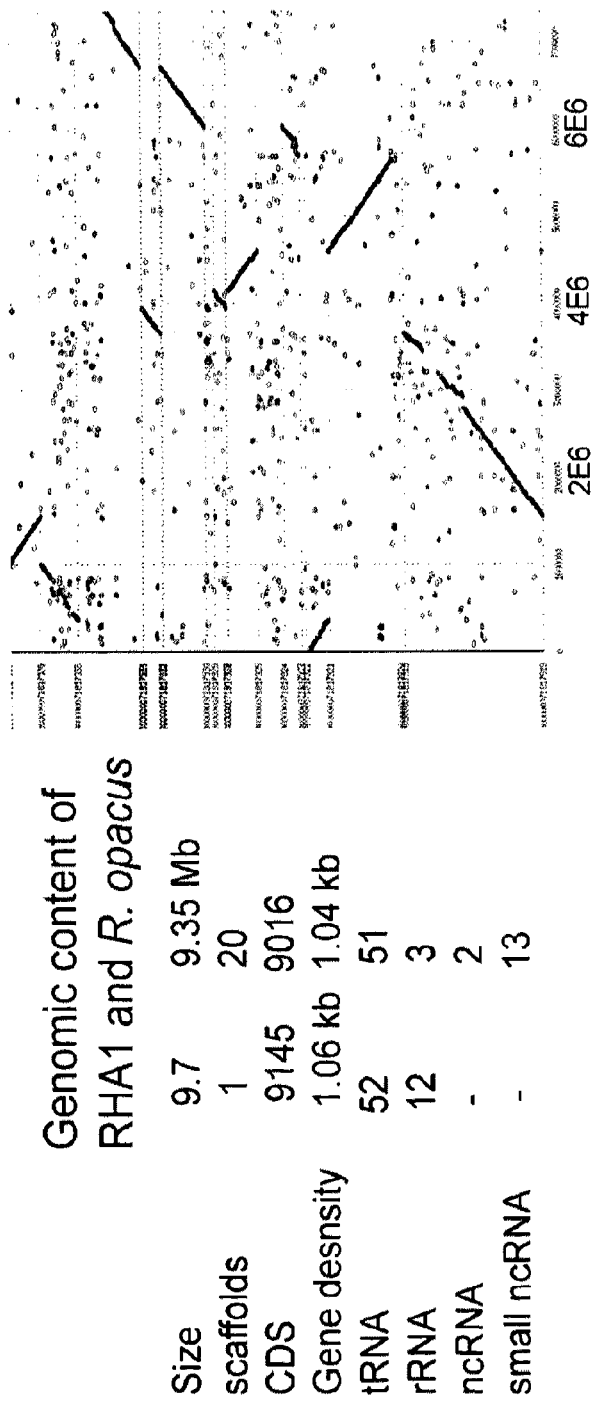
FIG. 14 depicts a genome alignment revealing synteny between *R. opacus* PD630 and *R. jostii* RHA 1 strains.
Figure 16:
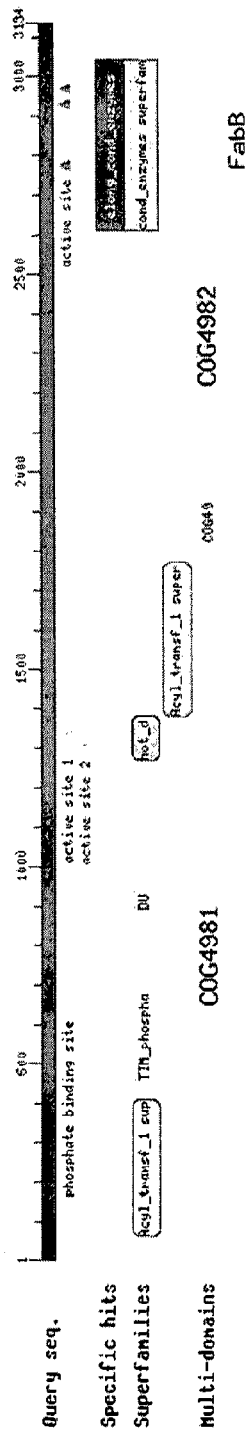
FIG. 16 is a schematic indicating a *Rhodococcus* genomic region.

The genome of R. opacus was analyzed. FIG. 13 presents phylogenetic analysis of actinomycetes in 16s rRNA in a variety of prokaryotic species. FIG. 14 reveals synteny between R. opacus PD630 and R. jostii RHA1 based on analysis of genome alignments. FIG. 15 summarizes data from assemblies of the R. opacus PD630 genome. FIG. 16 presents a schematic of an R. opacus PD630 genomic region. FIG. 17 summarizes a comparative genomics approach to identifying genes involved in lipid production.

Figure 18:
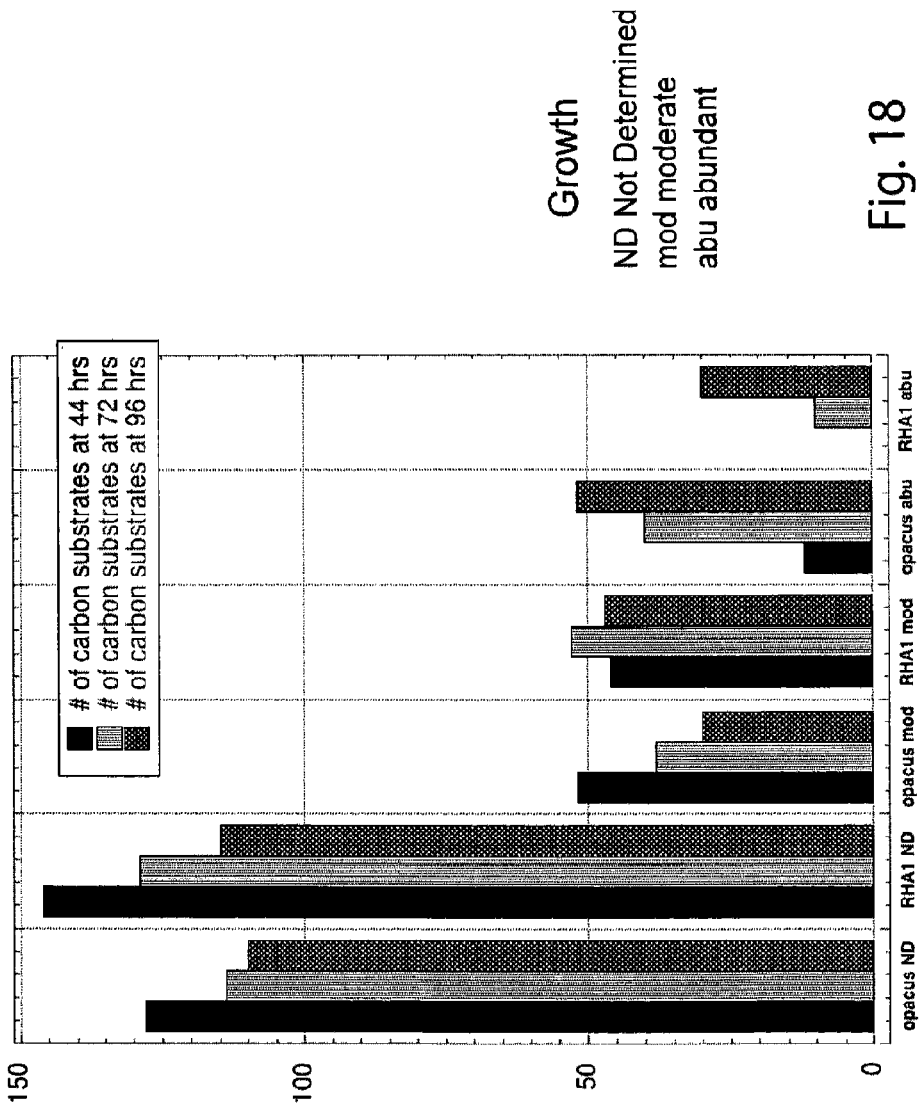
FIG. 18 is a graph depicting kinetics of biolog growth of *R. opacus* PD630 and *R. jostii* RHA1 on a variety of carbon substrates.
Figure 19:
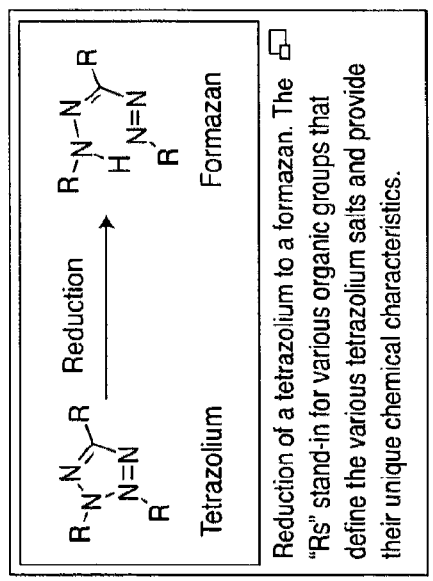
FIG. 19 presents a schematic and a table depicting the best carbon growth substrates assayed for *R. opacus* PD630 and *R. jostii* RHA1 using a cellular-respiration sensitive dye.
Figure 20:
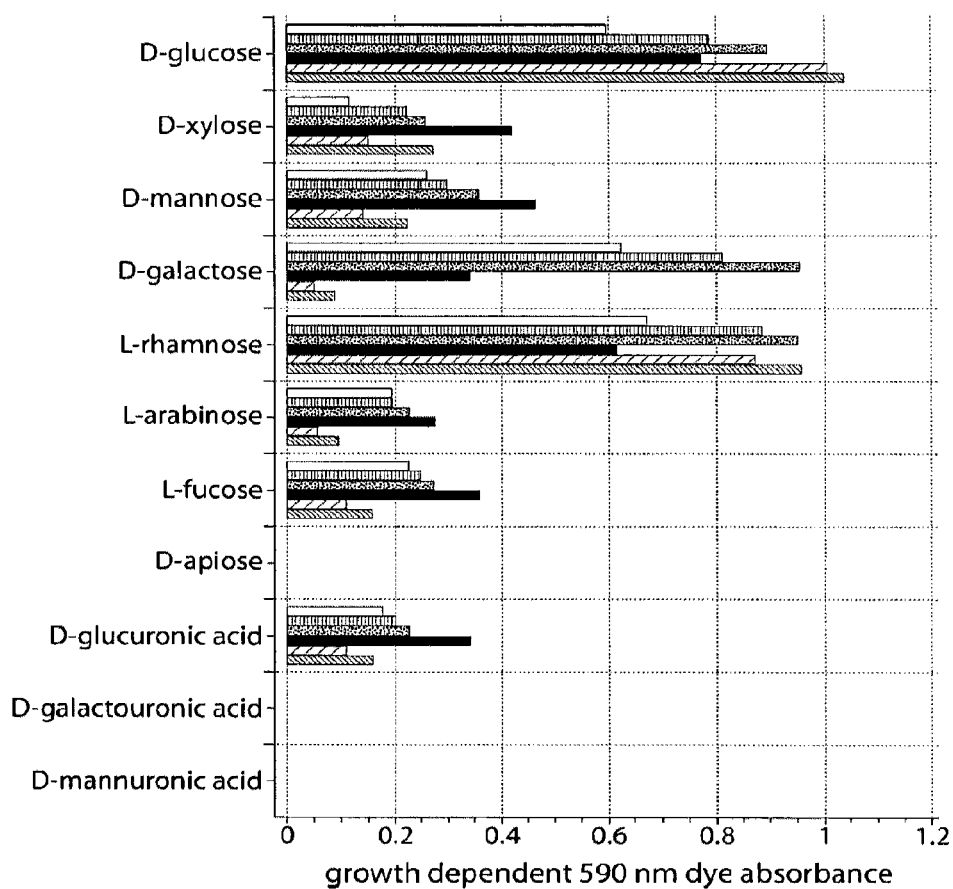
FIG. 20 presents a graph depicting catabolism of cellulytic sugars measured with biolog growth reactive dye D in *R. opacus* PD630 and *R. jostii* RHA1 strains.
Figure 21:
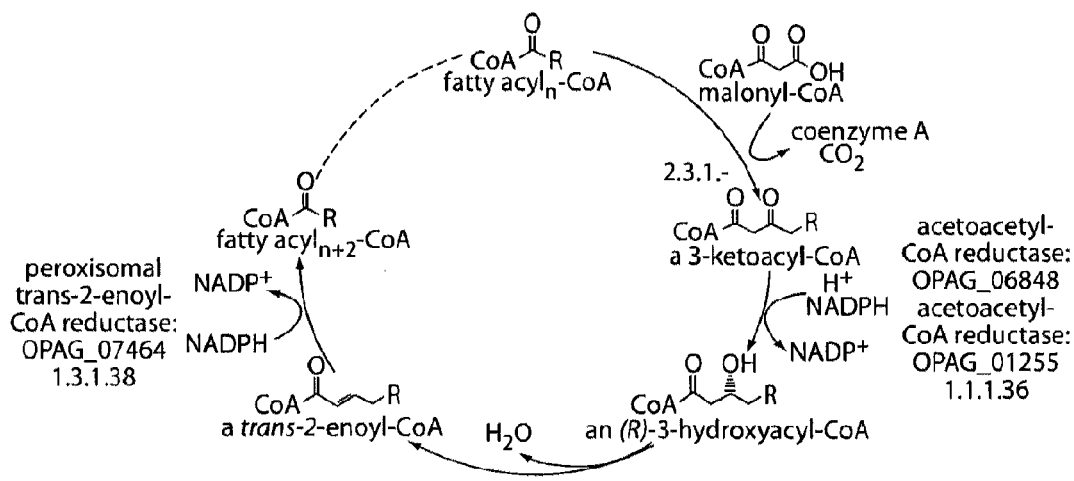
FIG. 21 is a schematic depicting fatty acid biosynthesis.

Growth of R. opacus PD630 and R. jostii RHA1 on a variety of carbon sources was evaluated (FIG. 18). FIG. 19 summarizes 10 carbon growth substrates that showed optimal results under specific conditions. Catabolism of cellulytic sugars was also measured (FIG. 20). FIG. 21 presents a schematic of long chain fatty acid biosynthesis.

Figure 10:
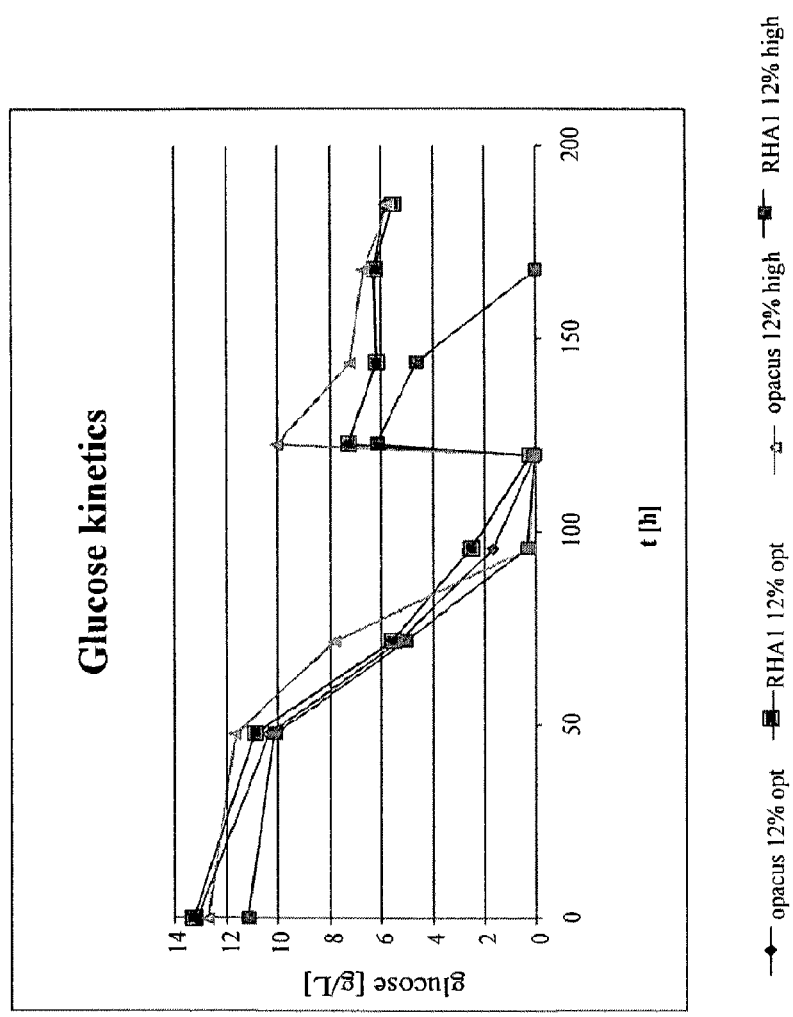
FIG. 10 is a graph depicting glucose kinetics in *R. opacus* PD630 and *R. jostii* RHA1 strains.

Time course analysis of growth of R. opacus PD630 and R. jostii RHA1 in 120 g l$^{-1}$ glucose and varying concentrations of $(NH_4)_2SO_4$ is shown in FIGS. 6-9. Addition of glucose at 120 hours increased total fatty acids and cell dry weight in the presence of 23.5 g l$^{-1}$ $(NH_4)_2SO_4$ (FIGS. 7, 9) but not in the presence of 6.7 l$^{-1}$ $(NH_4)_2SO_4$ (FIGS. 6, 8) indicating a dependence on $(NH_4)_2SO_4$. FIG. 10 is a graph depicting glucose kinetics in R. opacus PD630 and R. jostii RHA1 strains.

Flask Cultures on High Glucose Concentrations

Figure 22:
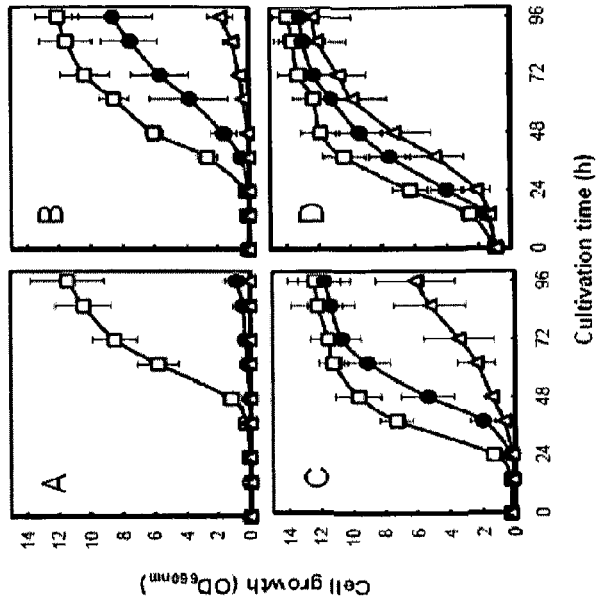
FIG. 22 depicts graphs indicating growth kinetics of *R. opacus* PD630 on high glucose concentrations in flask cultures. Glucose concentration of the defined medium tested were 200 g l$^{-1}$ (open square), 250 gl$^{-1}$ (closed circle), and 300 g l$^{-1}$ (open triangle). Initial inoculum densities were adjusted photometrically to obtain an OD$_{660}$ of 0.03 (A), OD$_{660}$ 0.1 (B), OD$_{660}$ 0.3 (C), and OD$_{660}$ 1.0 (D). The error bars represent the standard deviation of three separate replicates of each experiment.

To investigate the potential of R. opacus DSMZ 44193 for lipid production when grown on glucose, growth kinetics of this organism was tested in flask cultures on defined medium containing initial glucose concentrations of 200, 250 and 300 g $l^{-1}$ for 96 h. Different inocula sizes were also tested. The cell growth profiles which were obtained are shown in FIG. 22. When a flask culture was inoculated to reach an initial $OD_{660}$ of about 0.03, cell growth was observed only in medium containing 200 g $l^{-1}$ glucose, while when the inoculum size was increased to reach an $OD_{660}$ of 0.1 or 0.3 the strain grew in defined medium containing 200 and 250 g $l^{-1}$ glucose. With an initial $OD_{660}$ of about 1.0 the strain grew on media containing 200, 250 and 300 g $l^{-1}$ of glucose reaching stationary phase after 48, 72 and 96 h of cultivation, respectively.

Effect of Nitrogen Concentration on Cell Yield and Lipid Production

Figure 23:
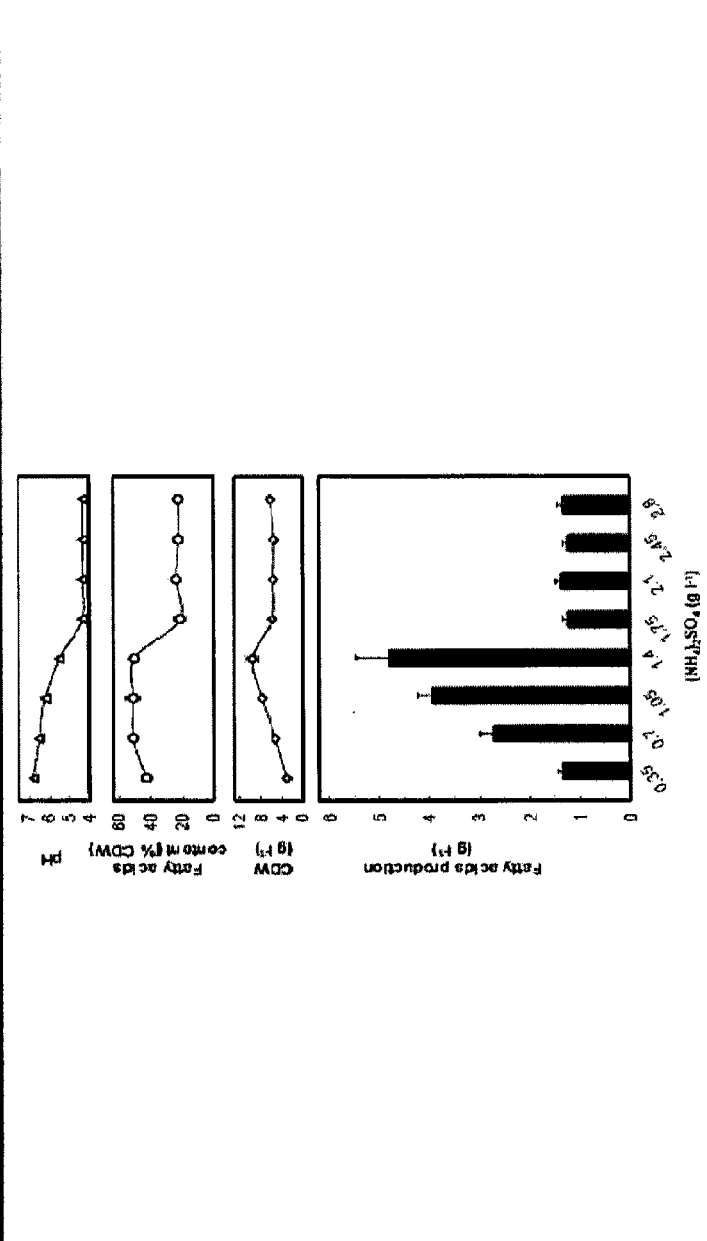
FIG. 23 depicts graphs indicating the effect of $(NH_4)_2SO_4$ concentration on lipid production by *R. opacus* PD630 in flask cultures. The strain was grown in defined medium with different $(NH_4)_2SO_4$ concentration for 4 days. The error bars represent the standard deviation of three separate replicates of each experiment.

In order to study the effect of carbon to nitrogen balance on cell lipid production and yield the amount of $(NH_4)_2SO_4$ in the medium was varied from 0.35 to 2.8 g $l^{-1}$, while maintaining a fixed initial glucose concentration of 40 g $l^{-1}$. As shown in FIG. 23, when the $(NH_4)_2SO_4$ concentration was increased from 0.35 to 1.4 g $l^{-1}$, the cell dry weight (CDW) and the fatty acids production increased from 3.1 to 9.6 g $l^{-1}$ and from 1.3 to 4.8 g $l^{-1}$, respectively, with a fatty acids content of the CDW of approximately 50%. However, when the $(NH_4)_2SO_4$ concentration of the medium was further increased to 1.75 g $l^{-1}$ the CDW and the fatty acids content decreased by 40% and 60%, respectively, resulting in a 75% drop in fatty acids production. When the final pH of this culture was measured, it was clear that an increase in $(NH_4)_2SO_4$ concentrations corresponded to much lower final pHs. The cell culture of *R. opacus* grown in defined medium containing 1.75 g $l^{-1}$ $(NH_4)_2SO_4$ had a final pH value of 4.3. This may account for the observed inhibition of cell growth and significant decrease in TAG production. The pH drop was not preventable even when the medium was strongly buffered with MOPS (data not shown).

Figure 25:
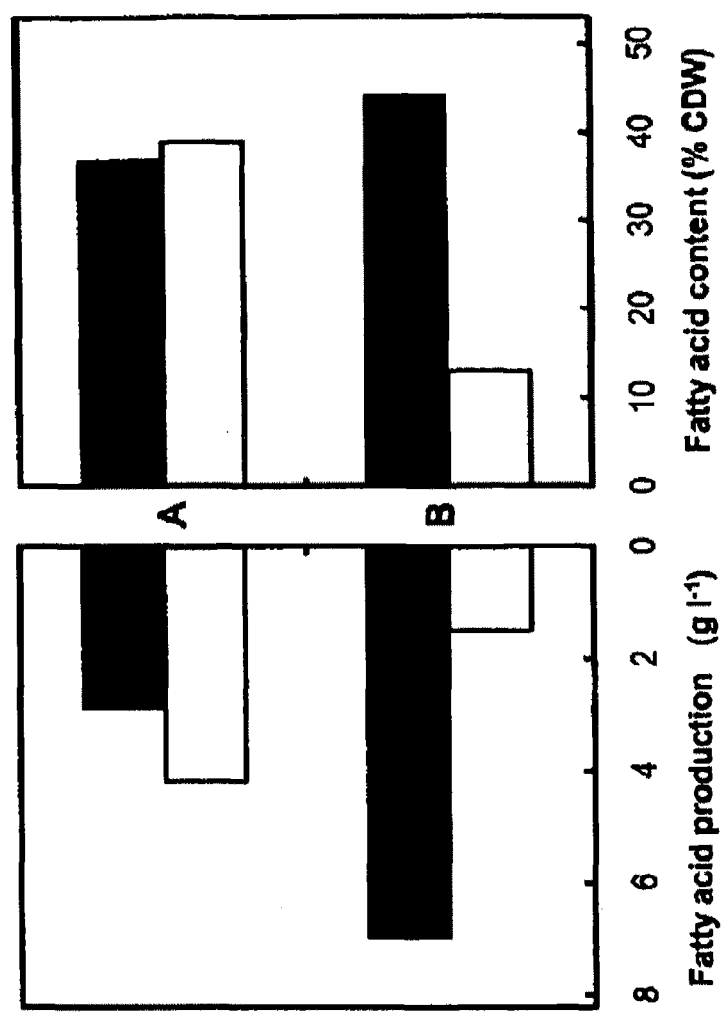
FIG. 25 presents graphs depicting lipid production of *R. opacus* PD630 in batch-culture fermentations with (black bars) or without (white bars) pH and oxygen control. Cells were grown in defined medium containing 1.4 g l$^-$(A) or 2.1 g l$^{-1}$ (B) $(NH_4)_2SO_4$ for 4 days.

To investigate whether cell yield and TAG production could be increased, batch-culture fermentations were performed in defined media containing 1.4 or 2.1 g $l^{-1}$ of $(NH_4)_2SO_4$ with and without pH and oxygen control. As shown in FIG. 25, a clear difference was observed between control and non-control fermentations. With the defined medium containing 1.4 g $l^{-1}$ of $(NH_4)_2SO_4$ there was a similar lipid production in the controlled and non-controlled fermentations of about 4.0 g $l^{-1}$ total fatty acids, representing about 40% of CDW (w/w). With the defined medium containing 2.1 g $l^{-1}$ of $(NH_4)_2SO_4$, lipid production in the strain cultivated in the non-controlled fermentation decreased to 1.7 g $l^{-1}$ total fatty acids (13% of CDW), while in the controlled fermentation, lipid production increased drastically 75% to 7.0 g $l^{-1}$ of total fatty acids (44% of CDW). These data demonstrate that the pH drop in the above-mentioned culture had led to a significant decrease in cell yield and TAG production and that production optimization studies needed to be performed under controlled environmental conditions.

Optimization of Fatty Acids Production by Response Surface Methodology

Preliminary results discussed above indicated that the carbon to nitrogen ratio (C/N) of glucose and $(NH_4)_2SO_4$ concentrations in defined medium and the inoculum size were factors associated with increasing lipid production while factors such as trace elements and different phosphate concentrations proved to be not statistically significant (data not shown). Since in previous experiments the limit in increasing lipid production had been reached by increasing the initial cell density to an $OD_{660}$ 1.0 (FIG. 22), to optimize and maximize lipid production with the fermentor system, glucose and $(NH_4)_2SO_4$ concentrations of the medium were selected as independent variables for the experimental design model. *R. opacus* DSMZ 44193 was cultivated in modified defined medium with varied amounts of glucose and $(NH_4)_2SO_4$ concentrations and the model equation used to calculate the optimum C/N ratio to obtain the maximum production of fatty acids was:

$$Y = -2.38 + 0.0706 X_1 + 2.05 X_2 - 0.000435 X_1^2 + 0.0135 X_1 X_2 - 0.196 X_2^2$$

where Y is the fatty acids production (g $l^{-1}$); $X_1$ and $X_2$ are the uncoded values of glucose and $(NH_4)_2SO_4$ concentrations (g $l^{-1}$), respectively. The experimental design model determined 9 different combinations of glucose and $(NH_4)_2SO_4$ concentrations with a central point (120 g $l^{-1}$ glucose, 7.5 g $(NH_4)_2SO_4$) to be run in triplicate for a total of 11 fermentations (Table 1). Besides these eleven fermentations, preliminary fermentations were run to determine the minimum and maximum concentrations of glucose and $(NH_4)_2SO_4$ to enter in the experimental design model. A triplicate set of independent fermentations of the theoretical optimal glucose to $(NH_4)_2SO_4$ ratio predicted by the model were run, for a total of 25 fermentations (Table 2). Data analysis with the software Stat-Graphics showed a high regression coefficient ($R^2=0.959$), suggesting that the quadratic equation was able to appropriately model the experimental data. The values of Y based on the range of $X_1$ and $X_2$ were calculated for all fermentations and illustrated in a response surface plot in FIG. 26.

Time Course Kinetics of Maximum Fatty Acids Production and Yield

Figure 26:
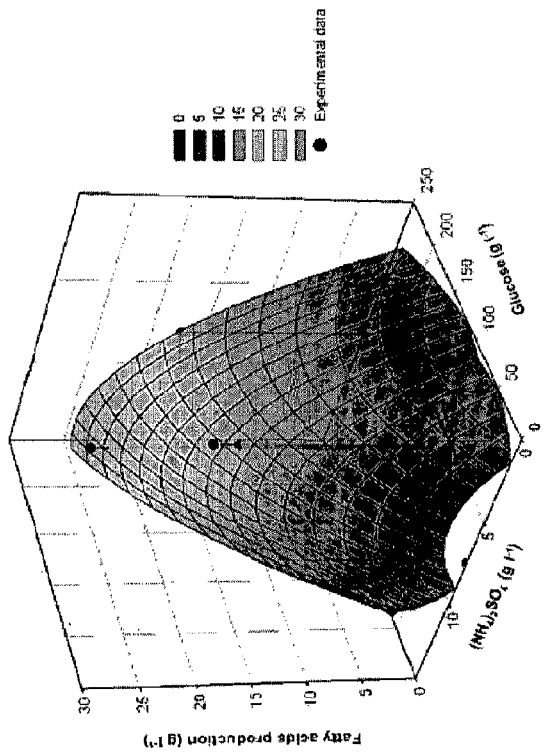
FIG. 26 depicts a response surface plot indicating the effect of glucose and $(NH_4)_2SO_4$ concentrations on lipid production by *R. opacus* PD630 cultures from batch-culture fermentations. (Points: experimental data; curves: calculated values).

The experimental design model adopted herein predicted that with the fermentor system a maximum production of fatty acids of 25.1 g $l^{-1}$ could be obtained with a defined medium including a C/N (w/w) balance of 17.8 containing 240.0 g $l^{-1}$ glucose and 13.45 g $l^{-1}$ $(NH_4)_2SO_4$ (FIG. 26).

Figure 27:
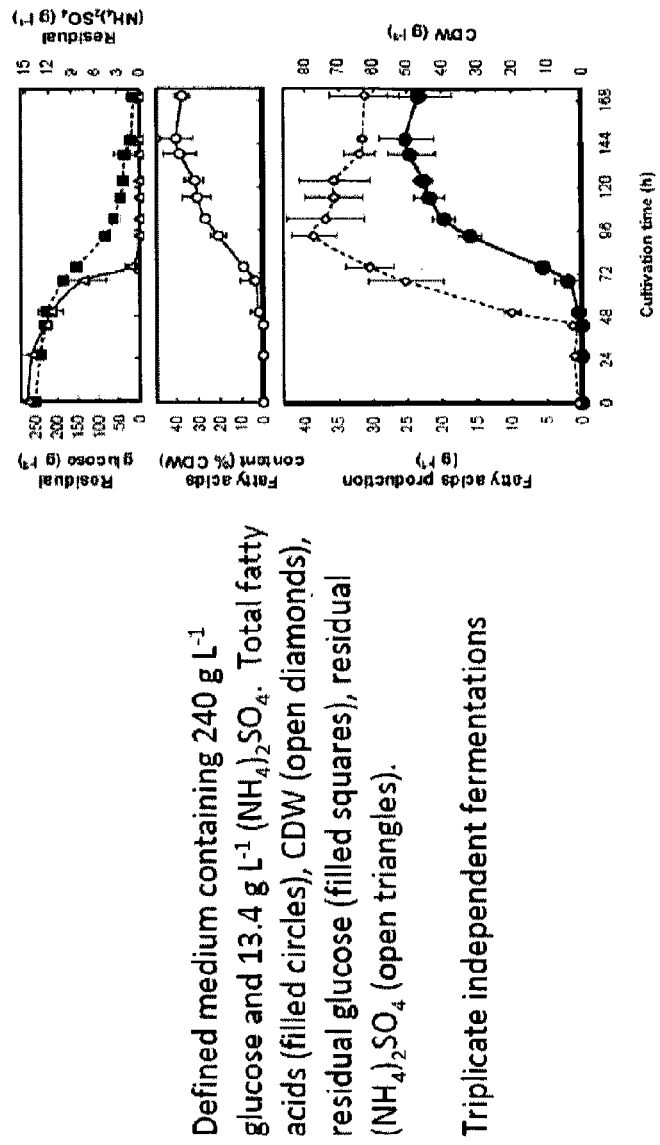
FIG. 27 presents graphs depicting a time course of fatty acid production by *R. opacus* PD630 carried out under the optimized growth conditions in batch-cultures fermentations. The strain was grown in modified defined medium containing 240 g l$^{-1}$ glucose and 13.4 g l$^{-1}$ $(NH_4)_2SO_4$. Total fatty acids (filled circles), CDW (open diamonds), residual glucose (filled squares), residual $(NH_4)_2SO_4$ (open triangles). The error bars represent the standard deviation of three independent replicates.
Figure 28:
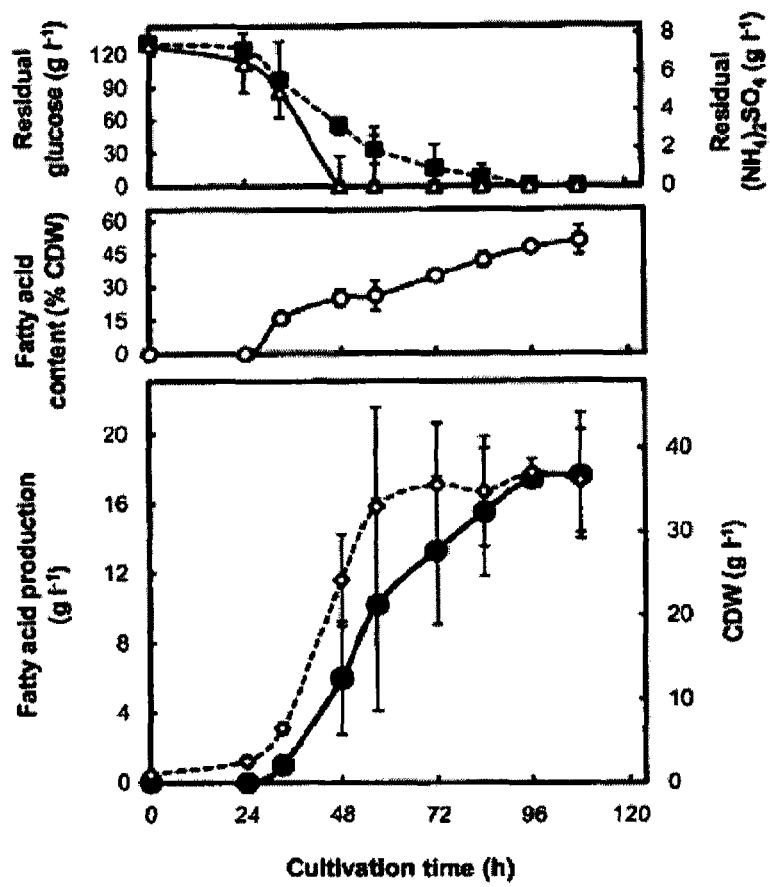
FIG. 28 presents graphs depicting a time course of fatty acid production by *R. opacus* PD630 grown in modified defined medium containing 120 g l$^{-1}$ glucose and 7.5 g l$^{-1}$ $(NH_4)_2SO_4$. Total fatty acids (filled circles), CDW (open diamonds), residual glucose (filled squares), residual $(NH_4)_2SO_4$ (open triangles). The error bars represent the standard deviation of three independent replicates.

To confirm this predicted optimal composition of the defined medium a triplicate set of controlled and independent batch-culture fermentions were run. Kinetics of fatty acids production, cell dry weight (CDW), fatty acids content in % of CDW and residues of glucose and $(NH_4)_2SO_4$ present in the culture broth are shown in FIGS. 27 and 28. Cell growth increased rapidly after 48 h of cultivation with a generation time of 11.9 ($\pm 2.0$) hours, reached stationary state at 77.6 ($\pm 7.3$) g CDW after 93 h of cultivation, and then slightly decreased. Fatty acids accumulation increased drastically after $(NH_4)_2SO_4$ was completely depleted after 76 h of cultivation with glucose consumption during the early log phase resulting mainly in cell mass increase. Fatty acids production increased further during the stationary growth phase after 93 h of cultivation. Maximum fatty acids accumulation of 25.2 ($\pm 3.9$) g $l^{-1}$ corresponding to 38.4 ($\pm 5.6$) % of the cell dry weight occurred after 147 h of cultivation, when residual glucose was close to complete consumption. With these growth conditions, the yield of total fatty acids per gram of glucose consumed was 0.1 ($\pm 0.02$) g. When *Rhodococcus opacus* PD630 reached the maximum accumulation of lipids, the fatty acid composition profile showed that the first three most abundant fatty acids (% of total fatty acids, w/w) were palmitic acid (27.7$\pm$0.9 0%), oleic acid (24.7$\pm$0.70%) and cis-10heptadecenoic acid (15.9$\pm$1.02%) (Table 3).

Figure 29:
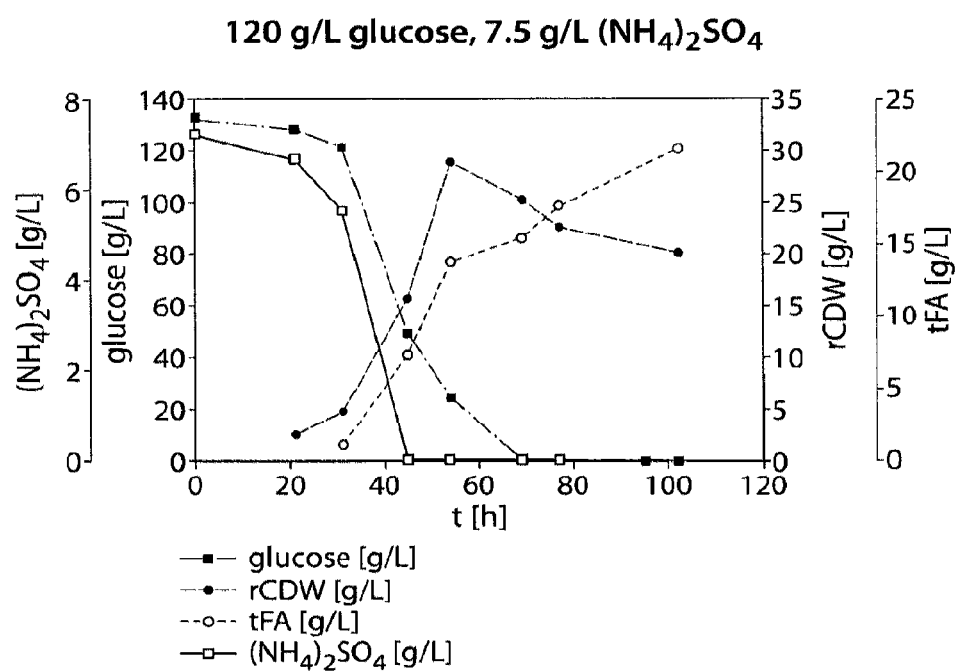
FIG. 29 presents a graph depicting a time course of fatty acid production by *R. opacus* PD630 grown in modified defined medium containing 120 g l$^{-1}$ glucose and 7.5 g l$^{-1}$ $(NH_4)_2SO_4$.

The maximum yield of 0.15 ($\pm 0.03$) g of total fatty acids per gram of glucose consumed was obtained with a defined medium with a C/N balance of 16 containing 120.0 g $l^{-1}$ glucose and 7.5 g $l^{-1}$ $(NH_4)_2SO_4$ (Table 2). Growth kinetics of *Rhodococcus opacus* PD630 growing under these conditions (FIG. 29) show that the culture had a shorter lag phase entering in exponential growth phase after 30 hours with a doubling time of 5.9 ($\pm 0.50$) hours, about half of that observed with the conditions for maximum total fatty acids production.

Growth kinetics showed again that lipid accumulation started when $(NH_4)_2SO_4$ was close to depletion and that maximum fatty acids accumulation of 17.6 (±3.3) representing 46.5 (±7.5) % of CDW was obtained during the stationary phase at 100 hours of growth when glucose was completely consumed. The fatty acids composition profile of Rhodococcus opacus PD630 was very similar to that of the maximum production conditions with the first three most abundant fatty acids (% of total fatty, w/w) being palmitic acid (29.4±0.82%), oleic acid (21.6±0.48%) and cis-10heptadecenoic acid (15.8±0.87%) (Table 3). FIG. 30 presents a summary of optimal conditions of the defined medium tested for fermentations for bioprocess production of triacylglycerols.

Discussion

Recently, there has been considerable interest in the production of microbial oils from oleaginous microorganisms, such as yeast, fungi, bacteria and microalgae (Li et al. 2008; Alvarez and Steinbüchel 2002; Hu et al. 2008). One of the major obstacles for the production of microbial oil is the relatively high cost of manufacturing, which is expected to be overcome by new technological developments (Antoni et al. 2007; Stephanopoulos 2007). High-cell-density cultivation is a prerequisite to maximize volumetric productions of microbial oil and therefore very important for the economic feasibility of biodiesel production (Park 2004; Riesenberg and Guthke 1999). To the best of our knowledge to date only a few microorganisms have been cultivated to cell-densities of 50 g $l^{-1}$ or higher, even in fed-batch culture systems (Riesenberg and Guthke 1999).

Here, the production of intracellular triacylglycerols by R. opacus PD630 grown with high glucose concentrations was investigated. Preliminary flask culture studies showed that high concentrations of $(NH_4)_2SO_4$ in the defined medium induced a decrease in the accumulation of lipids in the cells, while conversely during cultivation under strict nitrogen-limiting conditions, storage lipids were accumulated in the cytoplasm. It was determined herein that R. opacus PD630 has the uncommon capacity to grow in defined media containing glucose concentrations up to 300 g $l^{-1}$. Usually, fed-batch systems have been used to attain high cell-densities since high initial concentrations of glucose cause growth inhibition for the organism.

Results of cultivations under controlled growth conditions demonstrated that a decrease in pH caused growth inhibition and consequently a decrease in lipid accumulation. Batch-culture fermentations run under controlled environmental conditions allowed an increase of glucose and $(NH_4)_2SO_4$ in the culture medium that resulted in a dramatic increase in fatty acid production. These results also indicated that the carbon to nitrogen ratio (C/N, w/w) of glucose and $(NH_4)_2SO_4$ in the defined medium was an important factor associated with increasing lipid production. An experimental design protocol was used herein to determine the optimal culture conditions and the optimal C/N ratio to maximize total fatty acids production with the fermentor system described herein. Based on the experimental design results that obtained, the response surface method that was adopted predicted that an optimal production medium with a C/N ratio of 17.8, containing 240.0 g $l^{-1}$ glucose and 13.45 g $l^{-1}$ $(NH_4)_2SO_4$ would lead to a maximum production of 25.1 g $l^{-1}$ of fatty acids. These optimal growth conditions were validated experimentally in a triplicate set of batch-culture fermentations which resulted in a total fatty acids production of 25.2 g $l^{-1}$ confirming the validity of the experimental design model adopted.

Cells of R. opacus PD630 grown with the optimized defined mineral medium described herein, which did not contain expensive ingredients such as yeast extract, protein hydrolysates and other organic nutrients, entered exponential growth after a lag phase of 48 h. The culture reached rapidly stationary phase to a maximum CDW of 77.2 g $l^{-1}$ in 48 h. TAG synthesis increased drastically during the late log phase after about 72 h culture triggered by the depletion of a $(NH_4)_2SO_4$.

The bioprocess results described herein with R. opacus PD630 grown in batch-culture with high concentrations of glucose, up to 77.2 g $l^{-1}$ of cell dry weight, which contains about 40% TAGs indicate that this strain holds great potential for developing a biotechnological process for the production of industrial biodiesel from renewable biomass resources.

TABLE 1

Central composite experimental design matrix defining glucose and $(NH_4)_2SO_4$ concentration

| | Real values | | Coded values | | Fatty acid |
|---|---|---|---|---|---|
| Run | $X_1$ | $X_2$ | $X_1$ | $X_2$ | production (g $l^{-1}$) |
| 1 | 35.1 | 12.8 | −1 | 1 | 2.3 |
| 2 | 35.1 | 2.2 | −1 | −1 | 4.9 |
| 3 | 120.0 | 7.5 | 0 | 0 | 18.6 |
| 4 | 240.0 | 7.5 | 1.41 | 0 | 17.8 |
| 5 | 0.0 | 7.5 | −1.41 | 0 | 0.0 |
| 6 | 120.0 | 7.5 | 0 | 0 | 14.0 |
| 7 | 204.9 | 12.8 | 1 | 1 | 24.7 |
| 8 | 120.0 | 0.0 | 0 | −1.41 | 0.0 |
| 9 | 120.0 | 15.0 | 0 | 1.41 | 8.2 |
| 10 | 120.0 | 7.5 | 0 | 0 | 16.2 |
| 11 | 204.9 | 2.2 | 1 | −1 | 3.1 |

$X_1$, glucose concentration (g $l^{-1}$);
$X_2$, $(NH_4)_2SO_4$ concentration (g $l^{-1}$)

TABLE 2

Glucose, $(NH_4)_2SO_4$ and nitrogen to carbon ratio (C/N, w/w) of the defined medium tested for fermentations with for bioprocess production of triacylglycerols.

| glucose [g/l] | $(NH_4)_2SO_4$ [g/l] | C/N ratio [g/g] | $CDW^a$ [g/l] | $tFA^b$ [g/l] | FA [% CDW] | $Y_{glu}{}^c$ |
|---|---|---|---|---|---|---|
| 0 | 7.5 | 0.0 | 0 | 0 | 0 | 0.00 |
| 15.3 | 12.8 | 1.2 | 7.02 | 2.08 | 14.7 | 0.14 |
| 35.2 | 2.2 | 16.0 | 9.69 | 4.93 | 54.0 | 0.14 |
| 35.2 | 12.8 | 2.8 | 12.52 | 2.28 | 25.9 | 0.06 |
| 120 | 0 | 120.0 | 0 | 0 | 0 | 0.00 |
| 120 | 7.5 | 16.0 | 35.9 | 16.2 | 48.8 | 0.14 |
| 120 | 7.5 | 16.0 | 37.4 | 18.6 | 49.8 | 0.15 |
| 120 | 7.5 | 16.0 | 39.7 | 14.0 | 35.4 | 0.12 |
| 120 | 7.5 | 16.0 | 42.7 | 21.6 | 51.8 | 0.18 |
| 120 | 10 | 12.0 | 36.2 | 17.32 | 47.8 | 0.14 |
| 120 | 15 | 8.0 | 31.36 | 8.18 | 27.7 | 0.07 |
| 120 | 20 | 6.0 | 27.76 | 7.86 | 33.3 | 0.07 |
| 160 | 7.5 | 21.3 | 41.75 | 20.82 | 49.9 | 0.13 |
| 200 | 7.5 | 26.7 | 42.88 | 21.69 | 50.6 | 0.11 |
| 200 | 15 | 13.3 | 71.78 | 16.51 | 21.8 | 0.08 |
| 200 | 20 | 10.0 | 73.42 | 15.46 | 22.4 | 0.08 |
| 200 | 30 | 6.7 | 77.41 | 12.57 | 19.5 | 0.06 |
| 205 | 2.2 | 93.2 | 10.58 | 3.11 | 28.9 | 0.02 |
| 205 | 7.5 | 27.3 | 33.4 | 16.58 | 53.9 | 0.08 |
| 205 | 12.8 | 16.0 | 51.34 | 24.73 | 48.2 | 0.12 |
| 240 | 2.2 | 109.1 | 9.09 | 2.77 | 42.1 | 0.01 |
| 240 | 7.5 | 32.0 | 42.63 | 17.76 | 44.1 | 0.07 |
| 240 | 13.45 | 17.8 | 85.93 | 26.45 | 36.5 | 0.11 |
| 240 | 13.45 | 17.8 | 74.87 | 20.81 | 33.9 | 0.09 |
| 240 | 13.45 | 17.8 | 72.10 | 28.26 | 44.7 | 0.12 |

$^a$cell dry weight
$^b$total fatty acids
$^c$yield, g of fatty acids per gram of glucose consumed

TABLE 3

Fatty acids composition profile as % of total fatty acids (g/g) of R. opacus PD630 growing in optimal defined medium for maximum production (240 gl$^{-1}$ glucose, 13.45 gl$^{-1}$ (NH$_4$)$_2$SO$_4$ gl$^{-1}$; n = 3) and yield (120 gl$^{-1}$ glucose, 7.5 gl$^{-1}$ (NH$_4$)$_2$SO$_4$ gl$^{-1}$; n = 4) of fatty acids.

| | glucose (g) | |
|---|---|---|
| Facid Acid Species | 240 | 120 |
| Myristic acid (C14:0) | 1.9 (±0.13) | 2.0 (±0.07) |
| Pentadecanoic Acid (C15:00) | 5.6 (±0.28) | 7.4 (±1.29) |
| Palmitic acid (C16:0) | 27.7 (±0.90) | 27.8 (±0.06) |
| Palmitoleic acid (C16:1) | 10.8 (±1.31) | 10.7 (±0.04) |
| Heptadecanoic Acid (C17:00) | 8.7 (±0.34) | 10.2 (±0.04) |
| cis-10Heptadecenoic Acid (C17:1) | 15.9 (±1.02) | 17.2 (±0.88) |
| Stearic acid (C18:0) | 4.8 (±0.79) | 4.1 (±0.52) |
| Oleic acid (C18:1) | 24.7 (±0.70) | 20.7 (±2.82) |

References for Example 1

Alvarez H M, Mayer F, Fabritius D, Steinbüchel A (1996) Formation of intracytoplasmic lipid inclusions by *Rhodococcus opacus* strain PD630. Arch Microbiol 165:377-386

Alvarez H M, Steinbüchel A (2002) Triacylglycerols in prokaryotic microorganisms. Appl Microbiol Biotechnol 60:367-376

Antoni D, Zverlov V V, Schwarz W H (2007) Biofuels from microbes. Appl Microbiol Biotechnol 77:23-35

Bell K S, Philp J C, Aw D W, Christofi N (1998) The genus *Rhodococcus*. J Appl Microbiol 85:195-210.

Brandl H, Gross R A, Lenz R W, Fuller R C (1988) *Pseudomonas oleovorans* as a source of poly(β-hydroxyalkanoates) for potential applications as biodegradable polyesters. Appl Environ Microbiol 54:1977-1982

Canakci M, Sanli H (2008) Biodiesel production from various feedstocks and their effects on the fuel properties. J Ind Microbiol Biotechnol 35:431-441

Chartrain M, Jackey B, Taylor C, Sandford V, Gbewonyo K, Lister L, Dimichele L, Hirsch C, Heimbuch B, Maxwell C, Pascoe D, Buckland B, Greasham R (1998) Bioconversion of indene to cis (1S,2R) indandiol and trans (1R,2R) indandiol by *Rhodococcus* species. J Ferment Bioeng 86:550-558

Du W, Li W, Sun T, Chen X, Liu D (2008) Perspectives for biotechnological production of biodiesel and impacts. Appl Microbiol Biotechnol 79:331-337

Hu Q, Sommerfeld M, Jarvis E, Ghirardi M, Posewitz M, Seibert M, Darzins A (2008) Microalgal triacylglycerols as feedstocks for biofuel production: perspectives and advances. Plant J 54:621-639

Larkin M J, Kulakov L A, Allen C C (2005) Biodegradation and *Rhodococcus*—masters of catabolic versatility. Curr Opin Biotechnol 16:282-290

Li Q, Du W, Liu D (2008) Perspectives of microbial oils for biodiesel production. Appl Microbiol Biotechnol 80:749-756

Park E Y (2004) Recent progress in microbial cultivation techniques. Adv Biochem Eng Biotechnol 90:1-33

Riesenberg D, Guthke R (1999) High-cell-density cultivation of microorganisms. Appl Microbiol Biotechnol 51:422-430

Stein K (2007) Food vs biofuel. J Am Diet Assoc 107:1870-1878

Stephanopoulos G (2007) Challenges in engineering microbes for biofuels production. Science 315:801-804

Tollefson J (2008) Energy: not your father's biofuels. Nature 451:880-883

Vasudevan P T, Briggs M (2008) Biodiesel production—current state of the art and challenges. J Ind Microbiol Biotechnol 35:421-430

Voss I, Steinbüchel A (2001) High cell density cultivation of *Rhodococcus opacus* for lipid production at a pilot-plant scale. Appl Microbiol Biotechnol 55:547-555

Wältermann M, Luftmann H, Baumeister D, Kalscheuer R, Steinbüchel A (2000) *Rhodococcus opacus* strain PD630 as a new source of high-value single cell oil? Isolation and characterization of triacylglycerols and other storage lipids. Microbiology 146: 1143-1149

Example 2

Metabolic Engineering of *Rhodococcus opacus* PD630 to Produce Triacylglycerols on Xylose Herein, the oleaginous microorganism *Rhodococcus opacus* PD630 was metabolically engineered to broaden its substrate utilization range to include the pentose sugar xylose, which is commonly found in agricultural residues and other lignocellulosic biomass. Libraries were generated from *Streptomyces padanus* MITKK-103, a bacterium capable of utilizing xylose as a sole carbon source, and introduced into *R. opacus* PD630. The plasmid library was constructed by ligating *S. padanus* genome fragments, obtained by partial restriction digestion, into the plasmid pAL358 which carries a gentamicin resistance cassette and an origin of replication that allows for propagation in *R. opacus* PD630. Four transformants (Xsp1, 8, 10 and 12) were isolated that grew on xylose and accumulated triacylglycerol (TAGs). The strains had a 3603 bp insert on the plasmid, and sequencing of the fragment derived from *S. padanus* revealed the presence of two genes, xylA (1167 bp) and xylB (1938 bp). Xsp8 strain produced approximately 11.7 g of fatty acids per liter, accounting for 43% of the dried cell mass, after 5 days growth in defined medium containing 12% xylose in a pH controlled batch fermenter culture. These results suggest that the high cell density cultivation of the engineered strain on xylose could be promising for the industrial scale production of biodiesel from lignocellulosic biomass. Xylose utilization is an important trait for the economically feasible production of biofuels from lignocellulosic biomass by *R. opacus* PD630.

Materials and Methods

Strains, Plasmid and Media

*R. opacus* PD630 (DSMZ 44193) was obtained from Deutsche Sammlung von Mikroorganismen and Zellkulturen GmnH (DSMZ, Germany). *S. padanus* MITKK-103, which was isolated in our laboratory (Kurosawa et al. 2006), has been deposited with an accession number of NRRL30828. One Shot TOP 10 chemically competent *Escherichia coli*, which was used for gene library construction and DNA manipulation, was purchased from Invitrogen (Carlsbad, Calif.). The plasmid pAL358 (4363 bp) (supplied by PA Lessard) which carries a gentamicin resistance cassette and an origin of replication was used as a general cloning vector and for construction of the *S. padanus* genomic library. The culture media used tryptone-yeast extract broth (ISP medium No. 1) (Shirling and Gottlieb 1966), LB broth (Luria-Bertani), NBYE medium consisting of 8 g nutrient broth and 5 g yeast extract per liter of deionized water, and xylose defined medium which contained per liter: 16 g xylose, 1.0 g (NH$_4$)$_2$SO$_4$, 1.0 g MgSO$_4$.7H$_2$O, 0.015 g CaCl$_2$.2H$_2$O, 1.0 ml trace element solution, 1.0 ml stock A solution, 35.2 ml 1.0 M phosphate buffer and 10 mg gentamicin. The trace element solution stock A solution and phosphate buffer were the same as those described by Chartrain et al. (1998). Xylose, MgSO$_4$.7H$_2$O, CaCl$_2$.2H$_2$O and gentamicin were dissolved in deionized water and sterilized by autoclaving and then stock A, trace elements, and (NH$_4$)$_2$SO$_4$ were added to the cooled medium as filter sterilized stock solutions. Modifications of xylose defined medium are stated below in the text. For solid media, 2% (w/v) agar was added.

DNA Manipulation and Sequencing

Standard procedures were used for preparation of genomic DNA from *S. padanus* MITKK-103, restriction enzyme digestions, ligations and agarose gel electrophoresis (Sambrook and Russell 2001). Restriction endonucleases and T4 DNA ligase were purchased from New England BioLabs Inc., Ipswich, Mass. Plasmid DNA was isolated by using a Plasmid Midi Kit (QIAGEN) according to the manufacturer's instructions. The DNA fragments were purified with a GENECLEAN II KIT (BIO 101, La Jolla, Calif.). DNA sequencing was performed with the Big Dye terminator cycle sequencing kit (Applied BioSystems, Foster City, Calif.), and was analyzed with an ABI 3700 automated sequencer at the MIT biopolymers laboratory. Homologues of genes were identified using a BLAST search (blast.ncbi.nlm.nih.gov/Blast.cgi).

Electroporation

Plasmids containing the *S. padanus* genomic DNA library were introduced into *R. opacus* PD630 bp electroporation using a BIO-RAD Gene Pulser™ (BIO-RAD Laboratories, Inc., CA). To obtain electrocompetent cells of *R. opacus* PD630, 50 ml of NBYE medium containing 0.05% Tween-80 was inoculated with 0.5 ml of an overnight NBYE preculture and grown at 30° C. to an optical density of 0.5 at 660 nm. Cells were harvested, washed twice with ice-cold HG buffer containing 5 mM HEPES and 15% glycerol (pH 7.2) and concentrated 50-fold in ice-cold 10% glycerol. Competent cells were stored at −80° C. Immediately before the electroporation, 70 μl of competent cells were mixed with DNA (final concentration 0.1~1 μg/ml). The electroporation was performed in a 2 mm electroporation cuvette (VWR North America, West Chester, Pa.) and electroporated at 2.5 kV, 25 μF and 300 ohm. Pulsed cells were immediately diluted with 300 μl of NBYE and regenerated at 30° C. for 3 h before they were plated on xylose defined xylose agar plates.

Analytical Procedures

Cell growth was followed by measurement of the optical density at a wavelength of 660 nm (Spectronic 20 Genesys, Spectronic Instruments Inc., Rochester, N.Y.) or the cell dry weight (CDW). The CDW was determined after lyophilization of culture biomass obtained by centrifuging 10 ml of culture broth at 5,000 rpm for 15 min and washing the cell pellet twice in deionized water. The lyophilized cell pellet was also used to analyze the fatty acid concentrations. The supernatants of the culture broth were used for analyses of residual glucose and (NH$_4$)$_2$SO$_4$ after filtration through a 0.2-μm-pore-size filter. The residual xylose concentrations were measure by high-performance liquid chromatography (HPLC) (Agilent 1100 system) fitted with an Aminex HPX-87H column (300×7.8 mm, BIO-RAD, USA) coupled to a refractive index (RI) detector. The column was eluted with 5 mM H$_2$SO$_4$ as mobile phase at 40° C. and a flow rate of 0.6 ml/min. Residual ammonia concentrations were determined by the Ammonia Assay kit (Sigma, St. Louis, Mo.) according to the manufacturer's instructions. For the analysis of total lipids, fatty acids were converted to methyl esters by methanolysis followed by gas chromatography (GC) (Wältermann et al., 2000). An average of 10 mg of lyophilized cells were resuspended in 1 ml of methanol containing 15% (v/v) H$_2$SO$_4$ and 1 ml of chloroform. Methanolysis was carried out at 100° C. for 2.5 h. After cooling to room temperature, 0.5 ml deionized water was added to the solution and then vortexed for 1 min. The organic phase containing fatty acid methyl esters (FAMEs) was analyzed by using an Agilent 6850 series II GC system equipped with an Agilent DB-Wax column (30 m by 0.32 mm, 0.5 μm thick film) with hydrogen as the carrier gas. A 2 μl portion of the organic phase was injected with a 30:1 split ratio using the autosampler. The inlet was maintained at 250° C. The oven was held at 80° C. for 5 min, heated to 220° C. at 20° C./min, and then held at 220° C. for 5 min. Peak detection was performed by a flame ionization detector, which was maintained at 300° C. The fatty acids were identified and quantified by comparison to standard FAMEs (Sigma). Fatty acid content was defined as the percentage of the ratio of fatty acids to dry cell mass weight (% DCM).

Chemicals

All chemicals used were reagent-grade and obtained from Sigma-Aldrich (St. Louis, Mo.) unless otherwise noted. All medium components were purchased from BD Diagnostic Systems (Difco, Sparks, Md.).

Results

Construction of a *R. opacus* PD630 Xylose-Metabolizing Strain

Figure 32:
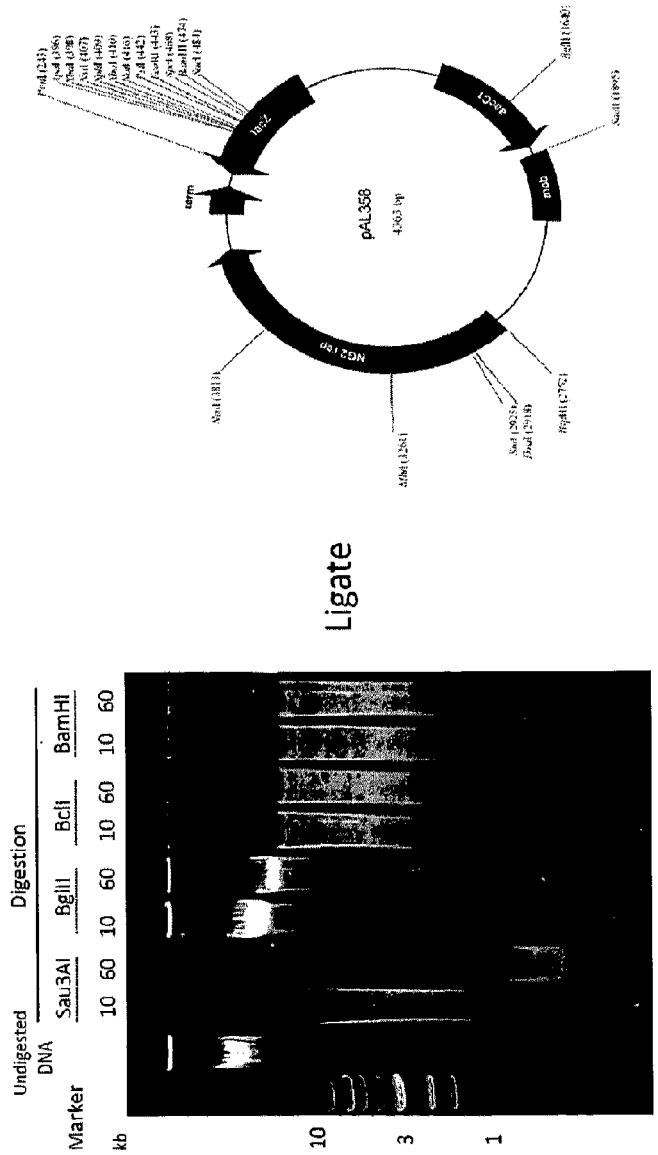
FIG. 32 presents an image of a gel and a schematic showing the restriction map of pAL358. Plasmid pAL358 carries a gentamicin resistance cassette and an origin of replication that allows for propagation in *Rhodococcus*.

While *R. opacus* PD630 is unable to catabolize xylose, *S. padanus* MITKK-103 utilizes xylose well as a sole carbon source (Kurosawa et al. 2006). In order to engineer a xylose utilizing strain of *R. opacus* PD630, an attempt was made to transfer the genes encoding enzymes involved in xylose metabolism in *S. padanus*, to *R. opacus*. Accordingly, *S. padanus* genomic DNA was partially digested with the restriction enzyme Sau3A. DNA fragments in the size range from 2 to 10 kbp were then isolated following gel electrophoresis. The isolated DNA fragments were ligated into the BamHI site of the pAL358 plasmid. The restriction map of plasmid pAL358 is given in FIG. 32. The resulting ligation mixture was transformed into One Shot TOP 10 chemically competent *E. coli*. *R. opacus* PD630 was transformed by electroporation with the resulting plasmid libraries from the *S. padanus*. Gentamicin resistant transformants were subsequently screened for growth on xylose as a sole carbon source. A total of 42 transformants were isolated on xylose defined agar plates.

Growth and Lipid Production on Xylose in *R. opacus* PD630 Transformants

The ability of the 42 transformants described above to produce lipids from xylose was to evaluated. The aforementioned transformants were used to inoculate 50 ml of defined media containing xylose as the sole carbon source and incubated on a rotary shaker (200 rpm) at 30° C. for 5 days. 13 of the transformants grew well, attaining an optical density (OD$_{660}$) of more than 5. To further confirm that these 13 strains were truly capable of utilizing xylose as a sole carbon source, the initial cultures were adjusted to an OD$_{660}$ of 5, and 0.5 ml of the cells was transferred to a xylose defined medium of 50 ml. Cultures were grown at 30° C. for 6 days. Four of 13 transformants, termed Xsp1, 8, 10 and 12, grew well on xylose, reaching an OD$_{660}$ of more than 10 and accumulating over 30% of the dried cell mass as fatty acids (Table 4).

Identification of Inserted Genes in Transformant *R. opacus* PD630 Strains

To understand xylose metabolism in the *R. opacus* PD630 xylose utilizing strains, the genes contained within the transformed plasmids were identified. Four transformants (Xsp1, 8, 10 and 12) were selected for further characterization, and their plasmids were isolated and sequenced. Restriction mapping demonstrated that all four plasmids contained 3603 bp insert within the pAL358 vector backbone. The isolated plasmid was designated pXsp. The nucleotide sequence of the whole insert (3603 bp fragment on pAL358) is shown in FIG. 33. Sequence analysis demonstrated that the insert contained two open reading frames predicted to encode a xylose isomerase (xylA) homolog and a xylulose kinase (xylB) homolog. Interestingly, the 3' region of the predicted xylB gene was absent, apparently replaced by the 5' region of a predicted cellulose binding protein.

Figure 41:
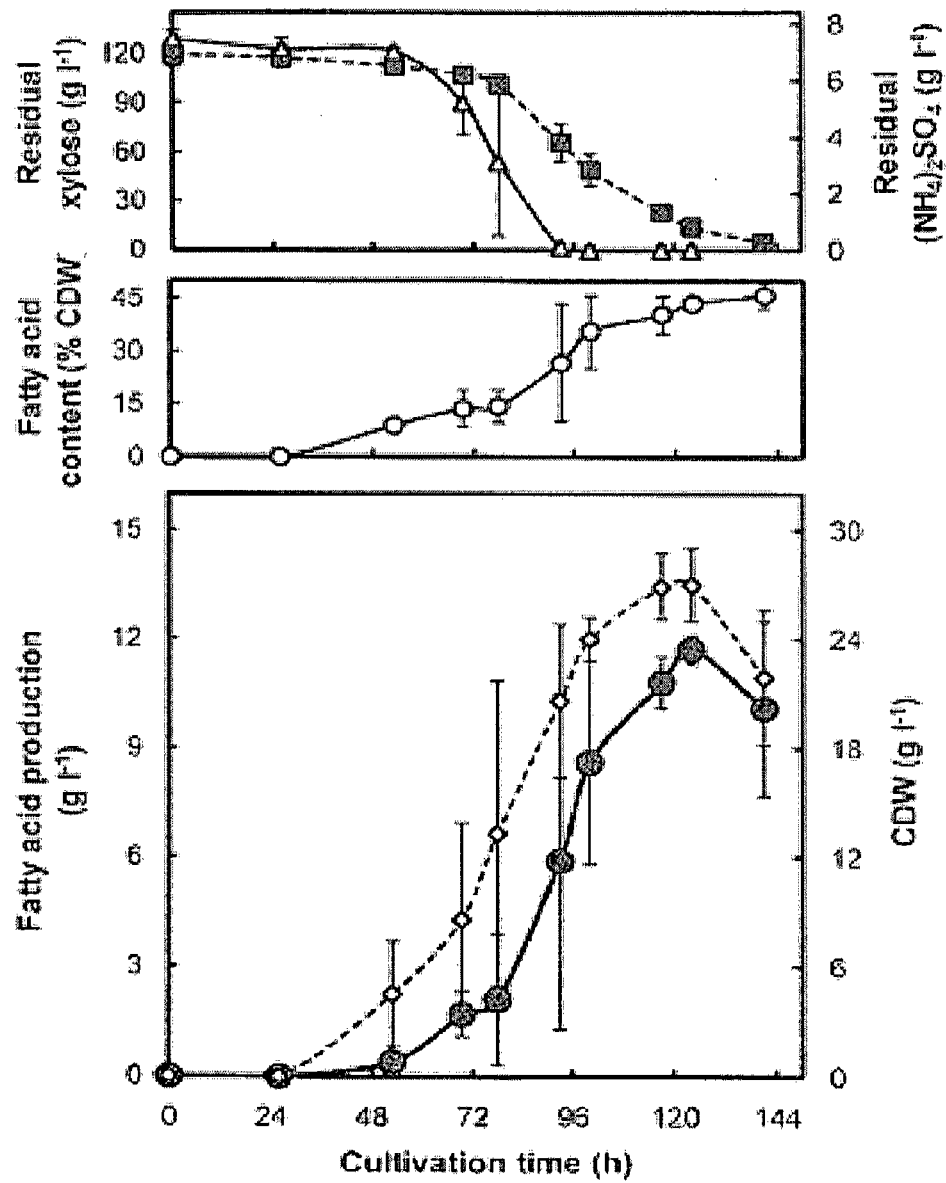
FIG. 41 presents graphs depicting a time course of fatty acid production by transformant strain Xsp8 grown in modified defined medium containing 120 g l$^{-1}$ xylose and 7.5 g l$^{-1}$ $(NH_4)_2SO_4$. Total fatty acid (filled circles), CDW (open diamonds), fatty acid content (open circles), residual xylose (filled squares), residual $(NH_4)_2SO_4$ (open triangles). The error bars represent the standard deviation of three independent replicates.

Time Course of Lipid Production on Xylose by Xsp8-Transformant in a Batch-Culture Fermentation High-cell-density cultivation is a prerequisite to maximize volumetric productivity of microbial oil fermentation (Park, 2004; Riesenberg and Guthke, 1999). Lipid production by the Xsp8-transformant grown with high xylose concentrations was investigated herein. Fermentor experiments were performed using a Sixfors bioreactor system (Infors AG CH-4103, Bottmingen, Switzerland) at 30° C. A loop of Xsp8-cells grown on an LB agar plate containing 10 μg/ml gentamicin at 30° C. for 3 days was inoculated into 100 ml of a xylose defined medium in a 500-ml baffled flask. The culture was incubated on a rotary shaker (200 rpm) at 30° C. for 5 days and the culture was adjusted to an $OD_{660}$ of 10. 10 ml of the cells were inoculated into 500 ml fermentor vessels containing 300 ml working volume of a modified defined medium containing per liter: 120 g xylose, 7.5 g $(NH_4)_2SO_4$, 3.0 g $MgSO_4.7H_2O$, 0.045 g $CaCl_2.2H_2O$, 3.0 ml trace element solution, 3.0 ml stock A solution, 17.6 ml 1.0 M phosphate buffer and 10 mg gentamicin. The pH value in the medium was maintained at 7.0±0.1 by the addition of 2 M NaOH. Dissolved oxygen was measured with an Ingold polarographic probe and maintained at above 80% $O_2$ saturation by adjusting the agitation speed up to 1200 rpm, and by automatically adjusting the mixture of air and pure oxygen flow via flow controllers while maintaining air gas flow at 0.1 VVM. When necessary to prevent foam formation, polypropylene glycol P 2'000 (Fluka) was manually added to each vessel. Fatty acid production kinetics, CDW, fatty acid content as a percent of CDW, and residual xylose and $(NH_4)_2SO_4$ present in the culture supernatants are shown in FIG. 41. After 72 h of cultivation, cell growth increased rapidly with a generation time of 19.6 (±3.2) hours and reached a stationary state at 26.9 (±1.8) g $l^{-1}$ CDW, followed by a slight decrease after 120 h of cultivation. Lipid accumulation increased dramatically after $(NH_4)_2SO_4$ was depleted. Maximum fatty acid accumulation of 11.7 (±0.4) g $l^{-1}$ corresponding to 43.4 (±1.7) % of the cell dry weight occurred after 124 h of cultivation, at which point the residual xylose was almost consumed.

Figure 38:
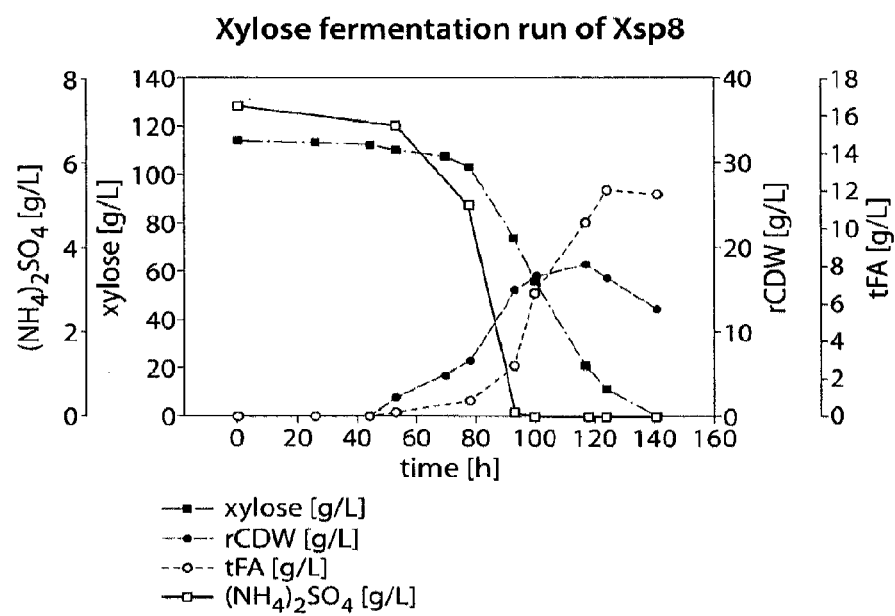
FIG. 38 presents a graph depicting a time course of fatty acid production in transformant strain Xsp8 grown in the presence of 120 g l$^{-1}$ xylose and 7.5 g l$^{-1}$ $(NH_4)_2SO_4$.
Figure 39:
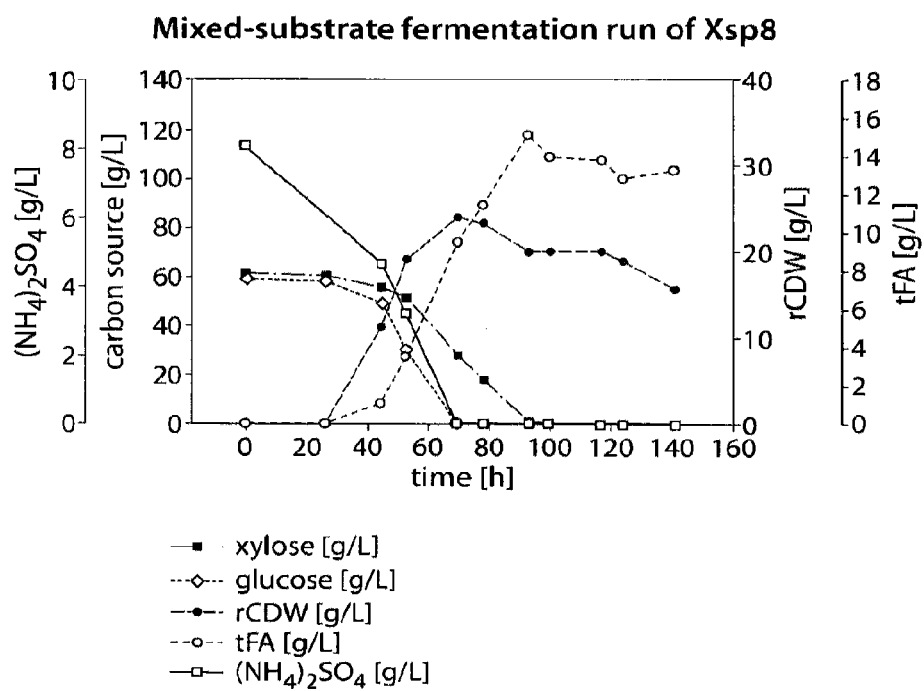
FIG. 39 presents a graph depicting a time course of fatty acid production in transformant strain Xsp8 using mixed-substrate fermentation including 60 g l$^{-1}$ xylose, 60 g l$^{-1}$ glucose and 7.5 g l$^{-1}$ $(NH_4)_2SO_4$.
Figure 40:
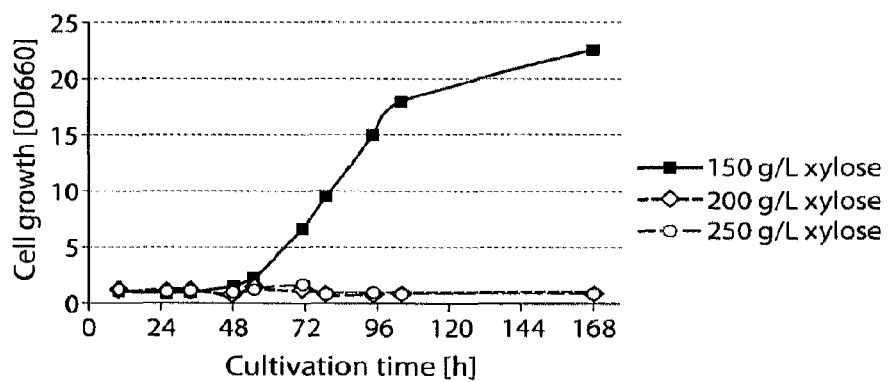
FIG. 40 presents a graph depicting growth of transformant strain Xsp8 in the presence of different xylose concentrations.
Figure 44:
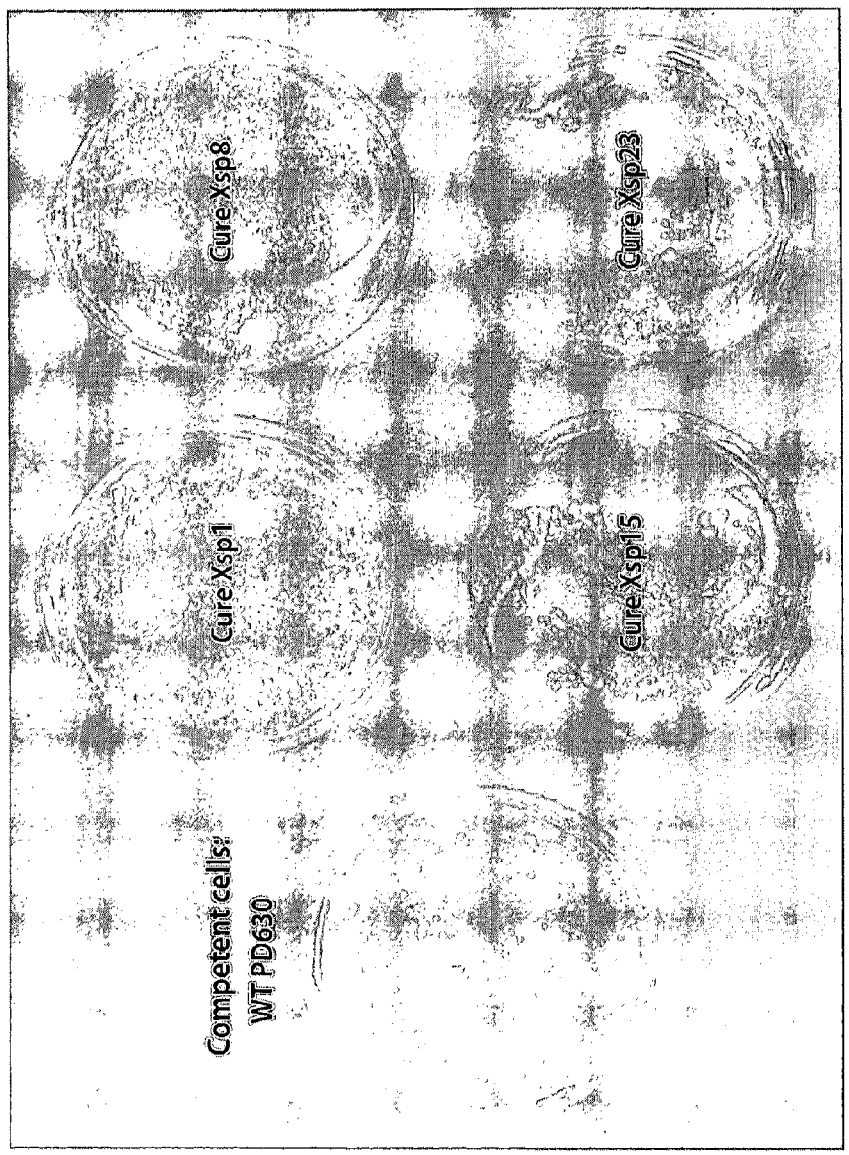
FIG. 44 presents an image of a plate assay in which *R. opacus* PD630 cells have been transformed with plasmids containing xylA and xylB.
Figure 46:
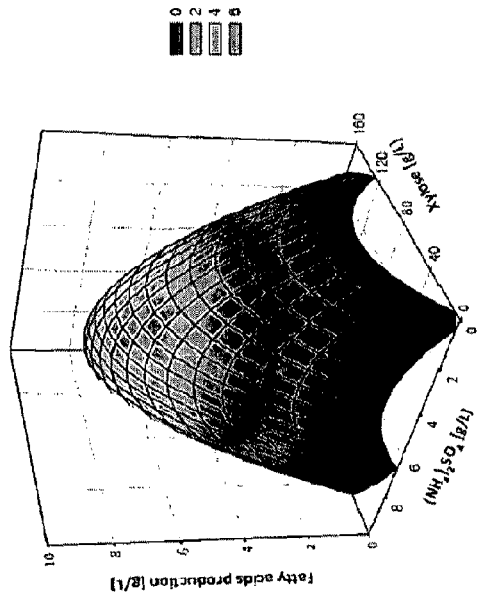
FIG. 46 presents a response surface plot depicting the optimal C/N ratio as determined by applying StatGraphics.
Figure 47:
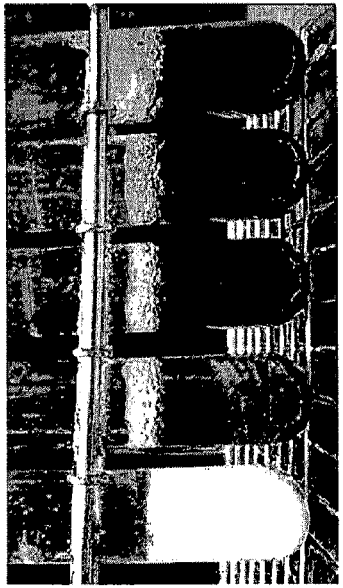
FIG. 47 presents an image of cell cultures during a lignin experiment used to identify an inhibiting effect.

Fatty acid production and fermentation results obtained with the transformants is shown in FIGS. 34 and 35. Fatty acid production and fermentation results obtained with co-metabolism of the transformants is demonstrated in FIGS. 36 and 37. Time course analyses of xylose fermentation, mixed-substrate fermentation and growth of Xsp8 in varying conditions is shown in FIGS. 38-40. Optimization of C/N ratios is presented in FIGS. 42 and 46. FIG. 43 presents an overview of the total fatty acids obtained in fermentations in differing C/N ratios. FIG. 44 demonstrates transformation of a plasmid with xylA and xylB into R. opacus and FIG. 45 demonstrates production of the Xsp8C-retransformants with the plasmid.

Figure 50:
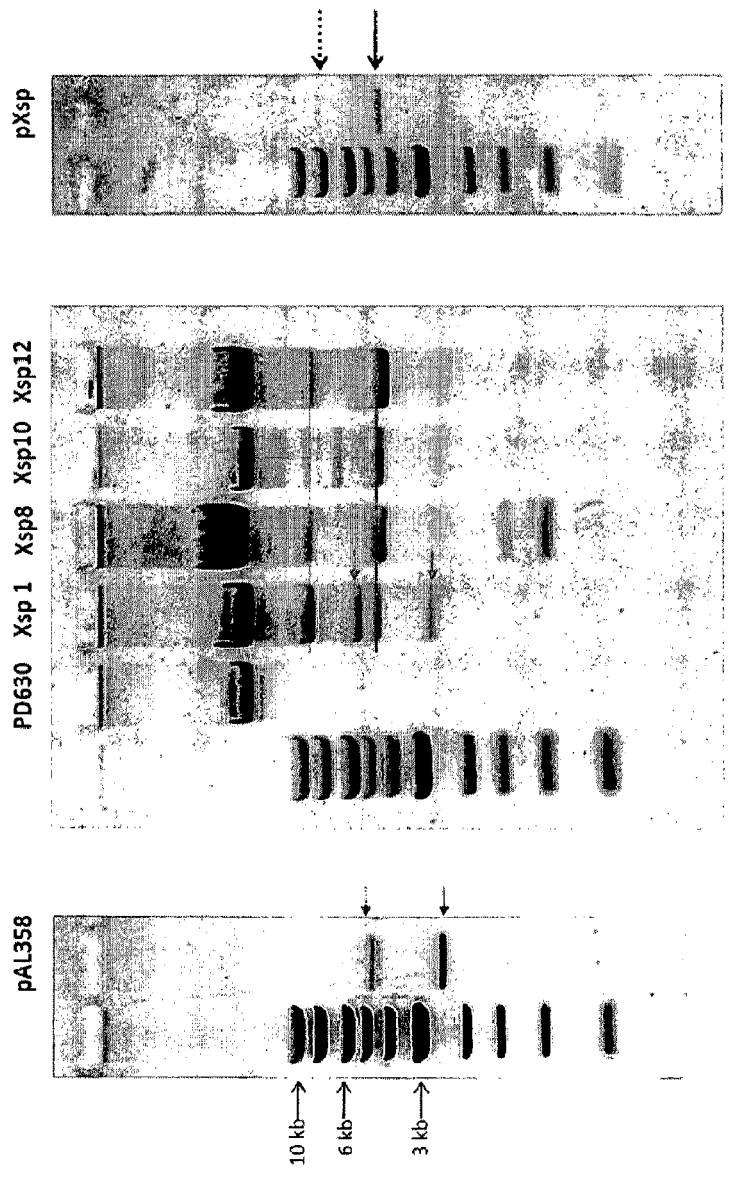
FIG. 50 presents an image of a DNA gel indicating analysis of genomic DNA in *R. opacus* PD630 cells and transformant engineered strains.
Figure 51:
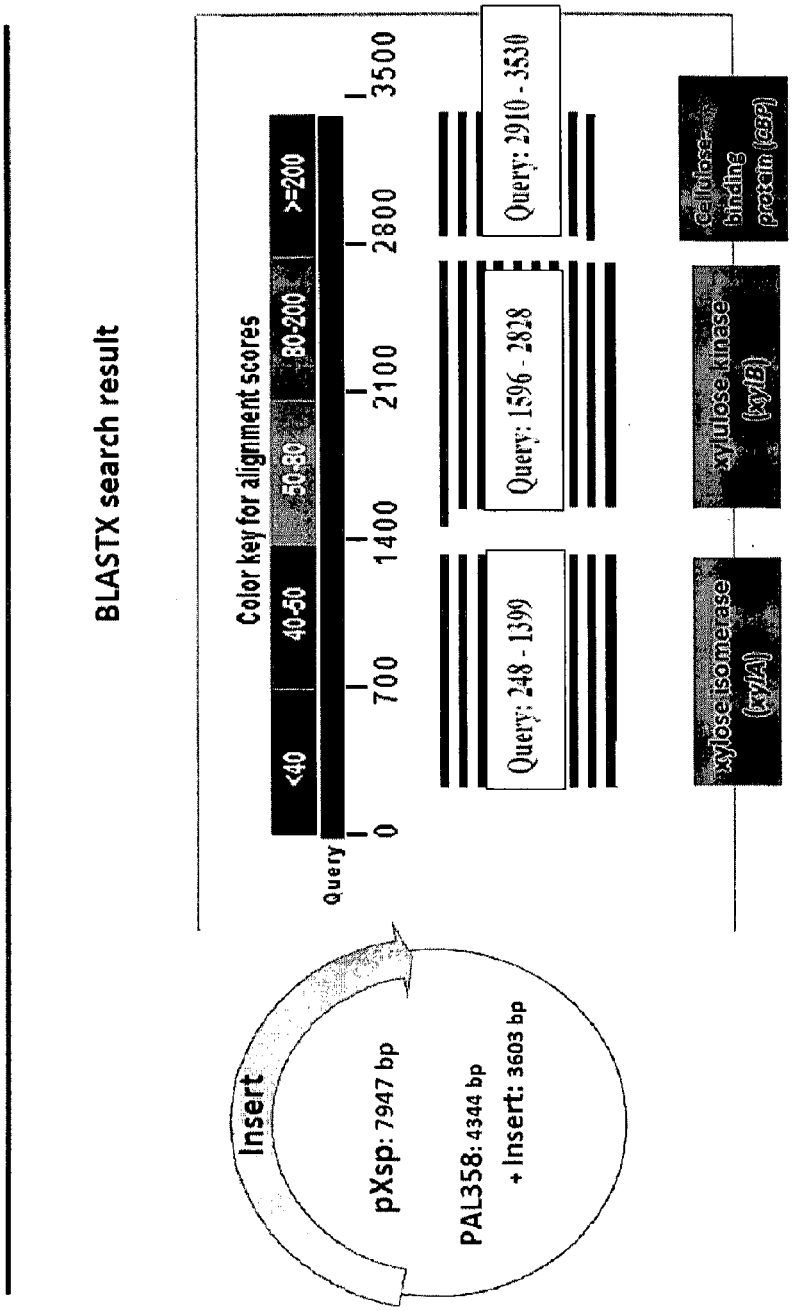
FIG. 51 presents a schematic of the sequence of the insert in the pXsp plasmid.
Figure 52:
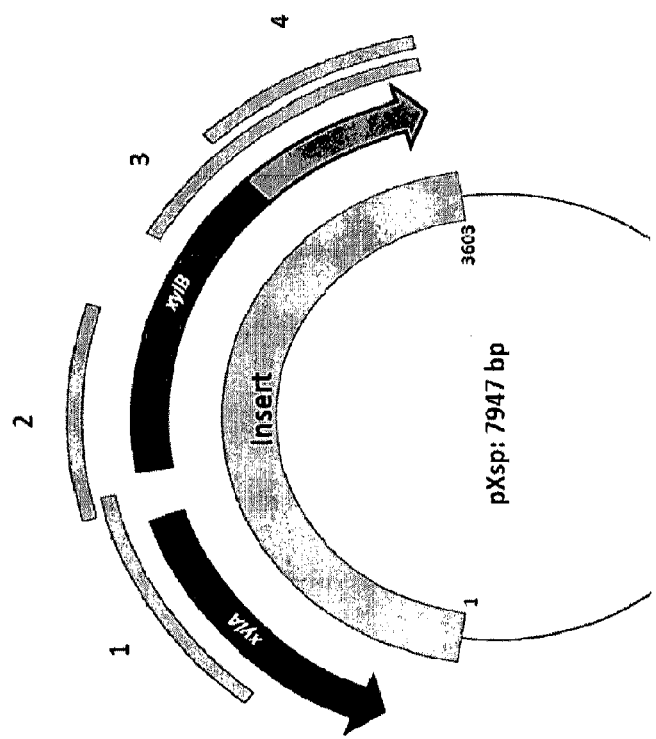
FIG. 52 presents a schematic of the xylA and xylB genes within the insert in the pXsp plasmid.
Figure 53:
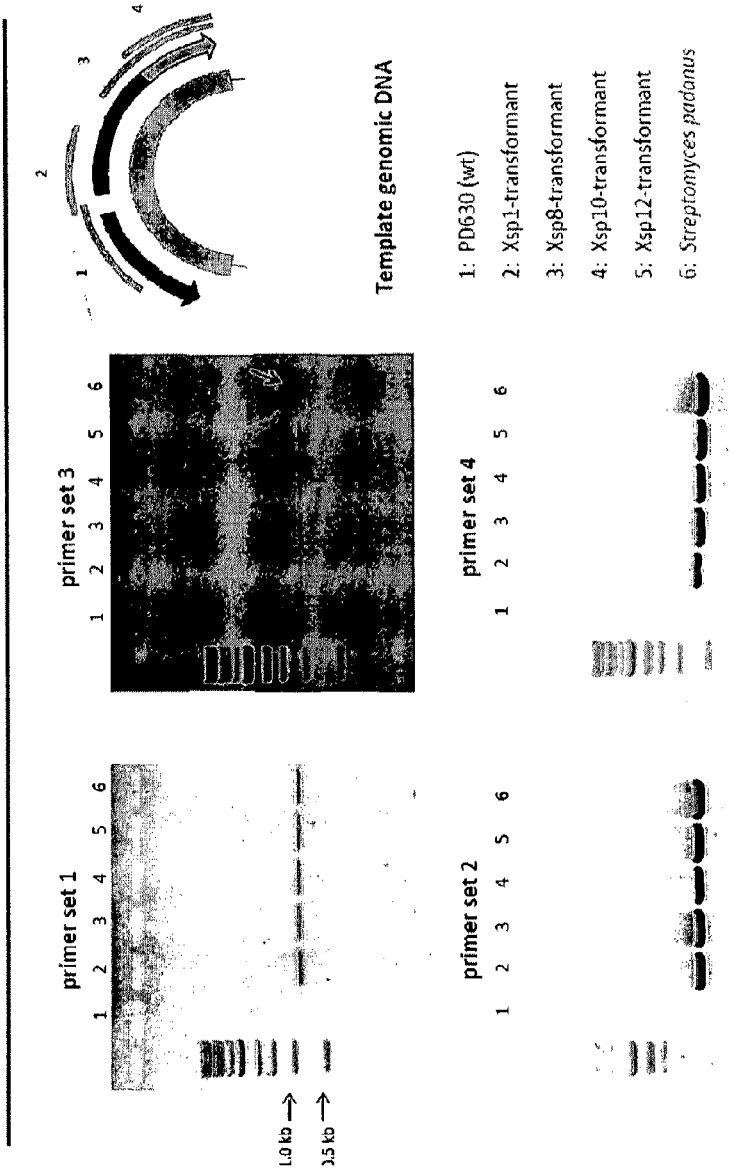
FIG. 53 presents images of gels revealing detection of the xylA and xylB genes by PCR. The location of PCR primer sets 1-4 are indicated in a schematic of the pXsp plasmid.
Figure 54:
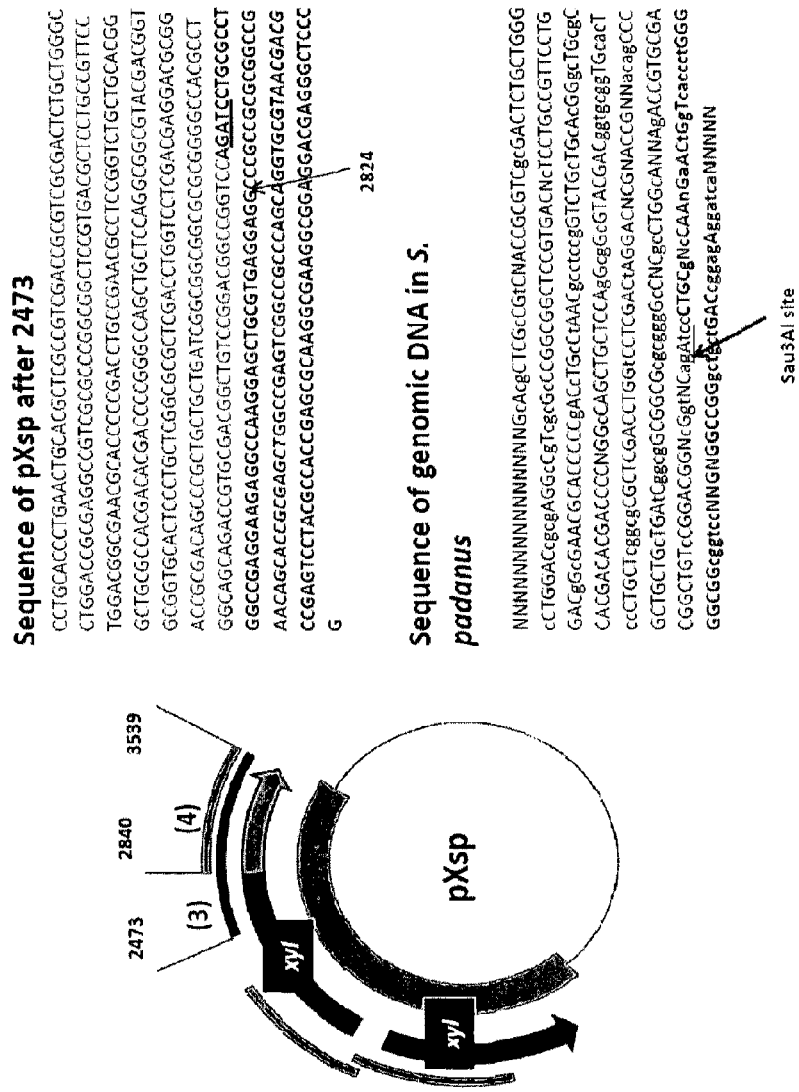
FIG. 54 presents a schematic of the pXsp plasmid containing the xylA and xylB inserts, and sequence data of the xylB gene from the insert revealing that within the pXsp plasmid, a portion of the xylB gene is fused to a different gene. The sequence of pXsp after 2473 is represented by SEQ ID NO:2, while the sequence of genomic DNA in *S. padanus* is represented as SEQ ID NO:3.
Figure 55:
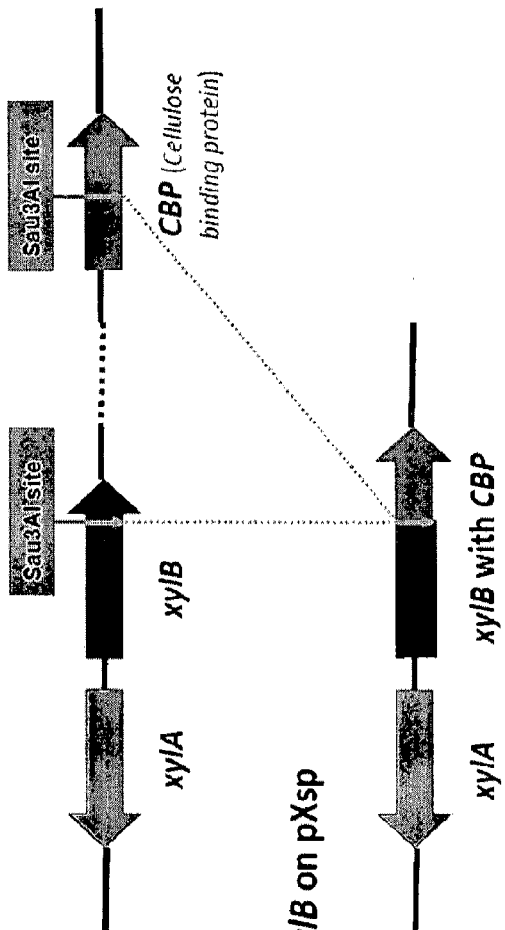
FIG. 55 presents a schematic of the xylB gene and the CBP gene in the *S. padanus* genome and a schematic of a fusion between the xylB gene and the CBP gene in the pXsp plasmid as a result of a recombination event.

FIG. 50 presents an analysis of the genomic DNA in the engineered strains. FIG. 51 describes the sequence of the plasmid insert and FIG. 52 presents an annotation of the sequence insert. FIG. 53 demonstrates detection of xylA and xylB by PCR in transformant strains. FIG. 54 provides sequence data for the plasmid insert and FIG. 55 presents a schematic depicting a recombination event within the insert region.

Genes encoding xylA and xylB were also obtained from S. coelicolor and S. avermitilis and introduced into R. opacus. A combination of xylA from S. coelicolor and xylB from S. avermitilis had the most beneficial effect for growth on xylose as a sole carbon source although the lipid accumulation from xylose was at a low level.

Discussion

Lignocellulosic biomass represents an abundant and cost-effective renewable energy source and a promising candidate as an alternative substrate for the biotechnological production of biodiesel. Lignocellulose hydrolysates include hexoses (glucose, galactose, and mannose), pentoses (xylose and arabinose) and noncarbohydrate polyphenolic compounds (Wiselogel et al. 1996). Despite the fact that typical lignocellulosic carbohydrate fractions are composed primarily of glucose, xylose represents a nonnegligible portion of the sugar fraction of lignocellulosic biomass, as it reaches the 5 to 20% range (Aristidou and Penttilä 2000). The capability to efficiently utilize xylose is a key attribute of microbial converters for optimizing the economics of lignocelluloses-based processes. Several microorganisms have been shown to grow aerobically on xylose, but relatively few wild-type strains can utilize xylose as a fermentable substrate (Jeffries and Jin 2000). Although recent extensive research efforts have been made to develop efficient industrial biotechnological schemes for deriving useful products from lignocelluloses, the bioconversion of xylose remains a limiting step (Willke and Vorlop 2004; Jeffries and Jin 2004).

In Example 1, it was demonstrated that R. opacus PD630 has the rare capability of accumulating large amounts of lipids (triacylglycerols) in a pH control batch-culture containing high glucose concentrations of more than 20% with a critical carbon to nitrogen ratio (Kurosawa et al. 2009). While R. opacus PD630 is unable to catabolize xylose, it holds great potential as a future source of industrial biodiesel derives from renewable biomass resources. In this study, the xylose metabolic pathway in R. opacus PD630 was manipulated by borrowing genes from S. padanus allowing utilization by R. opacus PD630 of xylose as a sole carbon source. One of the engineered strains, Xsp8, grown in a batch-culture including 12% xylose, reached a cell density of 26.9 g $l^{-1}$ CDW with fatty acids content of 43% of the CDW, accounting for 11.7 g of fatty acids per liter after 124 h of cultivation, at which point the residual xylose was almost consumed. These results indicate that lipid production of this strain is similar to that of the wild type R. opacus PD630 grown on glucose under similar conditions. Neither a wild-type strain nor an engineered strain capable of metabolizing xylose at a concentration of more than 10% has been developed previously, to our knowledge, although recent extensive metabolic engineering efforts that improve xylose metabolism for biofuels production have been done (Hahn-Hägerdal et al. 2007; Shaw A J et al. 2008).

In conclusion, demonstrated herein is a successful construction of an R. opacus PD630 transformant, by transferring xylose metabolite genes xylA and xylB from S. padanus, that is capable of efficiently utilizing xylose at high concentrations and accumulating TAGs. Taken together with the demonstration in Example 1 that R. opacus PD630 accumulates TAGs when grown on glucose, this constructed metabolically engineered strain could be the most promising producer in existence for biofuels production from lignocellulosic biomass.

TABLE 4

Analysis of growth and fatty acids production on in R. opacus PD630 transformants

| Strain | Culture $OD_{660}$ | CDW (g/L of culture) | Fatty acids (g/L of culture) | Fatty acids (% CDW) |
|---|---|---|---|---|
| Xsp1 | 10.0 ± 1.8 | 3.7 ± 0.9 | 1.2 ± 0.3 | 32.7 ± 0.6 |
| Xsp8 | 13.6 ± 1.1 | 5.3 ± 0.5 | 2.1 ± 0.5 | 39.0 ± 7.8 |
| Xsp10 | 10.5 ± 0.8 | 4.3 ± 0.2 | 1.2 ± 0.2 | 30.7 ± 3.1 |
| Xsp12 | 12.7 ± 1.1 | 4.9 ± 0.5 | 1.6 ± 0.3 | 32.0 ± 3.6 |

References for Example 2

Alvarez H M, Mayer F, Fabritius D, Steinbüchel A (1996) Formation of intracytoplasmic lipid inclusions by *Rhodococcus opacus* strain PD630. Arch Microbiol 165:377-386

Alvarez H M, Steinbüchel A (2002) Triacylglycerols in prokaryotic microorganisms. Appl Microbiol Biotechnol 60:367-376

Antoni D, Zverlov V V, Schwarz W H (2007) Biofuels from microbes. Appl Microbiol Biotechnol 77:23-35

Aristidou A, Penttilä (2000) Metabolic engineering applications to renewable resource utilization. Curr Opin Biotechnol 11:187-198

Canakci M, Sanli H (2008) Biodiesel production from various feedstocks and their effects on the fuel properties. J Ind Microbiol Biotechnol 35:431-441

Chartrain M, Jackey B, Taylor C, Sandford V, Gbewonyo K, Lister L, Dimichele L, Hirsch C, Heimbuch B, Maxwell C, Pascoe D, Buckland B, Greasham R (1998) Bioconversion of indene to cis (1S,2R) indandiol and trans (1R,2R) indandiol by *Rhodococcus* species. J Ferment Bioeng 86:550-558

Du W, Li W, Sun T, Chen X, Liu D (2008) Perspectives for biotechnological production of biodiesel and impacts. Appl Microbiol Biotechnol 79:331-337

Jeffries T W, Jin Y S (2000) Ethanol and thermotolerance in the bioconversion of xylose by yeasts. Adv Appl Microbiol 47:221-268

Jeffries T W, Jin Y S (2004) Metabolic engineering for improved fermentation of pentoses by yeasts. Appl microbiol Biotechnol 63:495-509

Hahn-Hägerdal B, Karhumaa K, Jeppsson M, Gorwa-Grauslund M F (2007) Metabolic engineering for pentose utilization in *saccharomyces cerevisiae*. Adv Biochem Eng Biotechnol 108:147-177

Hu Q, Sommerfeld M, Jarvis E, Ghirardi M, Posewitz M, Seibert M, Darzins A (2008) Microalgal triacylglycerols as feedstocks for biofuel production: perspectives and advances. Plant J 54:621-639

Kurosawa K, Bui V P, VanEssendelft J L, Willis L B, Lessard P A, Ghiviriga I, Sambandan T G, Rha C K, Sinskey A J (2006) Characterization of *Streptomyces* MITKK-103, a newly isolated actinomycin X2-producer. Appl Microbiol Biotechnol 72:145-154

Kurosawa K, Boccazzi P, Almeida N D, Sinskey A J (2009) High glucose cultivation of *Rhodococcus opacus* PD630 in batch-culture for biodiesel production. Appl Microbiol Biotechnol: preparation Li Q, Du W, Liu D (2008) Perspectives of microbial oils for biodiesel production. Appl Microbiol Biotechnol 80:749-756

Park E Y (2004) Recent progress in microbial cultivation techniques. Adv Biochem Eng Biotechnol 90:1-33

Riesenberg D, Guthke R (1999) High-cell-density cultivation of microorganisms. Appl Microbiol Biotechnol 51:422-430

Sambrook J, Russell D W (2001) Molecular Cloning: A laboratory Manual, third ed. Cold Spring Harbor Laboratory Press, Cold Spring Harbor, N.Y.

Shaw A J, Podkaminer K K, Desai S G, Bardsley J S, Rogers S R, Thorne P G, Hogsett D A, Lynd L R (2008) Metabolic engineering of a thermophilic bacterium to produce ethanol at high yield. Proc Natl Acad Sci USA 105:13769-13774

Shining E B, Gottlieb D (1969) Methods for characterization of *Streptomyces* species. Int J Syst Bacteriol 16:313-340

Stein K (2007) Food vs biofuel. J Am Diet Assoc 107:1870-1878

Tollefson J (2008) Energy: not your father's biofuels. Nature 451:880-883

Vasudevan P T, Briggs M (2008) Biodiesel production—current state of the art and challenges. J Ind Microbiol Biotechnol 35:421-430

Voss I, Steinbüchel A (2001) High cell density cultivation of *Rhodococcus opacus* for lipid production at a pilot-plant scale. Appl Microbiol Biotechnol 55:547-555

Wältermann M, Luftmann H, Baumeister D, Kalscheuer R, Steinbüchel A (2000) *Rhodococcus opacus* strain PD630 as a new source of high-value single cell oil? Isolation and characterization of triacylglycerols and other storage lipids. Microbiology 146: 1143-1149

Willke T, Vorlop K D (2004) Industrial bioconversion of renewable resources as an alternative to conventional chemistry. Appl Microbiol Biotechnol 66:131-142

Wiselogel A, Tyson S, Johnson D (1996) Biomass feedstock resources and composition. Taylor & Francis, Washington, D.C.

Example 3

Glycerol Utilization by *Rhodococcus opacus* for the Production of Biofuels

Biodiesel production in the United States has increased dramatically from 500,000 gallons in 1999 to 70 million gallons in 2005 (National Biodiesel Board, 2006). Synthesis of biodiesel from plant oil has led to the production of large quantities of glycerol. As world production of biodiesel is increasing exponentially, large quantities of low cost glycerol that could be used as a substrate for bioprocesses will be available. Growth of microorganisms such as *Rhodococcus* on renewable carbon sources and waste streams has the potential to produce oils, fatty acids, aldehydes, and alcohols. Described herein is the use of the microorganism *Rhodococcus opacus* to convert glycerol into longer chain fatty acids, primarily as triacyl glycerols (TAGs).

*Rhodococcus erythropolis* AN12 (*R. erythropolis* AN12) typically stores carbon as TAGs, which constitute approximately 30-70% of the cell dry weight. TAG-accumulating strains of *R. erythropolis* AN12 can grow well in culture media containing 4% (v/v) glycerol.

A series of mutants of *R. opacus* PD630 that could accumulate up to 76% of their cell dry weight in the form of TAGs when grown on gluconate has been developed previously (Waltermann et al. Microbiology 2000, 146:1143-9; Waltermann et al., FEMS Microbiol Lett 2000, 190:45-50). Therefore, *R. opacus* PD630 is a potentially useful microorganism because it accumulates as much as or more than 70% of its cell dry weight as oil (TAGs). However although this strain utilizes glucose and other carbon sources for growth, it does not utilize glycerol as sole carbon source.

Described herein is the construction of a plasmid that allows R. opacus PD630 to grow on glycerol as a sole carbon source. This was achieved through the expression of a plasmid in R. opacus PD630 cells. The plasmid was constructed by ligating a library of R. erythropolis AN12 genome fragments, obtained by partial restriction digestion, into the plasmid pAL358 which carries a gentamycin resistance cassette and an origin of replication that allows propagation in R. opacus PD630. The library of plasmids obtained were transformed into R. opacus PD630 cells that were then plated on defined medium plus gentamycin and glycerol as the sole carbon source to select for strains that would gain the function of growing on glycerol. A plasmid was obtained, pPB80, the expression of which allowed R. opacus PD630 to grow on glycerol. Sequencing of the 4,302 bp DNA fragment of R. erythropolis AN12 present in the plasmid revealed the presence of two genes: glycerol kinase (glpK) and glycerol-3-phosphate dehydrogenase (g3pdh) that allow R. opacus PD630 to grow on glycerol as a sole carbon source.

Materials and Methods

Figure 58:
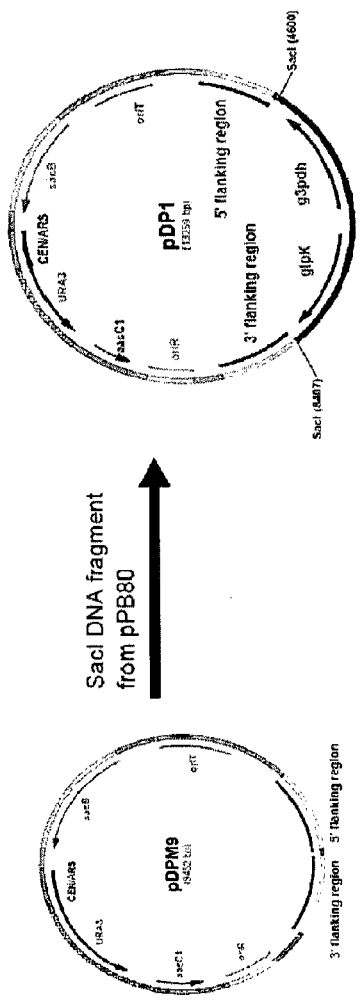
FIG. 58 presents a schematic depicting construction of the pDP1 plasmid and integration of glpK and g3pdh onto the *R. opacus* chromosome via homologous recombination.

Construction of the Integration Vector pDPM9 (FIG. 58)

In order to integrate foreign genes into the R. opacus PD630 genome, a neutral integration site was sought. BLAST homology searches identified a putative penP gene homolog, predicted to encode a beta-lactamase, within the R. opacus chromosome. Theoretically, deletion of the penP gene from the chromosome would have no effect on triacylglycerol production in this strain. Primers penP-1 and penP-2 were designed to amplify a 1 kb region from the R. opacus PD630 genome immediately 5' of the penP gene while primers penP-3 and penP-4 were designed to amplify a 1 kb region from the chromosome immediately 3' of the penP gene. Additionally, primers penP-2 and penP-3 were designed to insert a multiple cloning site (MCS) between the two amplified regions. The resulting amplicons were cloned into the vector pMQ30 (Shanks et al, 2006) using the previously described gap repair method (Shanks et al, 2006). The resulting plasmid, pDPM9, is a Sacharomyces cerevisiae/Escherichia coli shuttle vector incapable of replicating in R. opacus PD630, which expresses the aacC1 gene, encoding an gentamycin acetyl-transferase, hence according gentamycin resistance to the host strain. Additionally, this plasmid contains the mob element allowing for efficient conjugal transfer of the plasmid from a RP4 positive donor strain to a suitable recipient strain.

Construction of the Glycerol Integration Vector pDP1 (FIG. 58)

As described above, the integration vector pDPM9 is designed to integrate into the R. opacus PD630 genome at the penP locus, and contains a MCS between the penP flanking regions allowing for facile insertion of genes of interest into the integration vector and hence into the penP locus in the R. opcaus PD630 chromosome. Accordingly, the glpK and g3pdh genes were cloned from the plasmid pPB80 into pDPM9 using the restriction endonuclease SacI, inserting the glpK and g3pdh genes into the MCS of pDPM9, creating the plasmid pDP1.

Conjugal Transfer of pDP1 to R. opacus PD630

Conjugal transfer was used to introduce the pDP1 suicide vector into the R. opacus PD630 strain using standard techniques (Caiazza et al, 2004) except that the donor strain E. coli WM3064 was utilized instead of E. coli S17-1. Essentially, the plasmid pDP1 was transformed into the donor strain E. coli WM3064. The resulting diaminopimelic acid (DAP) auxotroph strain was grown in lysogeny broth (LB) (Bertani G, 2004) supplemented with DAP and gentamycin and then mixed with WT R. opacus PD630 cultures grown in LB at several ratios. Mixed cultures were then spotted on UV irradiated nitrocellulose filters and allowed to dry before placing on solid LB medium supplemented with 10 mM MgCl2 and 50 µM DAP. Conjugal matings were incubated at 30° C. for 24 hours. The nitrocellulose discs were then submerged in liquid LB medium and vortex vigorously to resuspend the bacteria. The bacteria were then washed two times in LB medium to remove any remaining DAP. Following washing, the bacteria were plated on solid medium rare supplemented with 0.15% $NH_4SO_4$, 2% glycerol and 10 µg/ml gentamycin and incubated at 30° C. for 3-5 days.

Total Fatty Acids Production by R. opacus Strains with Potential Chromosomal Integration of glpK and g3pdh Approximately 5 mg (+/−0.1 mg) of lyophilized cell pellets were weighed and resuspended in 2 mL of 1:1 $C_HCl_3$:MeOH. The sample was filtered through a 0.2 µm filter and 10 ul was spotted onto a 10×20 cm Silica TLC plate. The sample was developed with 70:30:1 Hexane:Diethyl Ether:Acetic Acid. After drying, the plate was sprayed with an aqueous cupriacetate/phosphoric acid solution and then charred at ~200° C. An image was taken in a gel box, then cropped and re-sized using Photoshop. Densitometry of TAG spots was performed using ImageJ software.

Results

Figure 56:
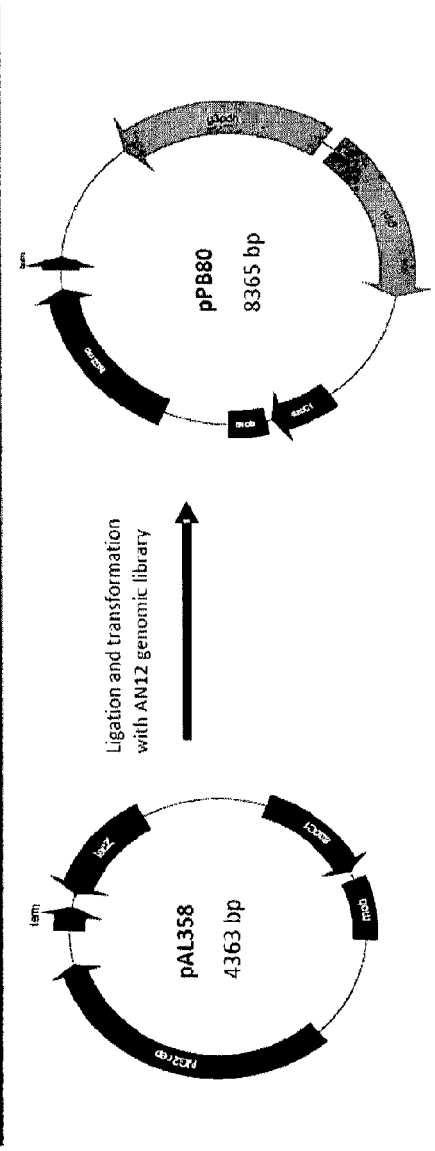
FIG. 56 depicts a schematic of the pAL358 plasmid and the pPB80 plasmid. Plasmid pAL358 carries the NG2 rep, which enables replication in both *E. coli* and *Rhodococcus* (Treadway et al., *Appl Microbiol Biotechnol* 1999, 51(6):786-93), RP4 mob, which enables transfer of the plasmid from suitable *E. coli* hosts to other bacteria, such as *Rhodococcus* via conjugation; and aacC1, which confers resistance to the antibiotic gentamycin. Plasmid pPB80 was constructed by cloning a 4,302 bp DNA fragment from a Sau3AI restriction digestion of *Rhodococcus erythropolis* AN12 chromosomal DNA into the BamHI site of pAL358.

It was hypothesized herein that some genes that enable R. erythropolis AN12 to grow in culture media containing 4% (v/v) glycerol could be transferred to the high TAG accumulating strain R. opacus PD630 so that this Rhodococcus strain could grow also on glycerol. To do this, a library of plasmids was constructed that contained DNA fragments of R. erythropolis AN 12 bp cloning a partial restriction digest of the chromosome of this organism into the plasmid pAL358 (FIG. 56). This plasmid carries a gentamycin resistance cassette and an origin of replication that allows propagation in R. opacus PD630.

R. erythropolis AN12 chromosomal DNA was digested for 25 minutes with the enzyme Sau3AI and cloned into a BamHI and gel-band purified pAL358. The library of plasmid thus obtained was then transformed into R. opacus PD630 and the transformed cells were then plated onto defined medium containing glycerol as sole carbon source and gentamycin. From this experiment several colonies were obtained; one R. opacus PD630 strain showed good growth on glycerol and was thus named RoGA, for R. opacus glycerol growing clone A. Plasmid isolation from this strain yielded the plasmid pPB80 of 8665 bp. Sequencing of the 4302 bp insert revealed that this DNA fragment contained two open reading frames which have high similarity to the glycerol 3 phosphate dehydrogenase (g3pdh) and glycerol kinase (glpK) genes of R. sp. RHA1 (FIG. 56).

Figure 59:
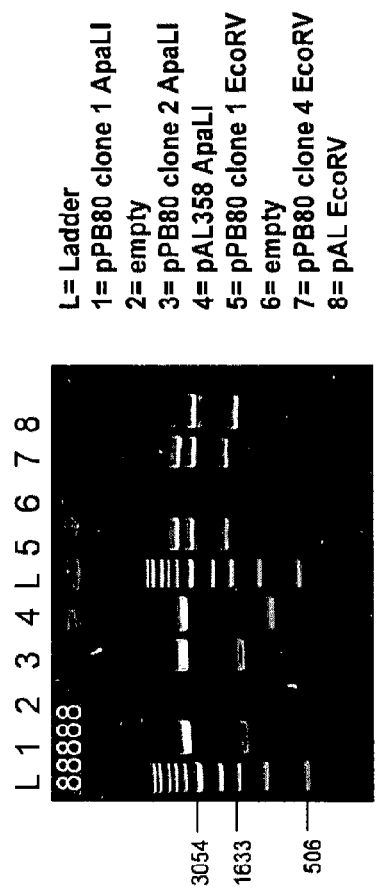
FIG. 59 presents a table and an image of a gel depicting ApaLI and RcoRV restriction digests of plasmids pPB80 and pAL358.

Upon obtaining the entire sequence of this plasmid, the composition of the plasmid was confirmed by restriction digestion analysis. Plasmid pAL358, used as a control, and plasmid pPB80 were digested with the restriction enzymes ApaLI and EcoRV and the expected restriction patterns are shown in FIG. 59. After restriction digest, samples of each digest were run on a 1% TAE gel and the results of the gel electrophoresis are shown in FIG. 59.

As confirmation, R. opacus PD630 was transformed with pAL358 and pPB80 and the cells were plated on defined medium containing gentamycin and glycerol as the sole carbon source. After 4 days of incubation at 30° C., plates that received R. opacus PD630 with pPB80 had well-defined colonies while plates that received R. opacus PD630 with pAL358 had very small colonies that once transferred into glycerol medium did not supported growth.

To confirm growth of strain R. opacus PD630 transformed with plasmid pPB80 (Strain RoGA) on glycerol, an experiment was conducted to determine TAG accumulation on glycerol, glucose and gluconate. Strain RoGA was cultured in 250 ml flasks on a rotary shaker operating at 200 rpm at 30° C. for 4 days in defined medium containing 1% (w/v) of different carbon sources and 0.07% (w/v) of $(NH_4)_2SO_4$. After 2 days of culture, an additional 2% (w/v) of different carbon sources were added to the cultures. After 4 days of culture, fatty acids that had accumulated were analyzed with a methanolysis protocol.

Results of this growth experiment (Table 5) show that R. opacus PD630 transformed with plasmid pPB80 that carries the g3pdh and glpK genes of R. erythropolis AN12 gains the ability to grow in defined medium containing glycerol as the sole carbon source to an OD of 4, and that some of the glycerol is transformed and stored as fatty acids. FIG. 57 summarizes total fatty acid production of R. opacus PD630 transformed with pPB80.

Figure 60:
FIG. 60 presents an image of a gel and a table depicting TAG production in six potential integrant strains in medium containing glycerol as the sole carbon source.
Figure 61:
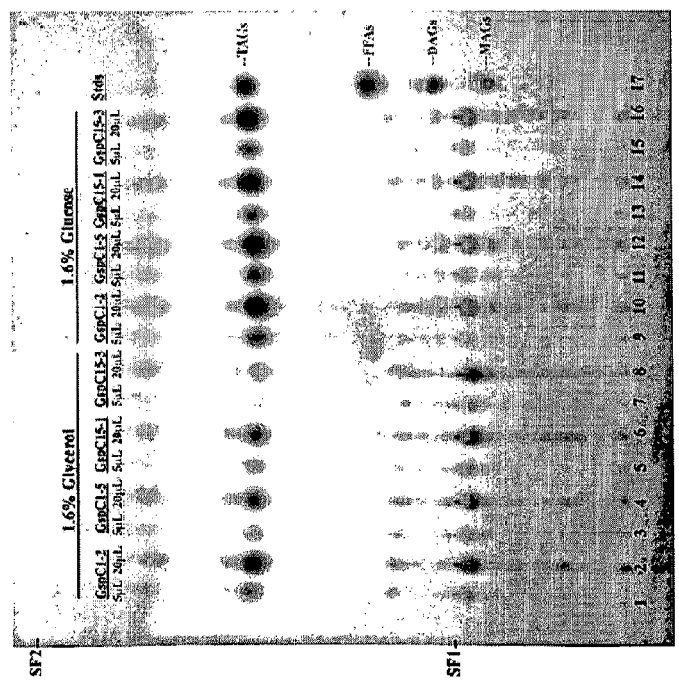
FIG. 61 presents an image of a gel depicting TAG production by *R. opacus* GspC transformants analyzed by thin-layer chromatography.
Figure 63:
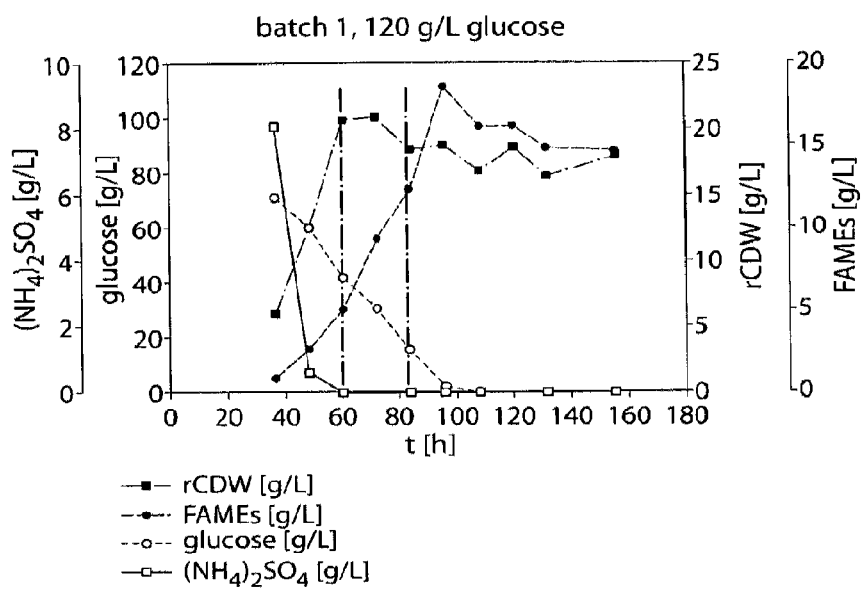
FIG. 63 presents a graph revealing fatty acid yield in *R. opacus* during TAG accumulation.

FIG. 60 summarizes TAG production by R. opacus glpK and g3pdh potential integrants. FIG. 61 shows TAG production by R. opacus GspC transformants analyzed by thin-layer chromatography. FIG. 62 demonstrates lipid accumulation in R. opacus GspC transformants analyzed by GC FAME. FIG. 63 reveals fatty acid yield in R. opacus during TAG accumulation. FIG. 64 demonstrates the fatty acid composition profile growing in the optimal conditions.

TABLE 5

FA production of R. opacus PD630 transformed with pPB80 (strain RoGA) on different carbon sources

| Initial carbon 1% | Bolus carbon 2% | Culture Days | Broth (pH) | ($OD_{660}$) | DCM (g/L) | Fatty acid production (g/L) | (% DCM) |
|---|---|---|---|---|---|---|---|
| RoGA | | | | | | | |
| Glycerol | Glycerol (after 2 days) | 4 | 6.7 | 3.9 | 1.0 | 0.1 | 8 |
| Glucose | Glycerol (after 2 days) | 4 | 6.5 | 10.5 | 4.0 | 0.9 | 23 |
| Gluconate | Glycerol (after 2 days) | 4 | 8.3 | 9.4 | 4.0 | 1.1 | 27 |
| Gluconate | Gluconate (after 2 days) | 4 | 8.8 | 7.6 | 4.0 | 1.7 | 42 |

Example 4

Multi-Phase (Fed Batch) Fermentations for Production and Harvest of Lipid Bodies from *Rhodococcus*

Figure 65:
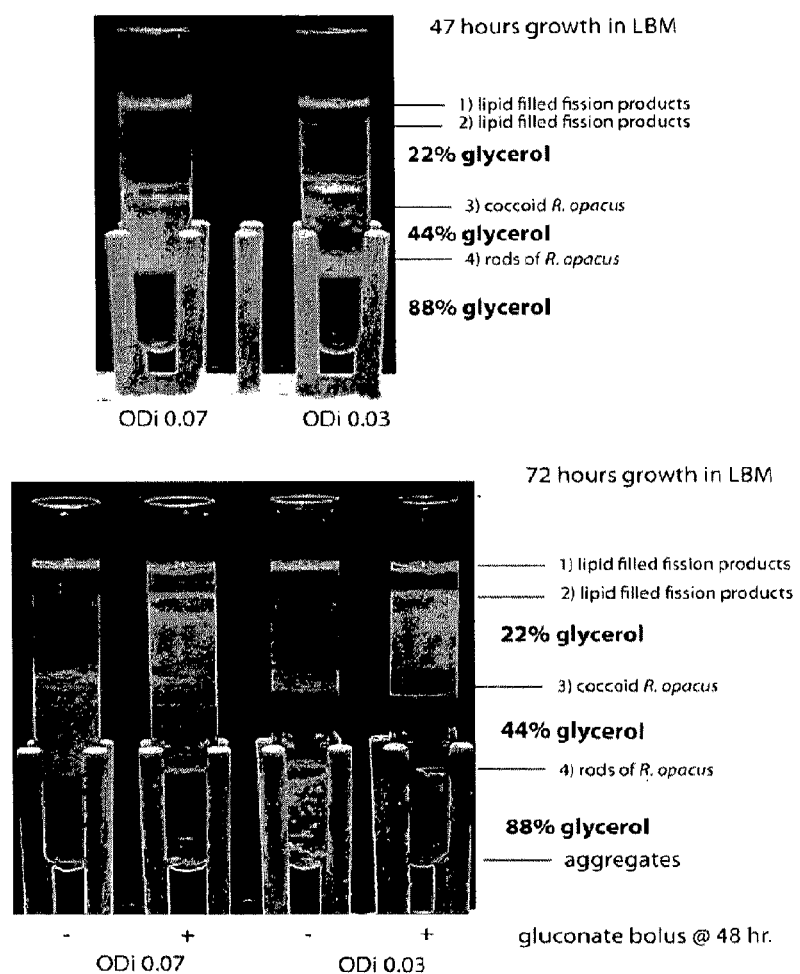
FIG. 65 presents glycerol step gradients demonstrating that bolus addition of gluconate drives the production of lipid filled fission products.
Figure 66:
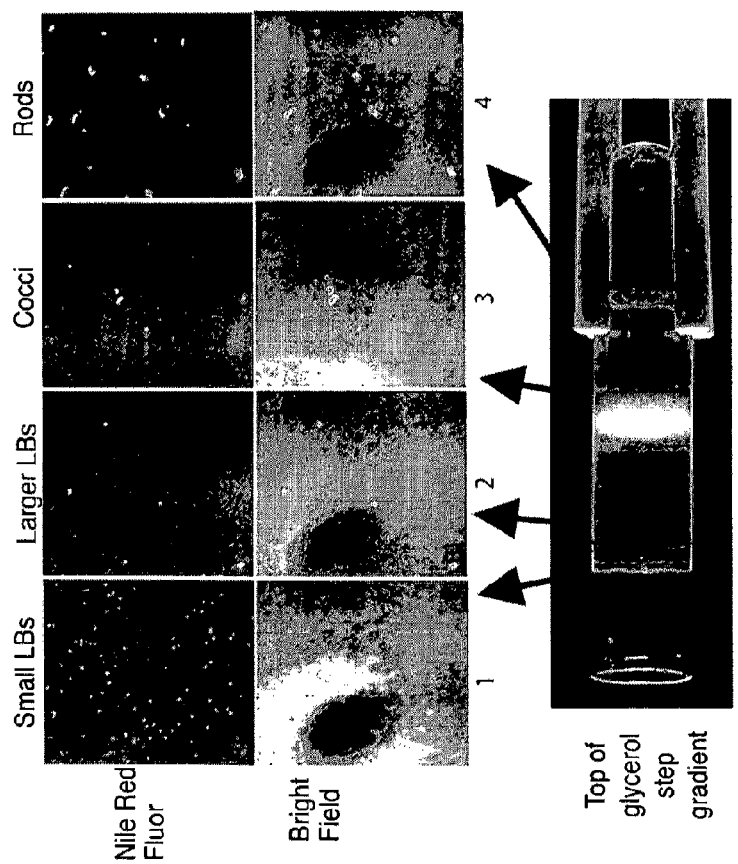
FIG. 66 presents fluorescence images of a glycerol gradient. Fractions from glycerol gradients were analyzed by fluorescence microscopy showing that smaller lipid filled fission products purified at the top of the glycerol step gradient.
Figure 67:
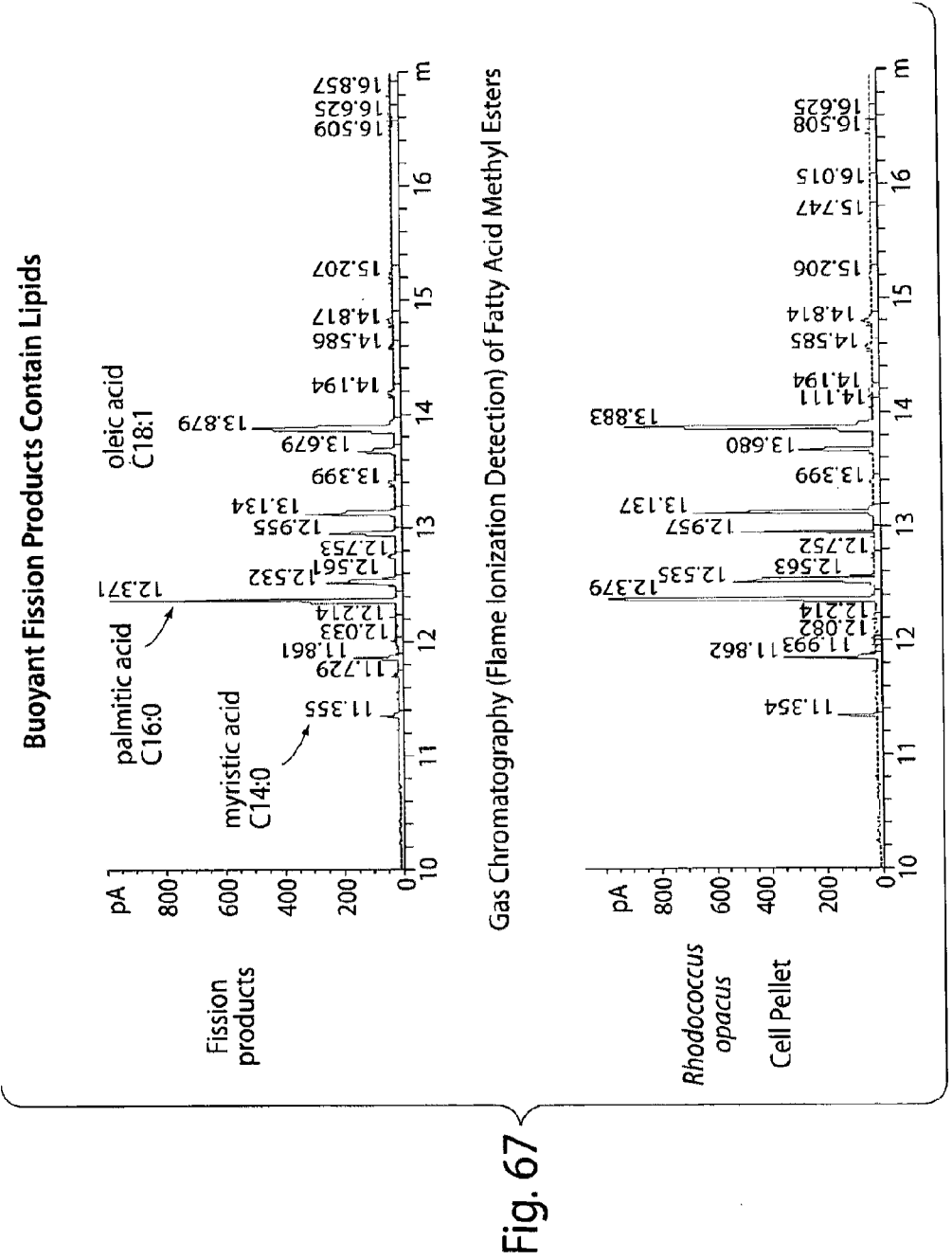
FIG. 67 presents Fatty Acid Methyl Esters (FAMEs) analyzed by gas chromatography.

The addition of sugar (gluconate) late in the growth of R. opacus PD630 led to an increase in lipid filled fission products that could be separated via density-gradient separations (FIG. 65). The lipid contents of these fission products were confirmed both microscopically using the lipophilic dye Nile Red (FIG. 66) and chemically by gas chromatography of Fatty Acid Methyl Esters (FAMEs) (FIG. 67).

Figure 68:
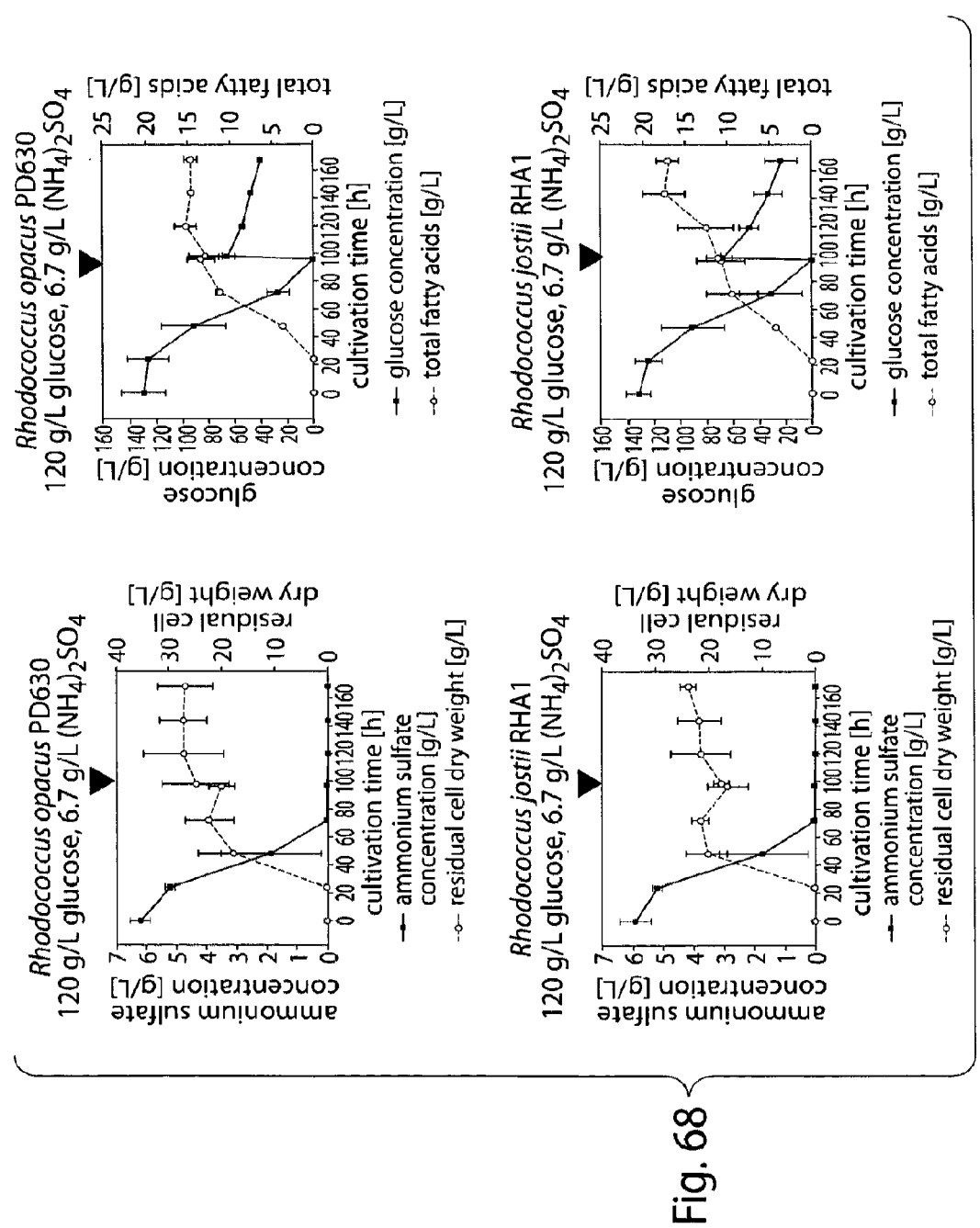
FIG. 68 presents graphs depicting analysis of fermentations comparing *Rhodococcus opacus* PD630 and *Rhodococcus jostii* RHA1 when grown in 120 g l$^{-1}$ glucose containing defined media with 1:17.9 G:G ammonium sulfate:glucose were fed 60 g l$^{-1}$ additional glucose (black triangle) after 96 hours of fermentation. Ammonium in the culture medium was measured using an enzyme assay with quantification standards. Residual Cell Dry Weight (rCDW) was determined as the Cell Dry weight—the lipid mass measured as Fatty Acid Methyl Esters. Consumption of glucose was determined by quantification of media after cells were removed by centrifugation using an HPLC assay. These values were presented as the average of 3 fermentations for each species.
Figure 69:
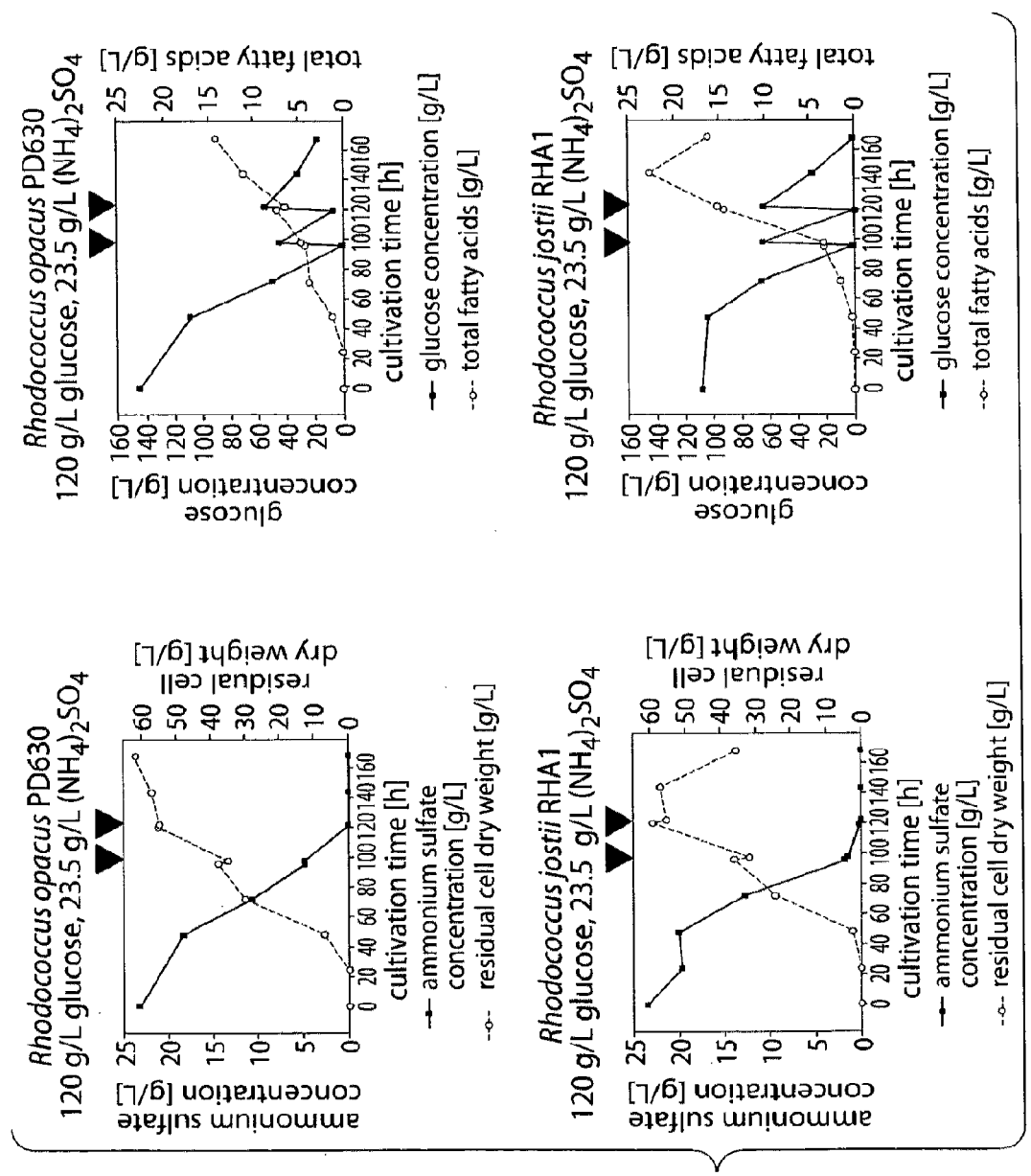
FIG. 69 presents graphs depicting analysis of fermentations comparing *Rhodococcus opacus* PD630 and *Rhodococcus jostii* RHA1 when grown in 120 g l$^{-1}$ glucose containing defined media with 1:5.1 G:G ammonium sulfate:glucose were fed 60 g l$^{-1}$ additional glucose (black triangle) after 96 and 120 hours of fermentation. Ammonium in the culture medium was measured using an enzyme assay with quantification standards. Residual Cell Dry Weight (rCDW) was determined as the Cell Dry weight—the lipid mass measured as Fatty Acid Methyl Esters. Consumption of glucose was determined by quantification of media after cells were removed by centrifugation using an HPLC assay.
Figure 70:
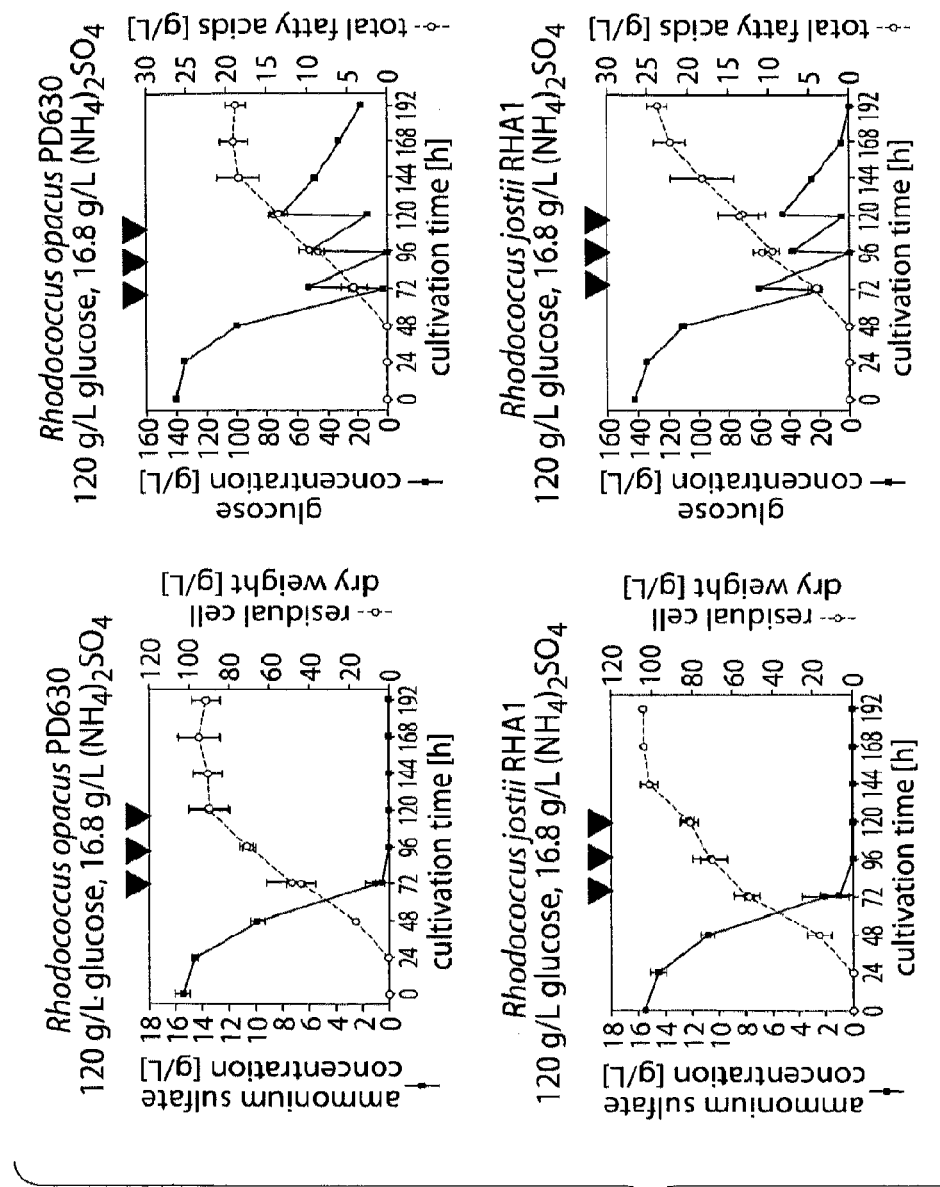
FIG. 70 presents graphs depicting analysis of fermentations comparing *Rhodococcus opacus* PD630 and *Rhodococcus jostii* RHA1 when grown in 120 g l$^{-1}$ glucose containing defined media with 7.1:1 G:G ammonium sulfate:glucose were fed 60 g l$^{-1}$ additional glucose (black triangle) after 72, 96, and 120 hours of fermentation. Ammonium in the culture medium was measured using an enzyme assay with quantification standards. Residual Cell Dry Weight (rCDW) was determined as the Cell Dry weight—the lipid mass measured as Fatty Acid Methyl Esters. Consumption of glucose was determined by quantification of media after cells were removed by centrifugation using an HPLC assay.
Figure 71:
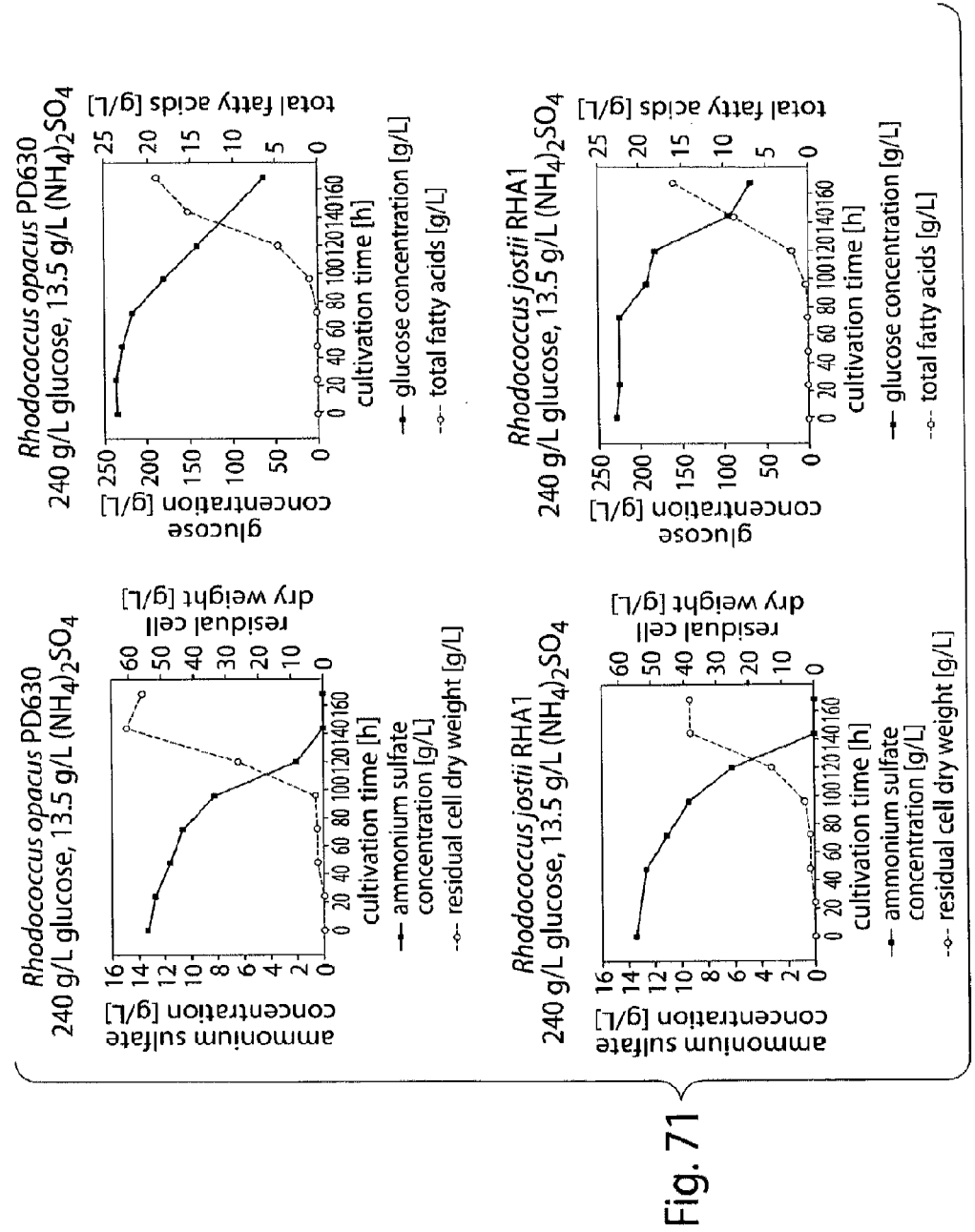
FIG. 71 presents graphs depicting analysis of fermentations comparing *Rhodococcus opacus* PD630 and *Rhodococcus jostii* RHA1 when grown in 240 g l$^{-1}$ glucose containing defined media with 1:17.9 G:G ammonium sulfate:glucose. Ammonium in the culture medium was measured using an enzyme assay with quantification standards. Residual Cell Dry Weight (rCDW) was determined as the Cell Dry weight—the lipid mass measured as Fatty Acid Methyl Esters. Consumption of glucose was determined by quantification of media after cells were removed by centrifugation using an HPLC assay.

The impact of bolus addition of glucose, a cellulosic sugar, late in fermentations was addressed under optimal (FIG. 68) or high Nitrogen:Carbon (N:C) ratio for both *Rhodococcus opacus* PD630 and *Rhodococcus jostii* RHA1 (FIG. 69). This approach yielded 4 major advantages over single-phase fermentations: 1) increased lipid yields, 2) increase in purity, 3) decrease in retention time in fermenter when compared to single phase high glucose fermentations (FIGS. 70 and 71) and 4) ease of separation of lipid products from viable cells by buoyant density separation.

In multiple sets of experiments, R. jostii RHA1 was found to have a more robust conversion of glucose after fed-batch feeding in both optimal and high N:C ratio fermentations. These multi-phase fermentations demonstrate an important proof of principle that the biomass of *Rhodococcus* retains significant catalytic activity for the biosynthesis of storage lipids long after free ammonium has disappeared from the culture medium. Late in fermentations, the residual dry cell weight that is defined by (dry cell weight-lipid fraction) indicates that the cells are turning over their intracellular contents to facilitate the production of storage lipids; thus yielding more carbon pure biomass.

Feeding fermentations of *Rhodococcus* grown in optimal N:C ratio at 96 hours indicated that the glucose had been consumed between 72 and 96 hours. The glucose-starved cell mass began to degrade itself, as seen by a decrease in residual cell dry weight (FIG. 68). These studies indicate that feeding glucose to cultures grown in this way at 72 hours would result in a more robust response as the cells will not change their physiologic state so dramatically as occurs upon starvation, but will instead continue to convert sugar into high level of storage lipids such as triacylglycerols.

Fermentations of *Rhodococcus* that were fed glucose at 72 hours prevented the observed decrease in residual cell dry weight with the 96 hour feedings. The positive benefit of earlier feeding resulted in linear increases in lipid production from 48 to 144 hours for R. opacus PD630 and from 48 to 168 hours for R. jostii RHA1. The nitrogen source ammonium in the defined media used for fermentations was largely consumed by 72 hours for both species. Upon nitrogen depletion in the growth media, the *Rhodococcus* strains had generated ~25% for R. opacus PD630 and ~20% for R. jostii RHA1 of the final lipid mass, indicating substantial enzymatic activity after the nitrogen had been consumed. The residual cell dry weight continued to increase to 120 hours for R. opacus PD630 and 144 hours for R. jostii RHA1. Once the plateau of increasing residual cell dry weight had been reached, the cell mass still contained significant enzymatic activity extending for 24 hours for R. opacus PD630; whereas R. jostii RHA1 continued to produce lipids for 48 hours and was interrupted by consumption of all available glucose totaling 300 g $l^{-1}$. These fermentations with feeding of glucose prior to glucose starvation indicate a substantial decrease in the residence time in the fermenter as R. jostii RHA1 was able to consume 300 g $l^{-1}$ of sugar in just over 168 hours whereas previous single phase fermentations had not consumed 240 g $l^{-1}$ sugar by 168 hours.

Example 5

Controlled Cell Weakening for Release of Lipid Bodies from *Rhodococcus*

Figure 72:
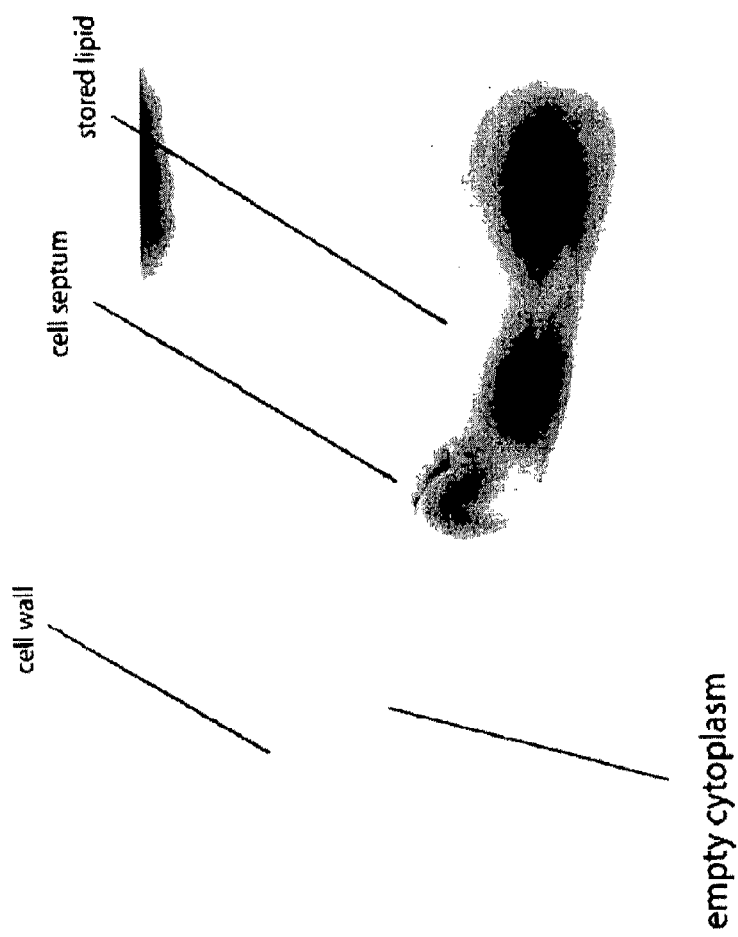
FIG. 72 presents time-lapse fluorescence-microscopy images showing weakening of cell walls following nitrogen starvation.
Figure 73:
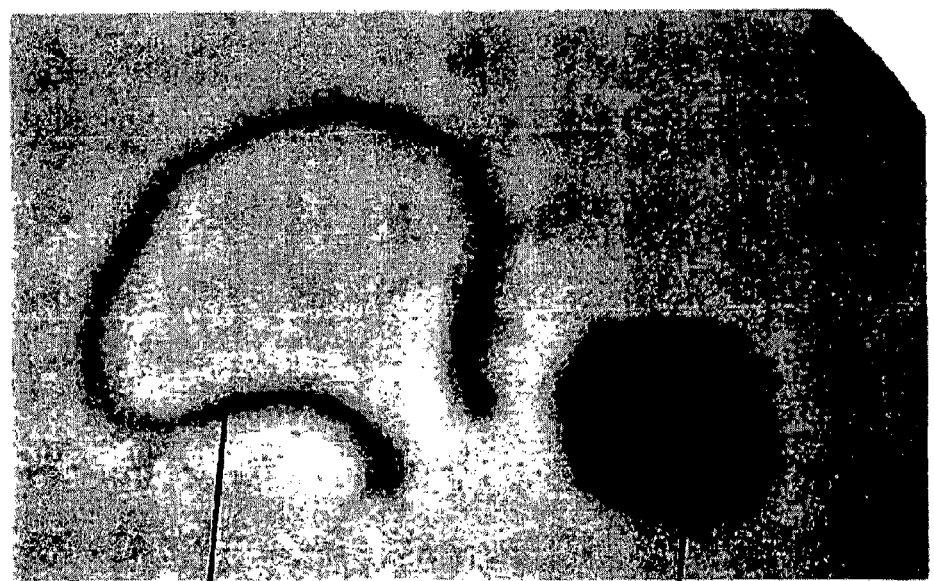
FIG. 73 presents electron-microscopy images showing weakening of cell walls following nitrogen starvation. Cells grown under conditions of storage lipid biosynthesis show emptying of intracellular contents are seen with transmission electron microscopy after metal staining of polyanions (black) and thin sectioning of biological samples.
Figure 74:
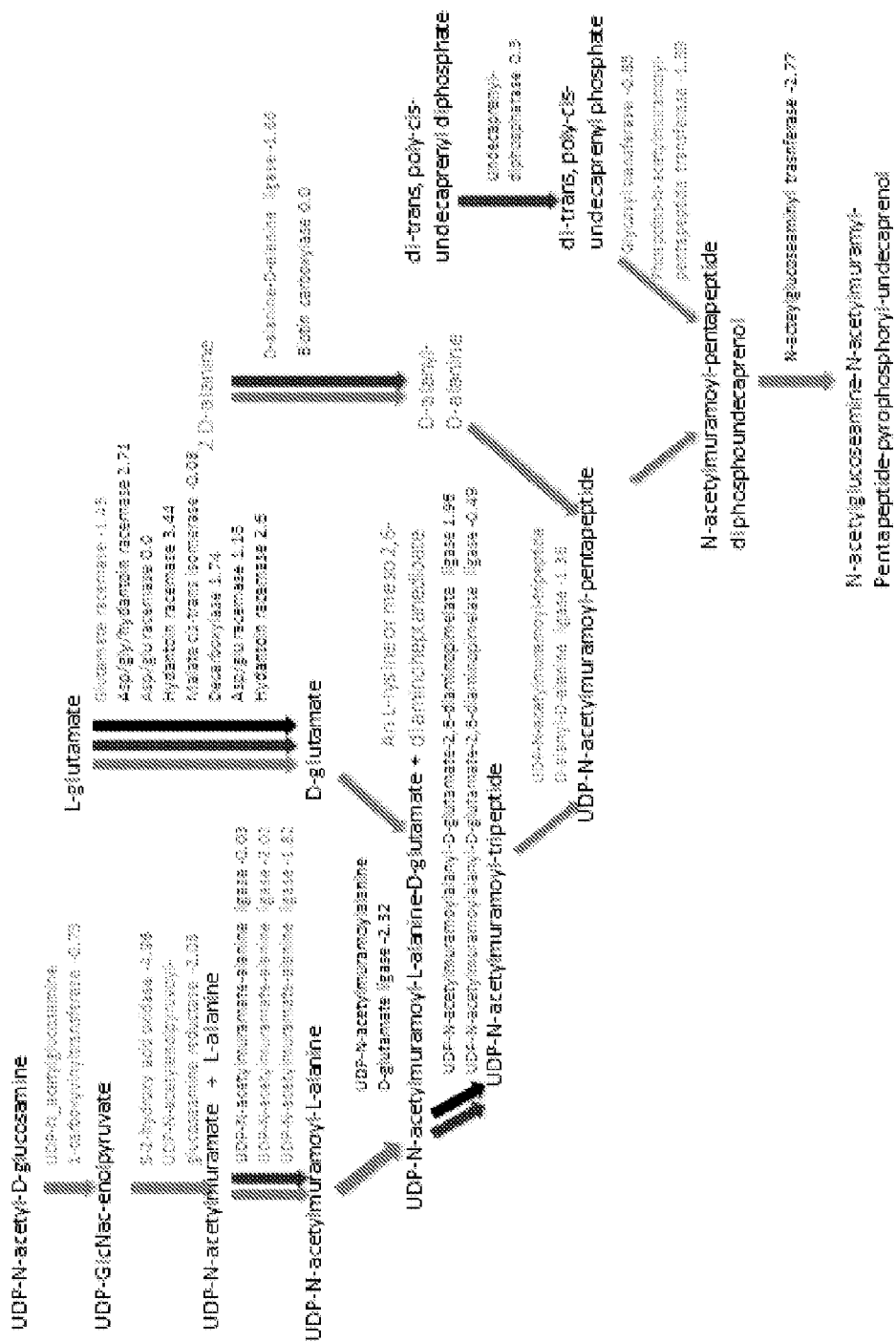
FIG. 74 presents a Pathway Tools reconstruction of peptidoglycan synthesis pathway with Loge expression values derived from microarray analysis. Elucidation of this pathway involved sequencing the genome of *R. opacus* PD630, annotating the genes within this genome, reconstructing the metabolic network from the gene annotations using pathway tools software, designing microarrays for probing the expression of all genes encoded in the genome, performing fermentations under conditions established for the timeline of storage lipid biosynthesis, extracting the RNA from cells grown under these conditions, and performing hybridizations to the designed microarray chips. Enzymes in a light shade of grey are below $\log_2$–0.6, enzymes in an intermediate shade of grey are between –0.6 and +0.6 $\log_2$ units, and enzymes in black are above 0.6 $\log_2$ units when compared to high nitrogen controls that repress the accumulation of storage lipids.

*Rhodococcus opacus* PD630 and *Rhodococcus jostii* RHA1 both have metabolisms capable of producing large amounts of neutral lipids that are stored intracellularly in organelle-like lipid bodies. Investigation into the cell physiology of these *Rhodococci* demonstrated that both organisms respond to limited nitrogen in their growth medium by activating a polygenetic pathway that results in lipid accumulation greater than 60% of the cell dry weight. Nitrogen limitation not only acts to stimulate the production of neutral lipids such as triacylglycerols, the most abundant component of the neutral lipids, but to also weaken the cell walls that house these valuable metabolic products. The weakening of cells after nitrogen starvation was observed by multiple methods including time-lapse fluorescence-microscopy (FIG. 72), electron-microscopy with thin sectioning (FIG. 73), and by demonstration that nearly the entire multistep-pathway for cell wall biosynthesis has been down-regulated at the RNA expression level (FIG. 74).

The bacterial cell wall is composed of peptidoglycan that is very nitrogen rich. Microscopy experiments both with light and electrons indicated that cells are getting weaker as they starve for nitrogen, as evidenced by lysis and empty compartments within the rods of Rhodococcus. Microarray gene expression analysis followed by visualization on a metabolic model generated by genome sequencing, annotation, and metabolic reconstruction has now demonstrated that peptidoglycan biosynthesis has been turned down at nearly every step along multiple pathways of peptidoglycan biosynthesis (FIG. 74). As the cells become weaker, recovery of intracellular contents becomes easier and likely less expensive.

Control of the media composition and characterization of the kinetics of storage lipid production and cell weakening has led to a process that can be taken advantage of for the production and harvesting of valuable stored lipids that can be used for the chemical conversion to Fatty. Acid Methyl Esters (FAMEs) routinely used as biodiesel fuel.

Example 6

The Predicted *Rhodococcus opacus* PD630 GapN Protein is Involved in Triacylglycerol Biosynthesis Abstract It is well known that most organisms store carbon when subjected to environmental stresses, i.e. nutrient limitation, desiccation, etc (23, 25, 30). For many bacteria, stored carbon exists as polyhydroxyalkanoate (PHA), starch, or glycogen (15, 22, 25). The Gram-positive Actinomycete *Rhodococcus opacus* strain PD630 is somewhat unique in that it stores carbon in the form of triacylglycerides (TAGs) under stress conditions, such as when nitrogen is limiting. Indeed, several studies have demonstrated that *R. opacus* PD630 can accumulate up to 76% of its cell dry weight (CDW) as TAGs when grown under nitrogen limiting conditions (2, 3). While this process is well-studied, the underlying molecular and biochemical mechanisms leading to TAG biosynthesis and subsequent storage are poorly understood. Described herein is a high-throughput genetic screen, utilizing transposon mutagenesis, to identify genes and their products required for TAG biosynthesis and storage in *R. opacus* PD630. This screen identified a putative aldehyde dehydrogenase as being essential for this process. Kinetic studies of TAG accumulation in both the wild-type and mutant strains demonstrated that the mutant accumulates up to 70-80% less TAGs than the wild-type strain. Further characterization of this gene and its product demonstrated that the protein is capable of oxidizing glyceraldehyde-3 phosphate (G3P) to 3-phosphoglycerate (3-PG) while reducing $NAD(P)^+$ to $NAD(P)H$, suggesting it is a homolog of the non-phosphorylating glyceraldehyde-3 phosphate dehydrogenase (G3PDH) GapN. Finally, $NAD(P)^+$-dependent G3PDH activity was measured in cells grown under nitrogen replete and limiting conditions and enzyme activity was found to be most pronounced in nitrogen limited cultures. Based on these data, it is hypothesized herein that during vegetative growth G3P is oxidized to 3PG via the phosphorylative branch of glycolysis yielding NADH and ATP, while the non-phosphorylative branch, yielding NAD(P)H, is utilized under lipid storage conditions, i.e. nitrogen limiting conditions. This would suggest that the transition from the phosphorylative to the non-phosphorylative G3PDH is a key switch in the shift from a vegetative state to a lipid storage phenotype.

Introduction

There are very few true generalities in biology, amongst which is that the vast majority of organisms are capable of storing excess carbon and often do so when other nutrients are limiting, i.e. nitrogen, phosphate, etc. Amongst bacteria, this stored carbon exists primarily as polyhydoxyalkanoate, though there are examples of other polymeric storage compounds including glycogen and polphosphate granules (12, 13, 17, 20, 24). Numerous members of the Actinomycete group, including *Mycobacterium tuberculosis*, several species of *Streptomyces* and *Rhodococcus opacus* strain PD630, have been shown to store excess carbon in the form of triacylglycerides (2-4, 11, 29). Indeed, *R. opacus* PD630 has previously been shown to accumulate up to 76% of its cell dry weight (CDW) as triacylglycerol when grown under nitrogen limiting conditions (2, 3). While several studies have been performed to characterize triacylglycerol biosynthesis and storage in *R. opacus* PD630 the underlying molecular and biochemical mechanisms remain poorly understood (1, 4, 18).

The non-phosphorylative glyceraldehyde 3-phosphate dehydrogenase (GapN) family of enzymes, a sub-family of the larger aldehyde dehydrogenase family, was originally associated with green eukaryotes, plants and algae primarily, wherein it catalyzes the irreversible oxidation of glyceradehyde-3-phosphate (G3P) to 3-phosphoglycerate while concomitantly reducing $NAD(P)^+$ to $NAD(P)H$ (14). This is in contrast to the canonical phosphorylative glyceraldehyde 3-phosphate dehydrogenase (GapA) which oxidizes G3P to 1,3-bisphosphoglycerate (1,3BPG) while reducing $NAD^+$ to NADH. 1,3-BPG is subsequently dephosphorylated to 3-phosphoglycerate (3-PG) by the enzyme phosphoglycerate kinase yielding one molecule of adenosine triphosphate (ATP) (FIG. 79). Thus instead of yielding one molecule of NADH and ATP, as would be the case in the phosphorylative branch of glycolysis, the non-phosphorylative branch yields a single molecule of NAD(P)H, an essential reducing equivalent in most biosynthetic pathways including fatty acid biosynthesis. While this family of enzymes was initially associated strictly with green eukaryotes, sequence and functional homologs have been identified in a number of eubacteria and archaea (7, 8, 16).

A genetic screen was performed seeking to identify genes and their products that are important in TAG biosynthesis and accumulation in *R. opacus* PD630. One of the mutants isolated in this screen has a transposon insertion in the 5' end of a gene predicted to encode an aldehyde dehydrogenase. Utilizing a variety of techniques it is demonstrated herein that the encoded product is in fact a NAD(P)H-dependent glyceraldehyde 3-phosphate dehydrogenase (GapN) homolog. Data suggest that the predicted GapN enzyme is necessary for the generation of NAD(P)H utilized in the biosynthesis of fatty acids. Furthermore, the data suggest that activation (or derepression) of the GapN protein may constitute an early switch from a vegetative lifestyle to a storage one. While several studies have identified genes that play a role in the later stages of triacylglycerol biosynthesis, this study may be the first to identify one of the initial steps in this process.

Materials and Methods
Bacterial Strains, Chemicals and Media

All of the bacterial strains and plasmids used in this study are listed in Tables 6-7. Primers used in this study are listed in Table 8. Bacteria were propagated in lysogeny broth (LB) (5) (Difco, Lawrence, Kans.) or minimal media unless otherwise noted. The minimal media used was prepared as previously described (19) and supplemented with 4% glucose and either 0.15% or 1.0% ammonium sulfate. Growth media was supplemented with kanamycin at a final concentration of 100 mg/ml. All restriction enzymes were purchased from New England Biolabs (Ipswich, Mass.). Chemicals were purchased from Sigma-Aldrich (St. Louis, Mo.). Plasmids were constructed in either Saccharomyces cerevisiae using in vivo recombinational cloning (27, 28) or in E. coli EC100D (Epicentre Biotechnologies, Madison, Wis.) using standard techniques. Plasmid DNA was mobilized into R. opacus PD630 using either conjugation or through electroporation as described below.

Electroporation and Conjugal Transfer of DNA into R. opacus PD630

Electrocompetent R. opacus cells were obtained by centrifuging 3 ml of 48 hour-old cultures grown in LB medium followed by several washes in 10% glycerol, cell pellets were then resuspended in 200 ml of 10% glycerol to which 1 mg of plasmid DNA was added. Electroporations were performed using a Biorad gene pulsor (Hercules, Calif.) apparatus set to 2.5 kV, 25 mF and 1000 ohms. Following electroporation, cells were immediately resuspended in 2 ml of LB medium and incubated at 30° C. for 2 hours prior to plating on selective medium. Conjugations were performed using the dap auxotrophic conjugal donor strain E. coli BW29427 (26). Briefly, 3 ml of R. opacus PD630 was mixed with 1 ml of the donor strain and centrifuged. The resulting cell pellet was spotted onto LB medium and incubated for 24-48 hours at 30° C. followed by plating on selective medium.

Transposon Mutagenesis and Screening

The EZ-Tn5 transposome system from Epicentre Biotechnologies (Madison, Wis.) was used to introduce random mutations throughout the R. opacus PD630 genome. Following transformation, as described above, with the transposome, transformants were plated on LB medium supplemented with kanamycin and incubated at 30° C. for 3-4 days. Colonies were transferred to 96 well plates containing LB medium supplemented with kanamycin and incubated at 30° C. for 4 days. Following growth, mutants were screened as described below.

TAG Accumulation Screen

Mutants were transferred from 96-well dishes to solid minimal media supplemented with 0.15% ammonium sulfate and grown for 120 hours at 30° C. Following growth, plates were flooded with 0.2% Sudan black in 95% ethanol and incubated at room temperature for 15 minutes followed by three 95% ethanol washes for 1, 5 and 15 minutes. Mutants were selected based on their inability to stain with the dye.

Lipid Extraction and Thin-Layer Chromatography

Extraction of lipids from cultures was performed as previously described with minor modifications (6). Briefly, cultures were centrifuged and the resulting pellets lyophilized. Lipids were extracted by adding a 1:1 chloroform:methanol solution to the dried pellets followed by incubation at room temperature for 60 minutes with agitation. Extracts were then filtered through a 0.2 mm filter to remove particulate matter. Thin layer chromatography experiments were performed using a two step resolution method as previously described (10, 21). 25 mg of lipid extract was spotted onto a glass backed silica gel 60 TLC plates (EMD Chemicals Inc., Gibbstown, N.J.) and dried under a constant stream of nitrogen. Samples were resolved using an initial polar buffer containing 60:35:5 chloroform:methanol: water, followed by a second buffer containing 70:30:1 hexane:diethyl ether:acetic acid. Plates were allowed to dry prior to charring by first exposing the plates to a 3% cupric acetate in an 8% aqueous phosphoric acid solution followed by baking in a 200° C. oven.

Methanolysis and Gas Chromatography of Lipids

Extraction of lipids and subsequent methanolysis to create fatty acid methyl esters (FAMES) was performed as previously described (19). Briefly, lyophilized cell pellets were resuspended in 1 ml of chloroform to which 1 ml of a 85:15 methanol:sulphuric acid solution was added. Samples were subsequently heated at 100° C. for 2.5 hours followed by rapid cooling on ice. The organic phase was washed once with water and filtered through a 0.2 mm filter to remove any particulate matter. Gas chromatography of FAMES (GC-FAMES) was performed using an Agilent Technologies 6850 series II network GC system (Agilent Technologies, Santa Clara, Calif.) as previously described (19).

Fluorescent Microscopy

Cultures were mixed 10:1 with a 75% glycerol solution containing 5 mg of Nile red and observed using a Carl Zeiss AX10 Imager A.1 fluorescent microscope using the GFP and cy3 filters. Images were recorded using a Carl Zeiss AxioCam MRm (Carl Zeiss microimagin Inc., Thornwood, N.Y.). Images were analyzed using Adobe Photoshop CS3.

NAD(P)H-Dependent Glyceraldehyse 3 Phosphate Activity Assay

NP-G3PDH activity was assayed as previously described with minor modifications (9). Briefly, reactions contained 1 mM NAD(P)+, 1 mM glyceraldehyde 3-phosphate and either 10 mg of purified TadD or 100 mg of crude bacterial lysate in a final volume of 1 ml. Reactions were incubated at 37° C. for one hour. Following incubation, the optical density of the reactions was measured at 340 nm. R. opacus cultures were grown in either lysogeny broth or MR medium supplemented with 4% glucose and 0.15% ammonium sulphate for 24 hours prior to mechanical disruption using a French pressure cell. Cellular debris was pelted by centrifugation at 20,000×g for 30 minutes.

Determination of NAD$^+$/NADH and NAD(P)$^+$/NAD(P)H Ratios

NAD+, NADH, NAD(P)+ and NAD(P)H concentrations were determined using the Biovision NAD+/NADH quantification and the Biovision NAD(P)+/NAD(P)H quatification kits, respectively (Mountain View, Calif.) per manufacturers instructions. Cell lysates of R. opacus PD630 were prepared as described above.

Results

Genetic Screen for Triacylglycerol Accumulation Deficient (tad) Mutants

A library of 5000 random Ez-Tn5 R. opacus PD630 mutants was generated and subsequently screened for triacylglycerol biosynthesis using a Sudan black-based screening method. Previous experiments by Kurasawa and colleagues as well as Alvarez and colleagues (19) (2, 3) demonstrated that R. opacus accumulates high concentrations of TAG when grown in media with a very low carbon: nitrogen ratio. Accordingly, herein, the Tn5 mutants were grown on minimal salts medium supplemented with 4% glucose and 0.15% ammonium sulfate for 120 hours, allowing for significant TAG accumulation. Accumulated TAGs were detected by staining the colonies with the lipophilic dye Sudan black. Following growth, the agar plates were flooded with a 0.2% Sudan black, 95% ethanol solution and incubated at room temperature for 15 minutes. The Sudan black dye was then removed and the plates washed three times with 95% ethanol. TAG accumulation is evidenced by very dark blue staining of a colony as can be seen in the wild type example in FIG. 75A, mutants deficient in TAG accumulation stained a much lighter color as is shown for the 44B2 mutant in FIG. 75A. From this initial screen, several mutants were identified that demonstrated varying degrees of decreased staining as compared to the wild type.

As decreased staining could readily be due to a variety of different factors other than a loss of TAG accumulation, mutants of interest were subjected to a second round of screening wherein they were grown in minimal media supplemented with 4% glucose and 0.15% ammonium sulfate in flasks for 120 hours and then analyzed for their TAG content using TLC. In addition to providing direct evidence of decreased TAG accumulation, this secondary screen also allowed for identification of mutants that had significant growth defects. Of the initial strains assayed one, designated 44B2, demonstrated wild type-like growth while accumulating greater than 70% less TAGs than the wild type strain.

Kinetics of TAG Accumulation in the Wild Type and 44B2 Mutant Strains

Figure 75:
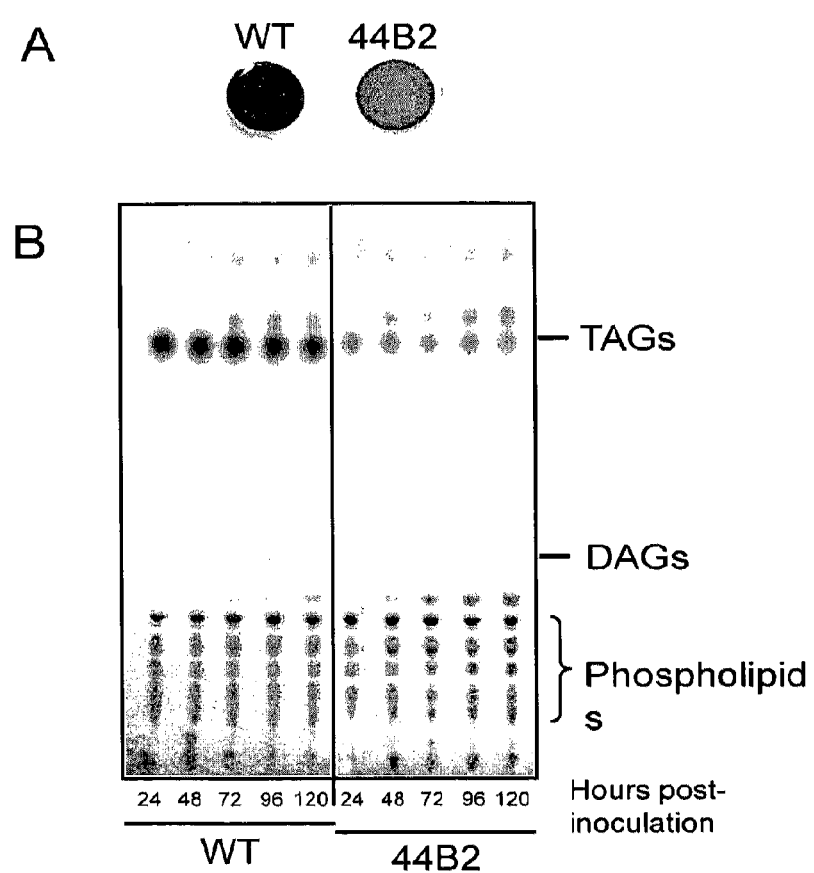
FIG. 75 demonstrates that the *R. opacus* PD630 44B2 transposon mutant accumulates less triacylglycerides (TAGs) than the wild type.

Following on the secondary screening, characterization of the 44B2 mutant was achieved by studying the kinetics of TAG accumulation. The wild type strain of *R. opacus* PD630, as well as the 44B2 mutant strain, were grown in minimal medium supplemented with 4% glucose and 0.15% ammonium sulfate. Samples were removed at 24, 48, 72, 96 and 120 hours to measure the optical density at 600 nm, determine the colony forming units, measure nitrogen and glucose concentrations as well as pH and to assess TAG accumulation. While the number of colony forming units as well as the consumption of nitrogen and glucose were identical between the two strains (data not shown) there was a distinct difference in the optical density and the amount of TAGs. The wild type strain had a significantly higher optical density at later time points (24 hrs, 1.185+/−0.15; 48 hrs, 6.015+/−0.21; 72 hrs, 8.75+/−0.34; 96 hrs, 8.80+/−0.47; and 120 hrs 9.075+/−0.26) as compared to the mutant strain (24 hrs, 2.48+/−0.29; 48 hrs, 6.115+/−0.18; 72 hrs, 6.53+/−0.43; 96 hrs, 6.115+/−0.19; and 120 hrs, 6.195+/−0.31). TLC analysis of the lipid content of the two strains demonstrated that while the concentrations of the polar lipids, thought to consist mainly of phospholipids and acting as a convenient loading control, remained similar between the two strains, the mutant strain demonstrated a large reduction in TAGs as compared to its wild type counterpart (FIG. 75B). Densitometrical analysis of the TLC results suggests a 70-80% reduction in TAG accumulation in the mutant strain.

While TLC is a simple, high throughput and powerful way to analyze lipid content in a given sample, it is limited to being mainly qualitative in nature. Accordingly, gas chromatography was utilized to analyze the fatty acid content of both the wild type and mutant strain. Cell pellets from kinetic experiments identical to those described above were lyophilized and the fatty acids extracted and converted to fatty acid methyl esters (FAMES) for use in GC. As with the TLC results, the mutant was found to accumulate 72.2% less fatty acids than the wild type, based on GC-FAMES analysis. Thus, GC-FAMES analysis confirmed that the 44B2 mutant accumulates greater than 70% less TAGs than the wild type strain.

Utilizing a marker rescue-like approach the transposon insertion site in the 44B2 mutant was identified as being at the far 5' end of a gene, termed herein tadD, predicted to encode a hypothetical protein with sequence similarity to the aldehyde dehydrogenase family of proteins.

Complementation of the tadD::Tn5 Mutant

Figure 48:
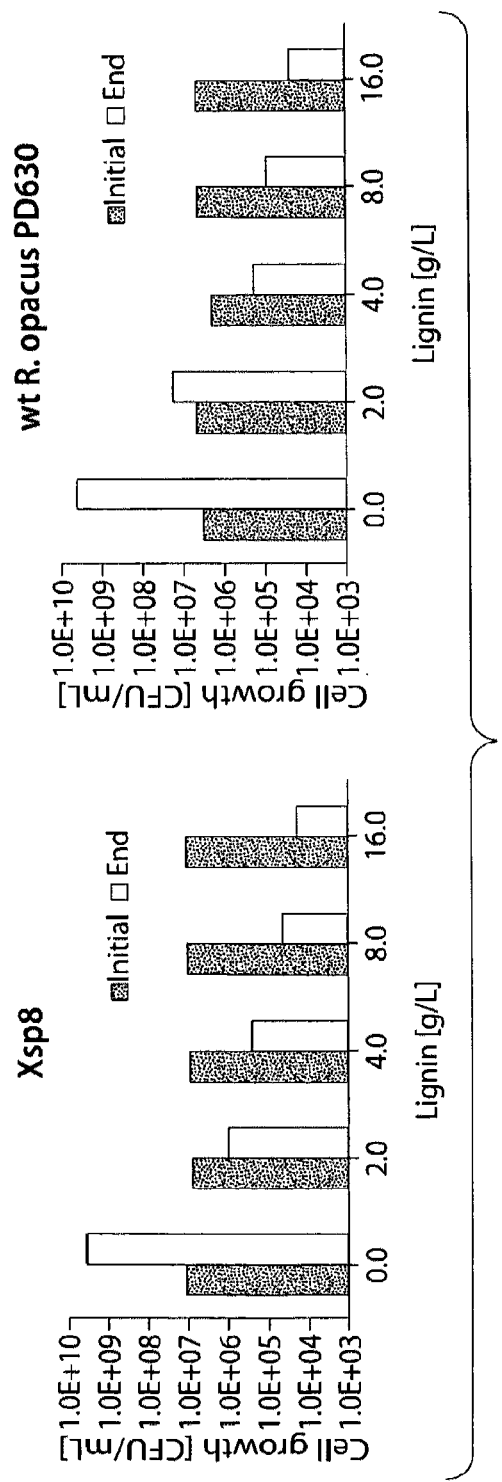
FIG. 48 presents graphs depicting the results of a lignin experiment and the effects on cell growth of wild type *R. opacus* PD630 cells and transformant Xsp8 cells.
Figure 49:
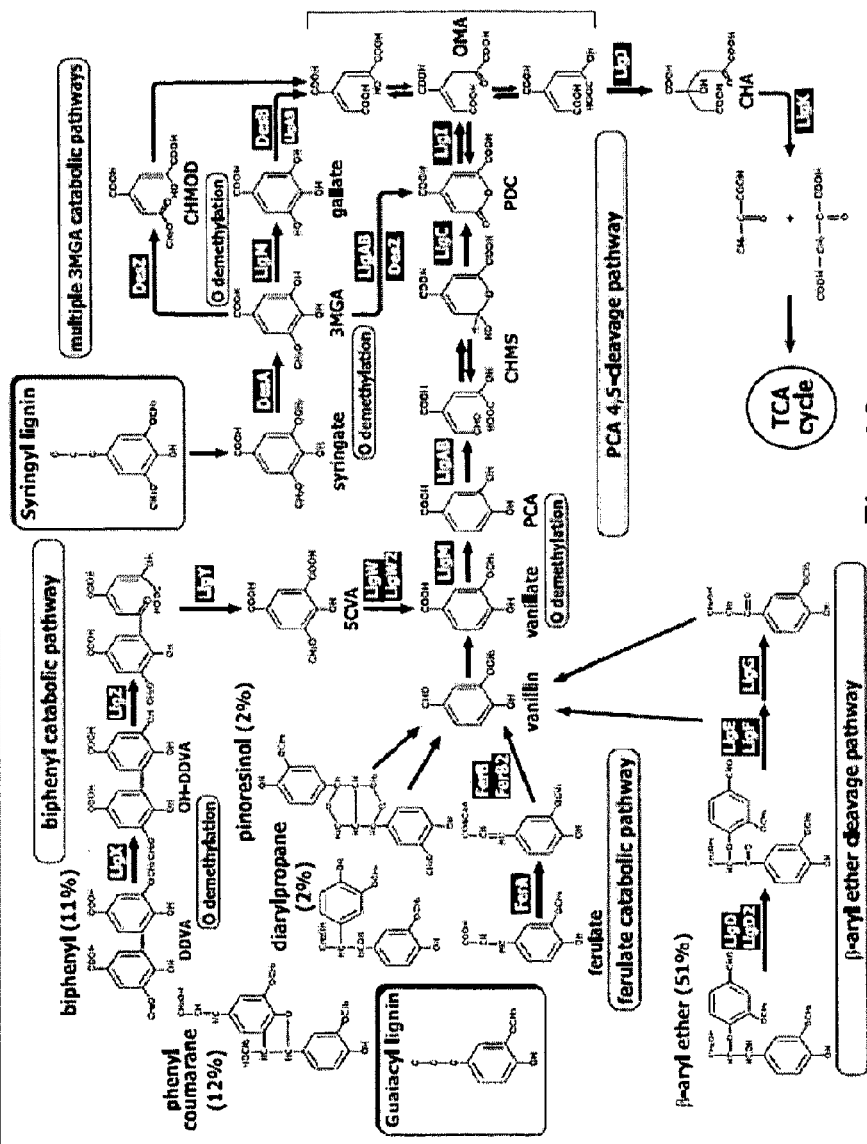
FIG. 49 presents a schematic of catabolic pathways for the degradation of lignin-derived compounds by *Sphingmonas paucimobilis*.

To demonstrate that the observed phenotype was the result of the mapped transposon insertion and not a random mutation elsewhere in the chromosome, the tadD gene was expressed from the tetracycline inducible promoter contained on the pSC86 plasmid. Since significant plasmid instability with this family of vectors has been observed in the past, cultures were grown for only 48 hours. As can be seen in FIG. 75B, 48 hours is more than adequate to establish significant TAG biosynthesis and accumulation.

Wild type *R. opacus* PD630 and the tadD::Tn5 mutant expressing either GFP or the tadD gene were grown in minimal rare medium supplemented with 4% glucose, 0.15% ammonium sulphate and spectinomycin for 48 hours prior to be diluted 1:10 into the same medium supplemented further with anhydrotetracycline. Cultures were then incubated at 30° C. with shaking for 48 hours prior to harvesting. TAG production was assayed using both TLC and GC-FAMES. Additionally, bacterial growth was monitored via CFU counts and observed no difference in the final number of bacteria in each culture. As expected, expression of GFP had little to no effect on the loss of TAG accumulation observed previously in the tadD::Tn5 mutant, however, extrachromosomal expression of the tadD gene in the mutant strain resulted in a significant increase in TAG accumulation, thus complementing the observed phenotype. Interestingly, overexpression of the tadD gene in the wild type strain resulted in a further increase in TAG production.

TadD has NAD(P)H-Dependent Glyceraldehyde 3-Phosphate Dehydrogenase Activity

With the demonstration that loss of tadD expression resulted in a significant decrease in TAG accumulation and that overexpression of this gene resulted in an increase of TAGs over what we observed in our control strain we sought to better understand the biochemical underpinnings of the TadD protein. Bioinformatic analysis of the TadD protein suggested that it may possess NAD(P)H-dependent glyceraldehyde 3-phosphate dehydrogenase activity (ND-G3PDH). This family of proteins were initially identified in and thought to occur exclusively in the so-called green eukaryotes. More recently, ND-G3PDH homologs have been identified in several Gram-positive organisms.

Figure 76:
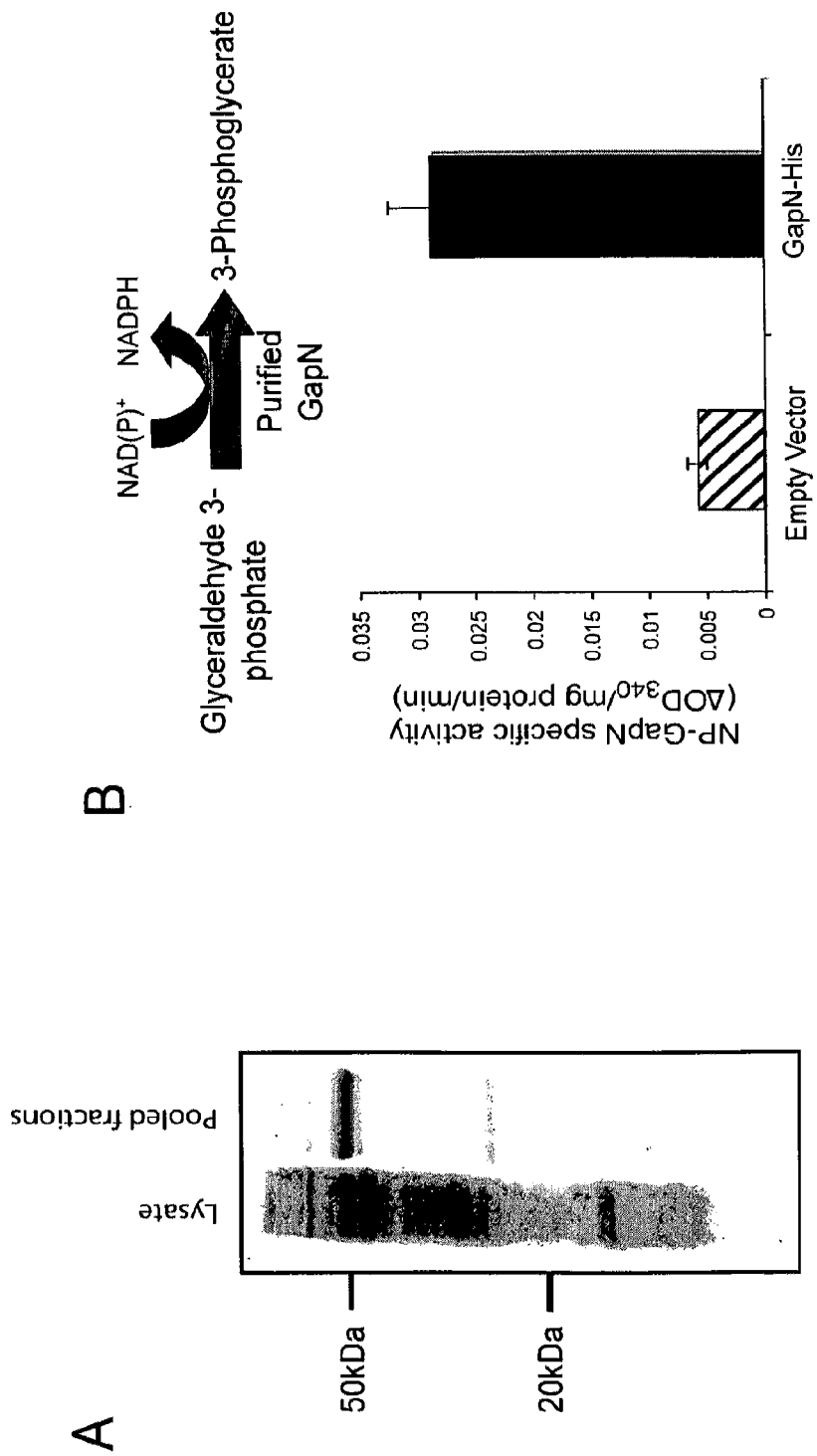
FIG. 76 shows that purified TadD demonstrates NAD(P)+-dependent glyceraldehyde 3-phosphate dehydrogenase (ND-G3PDH) activity.

To assess whether the TadD protein possessed ND-G3PDH activity we constructed a c-terminal hexa-histidine tagged variant of the TadD protein, expressed it in *E. coli* and purified the protein utilizing nickel affinity chromatography (FIG. 76A). Additionally, we fractionated supernatant from *E. coli* containing the parental plasmid which was used as an empty vector control. Fractions containing the histidine tagged TadD protein (and the corresponding fractions from the empty vector fractionation) were then used in ND-G3PDH activity assays. As shown in FIG. 76B reactions containing the purified TadD protein generated significantly more NAD(P)H than those containing extract from the empty vector strain as demonstrated by the increase in optical density at 340 nm suggesting that indeed TadD possesses ND-G3PDH activity.

TadD ND-G3PDH Activity is Induced Under Lipid Storage Conditions

With the demonstration that the TadD protein possessed ND-G3PDH activity we sought to determine whether this activity was coordinated with lipid biosynthesis. As NAD(P)H is essential to numerous biosynthetic pathways, specifically fatty acid biosynthesis, in many organisms, we hypothesized that we would see an increase in TadD-dependent ND-G3PDH activity in cells that have begun to accumulate TAGs.

Figure 77:
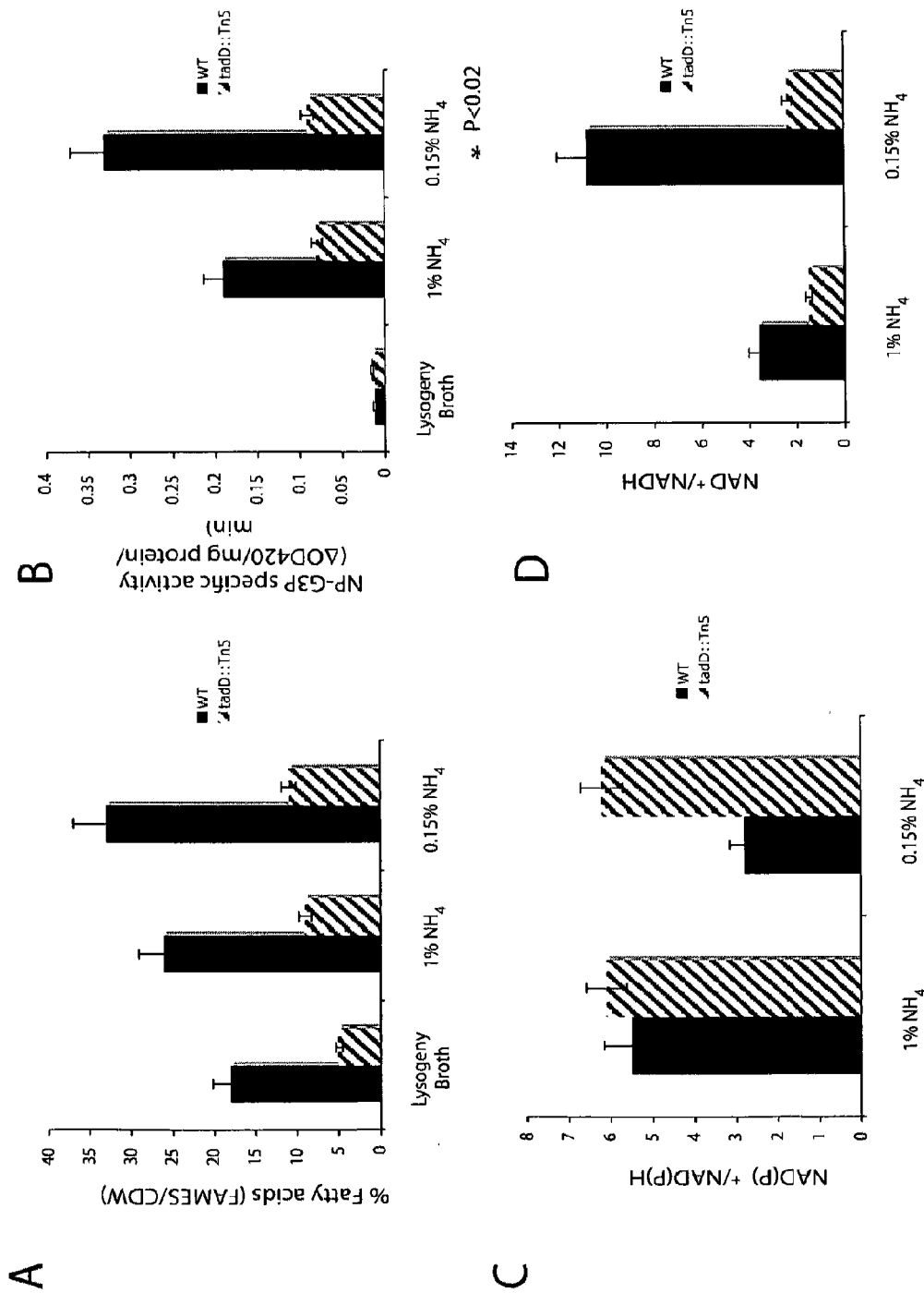
FIG. 77 presents graphs showing that TadD-dependent ND-G3PDH activity increases under lipid accumulation conditions in *R. opacus* PD630 resulting in an increase in NAD(P)H pools and a concomitant decrease in NADH pools.

To assess whether the observed TadD ND-G3PDH activity was induced under lipid storage conditions we grew the WT and the tadD transposon mutant in either rich LB medium (non-storage conditions) or MR medium supplemented with 4% glucose and either 1% (low storage conditions) or 0.15% (storage conditions) ammonium sulphate for 24 hours. As we sought to determine whether TadD-dependent ND-G3PDH activity changed under lipid storage versus non-storage conditions we first needed to determine whether there was in fact any difference in lipid accumulation under these three different conditions. To this end we assayed for the total fatty acid content of cultures grown under these three conditions using GC-FAMES (FIG. 77A). We found that, indeed, wild-type R. opacus accumulated significantly more fatty acids per mg of cell dry weight under the lipid storage conditions than either the high nitrogen or rich media conditions. Furthermore, as expected the tadD transposon mutant accumulated significantly less fatty acids than the wild type under all of the conditions tested.

These same cultures were then assayed for ND-G3PDH activity using the previously described assay. As we hypothesized, we saw a sharp increase in ND-G3PDH activity in cultures grown under lipid storage conditions (FIG. 77B). Interestingly, the ND-G3PDH activity is superimposable over the GC-FAMES data with very low activity and fatty acid accumulation in the LB grown cultures, an intermediate phenotype for both metrics under the high nitrogen conditions and high ND-G3PDH activity and fat storage under the nitrogen limiting condition. It is worth noting that there does appear to be some residual ND-G3PDH activity in the tadD transposon mutant. This could be the result of either partial activity of the mutant tadD gene product or the result of another protein with redundant or promiscuous ND-G3PDH activity.

While we have shown that TadD-dependent ND-G3PDH activity increases dramatically under conditions that promote lipid accumulation we wanted to determine if this translated into a change in the NAD(P)H and NADH pools within the cells. Accordingly, we grew wild type R. opacus and the tadD transposon mutant in minimal medium supplemented with 4% glucose and either 1% or 0.15% ammonium sulphate as described above. We then determined the concentration of NAD(P)$^+$ and NAD(P)H (FIG. 77C) or NAD$^+$ and NADH (FIG. 77D) which are expressed as the ratios of the oxidized form divided by the reduced form. Consistent with the changes in TadD-dependent ND-G3PDH activity described above we observed a dramatic decrease in the ratio of NAD(P)$^+$ to NAD(P)H with a concomitant increase in the NAD$^+$ to NADH ratio when comparing the wild type strain grown under nitrogen replete conditions to wild type grown under nitrogen limiting conditions. As expected we did not observe any significant difference in NAD(P)$^+$/NAD(P)H or NAD+/NADH ratios for the tadD mutant.

Overexpression of a Potential GapA Homolog Results in a Decrease in Fatty Acid Accumulation Many bacteria metabolize glucose via either the Emden-Meyerhof or the Entner-Doudoroff pathway. One of the key energy generating steps of these pathways is the NAD+-dependent dehydrogenation of glyceraldehyde 3-phosphate by the canonical glyceraldehyde 3-phosphate dehydrogenase GapA, followed by a subsequent substrate level phosphorylating by phosphoglycerate kinase, yielding one molecule of NADH, ATP and 3-phosphoglycerate. NAD(P)$^+$-dependent glyceraldehyde 3-phosphate dehydrogenases have been shown to bypass these two steps yielding a single molecule of NAD(P)H and 3-phosphoglycerate (FIG. 78A). Based on our data above we hypothesized that during vegetative growth, R. opacus PD630 metabolizes glucose and other hexoses via either of the two pathways described above utilizing the GapA-dependent pathway. However during lipid storage, we hypothesize that R. opacus switches to a GapN-dependent pathway thus yielding NAD(P)H, an essential cofactor in fatty acid biosynthesis. Accordingly, we hypothesized that overexpressing GapA should result in a decrease in available NAD(P)H and thus a decrease in lipid accumulation.

To this end we cloned a predicted GapA homolog (homologous the R. jostii ro07177 gene) into the E. coli/Rhodococcus expression vector pSC86 and mobilized it into wild type R. opacus PD630. Cultures of wild type R. opacus expressing either gfp, the gapA homolog or tadD were grown in minimal medium supplemented with 4% glucose, 0.15% ammonium sulphate, spectinomycin and anhydrotetracylcine for 48 hours at 30° C. Fatty acid content was assayed via TLC (FIG. 78B). We observed that, as predicted, overexpression of the GapA homolog resulted in a dramatic decrease in total fatty acids while, as shown above, overexpression of TadD resulted in an increase in TAG accumulation.

Protein Sequence for R. opacus TadD/GapN:

(SEQ ID NO: 4)
M S I A A D S L S N I T P P G L T I D G E I T T T
A A V I P V I N P A T E S A F I E V P D A G V E Q
L D A A V S A A R R A A K H W A T H D L P F R Q G
I V L R L V D H V R A N I D E L A R L V T L E Q G
K P L A K A A G E I E S G L R G L E R Y A S W D I
P V E V I R D N D D E L I E V H R A P V G V V G G
I T A W N Y P L L L A L W K I G P A L I T G N P I
I V K P S P L T P V A T L R L G E L A Q Q I L P P
G V L Q V L S G G D D L G R A M T A H T G I D K I
T F T G S E R A G K S I M A G A G A T L K R L T L
E L G G N D P G I V L D D V D V A S I A A D L Y W
G A L S N C G Q V C A G L K R L Y V P Q H L A P A
I E E A L A E V A K G V K V G N G L D D G V D M G
P V Q N A A Q F T K V R G Y V D D A A N R G A D V
Y F R G E V P E G P G Y F H P V T L V R G V D D S
V P L V R E E Q F G P V L P I L T Y T D I D D V I
A R A N D S E L A L G A S V W S S D E Q R A T E V
A E R V E A G T V W V N Q H P M L S S D V P F G G
V K Q S G L G V E Q S I H G V L E Y T N Y R V L R
V K R

TABLE 6

Strains used in Example 6

| Strain | Relevant Genotype | Source |
|---|---|---|
| Rhodococcus | | |
| R. opacus PD630 | Wild type strain | (19) |
| DPM30 | tadD::Tn5 | This Study |
| DPM173 | WT + pSC93 | This Study |

TABLE 6-continued

Strains used in Example 6

| Strain | Relevant Genotype | Source |
|---|---|---|
| DPM206 | WT + pDPM46 | This Study |
| DPM205 | DPM30 + pSC93 | This Study |
| DPM207 | DPM30 + pDPM46 | This Study |
| DPM208 | WT + pDPM47 | This Study |
| E. coli | | |
| E. coli TOP10 | Δ(ara, leu)7697 pir-116(DHFR) | Invitrogen |
| DPM54 | E. coli EC100D + pMQ70 | This Study |
| DPM55 | E. coli EC100D + pDPM21 | This Study |

TABLE 7

Plasmids used in Example 6

| Plasmids | Relevant Genotype | Source |
|---|---|---|
| pMQ70 | pMB1 ori, oriT, bla, araC, ParaBAD | (27) |
| pDPM21 | pMQ70 + tadD | This Study |
| pSC93 | NG2 ori, RP4 mob, aadA, tetR, gfp, Psmyc-tetRO | This Study |
| pDPM46 | pSC93 + tadD | This Study |
| pDPM47 | pSC93 + ro07177 | This Study |

TABLE 8

Primers used in Example 6

| Primers | Sequence |
|---|---|
| pSC86-tadD for | GCG GCT GCA GAT GAG TAT CGC CGC AGA TTC TCT GTC (SEQ ID NO: 5) |
| pSC86-tadD rev | CCG CGG AAT TCT TTA TCG TTT GAC CCG CAG CAC TCT G (SEQ ID NO: 6) |
| pSC86-gapA for | GCG GCT GCA GAT GAC TGT CCG GGT AGG CGT AAA CG (SEQ ID NO: 7) |
| pSC86-gapA rev | CCG CGG AAT TCT TTA GAG AGA CTT GGC GAC GAG ACC GAT G (SEQ ID NO: 8) |
| pMQ70-tadD-his for | GCGGGAATTCAGGAGGTCTCTCTCAT GAGTATCGCCGCAGATTCTCTGTCC (SEQ ID NO: 9) |
| pMQ70-tadD-his rev | CCGCAAGCTTTTAATGATGATGATGAT GATGTCGTTTGACCCGCAGCACTCTAG (SEQ ID NO: 10) |

References for Example 6

1. Alvarez, A. F., H. M. Alvarez, R. Kalscheuer, M. Waltermann, and A. Steinbuchel. 2008. Cloning and characterization of a gene involved in triacylglycerol biosynthesis and identification of additional homologous genes in the oleaginous bacterium *Rhodococcus opacus* PD630. Microbiology 154:2327-2335.
2. Alvarez, H. M., R. Kalscheuer, and A. Steinbuchel. 2000. Accumulation and mobilization of storage lipids by *Rhodococcus opacus* PD630 and *Rhodococcus ruber* NCIMB 40126. Appl Microbiol Biotechnol 54:218-223.
3. Alvarez, H. M., F. Mayer, D. Fabritius, and A. Steinbuchel. 1996. Formation of intracytoplasmic lipid inclusions by *Rhodococcus opacus* strain PD630. Arch Microbiol 165: 377-386.
4. Arabolaza, A., E. Rodriguez, S. Altabe, H. Alvarez, and H. Gramajo. 2008. Multiple pathways for triacylglycerol biosynthesis in *Streptomyces coelicolor*. Appl Environ Microbiol 74:2573-2582.
5. Bertani, G. 2004. Lysogeny at mid-twentieth century: P1, P2, and other experimental systems. J Bacteriol 186:595-600.
6. Bligh, E. G., and W. J. Dyer. 1959. A rapid method of total lipid extraction and purification. Can J Biochem Physiol 37:911-917.
7. Brunner, N. A., D. A. Lang, M. Wilmanns, and R. Hensel. 2000. Crystallization and preliminary X-ray diffraction analysis of the NAD-dependent non-phosphorylating GAPDH of the hyperthermophilic archaeon *Thermoproteus tenax*. Acta Crystallogr D Biol Crystallogr 56:89-91.
8. Cobessi, D., F. Tete-Favier, S. Marchal, G. Branlant, and A. Aubry. 2000. Structural and biochemical investigations of the catalytic mechanism of an NADP-dependent aldehyde dehydrogenase from *Streptococcus mutans*. J Mol Biol 300:141-152.
9. Crow, V. L., and C. L. Wittenberger. 1979. Separation and properties of NAD+- and NADP+-dependent glyceraldehyde-3-phosphate dehydrogenases from *Streptococcus mutans*. J Biol Chem 254:1134-1142.
10. Downing, D. T. 1968. Photodensitometry in the thin-layer chromatographic analysis of neutral lipids. J Chromatogr 38:91-99.
11. Garton, N. J., S. J. Waddell, A. L. Sherratt, S. M. Lee, R. J. Smith, C. Senner, J. Hinds, K. Rajakumar, R. A. Adegbola, G. S. Besra, P. D. Butcher, and M. R. Barer. 2008. Cytological and transcript analyses reveal fat and lazy persister-like bacilli in *tuberculous* sputum. PLoS Med 5:e75.
12. Gomez, C., M. A. Aon, and A. A. Iglesias. 1999. Ultrasensitive glycogen synthesis in Cyanobacteria. FEBS Lett 446:117-121.
13. Gomez Casati, D. F., M. A. Aon, S. Cortassa, and A. A. Iglesias. 2001. Measurement of the glycogen synthetic pathway in permeabilized cells of cyanobacteria. FEMS Microbiol Lett 194:7-11.
14. Habenicht, A. 1997. The non-phosphorylating glyceraldehyde-3-phosphate dehydrogenase: biochemistry, structure, occurrence and evolution. Biol Chem 378:1413-1419.
15. Hai, T., S. Hein, and A. Steinbuchel. 2001. Multiple evidence for widespread and general occurrence of type-III PHA synthases in cyanobacteria and molecular characterization of the PHA synthases from two thermophilic cyanobacteria: *Chlorogloeopsis fritschii* PCC 6912 and *Synechococcus* sp. strain MA19. Microbiology 147:3047-3060.
16. Iddar, A., F. Valverde, O. Assobhei, A. Serrano, and A. Soukri. 2005. Widespread occurrence of non-phosphorylating glyceraldehyde-3-phosphate dehydrogenase among gram-positive bacteria. Int Microbiol 8:251-258.
17. Jendrossek, D. 2009. Polyhydroxyalkanoate granules are complex subcellular organelles (carbonosomes). J Bacteriol 191:3195-3202.
18. Kalscheuer, R., M. Waltermann, M. Alvarez, and A. Steinbuchel. 2001. Preparative isolation of lipid inclusions from *Rhodococcus opacus* and *Rhodococcus ruber* and identification of granule-associated proteins. Arch Microbiol 177:20-28.

19. Kazuhiko, K., Boccazzi, P., de Almeida, N., Sinskey, A. J. 2009. High Glucose Cultivation of *Rhodococcus opacus* PD630 in batch-culture for biodiesel production. In preparation.
20. Kessler, B., and B. Witholt. 2001. Factors involved in the regulatory network of polyhydroxyalkanoate metabolism. J Biotechnol 86:97-104.
21. King, R. J., H. Martin, D. Mitts, and F. M. Holmstrom. 1977. Metabolism of the apoproteins in pulmonary surfactant. J Appl Physiol 42:483-491.
22. Kranz, R. G., K. K. Gabbert, T. A. Locke, and M. T. Madigan. 1997. Polyhydroxyalkanoate production in *Rhodobacter capsulatus*: genes, mutants, expression, and physiology. Appl Environ Microbiol 63:3003-3009.
23. Owen, O. E., G. A. Reichard, Jr., M. S. Patel, and G. Boden. 1979. Energy metabolism in feasting and fasting. Adv Exp Med Biol 111:169-188.
24. Rehm, B. H. 2006. Genetics and biochemistry of polyhydroxyalkanoate granule self-assembly: The key role of polyester synthases. Biotechnol Lett 28:207-213.
25. Roach, P. J., C. Cheng, D. Huang, A. Lin, J. Mu, A. V. Skurat, W. Wilson, and L. Zhai. 1998. Novel aspects of the regulation of glycogen storage. J Basic Clin Physiol Pharmacol 9:139-151.
26. Scheffel, A., and D. Schuler. 2007. The acidic repetitive domain of the *Magnetospirillum gryphiswaldense* MamJ protein displays hypervariability but is not required for magnetosome chain assembly. J Bacteriol 189:6437-6446.
27. Shanks, R. M., N. C. Caiazza, S. M. Hinsa, C. M. Toutain, and G. A. O'Toole. 2006. *Saccharomyces cerevisiae*-based molecular tool kit for manipulation of genes from gram-negative bacteria. Appl Environ Microbiol 72:5027-5036.
28. Shanks, R. M., D. E. Kadouri, D. P. MacEachran, and G. A. O'Toole. 2009. New yeast recombineering tools for bacteria. Plasmid 62:88-97.
29. Sirakova, T. D., V. S. Dubey, C. Deb, J. Daniel, T. A. Korotkova, B. Abomoelak, and P. E. Kolattukudy. 2006. Identification of a diacylglycerol acyltransferase gene involved in accumulation of triacylglycerol in *Mycobacterium tuberculosis* under stress. Microbiology 152:2717-2725.
30. Wang, Z. T., N. Ullrich, S. Joo, S. Waffenschmidt, and U. Goodenough. 2009. Algal Lipid Bodies: Stress Induction, Purification, and Biochemical Characterization in Wild-type and Starch-less *Chlamydomonas reinhardtii*. Eukaryot Cell.

Example 7

The *Rhodococcus opacus* PD630 Heparin-Binding Hemagglutinin Homolog TadA Mediates Lipid Body Formation Introduction Carbon storage is universal within nature with the vast majority of organisms storing excess carbon in one form or another (2, 8, 35, 50, 54). For most organisms carbon storage is triggered by an environmental stress, including nutrient limitation, desiccation, presence of xenobiotics and others (2-4, 30, 32, 50, 54). In eukaryotic organisms, excess carbon is typically stored in the form of triacylglycerides (TAGs), starch or glycogen. The vast majority of prokaryotic organisms store carbon in the form of polymeric polyhydroxyalkanoate (PHA) (22, 32, 49, 50). As is the case with most carbon storage pathways, biosynthesis of PHA typically occurs as the result of nutrient deprivation (28, 32). PHA biosynthesis has been extensively studied in many different microbes and the key enzymes required for this pathway have been identified and characterized (for review see (43)). PHA is stored in conspicuous inclusion bodies, known as granules, that localize to the cytoplasm (26, 41, 57, 58). It has been demonstrated that PHA granules are highly organized structures and that their formation is regulated by the presence and relative abundance of a family of proteins known as phasins. The phasin protein PhaP is believed to coat the exterior of PHA granules and, by an as yet identified mechanism, regulate granule size and abundance (49, 57, 58).

While the majority of eubacteria (26, 44), and indeed many archaea (24, 44), store carbon as PHA, a small subset of organisms, primarily actinomycetes, are capable of storing carbon in the form of TAGs. TAG biosynthesis and storage has been observed in members of the genera *Mycobacterium, Rhodococcus, Streptomyces, Nocardia* and others. Of these to organisms, TAG biosynthesis and storage has been most extensively studied in the Gram-positive, non-spore forming actinomycete *Rhodococcus opacus*, strain PD630 (1-3, 5-7, 13, 15, 20, 21, 27, 47, 52-55).

Several studies have demonstrated that *R. opacus* PD630 is capable of accumulating up to 76% of its cell dry weight as TAGs (3). As is the case for PHA biosynthesis, TAG accumulation occurs during nitrogen starvation when carbon is in excess (1-3, 30, 55). Paralleling PHA biosynthesis further, TAGs are stored in *R. opacus* PD630 in distinct inclusion bodies, termed lipid bodies (2, 3, 27, 52, 54). While several studies have sought to identify the underlying molecular and biochemical mechanisms behind TAG biosynthesis and storage in the form of lipid bodies, very little is known concerning these processes. It is likely that these pathways are very complex as supported by the predicted gene redundancy within the closely related, recently sequenced, *Rhodococcus jostii* RHA1 genome (34).

Herein, genes and their products that are involved in lipid metabolism in *R. opacus* PD630 were identified. Utilizing a forward genetic approach a conserved hypothetical gene was identified, termed herein tadA (triacylglycerol accumulation deficient), which is predicted to encode a protein with sequence similarity to the heparin-binding hemagglutinin family of proteins from the genus *Mycobacterium*. The tadA::Tn5 mutant accumulates 30-40% less TAGs than the parental strain. As demonstrated herein, this deficiency is most likely the result of altered lipid body formation and morphology. Through biochemical studies, it is further demonstrated herein that the predicted heparin-binding activity of this protein is required for its activity both in vivo and in vitro. Thus, it is believed that this is the first protein shown to regulate lipid body assembly and maturation in prokaryotes.

Materials and Methods

Bacterial Strains, Chemicals and Media

All bacterial strains, plasmids and oligonucleotides used in this study are listed in Table 9. Bacteria were propagated in lysogeny broth (LB) (9) (Difco, Lawrence, Kans.) or minimal media, unless otherwise noted. The minimal media was prepared as previously described (30) and supplemented with 4% glucose and 0.15% ammonium sulfate. Growth media was supplemented with kanamycin (100 µg/ml), gentamycin (10 µg/ml), ampicillin (150 µg/ml) and/or arabinose (0.2%). All restriction enzymes were purchased from New England Biolabs (Ipswich, Mass.). Chemicals were purchased from Sigma-Aldrich (St. Louis, Mo.). Plasmids were constructed in either *Saccharomyces cerevisiae* using in vivo recombinational cloning (45, 46) or in *E. coli* EC100D (Epicentre Biotechnologies, Madison, Wis.) using standard techniques. Plasmid DNA was mobilized into *R. opacus* PD630 using electroporation as described below. Plasmid DNA was purified from cells using Qiagen Mini-Prep kits (Qiagen, Valencia, Calif.) per manufacturer's instructions.

Electroporation of DNA into *R. opacus* PD630

Electrocompetent *R. opacus* cells were obtained by centrifuging 3 ml of 48 hour-old cultures grown in LB medium supplemented with 1% casamino acids followed by several washes in sterile dH$_2$O, cell pellets were then resuspended in 200 µl of sterile dH$_2$O to which 1 µg of plasmid DNA was added. Electroporations were performed using a Bio-Rad gene pulser (Hercules, Calif.) apparatus set to 2.5 kV, 25 µF and 600 ohms. Following electroporation cells were immediately resuspended in 2 ml of LB medium and incubated at 30° C. for 2 h prior to plating on selective medium.

Transposon Mutagenesis and Screening

The EZ-Tn5 transposome system from Epicentre Biotechnologies (Madison, Wis.) was used to introduce random mutations throughout the *R. opacus* PD630 genome. Following electroporation, as described above, with the transposome, transformants were plated on solidified LB medium supplemented with kanamycin and incubated at 30° C. for 3-4 days. Colonies were transferred to 96 well plates containing LB medium supplemented with kanamycin and incubated at 30° C. for 4 days. Following growth, mutants were screened as described below.

Mapping Transposon Insertion Sites

Identification of the transposon insertion site was performed using a modified marker rescue technique as described by the manufacturer. Genomic DNA was purified as previously described (25). Following purification, genomic DNA was digested with the restriction endonuclease AgeI. Digested genomic DNA was then ligated using T4 DNA ligase and electroporated into *E. coli* EC 100D cells and grown on solid LB medium supplemented with kanamycin. Following growth, single colonies were grown in liquid LB medium supplemented with kanamycin, from which plasmid DNA was purified and sequenced using primers provided by the transposome manufacturer.

TAG Accumulation Screen

Mutants were transferred from 96-well dishes to solid minimal media supplemented with 4% glucose and 0.15% ammonium sulfate and grown for 120 hours at 30° C. Following growth, plates were flooded with 0.2% Sudan black in 95% ethanol and incubated at room temperature for 15 min followed by three 95% ethanol washes for 1, 5 and 15 min. Mutants were selected based on their reduced staining with the dye.

Lipid Extraction and Thin-Layer Chromatography

Extraction of lipids from cultures was performed as previously described with minor modifications (10). Briefly, cultures were centrifuged and the resulting pellets lyophilized. Lipids were extracted by adding a 1:1 chloroform:methanol solution to the dried pellets followed by incubation at room temperature for 60 min with agitation. Extracts were then filtered through a 0.2 µm filter to remove particulate matter. Thin layer chromatography experiments were performed using a two-step resolution method as previously described (16, 29). Equal volumes of lipid extract were spotted onto a glass-backed silica gel 60 TLC plates (EMD Chemicals Inc., Gibbstown, N.J.) and dried under a constant stream of nitrogen. Samples were resolved using an initial polar buffer consisting of 60:35:5 chloroform:methanol:water, dried and then further resolved using a second buffer containing 70:30:1 hexane:diethyl ether:acetic acid. Plates were developed by charring by first exposing the plates to a 3% cupric acetate, 8% aqueous phosphoric acid solution followed by baking in a 200° C. oven. Glycerol monooleate, glycerol dioleate and glycerol trioleate were used as standards.

Gas Chromatography of Fatty Acid Methyl Esters (GC-FAMES)

Cell pellets for GC-FAMES analysis were lyophilized overnight. Extraction and subsequent transesterification of fatty acids was performed as previously described (11, 30). Briefly, 10 mg of dried cell mass was resuspended in 1 ml of chloroform to which 1 ml of methanol:sulfuric acid (85:15) was added. Samples were then heated to 100° C. for 2.5 hours and promptly cooled on ice. Phases were separated by centrifugation at 2000×g for 5 minutes. The organic phase was removed and dried using anhydrous sodium sulphate and filtered through a 0.22 µm filter. Samples were analyzed using a Hewlett Packard 6890 gas chromatograph with an Agilent DB-Wax megabore column (30 m×0.53 mm×1 µm). Methyl esters were detected using a flame ionization detector. Oven temperature was ramped form 70 to 220° C. for all samples. Total fatty acids as well as the abundance of various species were determined by comparing the resulting chromatograph peak areas to a series of standards.

Construction of Plasmids pDPM70, pDPM78 and pDPM80

The *Rhodococcus/E. coli/S. cerevisiae* expression vector pDPM70 was constructed using in vivo recombination as previously described (45, 46). Initially, the URA3 gene and the CEN6/ARSH4 *S. cerevisiae* origin of replication from pMQ30 (45) was amplified using the primers pDPM13 for and pDPM13 rev and subsequently cloned into the *Rhodococcus/E. coli* shuttle vector pAL358 creating the *Rhodococcus/E. coli/S. cerevisiae* shuttle vector pDPM13. The Psmyc-tetRO promoter and cognate ribosome binding site were amplified from pMSG374 (17, 48) using primers pDPM65 for and pDPM65 rev and was cloned into pDPM13, which had previously been linearized via restriction digest.

Full-length tadA was amplified from the *R. opacus* PD630 chromosome and integrated downstream of the Psmyc promoter in pDPM70 using primers pDPM66 for and pDPM66 rev to create the *Rhodococcus* tadA expression plasmid pDPM78. To create the ΔC-terminal TadA mutant protein (or mutein), the tadA gene was amplified from the *R. opacus* PD630 chromosome using primers pDPM66 for and pDPM80 rev and cloned into pDPM70 thus creating plasmid pDPM80.

Plasmid pDPM72 containing the full-length WT tadA open reading frame with a C-terminal hexa-histidine tag, was created using in vivo recombination cloning. The tadA gene was amplified from the *R. opacus* PD630 chromosome using primers pDPM72 for and pDPM72 rev and subsequently cloned into pDPM77 (33) which had been previously linearized via restriction digest. To create pDPM75, containing a hexa-histidine tagged C-terminal truncation of TadA, pDPM72 was linearized utilizing the restriction enzyme SphI, which cleaves pDPM72 within the 3' end of the tadA open reading frame, and subsequently recombined with the primer pDPM75 rev in *S. cerevisiae*.

Fluorescent Microscopy

Nile red staining of cells was performed as previously described (19, 23). Briefly, cultures were mixed 10:1 with a 75% glycerol solution containing 5 µg of the lipophilic flurophore Nile red and observed using a Carl Zeiss AX10 Imager A.1 fluorescent microscope using the GFP and cy3 filters. Images were recorded using a Carl Zeiss AxioCam MRm (Carl Zeiss Microimaging Inc., Thornwood, N.Y.) and subsequently analyzed using Adobe Photoshop CS3.

Purification of Lipid Bodies

Lipid bodies were purified from *R. opacus* PD630 as previously described (27) with minor modifications. Briefly, *R. opacus* was grown for 96 h in minimal media supplemented with 4% glucose and 0.15% ammonium sulphate. Cultures were harvested via centrifugation at 6000×g for 20 minutes. Cell pellets were resuspended in 25 ml of PBS and lysed by passing through a French pressure cell set at 18,000 psi 5 times. An equal volume of 80% glycerol was added to lysates followed by centrifugation at 6000×g for 3 h at 4° C. Following centrifugation, the upper layer (lipid body fraction) was removed to 40 ml of 40% glycerol (tube #1) and the pellet (cell debris) was resuspended in 40 ml of 40% glycerol (tube #2) followed by a second centrifugation at 6000×g for 3 h. The lipid body layer (upper layer) from tube #1 was removed to 20 ml PBS and the cell debris (pellet) from tube #2 was resuspended in 20 ml of PBS followed by centrifugation at 7500×g for 30 min. All fractions were then resuspended in 5 ml of PBS and used immediately.

Purification of TadA

TadA was purified using nickel affinity chromatography as previously described (33, 40). Overnight cultures of *E. coli* Top10 cells harboring either pDPM72 or pDPM75 grown in LB medium supplemented with ampicillin were diluted 1:1000 in 500 ml LB medium supplemented with ampicillin and arabinose and grown for 18 h at 37° C. with shaking. Cells were pelleted via centrifugation at 5000×g for 10 minutes, resuspended in 20 mM sodium phosphate, 500 mM sodium chloride, 20 mM imidazole buffer (pH7.0) and lysed via passage through a French pressure cell. Cell lysates were subsequently centrifuged at 20,000×g for 30 minutes and passed through a 0.22 µm filter. Filtered lysates were then fractionated over a 5 ml HisTrap FF nickel affinity column (GE Healthcare, Piscataway, N.J.) using a 20-500 mM linear imidazole gradient. It was determined using SDS-PAGE that all three variants of TadA-His eluted between 100 and 250 mM imidazole. TadA-containing fractions were pooled and concentrated using Vivaspin15R columns with a 10,000 molecular weight cutoff (Sartorius Stedim, Goettingen, Germany) and dialyzed against 20 mM Tris (pH7.0) 100 mM NaCl using Slide-A-Lyzer dialysis cassettes (Thermo Scientific, Rockford, Ill.). Protein concentrations were determined using the Bio-Rad protein assay kit (Bio-Rad, Hercules, Calif.) per manufacturer's instructions with bovine serum albumin serving as a protein standard.

Heparin-Sepharose Binding

Purified TadA was diluted to a final concentration of 500 µg/ml in dialysis buffer. 100 mg of Heparin-sepharose CL-6B (GE Healthcare, Piscataway, N.J.) was resuspended in 5 ml of Tris buffer (20 mM Tris (pH7.0), 100 mM NaCl) and allowed to rehydrate with gentle agitation for 1 h. Following rehydration, the resin was pelleted via centrifugation at 1000×g for 2 minutes and subsequently washed 3 times in the same buffer. The resin was resuspended in 1 ml of Tris buffer to which 500 µg of purified TadA was added. The Sepharose-TadA slurry was incubated at 4° C. for 1 h with gentle agitation. Following incubation, the resin was pelleted, an aliquot of the supernatant was removed (flow-through fraction), the Sepharose was washed 5 times with Tris buffer and an aliquot of the supernatant from the final wash was removed (wash fraction). The remaining heparin-sepharose was resuspended in 1 ml of Tris buffer from which an aliquot was removed (beads fraction). 5× SDS-PAGE loading buffer was added to each aliquot, which were then boiled for 5 min. Samples were resolved using 10% acrylamide Ready gel Tris-HCl SDS-PAGE gels (Bio-Rad, Hercules, Calif.) and stained using colloidal coomassie as previously described (18, 31).

Lipid Aggregation Assays

Purified lipid bodies were diluted to a final optical density of 10 at 600 nm and mixed with either 20 mM Tris, 100 mM NaCl or purified TadA in a round bottom 96-well dish and incubated at room temperature for 12 h. Wells were imaged using a Canon Powershot SD1200 IS digital camera (Canon, Lake Success, N.Y.). To obtain a more quantitative measure of aggregation, 2 µl of the supernatant was removed from each well and the optical density at 600 nm was determined using a Nano-Drop spectrophotometer (Thermo Scientific, Wilmington, Del.).

Western Blotting

All Western-blotting was performed as previously described (12, 33). Qiagen Penta-His Antibodies (Qiagen, Valencia, Calif.) were used at a dilution of 1:3000 as the primary antibody in all Western blots. Goat anti-rabbit HRP conjugated antibodies (Bio-Rad, Hercules, Calif.) were used as the secondary antibody for all Westerns.

Results

Genetic Screen for Triacylglycerol Accumulation Deficient (tad) Mutants

Figure 80:
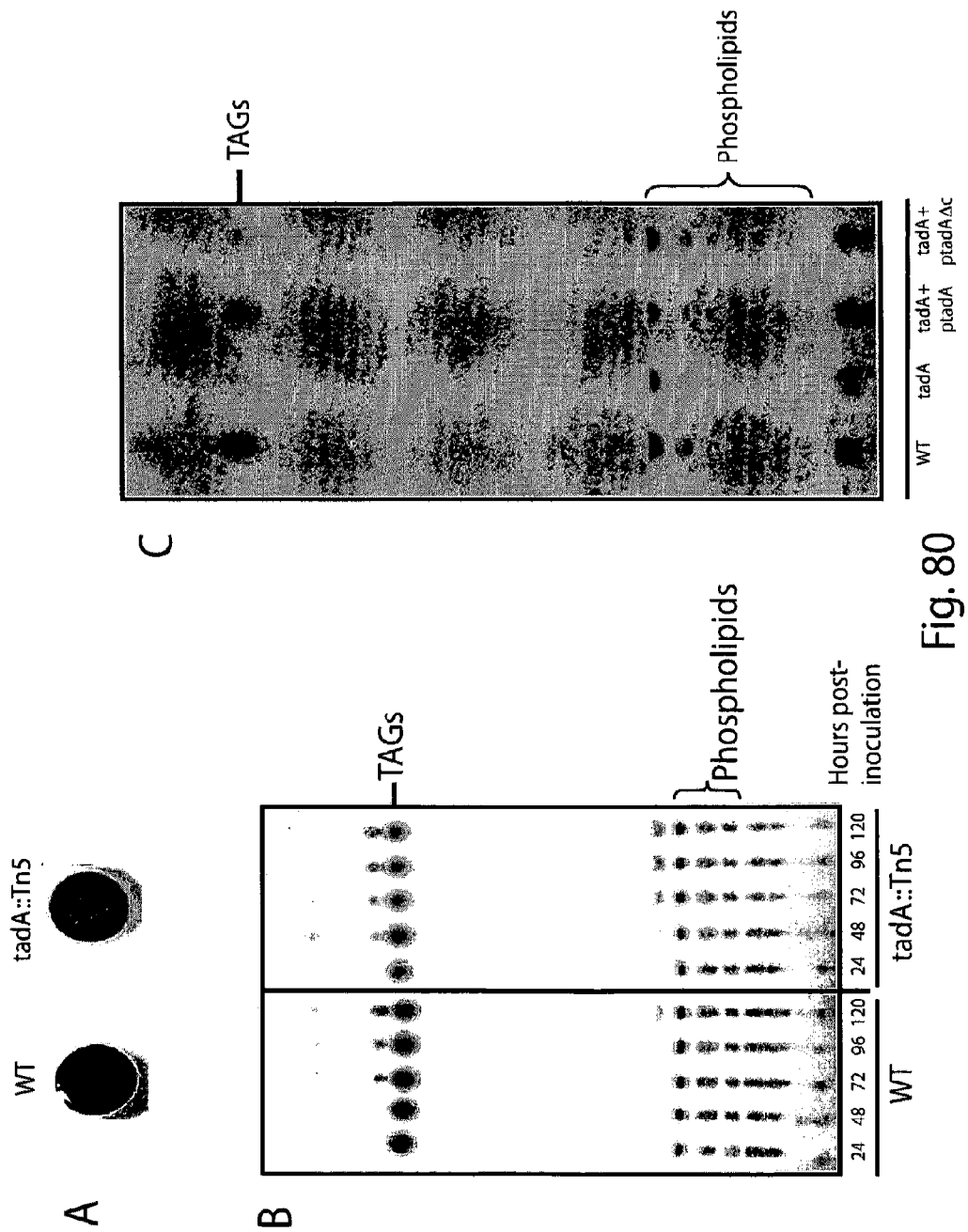
FIG. 80 The tadA::Tn5 mutant is deficient for TAG accumulation.
Figure 81:
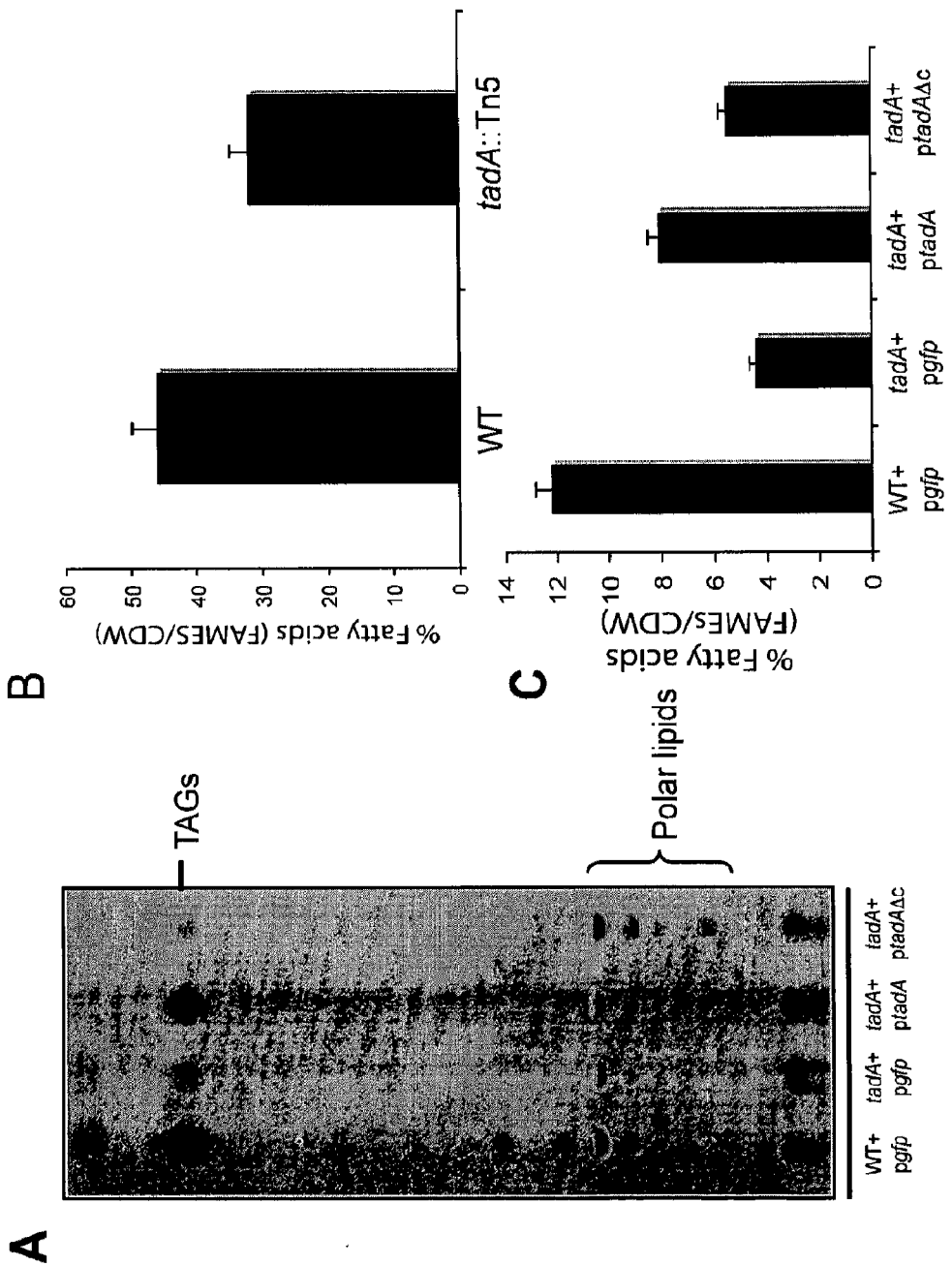
FIG. 81 demonstrates reduced TAG accumulation in tadA mutants and complementation of the tadA::Tn5 mutant.

A library of 5000 random Ez-Tn5 *R. opacus* PD630 mutants was generated and subsequently screened for triacylglycerol biosynthesis using a Sudan black-based screening method. Previous experiments by Kurasawa and colleagues as well as Alvarez et al (2, 3) demonstrated that *R. opacus* accumulates high concentrations of TAG when grown in media with a low carbon:nitrogen ratio. Accordingly, the Tn5 mutants were grown on minimal salts medium supplemented with 4% glucose and 0.15% ammonium sulfate for 120 h, allowing for significant TAG accumulation. Following growth, accumulated TAGs were detected by staining the colonies with the lipophilic dye Sudan Black B. TAG accumulation was exhibited by dark blue staining of the colonies as seen in the wild-type example in FIG. 80A; mutants deficient in TAG accumulation exhibited less staining as is shown for the 19A3 mutant in FIG. 80A and lower percent fatty acid production (FIG. 81). From this initial screen several mutants were identified that demonstrated varying degrees of decreased staining as compared to the wild type.

As decreased staining could readily be due to a variety of different factors other than a loss of TAG accumulation, mutants of interest were subjected to a second round of screening wherein they were grown in minimal media in flasks for 120 h and then analyzed for their TAG content using TLC. Of the initial strains assayed one, designated 19A3, demonstrated wild type-like growth while accumulating 35% less TAGs than the wild-type strain.

Kinetics of TAG Accumulation in the Wild Type and 19A3 Mutant Strains

Following on the secondary screening, the 19A3 mutant was characterized by studying the kinetics of TAG accumulation. The wild-type strain of *R. opacus* PD630, and the 19A3 mutant strain, were grown in minimal medium supplemented with 4% glucose and 0.15% ammonium sulfate. Samples were removed at 24, 48, 72, 96 and 120 h to measure the culture turbidity (A=600 nm), determine the colony forming units, measure nitrogen and glucose concentrations as well as pH and to assess TAG accumulation. Whereas, the number of colony forming units, as well as the consumption of nitrogen and glucose, were identical between the two strains, there was a distinct difference in the culture turbidity and the amount of TAGs accumulated. The wild-type strain had a higher optical density at later time points (72 h, 8.75+/−0.34; 96 h, 8.80+/−0.47; and 120 h, 9.08+/−0.26) as compared to the mutant strain (72 h, 8.22+/−0.43; 96 h, 8.31+/−0.19; and 120 h, 8.09+/−0.31). TLC analysis of the lipid content of the two strains demonstrated that the concentrations of the polar lipids, thought to consist primarily of phospholipids and acting as a convenient loading control, remained similar between the two strains. However, the mutant strain demonstrated a reduction in TAGs as compared to its wild type counterpart (FIG. 80B). Densitometric analysis of the TLC results suggests a 30-40% reduction in TAG accumulation in the mutant strain. The optical density difference between the two strains was most likely the result of the decreased accumulation of TAGs in the mutant strain and not a difference in growth, a point which was confirmed by CFU counts (data not shown). Interestingly, similar discrepancies in optical density have been described in bacteria accumulating PHAs.

Gas chromatography was utilized as a second method to analyze the fatty acid content of both the wild type and mutant strain. Cell pellets from kinetic experiments identical to those described above were lyophilized and the fatty acids extracted and converted to fatty acid methyl esters (FAMES) for use in GC. Consistent with the TLC results, the mutant accumulated 38% (+/−2.8%) less fatty acids than the wild type at the 96-h time point. Thus, GC-FAMES analysis confirmed that the 19A3 mutant accumulates 35-40% less TAGs than the wild-type strain.

Utilizing a marker rescue-like approach, the transposon insertion site was identified in the 19A3 mutant as being 150 nucleotides downstream of the predicted start codon of a gene, termed herein tadA (triacylglycerol accumulation deficient), which is predicted to encode a hypothetical protein with sequence similarity to the heparin-binding hemagglutinin family of proteins from *Mycobacterium smegmatis* (FIG. 82). BLAST analysis of the nucleotide sequence of the tadA gene against the *R. jostii* RHA1 genome (www.*rhodococcus*.ca) identified a homolog with 97.46% identity at the nucleotide level and 100% identity at the amino acid level annotated as ro02104.

Complementation of the tadA::Tn5 Mutant

To demonstrate that the observed phenotype was the result of the mapped transposon insertion and not a random mutation elsewhere in the chromosome, the tadA gene was expressed from the Psmyc promoter contained on the pDPM78 plasmid. As significant plasmid instability has been observed with this family of vectors in the past, cultures were grown for only 48 h prior to analysis. As can be seen in FIGS. 80B and C, 48 h is more than adequate to establish significant TAG biosynthesis and accumulation.

Wild-type *R. opacus* PD630 and the tadA::Tn5 mutant containing either the empty vector pDPM70, the WT TadA expressing plasmid pDPM78 (ptadA) or the ΔC-terminal TadA (highlighted region in FIG. 82) expressing plasmid pDPM80 (ptadAΔC) were grown in minimal medium supplemented with gentamycin for 48 h prior to being diluted 1:10 into baffled flasks containing the same medium. Cultures were then incubated at 30° C. with shaking for 48 h prior to harvesting. TAG production was assayed using TLC (FIG. 80C). Additionally, bacterial growth was monitored by assessing colony forming units counts and no difference was observed in the final number of bacteria in each culture. Extrachromosomal expression of the wild-type tadA gene in the 19A3 mutant strain resulted in an obvious and reproducible increase in TAG accumulation, thus complementing the observed phenotype, while expression of ΔC-terminus mutant of tadA did not have any impact on TAG accumulation (FIG. 80C).

Figure 83:
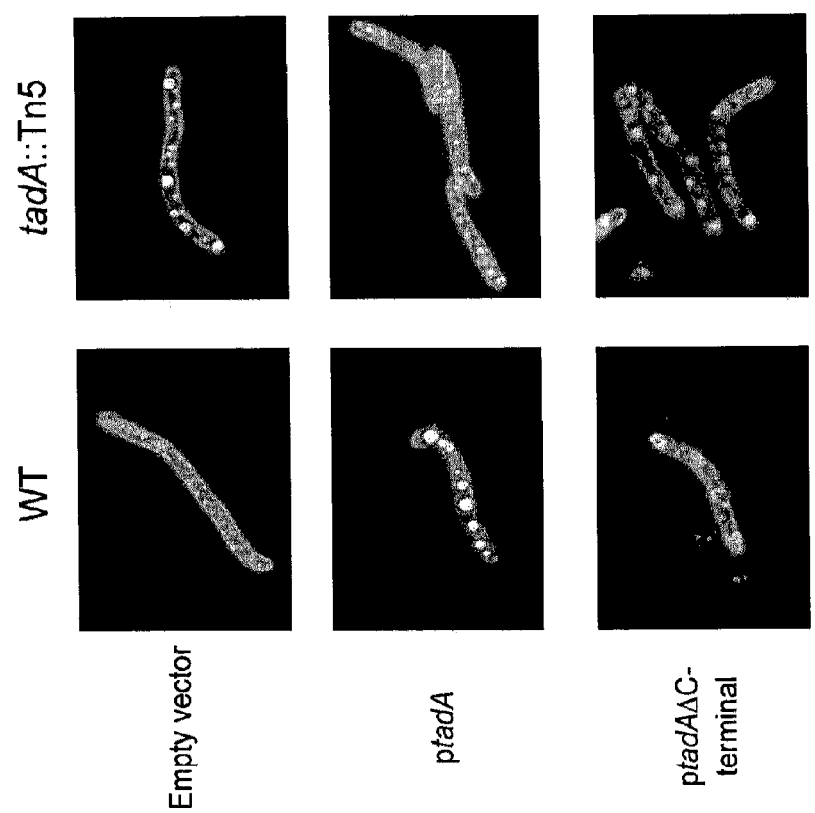
FIG. 83 reveals that the tadA::Tn5 mutant demonstrates altered lipid body morphology. Micrographs of bacteria stained with the lipophilic fluorophore Nile Red. Shown are the isogenic wild-type *R. opacus* (left) and the tadA mutant strains (right) containing the empty vector pDPM70 or expressing either wild-type tadA or the gene encoding the C-terminally truncated tadA were grown in minimal medium for 48 hours.

Lipid Bodies in the tadA Mutant are Morphologically Different than Those Formed in the Parental Strain To better assess the TAG accumulation deficiency observed in the tadA mutant, fluorescent microscopy was utilized to visualize lipid bodies formed in the wild type and mutant containing the empty vector pDPM70. Cultures of both strains were grown in minimal medium supplemented with gentamycin for 48 hours and lipid bodies were stained with the lipophilic fluorophore Nile Red. Lipid bodies formed in the tadA mutant were observed to be morphologically different than those formed by the wild type. As shown in FIG. 83 the wild type has numerous small lipid bodies which virtually fill the cytoplasm of the cell while the tadA mutant is characterized by fewer, but slightly larger lipid bodies that appear to localize primarily to the cytoplasmic side of the cell membrane. Additionally, the mutant lipid bodies have a sharper appearance with more delineated edges as compared to the wild-type bacterium.

With the demonstration that the TAG deficiency observed in the tadA mutant was most likely the result of a defect in the lipid body formation pathway, it was hypothesized that overexpression of the tadA gene in the parental strain, shown above to complement the mutant phenotype, would result in increased lipid body size. To this end, the wild-type TadA protein as well as the ΔC-terminal TadA were expressed in wild type *R. opacus* and the tadA::Tn5 mutant. Interestingly, overexpression of the tadA gene in the wild type resulted in the formation of large lipid bodies that appear to line up along the middle of the cells while the truncated TadA had no effect (FIG. 82). As would be predicted by the TLC analysis, expression of the wild-type TadA protein in the 19A3 mutant resulted in wild type-like lipid bodies while the ΔC-terminus variant of TadA did not appear to compliment the mutant phenotype.

TadA Localizes to Lipid Bodies

Figure 84:
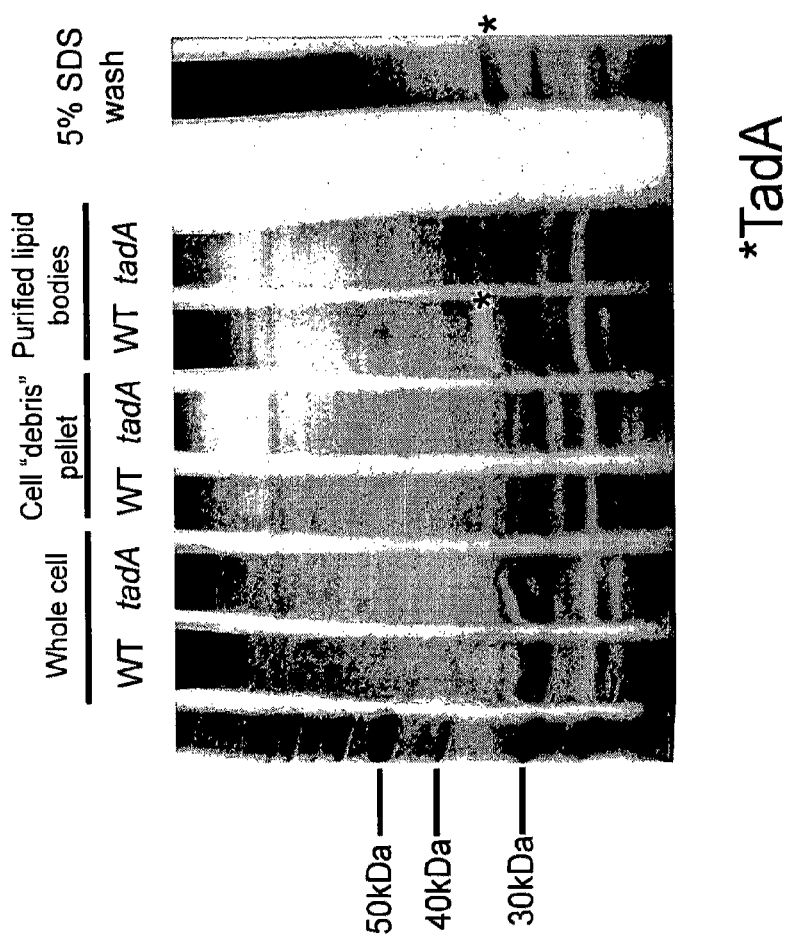
FIG. 84 demonstrates that TadA is enriched in lipid body containing cellular fractions. Wild-type *R. opacus* and the tadA::Tn5 mutant were grown in minimal medium for 120 h followed by lysis and subsequent separation of the lipid bodies by centrifugation. Samples of the unlysed cells, the cellular material depleted of lipid bodies (cell "debris" pellet), the purified lipid bodies and lipid bodies washed in 5% SDS were normalized to total protein concentration and then resolved using SDS-PAGE followed by silver staining.

With the demonstration that expression of the tadA gene is linked to lipid body morphology, it was hypothesized that it may act to structurally regulate lipid body formation or maturation. Key to this hypothesis would be localization of the TadA protein to lipid bodies. To assess the localization of the TadA protein, specifically to determine whether the protein localizes to lipid bodies, lipid bodies were purified from both the wild type and the tadA mutant as previously described (27). Both the wild type and the tadA::Tn5 mutant were grown under TAG inducing conditions and lipid bodies were harvested. SDS-PAGE analysis of the lipid body fraction showed a highly enriched protein present in the wild-type strain that was conspicuously absent in the mutant (FIG. 84). Mass spectrometric analysis of this band identified it as being the TadA protein, suggesting that the TadA protein localizes to lipid bodies.

Numerous proteins were observed to co-purify with the lipid bodies, which could be an artifact of the purification technique. In order to dissociate those proteins which were loosely associated with the lipid bodies the lipid body fraction was washed twice in 5% SDS, followed by SDS-PAGE analysis. Washing the lipid body-containing fraction in SDS resulted in a decrease in the total number of proteins associated with this fraction. As can be seen in FIG. 84, once again a protein was observed that migrated at approximately the appropriate size corresponding to the TadA protein (arrows in FIG. 84). Mass spectrometric analysis once again identified this protein as TadA. Thus it appears as if the TadA protein associates very tightly with the lipid body-containing fraction.

TadA Binds Heparin in vitro

As shown in FIG. 82, the TadA protein shares a high level of similarity with the heparin-binding hemagglutinin (HBHA) protein from *Mycobacterium smegmatis* at the amino acid level. Of particular interest was the high level of similarity at the predicted C-terminal end of the protein, which in *M. smegmatis* and other *Mycobacteria* has been shown to be essential for heparin-binding activity both in vitro and in vivo. Based on these similarities as well as previous data in various *Mycobacteria* it was hypothesized that the TadA protein may also possess heparin-binding activity.

Figure 86:
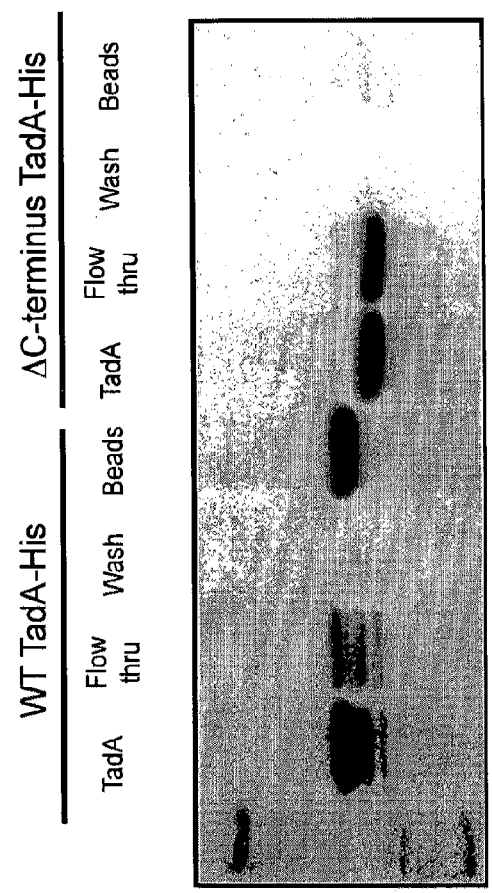
FIG. 86 demonstrates that the TadA protein binds heparin in vitro. Wild-type and the ΔC-terminus TadA were purified using nickel affinity chromatography and subsequently assayed for their ability to bind to heparin-sepharose. Purified TadA was incubated with heparin sepharose. Following centrifugation, the supernatant was removed (flow through) and the resin was washed 5 times (wash). The resin was then resuspended in SDS-PAGE loading buffer and boiled (Beads). Samples were resolved using SDS-PAGE and stained with colloidal coomassie. WT TadA is visible in the heparin-sepharose fraction suggesting it binds to heparin while the ΔC-terminus mutant was not detected in this fraction.

To test whether the TadA protein was capable of binding heparin, a TadA hexa-histidine fusion protein was expressed in *E. coli* and the protein was purified via nickel-affinity chromatography. Following purification this protein was incubated with heparin-sepharose and heparin binding was assessed. As can be seen in FIG. 86, while some of the protein did not bind to the heparin-sepharose, as indicated by the presence of the TadA protein in the flow through fraction, the majority of the protein was found associated with the heparin-sepharose ("beads"). Previous reports have suggested that the lysine-rich C-terminal domain of heparin-binding hemagglutinins is particularly sensitive to proteolytic cleavage. This is likely to be the case for the TadA protein as well since the flow-through fraction seemed to be enriched with what appears to be proteolytic products. These products are absent in the heparin-sepharose bound fraction.

As previous studies have demonstrated that heparin-binding activity is the result of the C-terminal, lysine-rich region of heparin-binding hemagglutinins, it was proposed that this would also be the case for the TadA protein. To this end, a variant of the TadA protein was constructed and purified which had been truncated at amino acid 231 (ΔC-terminus TadA) thus eliminating the 11 lysine residues found in the C-terminus, and assessed its ability to bind to heparin-sepharose. Abundant levels of the TadA protein were observed in the flow through fraction while no protein was detected associated with the heparin matrix, thus suggesting that this domain is necessary for heparin-binding (FIG. 86). As an additional control, to ensure that the association of TadA with the heparin-sepharose resin was not the result of a non-specific interaction, the heparin-binding assay was performed in the presence of pure heparin and it was found that this completely abrogated any binding of TadA to the heparin-sepharose matrix. Results of a TadA yeast agglutination assay are presented in FIG. 85.

TadA Aggregates Purified Lipid Bodies in vitro

With both the demonstration that the absence or overexpression of tadA results in altered lipid body formation, as well as the observation that the TadA protein is enriched in lipid body-containing cellular fractions, next it was investigated whether the TadA protein could aggregate purified lipid bodies in vitro. To this end, lipid bodies were purified from wild type *R. opacus*, as previously described. Purified lipid bodies were incubated with purified TadA in a round bottom 96 well dish similar to classic hemagglutinin assays. As hypothesized, wild-type TadA was observed to be capable of inducing lipid body aggregation and subsequent flocculation in a dose-dependent manner (FIG. 87A). This activity required the presence of the C-terminal heparin-binding domain, as incubation of purified lipid bodies with the purified ΔC-terminus TadA variant did not result in aggregation. To better quantify this assay, 2 μl of the supernatant from each well was removed and the optical density at 600 nm measured. As can be seen in FIG. 87B, the optical density of the supernatants decreases as protein concentration increases, suggesting increased aggregation and flocculation of the lipid bodies with increased concentrations of wild-type TadA. A similar pattern was not observed for the ΔC-terminus mutant further supporting the hypothesis that the C-terminus is essential for lipid body aggregation.

It was speculated that this increased flocculation was the result of increased aggregation of the lipid bodies in the presence of TadA. To address this, samples were observed from the various wells using fluorescent microscopy. Lipid bodies from the aggregation experiments were stained with the lipophilic fluorphore Nile Red. For both the no-protein controls as well as for lipid bodies incubated with the ΔC-terminal variant of TadA, the lipid bodies existed primarily as small to medium sized aggregates. However, when lipid bodies incubated with wild type TadA were observed it was found that the lipid bodies had aggregated into very large clumps often filling the field of view (FIG. 87C).

Based on the belief that the TadA protein localizes to lipid bodies in vivo and that the aggregation activity is dependent on this localization, next it was investigated whether the TadA protein added to the purified lipid bodies during the aggregation assays was associating with the lipid bodies. Conveniently, as the TadA used in these assays contains a hexa-histidine tag, anti-penta-histidine antibodies were used to probe the lipid bodies used in the aggregation assays for the presence of the added, recombinant TadA. Lipid bodies from the aggregation assay were harvested, supernatants removed and the lipid bodies washed prior to resolving both the supernatant and lipid body fractions using SDS-PAGE followed by Western blotting using anti-penta-histidine antibodies. Both the wild-type TadA and the ΔC-terminus mutant proteins were detected in both the supernatant as well as the lipid body fractions suggesting that they associate with lipid bodies during the assay (FIG. 87D).

Regulation of tadA

Figure 88:
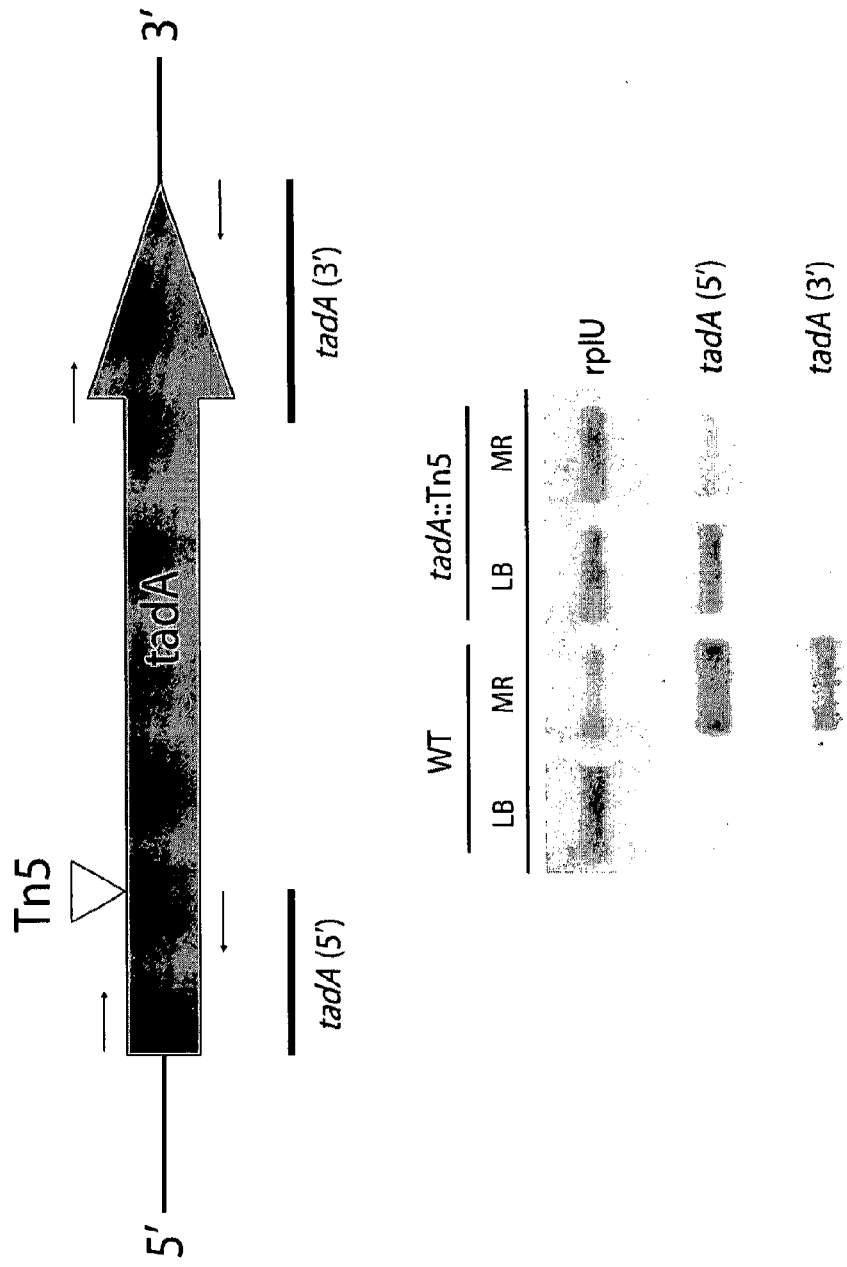
FIG. 88 presents a schematic and a gel depicting transcriptional regulation of tadA.
Figure 90:
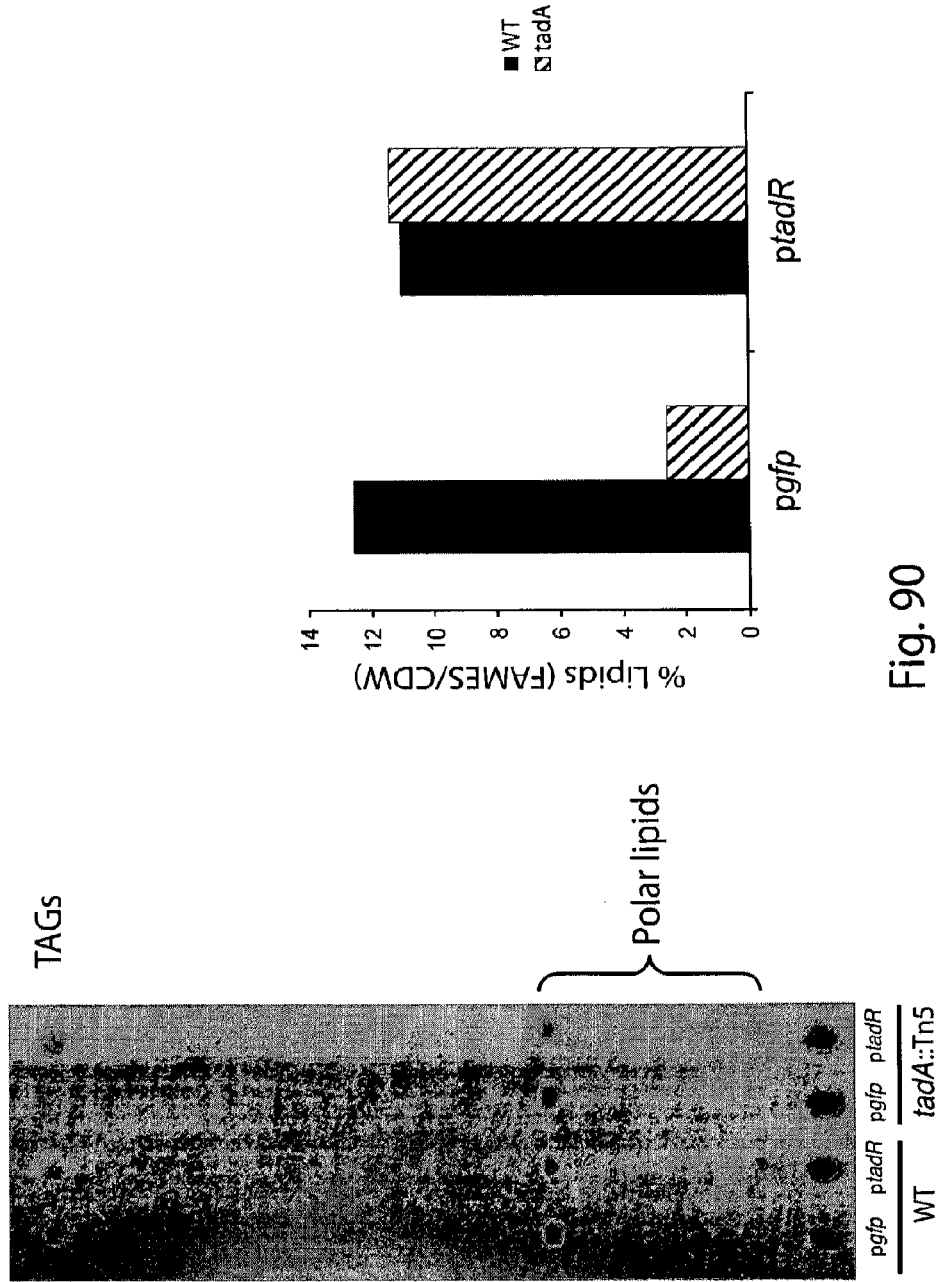
FIG. 90 demonstrates accumulation of TAGs in tadR mutants independent of tadA.
Figure 91:
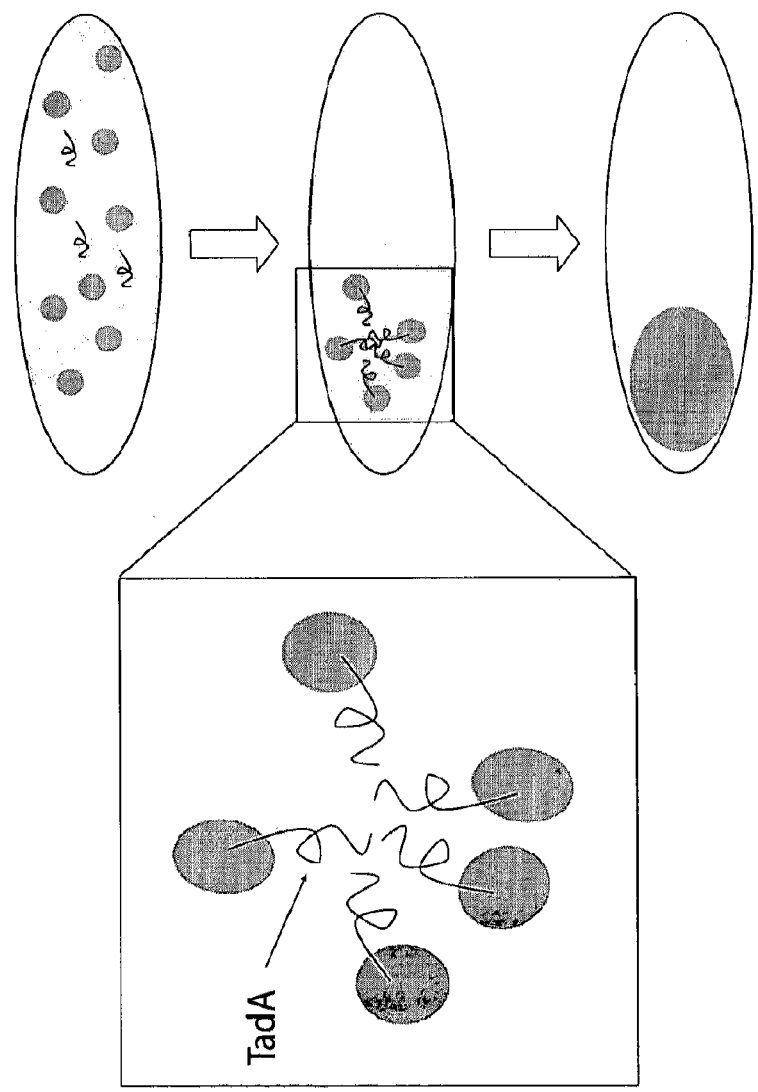
FIG. 91 presents a schematic depicting a proposed model for TAG accumulation.

Regulation of tadA was also investigated. A schematic depicting the tadA gene and the site of insertion of the Tn5 mutant is presented in FIG. 88. FIG. 89 depicts the chromosomal region surrounding the tadA gene. Immediately upstream of the tadA gene is an open reading frame referred to as ro02105, named herein tadR. The tadR gene encodes for a predicted DNA binding protein, containing an XRE HTH DNA binding domain. The protein sequence for TadR is provided below. FIG. 89 reveals that tadR upregulates expression of tadA. Significantly, FIG. 90 demonstrates that tadR can rescue the TAG accumulation defect of tadA mutants. tadR was found to induce TAG accumulation independently of tadA, suggesting that it has other downstream targets other than tadA. tadA transcript levels were also found to be increased in cells grown in MR medium relative to LB medium (FIG. 89). A proposed model for TadA activity is shown in FIG. 91. In this model, expression of TadA leads to lipid body coalescence. Increased coalescence of lipid bodies is significant because it represents a means to increase efficiency of TAG purification from cells.

Other genes within the surrounding chromosomal region of tadA are shown in FIG. 92. The functions of these genes were also investigated. Immediately upstream of tadA is the gene tadR, discussed above. Immediately upstream of tadR is a gene designated as ro02106, which is a predicted membrane protein. Upstream of ro02106 is a gene designated as ro02107 which is an AcrR family transcriptional regulator. Immediately downstream from tadA is a gene designated as ro02103, and is named herein tadB. The protein sequence for TadB is provided below. Significantly, when overexpressed, the tadB gene was also found to produce increased TAG accumulation (FIG. 93).

Thus, a new operon of genes was identified and described herein to be involved in TAG production. Overexpression of tadR, tadA and/or tadB leads to increased production of TAGs in cells, representing a means for engineering cells to improve yield and efficiency of TAG production.

Discussion

Numerous studies have sought to identify the mechanisms by which various carbon storage molecules are actually compartmentalized within the cell. Much attention has been given to the PHA storage pathways and the phasins that mediate the formation of the PHA granules. Indeed, it is well documented that PHA storage and granule formation is a regulated and ordered process (57, 58). In oleaginous seeds and plants, oleosins have been implicated in playing a role in lipid body formation (42, 59). However, despite several studies, there is a relative dearth of knowledge concerning the topic in oleaginous bacteria such as R. opacus. This gap in knowledge has led some to speculate that the process of lipid body formation is not regulated but is simply the result of TAGs accumulating and blebbing from the cytoplasmic membrane in a disordered and random manner (52). Previous attempts to purify lipid bodies from R. opacus and identify proteins associated with them yielded several promising candidates, but little has followed on these initial reports (27). Interestingly, in these earlier reports, the TadA protein was not identified. The discrepancy between our data and previous works could be the result of different carbon sources provided in the medium (gluconate vs. glucose) or other culture conditions. However, we have observed that the 19A3 mutant demonstrates decreased TAG accumulation when grown with gluconate as the sole carbon source suggesting it plays a role in lipid body formation under these conditions as well.

The genetic screen described herein identified the 19A3 transposon mutant, which accumulated approximately 35% less TAGs as compared to the wild-type strain. Mapping of the mutation revealed a transposon insertion ~150 nucleotides into the 5' end of a gene, which is termed tadA. Additionally, 2 other mutants with Tn insertions within the tadA gene were identified. All of the mutants isolated demonstrated a similar decrease in TAG accumulation and a similar lipid body phenotype. The R. jostii RHA1 tadA homolog ro02104 is flanked by the ro02103 gene predicted to encode a membrane associated protein and the ro02105 gene predicted to encode a transcriptional regulator. The spacing and orientation of these three genes, ro02105, ro02104 and ro02103, suggests they may be co-expressed as an operon. The tadA gene is predicted to encode a conserved hypothetical protein with significant similarity to the HBHA protein from M. smegmatis. This mutation did not appear to have any effect on the growth rate, sugar metabolism or nitrogen utilization nor did it seem to have any effect on the metabolism of other lipids as evidenced by our TLC analysis of this strain (FIG. 80B). A distinct change however was observed in the lipid body morphology for this mutant as compared to the wild type. Lipid bodies appeared to be slightly larger in the mutant, especially at early time points, and appear to localize primarily to the cell membrane while lipid bodies in the wild type appear to localize throughout the cell (FIG. 83). At later time points lipid bodies in the wild type had begun to coalesce into larger lipid bodies that were evenly distributed throughout the cell, consistent with earlier reports, while in the mutant the size, shape and relative distribution of the lipid bodies was unchanged. Furthermore, overexpression of the TadA protein in the wild-type strain resulted in the formation of very large lipid bodies, which appear to localize to the central axis of the cell (FIG. 83). Thus it is likely that the TadA protein plays a role in lipid body assembly and/or formation rather than in lipid biosynthesis itself.

Figure 87:
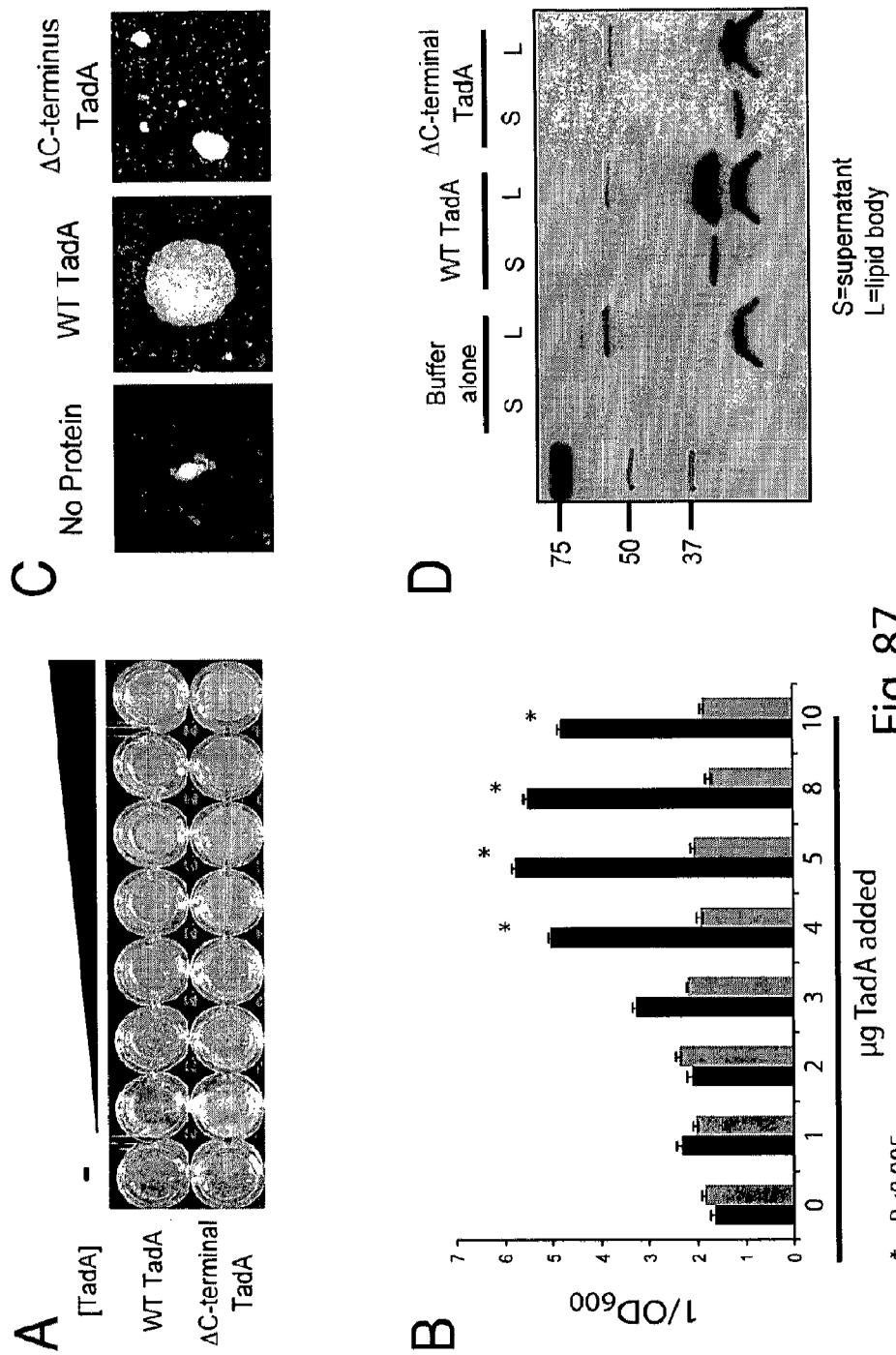
FIG. 87 demonstrates aggregation of purified lipid bodies.

Interestingly, this activity requires the heparin-binding capability of the protein. Loss of the C-terminal heparin-binding domain not only results in an inability to bind heparin in vitro (FIG. 86) but also an inability to function in vivo as evidenced by both the inability of the truncated protein to compliment the 19A3 mutant or induce the overexpression phenotype in the wild type strain (FIG. 83). Furthermore, despite localizing to purified lipid bodies in vitro, the ΔC-terminal TadA protein was incapable of inducing lipid body aggregation in our in vitro assay (FIG. 87).

It is noteworthy that the TadA homolog HBHA is found in both pathogenic and non-pathogenic Mycobacteria and has previously been shown to act as a virulence factor in Mycobacterium tuberculosis, wherein it is believed to promote dissemination during later stages of infection (14, 36-39). Interestingly, M. tuberculosis has been shown to accumulate TAGs and store them in conspicuous inclusion bodies similar to those seen in Rhodococcus (15, 20, 21). In this organism, lipid biosynthesis and storage has been linked to pathogenesis (15, 20, 21, 47). It is possible that much like TadA in Rhodococcus, HBHA in Mycobacteria serves to facilitate lipid body formation and maturation in addition to its predicted role in cyto-adherence and dissemination. Even more tantalizing, the observed decreased virulence in M. tuberculosis HBHA mutants in vivo could be attributed to an inability to functionally store lipids rather than the observed cyto-adherence. Most likely, neither function is the sole reason for the observed reduction in virulence, but rather it is a combination of the two.

The activity of the C-terminal heparin-binding domain is critical for TadA functionality both in vivo and in vitro suggesting that the protein may interact with a lipid-body associated polyanion in vivo thus nucleating lipid bodies and allowing for their previously observed coalescence during later stages of lipid storage. Of additional interest is the localization of lipid bodies both in the 19A3 transposon mutant, around the perimeter of the cell, and in the wild type over expressing TadA, along the center of the cell. It would seem that the TadA protein both acts to aggregate lipid bodies but also acts to localize them within the cell. Without wishing to be bound by any theory, the TadA protein may interact with the bacterial cytoskeleton to both localize and subsequently coalesce lipid bodies. Indeed, previous reports have shown that M. tuberculosis HBHA is capable of binding to actin, the eukaryotic homolog of the bacterial cytoskeletal protein MreB, both in vitro and in vivo. Furthermore, HBHA shares some similarity with actin binding proteins including tropomyosin 1 and ezrin 1, at the amino acid level (37, 51). One can readily envision a model wherein TAGs are synthesized at the cell membrane, as has previously been predicted (2, 52), TadA associates with the growing, membrane-bound lipid bodies at which point the C-terminus interacts with components of the bacterial cytoskeleton which is followed by release of the nascent lipid bodies from the membrane. The bacterial cytoskeleton may act to facilitate both coalescence of lipid bodies as well as their eventual cellular localization.

Thus, presented herein is the first demonstration of a protein that not only localizes to lipid bodies in bacteria, but also acts to mediate their assembly and/or maturation. Based on these data, the process of lipid body assembly and maturation, much like numerous other cellular processes, appears to be highly regulated.

Protein Sequence for R. opacus TadA:

```
                                            (SEQ ID NO: 11)
M T D Q K T I D S V K T S L Y A A V G A G D V V V

Q A V A D V V A Q V R S R A E S T Q G D V E E R V

G G A K E R I A G L Q E E V T E G V E N L R D R L

A G L P S E L P E E L A E L R E K F T A D E L R K

V A E A Y L K V A S D L Y T S L A E R G E D T V E
```

R I R K Q P V V E E G I G R A E T A F G D A V E L
T E E A L G T V A R Q T R A V G E Q A A K L A G R
A S G R I S D T A E G L G E A I A D A G D E A A L
K V L D L G D Q A E E A S K D A A D R V A A T A A
D V Q A Q A D K A A Q A K H A A P A K K A A P A K
A A A T P A P A P A K K V A A P A K K A A P A K K
A

Protein Sequence for *R. opacus* TadB:

(SEQ ID NO: 12)
MIQVDGVVSVILLVIRIVALGGAAYALFHAARQRKDAFTAVDKLSKPIW
LSILAVAFLVLLLFPAVQLFGIVAVVAVCVYLVDVRPRVDDVQRGPRW

Protein Sequence for *R. opacus* TadR:

(SEQ ID NO: 13)
MASDDRDAAGAGDLAARVVSNAAHDIGGFIRAQREAAQVSMRQLAQLAG
VSNPYLSQIERGLRKPSAEVLGQIAKGLRVSSEVLYVQAGYLEQRPHGP
LRDALLADTAITERQKQVLLEIYESFCRENESAEAAESRTSELRTEEHQ
RSDSQTPEPEPPTVEQEKADD

TABLE 9

Strains, plasmids and primers used in Example 7

| Strain | Relevant genotype | Source or reference |
| --- | --- | --- |
| *E. coli*: | | |
| *E. coli* TOP10 | | Invitrogen |
| DPM229 | *E. coli* Top10, pDPM72 | This study |
| DPM238 | *E. coli* Top10, pDPM75 | This study |
| *Rhodococcus*: | | |
| *R. opacus* PD630 | Wild type | (3) |
| DPM245 | Wild type *R. opacus*, pDPM70 | This study |
| DPM246 | Wild type *R. opacus*, pDPM78 | This study |
| DPM247 | Wild type *R. opacus*, pDPM80 | This study |
| DPM248 | tadA::Tn5, pDPM70 | This study |
| DPM249 | tadA::Tn5, pDPM78 | This study |
| DPM250 | tadA::Tn5, pDPM80 | This study |
| Plasmids | Relevant genotype | Source or reference |
| pAL358 | *Rhodococcus*/*E. coli* shuttle vector, GmR | (56) |
| pMSG374 | *Mycobacterium* expression vector | (48) |
| pMQ70 | *S. cerevisiae*/*E. coli* expression vector, ApR | (45) |
| pDPM70 | *S. cerevisiae*/*Rhodococcus*/*E. coli* expression vector, GmR. | This study |
| pDPM78 | pDPM70 + *R. opacus* PD630 tadA, GmR | This study |
| pDPM80 | pDPM70 + ΔC-terminus tadA, GmR | This study |
| pDPM72 | pMQ70 + tadA-C-terminal 6x histidine fusion, ApR | This study |
| pDPM76 | pMQ70 + TadA ΔC-terminus C-terminal 6x histidine fusion, ApR | This study |

TABLE 9-continued

Strains, plasmids and primers used in Example 7

| Primers | Sequence |
|---|---|
| pDPM65 for | 5'-CGGATCTGCCCTGGCTTCAGGAGATCGGAAGAC<br>GTGAGCGGATAACAATTTCACACAGG-3'<br>(SEQ ID NO: 14) |
| pDPM65 rev | 5'-CGAATTGCTGCGCGTAACCACCACACCCGCCGCGC<br>TTAGGATCGTCGGCACCGTCACGG-3'<br>(SEQ ID NO: 15) |
| pDPM66 for | 5'-GCTCGAGGCATGCAGAAAGGAGGCCATATGGGACT<br>GCATGCATCATCATCATCATATGACTGACCAGAAG<br>ACCATCGAC-3'<br>(SEQ ID NO: 16) |
| pDPM66 rev | 5'-CCATGATTACGCCAAGCTTGGTACCGAGCTCG<br>GTTCAAGCCTTCTTGGCCGGAGCAGCC-3'<br>(SEQ ID NO: 17) |
| pDPM80 rev | 5'-ATGACCATGATTACGCCAAGCTTGGTACCGA<br>GCTCGGTTCAGTCGGCCTGAGCCTGGACGTCGG-3'<br>(SEQ ID NO: 18) |
| pDPM65 seq for | 5'-GGCAAAATGGTGGAAGGGCG-3'<br>(SEQ ID NO: 19) |
| pDPM65 seq rev | 5'-GGCCTTGCTGTTCTTCTACGGC-3'<br>(SEQ ID NO: 20) |
| pDPM72 for | 5'-CAAAACAGCCAAGCTTTTAATGATGATGATGATG<br>AGCCTTCTTG GCCGGAGCAGCC-3'<br>(SEQ ID NO: 21) |
| pDPM72 rev | 5'-TACCCGTTTTTTTGGGCAGCGAATTCAGGAGGTCTCTC<br>TCATGACTGACCAGAAGACCATCGACAGC-3'<br>(SEQ ID NO: 22) |
| pDPM75 rev | 5'-CGCCAAAACAGCCAAGCTTTTAATGATGATGATGAT<br>GATGGTCGGCCTGAGCCTGGACGTCGGCAGCGGTGGC<br>GGCGACGC-3'<br>(SEQ ID NO: 23) |
| pMQ70 seq for | 5'-CAGACCGCT TCTGCGTTCTGATTTAATCTG-3'<br>(SEQ ID NO: 24) |
| pMQ70 seq rev | 5'-CGCTAACCAAACCGGTAACCCCGC-3'<br>(SEQ ID NO: 25) |

References for Example 7

1. Alvarez, A. F., H. M. Alvarez, R. Kalscheuer, M. Waltermann, and A. Steinbuchel. 2008. Cloning and characterization of a gene involved in triacylglycerol biosynthesis and identification of additional homologous genes in the oleaginous bacterium *Rhodococcus opacus* PD630. Microbiology 154:2327-2335.
2. Alvarez, H. M., R. Kalscheuer, and A. Steinbuchel. 2000. Accumulation and mobilization of storage lipids by *Rhodococcus opacus* PD630 and *Rhodococcus ruber* NCIMB 40126. Appl Microbiol Biotechnol 54:218-223.
3. Alvarez, H. M., F. Mayer, D. Fabritius, and A. Steinbuchel. 1996. Formation of intracytoplasmic lipid inclusions by *Rhodococcus opacus* strain PD630. Arch Microbiol 165:377-386.
4. Alvarez, H. M., R. A. Silva, A. C. Cesari, A. L. Zamit, S. R. Peressutti, R. Reichelt, U. Keller, U. Malkus, C. Rasch, T. Maskow, F. Mayer, and A. Steinbuchel. 2004. Physiological and morphological responses of the soil bacterium *Rhodococcus opacus* strain PD630 to water stress. FEMS Microbiol Ecol 50:75-86.
5. Alvarez, H. M., M. F. Souto, A. Viale, and O. H. Pucci. 2001. Biosynthesis of fatty acids and triacylglycerols by 2,6,10,14-tetramethyl pentadecane-grown cells of *Nocardia globerula* 432. FEMS Microbiol Lett 200:195-200.
6. Alvarez, H. M., and A. Steinbuchel. 2002. Triacylglycerols in prokaryotic microorganisms. Appl Microbiol Biotechnol 60:367-376.
7. Arabolaza, A., E. Rodriguez, S. Altabe, H. Alvarez, and H. Gramajo. 2008. Multiple pathways for triacylglycerol biosynthesis in *Streptomyces coelicolor*. Appl Environ Microbiol 74:2573-2582.
8. Arrese, E. L., and J. L. Soulages. Insect fat body: energy, metabolism, and regulation. Annu Rev Entomol 55:207-225.
9. Bertani, G. 2004. Lysogeny at mid-twentieth century: P1, P2, and other experimental systems. J Bacteriol 186:595-600.
10. Bligh, E. G., and W. J. Dyer. 1959. A rapid method of total lipid extraction and purification. Can J Biochem Physiol 37:911-917.
11. Brandl, H., R. A. Gross, R. W. Lenz, and R. C. Fuller. 1988. *Pseudomonas oleovorans* as a Source of Poly(beta-Hydroxyalkanoates) for Potential Applications as Biodegradable Polyesters. Appl Environ Microbiol 54:1977-1982.

12. Burnette, W. N. 1981. "Western blotting": electrophoretic transfer of proteins from sodium dodecyl sulfate-polyacrylamide gels to unmodified nitrocellulose and radiographic detection with antibody and radioiodinated protein A. Anal Biochem 112:195-203.

13. Daniel, J., C. Deb, V. S. Dubey, T. D. Sirakova, B. Abomoelak, H. R. Morbidoni, and P. E. Kolattukudy. 2004. Induction of a novel class of diacylglycerol acyltransferases and triacylglycerol accumulation in *Mycobacterium tuberculosis* as it goes into a dormancy-like state in culture. J Bacteriol 186:5017-5030.

14. de Lima, C. S., M. A. Marques, A. S. Debrie, E. C. Almeida, C. A. Silva, P. J. Brennan, E. N. Sarno, F. D. Menozzi, and M. C. Pessolani. 2009. Heparin-binding hemagglutinin (HBHA) of *Mycobacterium leprae* is expressed during infection and enhances bacterial adherence to epithelial cells. FEMS Microbiol Lett 292:162-169.

15. Deb, C., C. M. Lee, V. S. Dubey, J. Daniel, B. Abomoelak, T. D. Sirakova, S. Pawar, L. Rogers, and P. E. Kolattukudy. 2009. A novel in vitro multiple-stress dormancy model for *Mycobacterium tuberculosis* generates a lipid-loaded, drug-tolerant, dormant pathogen. PLoS One 4:e6077.

16. Downing, D. T. 1968. Photodensitometry in the thin-layer chromatographic analysis of neutral lipids. J Chromatogr 38:91-99.

17. Ehrt, S., X. V. Guo, C. M. Hickey, M. Ryou, M. Monteleone, L. W. Riley, and D. Schnappinger. 2005. Controlling gene expression in mycobacteria with anhydrotetracycline and Tet repressor. Nucleic Acids Res 33:e21.

18. Fishbein, W. N. 1972. Quantitative densitometry of 1-50 g protein in acrylamide gel slabs with Coomassie blue. Anal Biochem 46:388-401.

19. Fowler, S. D., and P. Greenspan. 1985. Application of Nile red, a fluorescent hydrophobic probe, for the detection of neutral lipid deposits in tissue sections: comparison with oil red O. J Histochem Cytochem 33:833-836.

20. Garton, N. J., H. Christensen, D. E. Minnikin, R. A. Adegbola, and M. R. Barer. 2002. Intracellular lipophilic inclusions of mycobacteria in vitro and in sputum. Microbiology 148:2951-2958.

21. Garton, N. J., S. J. Waddell, A. L. Sherratt, S. M. Lee, R. J. Smith, C. Senner, J. Hinds, K. Rajakumar, R. A. Adegbola, G. S. Besra, P. D. Butcher, and M. R. Barer. 2008. Cytological and transcript analyses reveal fat and lazy persister-like bacilli in *tuberculous* sputum. PLoS Med 5:e75.

22. Gerngross, T. U., K. D. Snell, O. P. Peoples, A. J. Sinskey, E. Csuhai, S. Masamune, and J. Stubbe. 1994. Overexpression and purification of the soluble polyhydroxyalkanoate synthase from *Alcaligenes eutrophus*: evidence for a required posttranslational modification for catalytic activity. Biochemistry 33:9311-9320.

23. Greenspan, P., E. P. Mayer, and S. D. Fowler. 1985. Nile red: a selective fluorescent stain for intracellular lipid droplets. J Cell Biol 100:965-973.

24. Han, J., Q. Lu, L. Zhou, H. Liu, and H. Xiang. 2009. Identification of the polyhydroxyalkanoate (PHA)-specific acetoacetyl coenzyme A reductase among multiple FabG paralogs in *Haloarcula hispanica* and reconstruction of the PHA biosynthetic pathway in *Haloferax volcanii*. Appl Environ Microbiol 75:6168-6175.

25. Hoffman, C. S., and F. Winston. 1987. A ten-minute DNA preparation from yeast efficiently releases autonomous plasmids for transformation of *Escherichia coli*. Gene 57:267-272.

26. Jendrossek, D. 2009. Polyhydroxyalkanoate granules are complex subcellular organelles (carbonosomes). J Bacteriol 191:3195-3202.

27. Kalscheuer, R., M. Waltermann, M. Alvarez, and A. Steinbuchel. 2001. Preparative isolation of lipid inclusions from *Rhodococcus opacus* and *Rhodococcus ruber* and identification of granule-associated proteins. Arch Microbiol 177:20-28.

28. Kessler, B., and B. Witholt. 2001. Factors involved in the regulatory network of polyhydroxyalkanoate metabolism. J Biotechnol 86:97-104.

29. King, R. J., H. Martin, D. Mitts, and F. M. Holmstrom. 1977. Metabolism of the apoproteins in pulmonary surfactant. J Appl Physiol 42:483-491.

30. Kurosawa, K., Boccazzi, P., de Almeida, N., Sinskey, A. J. 2010. High glucose cultivation of *Rhodococcus opacus* PD630 in batch-culture for biodiesel production Journal of Biotechnology. In press.

31. Laemmli, U. K. 1970. Cleavage of structural proteins during the assembly of the head of bacteriophage T4. Nature 227:680-685.

32. Lawrence, A. G., J. Schoenheit, A. He, J. Tian, P. Liu, J. Stubbe, and A. J. Sinskey. 2005. Transcriptional analysis of *Ralstonia eutropha* genes related to poly-(R)-3-hydroxybutyrate homeostasis during batch fermentation. Appl Microbiol Biotechnol 68:663-672.

33. MacEachran, D. P., S. Ye, J. M. Bomberger, D. A. Hogan, A. Swiatecka-Urban, B. A. Stanton, and G. A. O'Toole. 2007. The *Pseudomonas aeruginosa* secreted protein PA2934 decreases apical membrane expression of the cystic fibrosis transmembrane conductance regulator. Infect Immun 75:3902-3912.

34. McLeod, M. P., R. L. Warren, W. W. Hsiao, N. Araki, M. Myhre, C. Fernandes, D. Miyazawa, W. Wong, A. L. Lillquist, D. Wang, M. Dosanjh, H. Hara, A. Petrescu, R. D. Morin, G. Yang, J. M. Stott, J. E. Schein, H. Shin, D. Smailus, A. S. Siddiqui, M. A. Marra, S. J. Jones, R. Holt, F. S. Brinkman, K. Miyauchi, M. Fukuda, J. E. Davies, W. W. Mohn, and L. D. Ellis. 2006. The complete genome of *Rhodococcus* sp. RHA1 provides insights into a catabolic powerhouse. Proc Natl Acad Sci USA 103:15582-15587.

35. Meex, R. C., P. Schrauwen, and M. K. Hesselink. 2009. Modulation of myocellular fat stores: lipid droplet dynamics in health and disease. Am J Physiol Regul Integr Comp Physiol 297:R913-924.

36. Menozzi, F. D., R. Bischoff, E. Fort, M. J. Brennan, and C. Locht. 1998. Molecular characterization of the mycobacterial heparin-binding hemagglutinin, a mycobacterial adhesin. Proc Natl Acad Sci U S A 95:12625-12630.

37. Menozzi, F. D., V. M. Reddy, D. Cayet, D. Raze, A. S. Debrie, M. P. Dehouck, R. Cecchelli, and C. Locht. 2006. *Mycobacterium tuberculosis* heparin-binding haemagglutinin adhesin (HBHA) triggers receptor-mediated transcytosis without altering the integrity of tight junctions. Microbes Infect 8:1-9.

38. Menozzi, F. D., J. H. Rouse, M. Alavi, M. Laude-Sharp, J. Muller, R. Bischoff, M. J. Brennan, and C. Locht. 1996. Identification of a heparin-binding hemagglutinin present in mycobacteria. J Exp Med 184:993-1001.

39. Pethe, K., M. Aumercier, E. Fort, C. Gatot, C. Locht, and F. D. Menozzi. 2000. Characterization of the heparin-binding site of the mycobacterial heparin-binding hemagglutinin adhesin. J Biol Chem 275:14273-14280.

40. Petty, K. J. 2001. Metal-chelate affinity chromatography. Curr Protoc Protein Sci Chapter 9:Unit 9 4.

41. Prieto, M. A., B. Buhler, K. Jung, B. Witholt, and B. Kessler. 1999. PhaF, a polyhydroxyalkanoate-granule-associated protein of *Pseudomonas oleovorans* GPo1 involved in the regulatory expression system for pha genes. J Bacteriol 181:858-868.
42. Purkrtova, Z., P. Jolivet, M. Miguel, and T. Chardot. 2008. Structure and function of seed lipid-body-associated proteins. C R Biol 331:746-754.
43. Rehm, B. H. 2006. Genetics and biochemistry of polyhydroxyalkanoate granule self-assembly: The key role of polyester syntliases. Biotechnol Lett 28:207-213.
44. Rehm, B. H., and A. Steinbuchel. 1999. Biochemical and genetic analysis of PHA synthases and other proteins required for PHA synthesis. Int J Biol Macromol 25:3-19.
45. Shanks, R. M., N. C. Caiazza, S. M. Hinsa, C. M. Toutain, and G. A. O'Toole. 2006. *Saccharomyces cerevisiae*-based molecular tool kit for manipulation of genes from gram-negative bacteria. Appl Environ Microbiol 72:5027-5036.
46. Shanks, R. M., D. E. Kadouri, D. P. MacEachran, and G. A. O'Toole. 2009. New yeast recombineering tools for bacteria. Plasmid 62:88-97.
47. Sirakova, T. D., V. S. Dubey, C. Deb, J. Daniel, T. A. Korotkova, B. Abomoelak, and P. E. Kolattukudy. 2006. Identification of a diacylglycerol acyltransferase gene involved in accumulation of triacylglycerol in *Mycobacterium tuberculosis* under stress. Microbiology 152:2717-2725.
48. Stephanou, N. C., F. Gao, P. Bongiorno, S. Ehrt, D. Schnappinger, S. Shuman, and M. S. Glickman. 2007. Mycobacterial nonhomologous end joining mediates mutagenic repair of chromosomal double-strand DNA breaks. J Bacteriol 189:5237-5246.
49. Stubbe, J., and J. Tian. 2003. Polyhydroxyalkanoate (PHA) hemeostasis: the role of PHA synthase. Nat Prod Rep 20:445-457.
50. Timm, A., and A. Steinbuchel. 1992. Cloning and molecular analysis of the poly(3-hydroxyalkanoic acid) gene locus of *Pseudomonas aeruginosa* PAO1. Eur J Biochem 209:15-30.
51. Verbelen, C., V. Dupres, D. Raze, C. Bompard, C. Locht, and Y. F. Dufrene. 2008. Interaction of the mycobacterial heparin-binding hemagglutinin with actin, as evidenced by single-molecule force spectroscopy. J Bacteriol 190:7614-7620.
52. Waltermann, M., A. Hinz, H. Robenek, D. Troyer, R. Reichelt, U. Malkus, H. J. Galla, R. Kalscheuer, T. Stoveken, P. von Landenberg, and A. Steinbuchel. 2005. Mechanism of lipid-body formation in prokaryotes: how bacteria fatten up. Mol Microbiol 55:750-763.
53. Waltermann, M., H. Luftmann, D. Baumeister, R. Kalscheuer, and A. Steinbuchel. 2000. *Rhodococcus opacus* strain PD630 as a new source of high-value single-cell oil? Isolation and characterization of triacylglycerols and other storage lipids. Microbiology 146 (Pt 5):1143-1149.
54. Waltermann, M., and A. Steinbuchel. 2005. Neutral lipid bodies in prokaryotes: recent insights into structure, formation, and relationship to eukaryotic lipid depots. J Bacteriol 187:3607-3619.
55. Waltermann, M., T. Stoveken, and A. Steinbuchel. 2007. Key enzymes for biosynthesis of neutral lipid storage compounds in prokaryotes: properties, function and occurrence of wax ester synthases/acyl-CoA: diacylglycerol acyltransferases. Biochimie 89:230-242.
56. Yang, J. C., P. A. Lessard, and A. J. Sinskey. 2007. Characterization of the mobilization determinants of pAN12, a small replicon from *Rhodococcus erythropolis* AN12. Plasmid 57:71-81.
57. York, G. M., B. H. Junker, J. A. Stubbe, and A. J. Sinskey. 2001. Accumulation of the PhaP phasin of *Ralstonia eutropha* is dependent on production of polyhydroxybutyrate in cells. J Bacteriol 183:4217-4226.
58. York, G. M., J. Stubbe, and A. J. Sinskey. 2001. New insight into the role of the PhaP phasin of *Ralstonia eutropha* in promoting synthesis of polyhydroxybutyrate. J Bacteriol 183:2394-2397.
59. Zweytick, D., K. Athenstaedt, and G. Daum. 2000. Intracellular lipid particles of eukaryotic cells. Biochim Biophys Acta 1469:101-120.

EQUIVALENTS

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

What is claimed is:

1. A method for producing triacylglycerols, the method comprising
   culturing a population of cells in culture medium comprising a glucose, xylose, or glycerol concentration between 40 g $l^{-1}$ and 300 g $l^{-1}$ and a carbon/nitrogen ratio between 1.2/1 and 109/1 for a time sufficient for the cells to produce triacylglycerols, and
   optionally collecting the triacylglycerols from the culture medium.

2. The method of claim 1, wherein the cells are oleaginous cells.

3. The method of claim 2, wherein the oleaginous cells are bacterial cells.

4. The method of claim 3, wherein the bacterial cells are *Actinomycetes* cells.

5. The method of claim 4, wherein the *Actinomycetes* cells are *Rhodococcus* cells.

6. The method of claim 5, wherein the *Rhodococcus* cells are *Rhodococcus opacus* cells.

7. The method of claim 6, wherein the *Rhodococcus opacus* cells are *Rhodococcus opacus* PD630 cells.

8. The method of claim 5, wherein the *Rhodococcus* cells are *Rhodococcus* sp. RHA1 cells.

9. The method of claim 1, wherein the glucose concentration is between 60 g $l^{-1}$ and 300 g $l^{-1}$.

10. The method of claim 9, wherein the glucose concentration is between 120 g $l^{-1}$ and 300 g $l^{-1}$.

11. The method of claim 1, wherein the carbon to nitrogen ratio is between 10/1 and 20/1.

12. The method of claim 11, wherein the carbon to nitrogen ratio is approximately 17.8/1.

13. The method of claim 1, wherein the cell is cultured in medium with a pH between 4.0 and 9.0.

14. The method of claim 13, wherein the pH is approximately 7.0.

15. The method of claim 1, wherein the cell is cultured at a temperature of between 20° C. and 45° C.

16. The method of claim 15, wherein the temperature is approximately 30° C.

17. The method of claim 1, wherein the cell is cultured in the presence of xylose.

18. The method of claim 1, wherein the cell is cultured in the presence of glycerol.

* * * * *

UNITED STATES PATENT AND TRADEMARK OFFICE
CERTIFICATE OF CORRECTION

PATENT NO. : 8,679,782 B2  Page 1 of 1
APPLICATION NO. : 13/378479
DATED : March 25, 2014
INVENTOR(S) : Sinskey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this

Twenty-ninth Day of September, 2015

Michelle K. Lee
*Director of the United States Patent and Trademark Office*